US007928127B2

(12) United States Patent
Lee et al.

(10) Patent No.: US 7,928,127 B2
(45) Date of Patent: Apr. 19, 2011

(54) INHIBITORS OF MATRIX METALLAPROTEINASES

(75) Inventors: Mijoon Lee, Seoul (KR); Masahiro Ikejiri, Osaka (JP); Mayland Chang, Granger, IN (US); Rafael Fridman, West Bloomfield, MI (US); Shahriar Mobashery, Granger, IN (US)

(73) Assignees: Notre Dame University, Notre Dame, IN (US); Wayne State University, Detroit, MI (US)

( * ) Notice: Subject to any disclaimer, the term of this patent is extended or adjusted under 35 U.S.C. 154(b) by 192 days.

(21) Appl. No.: 11/914,933

(22) PCT Filed: May 19, 2006

(86) PCT No.: PCT/US2006/019656
§ 371 (c)(1),
(2), (4) Date: Jul. 31, 2008

(87) PCT Pub. No.: WO2006/125208
PCT Pub. Date: Nov. 23, 2006

(65) Prior Publication Data
US 2009/0005420 A1 Jan. 1, 2009

Related U.S. Application Data

(60) Provisional application No. 60/743,467, filed on Mar. 13, 2006.

(51) Int. Cl.
*A61K 31/4427* (2006.01)
*A61K 31/38* (2006.01)
*A61K 31/336* (2006.01)
*C07D 409/02* (2006.01)
*C07D 331/02* (2006.01)
*C07D 303/34* (2006.01)

(52) U.S. Cl. ..... 514/336; 514/430; 514/475; 546/279.7; 549/90; 549/556

(58) Field of Classification Search .................. 514/430, 514/475, 336; 549/556, 90; 546/279.7
See application file for complete search history.

(56) References Cited

U.S. PATENT DOCUMENTS

| 2,949,474 | A | 8/1960 | Murdoch et al. |
| 2,965,651 | A | 12/1960 | Kosmin et al. |
| 3,222,326 | A | 12/1965 | Brodoway |
| 4,797,218 | A | 1/1989 | Steinberg et al. |
| 5,288,722 | A | 2/1994 | Kishimoto et al. |
| 5,981,763 | A | 11/1999 | Garapon et al. |
| 6,703,415 | B2 | 3/2004 | Mobashery et al. |

FOREIGN PATENT DOCUMENTS

| WO | WO-95/35275 | 12/1995 |
| WO | WO-97/18231 | 5/1997 |
| WO | WO-98/33788 | 8/1998 |
| WO | WO-2006125208 A1 | 11/2006 |

OTHER PUBLICATIONS

Schafer et al. (Drug Discovery Today 2008, 13 (21/22), 913-916).*
Horig et al. Journal of Translational Medicine 2004, 2(44).*
Catterall et al., Arthritis Research & Therapy 2003, 5(1), 12-24.*
"Application Serial No. PCT/US2006/019656, Int'l Preliminary Examination Report Mailed Feb. 20, 2009" 6 pgs.
"International Application Serial No. PCT/US06/19656, International Search Report mailed Oct. 2, 2006", 6 pgs.
"International Application Serial No. PCT/US06/19656, Written Opinion mailed Oct. 2, 2006", 5 pgs.
Beckett, R. Paul, et al., "Recent Advances in Matrix Metalloproteinase Inhibitor Research", *Drug Discovery Today*, 1(1), (Jan. 1996), 16-26.
Brew, K., et al., "Tissue Inhibitors of Metalloproteinases: Evolution, Structure and Function", *Biochimica et Biophysica Acta*, 1477(1-2), (Mar. 7, 2000), 267-283.
Brown, Stephen, et al., "Potent and Selective Mechanism-Based Inhibition of Gelatinases", *Journal of the American Chemical Society*, 122(28), (Jul. 19, 2000), 6799-6800.
Bruce, Colleen, et al., "The effect of marimastat, a metalloprotease inhibitor, on allergen-induced asthmatic hyper-reactivity", *Toxicology and Applied Pharmacology 205*, (2005), 126-132.
Bulychev, A., et al., "N-Sulfonyloxy-beta-lactam Inhibitors for beta-Lactamases", *Tetrahedron*, 56(31), (Jul. 28, 2000), 5719-5728.
Dalberg, Kristina, et al., "Gelatinase A, Membrane Type 1 Matrix Metalloproteinase, and Extracellular Matrix Metalloproteinase Inducer mRNA Expression: Correlation with Invasive Growth of Breast Cancer", *World Journal of Surgery*, 24(3), (Mar. 2000), 334-340.
Demedts, Ingel K, et al., "Matrix metalloproteinases in asthma and COPD", *Current Opinion in Pharmacology*, (2005), 257-263.
Dumas, V., et al., "Expression of basement membrane antigens and matrix metalloproteinases 2 and 9 in cutaneous basal and squamous cell carcinomas", *Anticancer Research*, 19(4B), (Jul.-Aug. 1999), 2929-2938.
Forget, Marie-Annick, et al., "Physiological roles of matrix metalloproteinases: implications for tumor growth and metastasis", *Canadian Journal of Physiology and Pharmacology*, 77, (1999), 465-480.
Freskos, J., et al., "Discovery of a Novel Series of Selective MMP Inhibitors: Identification of the γ-Sulfone-Thiols", *Bioorganic & Medicinal Chemistry Letters*, 9(7), (Apr. 5, 1999), 943-948.
Fridman, R., et al., "Domain structure of human 72-kDa gelatinase/type IV collagenase. Characterization of proteolytic activity and identification of the tissue inhibitor of metalloproteinase-2 (TIMP-2) binding regions", *Journal of Biological Chemistry*, 267(22), (Aug. 5, 1992), 15398-15405.
Fridman, R., et al., "Expression of human recombinant 72 kDa gelatinase and tissue inhibitor of metalloproteinase-2 (TIMP-2): characterization of complex and free enzyme", *Biochemical Journal*, 289( Pt 2), (Jan. 15, 1993), 411-416.

(Continued)

*Primary Examiner* — Jason M Nolan
(74) *Attorney, Agent, or Firm* — Clise, Billion & Cyr, P.A.; Michael H. Haukaas

(57) ABSTRACT

The present invention provides novel compounds of formulas I-IX, as described herein. Also provided are compositions of compounds of formulas I-IX, methods of making compounds of formulas I-IX, and methods of using compounds of formulas I-IX. The compounds of the invention can be used to inhibit matrix metalloproteinases, and are useful to treat conditions and diseases associated therewith.

20 Claims, 12 Drawing Sheets

OTHER PUBLICATIONS

Greenwald, R A., et al., "Thirty-six Years in the Clinic without an MMP Inhibitor: What Hath Collagenase Wrought?", *Annals of the New York Academy of Sciences*, 878, (Jun. 1999), 412-419.

Hasaneen, Nadia A, et al., "Cyclic mechanical strain-induced proliferation and migration of human airway smooth muscle cells: role of EMMPRIN and MMPs", *The FASEB Journal*, (Sep. 2005), 1507-1509.

Ikeijiri, et al., "Design, Synthesis, and Evaluation of a Mechanism-Based Inhibitor for Gelatinase A", *J.Org Chem.*, 70, (2005), 5709-5712.

Knight, C G., "Fluorimetric assays of proteolytic enzymes", *Methods in Enzymology*, 248, (1995), 18-34.

Leath, Thomas M, et al., "Novel and emerging therapies for asthma", *DDT* vol. 10, No. 23/24, (Dec. 2005), 1647-1655.

Lee, Mijoon, et al., "Synthesis of Chiral 2-(4-Phenoxyphenylsulfonylmethyl)thiiranes as Selective Gelatinase Inhibitors", *Organic Letters* vol. 7, No. 20, (2005), 4463-4465.

Lim, Taek, et al., "A convenient Synthesis of a Selective Gelatinase Inhibitor as an Antimetastatic Agent", *J. Org. Chem. 69*, (2004), 3572-3573.

Marshall, D.C.L., et al., "Introduction of matrix metalloproteinase-2 in human immunodeficiency virus-1 glycoprotein 120 transgenic mouse brains", *Neuroscience Letters 254*, (1998), 97-110.

Massova, Irina, et al., "Matrix Metalloproteinases: Structures, Evolution, and Diversification", *FASEB Journal*. 12(12), (Sep. 1998), 1075-1095.

Massova, Irina, et al., "Structural Insights into the Catalytic Domains of Human Matrix Metalloprotease-2 and Human Matrix Metalloprotease-9: Implications for Substrate Specificities", *Journal of Molecular Modeling*, 3(1), (Jan. 1997), 17-30.

McMillan, Sarah J, et al., "Matrix Metalloproteinase-9 Deficiency Results in Enhanced Allergen-Induced Airway Inflammation", *The Journal of Immunology 172*, (2004), 2586-2594.

Michaelides, M. R., et al., "Recent advances in matrix metalloproteinase inhibitors research", *Current Pharmaceutical Design*, 5(10), (Oct. 1999), 787-819.

Misse, Dorothee, et al., "HIV-1 glycoprotein 120 induces the MMP-9 cytopathogenic factor production that is abolished by inhibition of the p38 mitogen-activated protein kinase signaling pathway", *Blood*, vol. 98, No. 3, (Aug. 1, 2001), 541-547.

Morgunova, Ekaterina, et al., "Structure of Human Pro-Matrix Metalloproteinase-2: Activation Mechanism Revealed", *Science*, 284(5420), (Jun. 4, 1999), 1667-1670.

Nelson, Amy R., et al., "Matrix Metalloproteinases: Biologic Activity and Clinical Implications", *Journal of Clinical Oncology*, 18(5), (Mar. 1, 2000), 1135-1149.

Olson, Matthew W, "Characterization of the monomeric and dimeric forms of latent and active matrix metalloproteinase-9. Differential rates for activation by stromelysin 1", *Journal of Biological Chemistry*, 275(4), (Jan. 28, 2000), 2661-2668.

Pyke, C., et al., "Localization of messenger RNA for Mr 72,000 and 92,000 type IV collagenases in human skin cancers by in situ hybridization", *Cancer Research*, 52(5), (Mar. 1, 1992), 1336-1341.

Salo, Tuula, et al., "Purification and Characterization of a Murine Basement Membrane Collagen-degrading Enzyme Secreted by Metastatic Tumor Cells", *Journal of Biological Chemistry* 258(5), (Mar. 10, 1983), 3058-3063.

Suryadevara, Radhika, et al., "Regulation fo Tissue Inhibitor of Metalloproteinase-1 by Astrocytes", *GLIA4 44*, (2003), 47-56.

Tamura, Y., "Highly Selective and Orally Active Inhibitors of Type IV Collagenase (MMP-9 and MMP-2): N-Sulfonylamino Acid Derivatives", *Journal of Medicinal Chemistry*, 41(4), (Feb. 12, 1998), 640-649.

Toft-Hansen, Henrik, et al., "Key Metalloproteinases Are Expressed by Specific Cell Types in Experimental Autoimmune Encephalomyelitis", *The Journal of Immunology*, (2004), 5209-5218.

Vermaelen, Karim Y, et al., "Matrix Metalloproteinase-9-Mediated Dendritic Cell Recruitment into the Airways Is a Critical Step in a Mouse Model of Asthma", *The Journal of Immunology*, (2003), 1016-1022.

Westermarck, Jukka, et al., "Regulation of Matrix Metalloproteinase Expression in Tumor Invasion", *FASEB Journal*, 13(8), (May 1999), 781-792.

Zhang, Kunyan, et al., "HIV-induced metalloproteinase processing of the chemokine stromal cell derived factor-1 causes neurodegeneration", *Nature Neuroscience* vol. 6, No. 10, (Sep. 21, 2003), 1064-1071.

\* cited by examiner

A

B

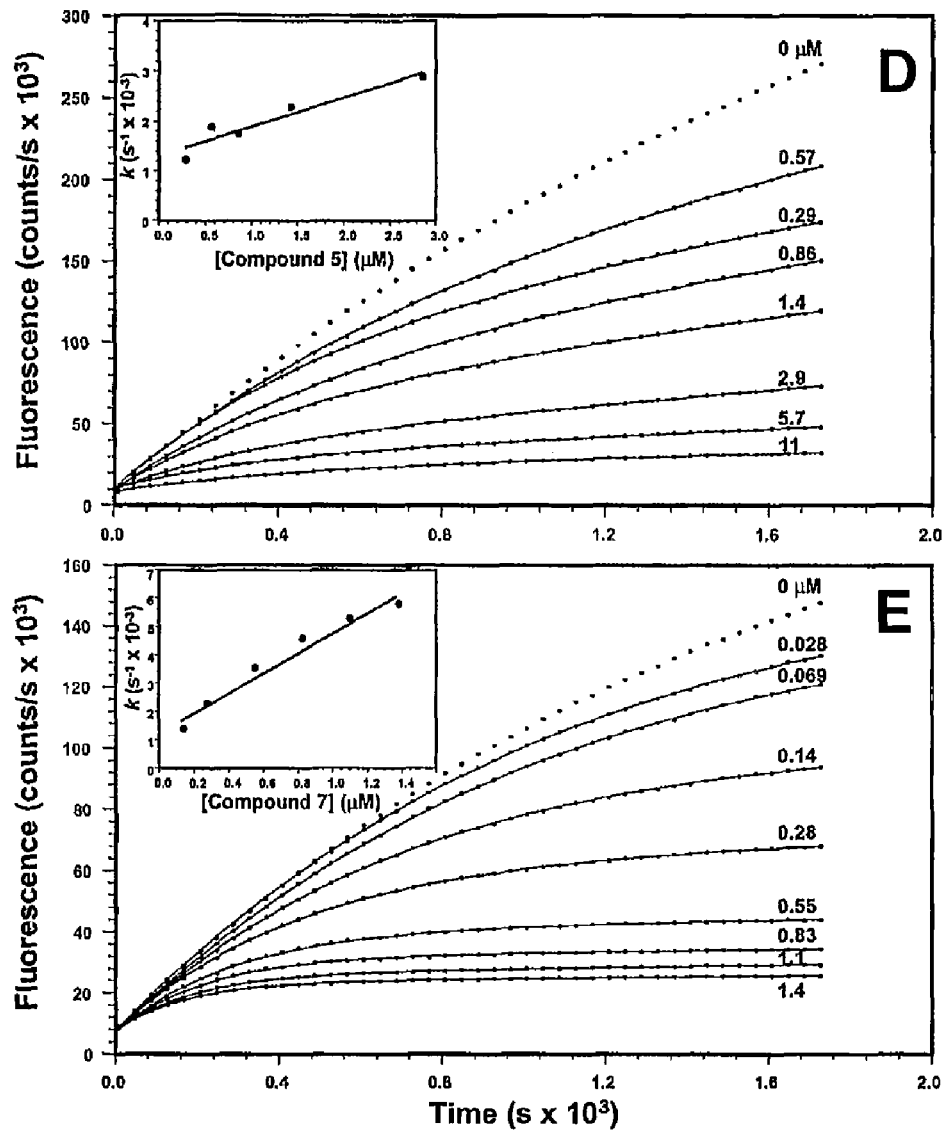
*FIG. 4*, cont'd

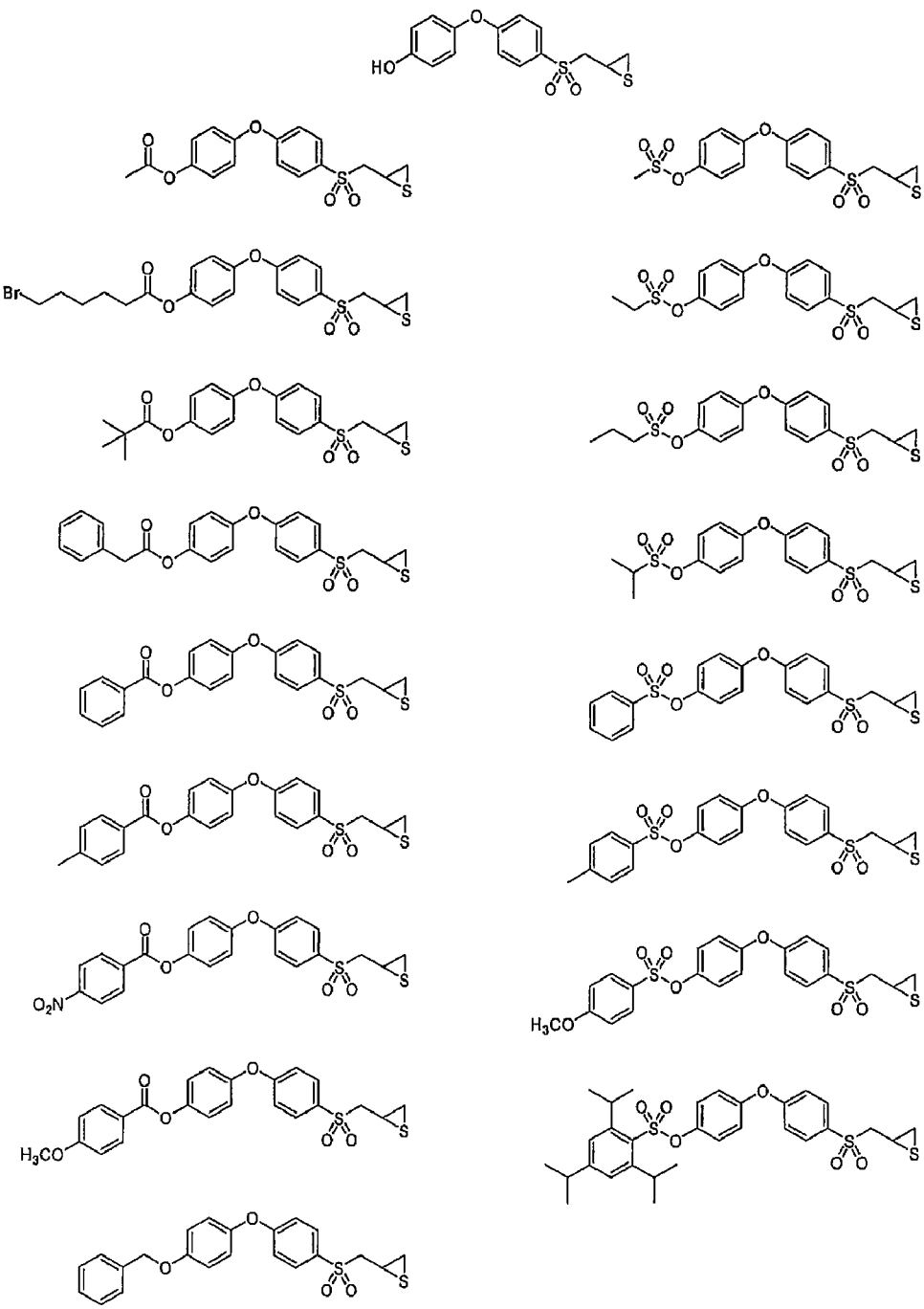
FIG. 8, cont'd

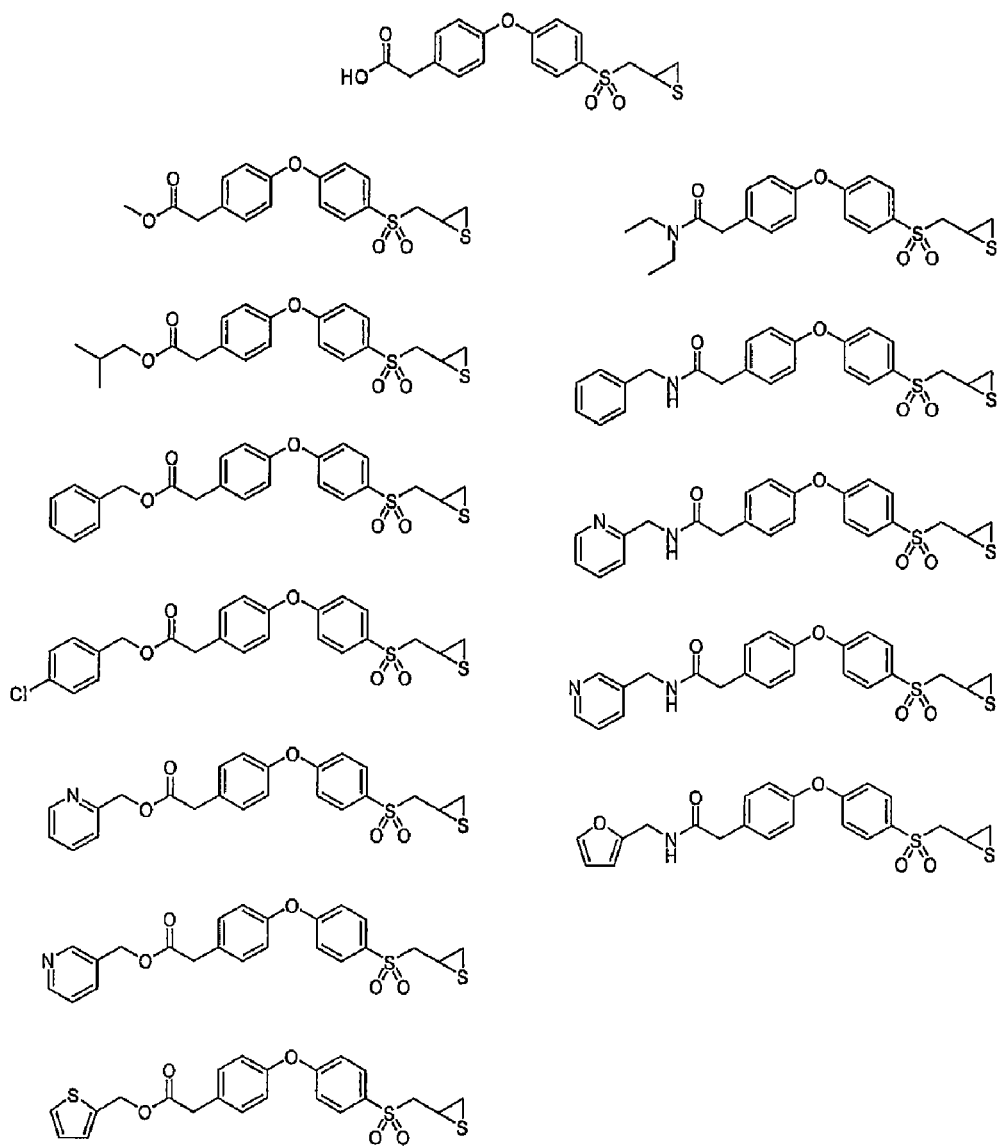
FIG. 8, cont'd

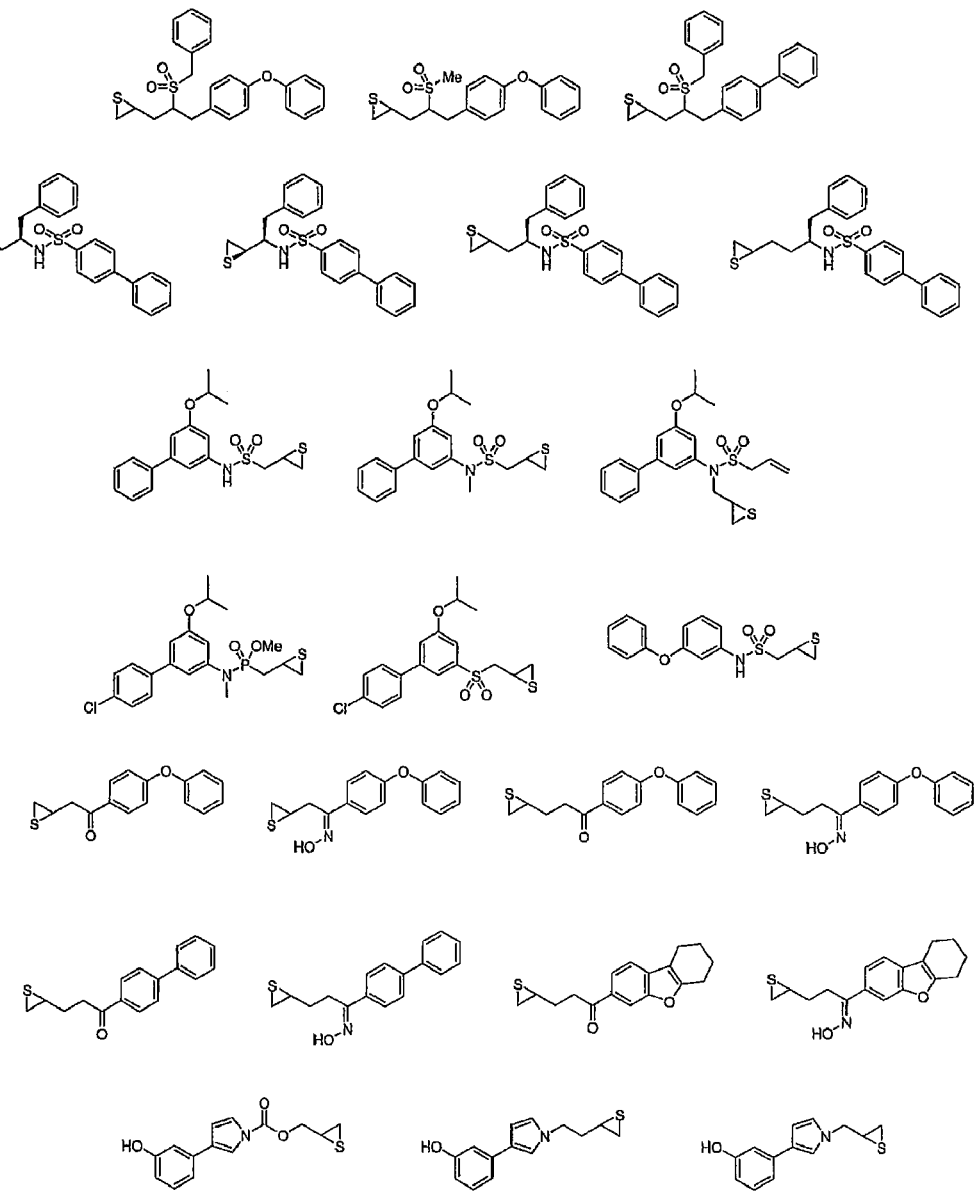
FIG. 8, cont'd

INHIBITORS OF MATRIX METALLAPROTEINASES

RELATED APPLICATIONS

This application is a U.S. National Stage Filing under 35 U.S.C. 371 from International Application Number PCT/US2006/019656, filed May 19, 2006 and published in English as WO 2006/125208 on Nov. 23, 2006, which claims the benefit of U.S. Provisional Application Ser. No. 60/743,467, filed Mar. 13, 2006, under 35 U.S.C. 119(e), which applications and publication are incorporated herein by reference.

GOVERNMENT FUNDING

This invention was made with Government support under grant NCI-CA100475 awarded by the National Institutes of Health. The United States Government has certain rights in this invention.

BACKGROUND OF THE INVENTION

Specific interactions of cells within the extracellular matrix are critical for the normal function of organisms. Alterations of the extracellular matrix are carried out by a family of zinc-dependent endopeptidases called matrix metalloproteinases (MMPs). The alterations are carried out in various cellular processes such as organ development, ovulation, fetus implantation in the uterus, embryogenesis, wound healing, and angiogenesis.

Twenty-six different MMPs are currently known. MMPs consist of five major groups of enzymes: gelatinases, collagenases, stromelysins, membrane-type MMPs, and matrilysins. The activities of MMPs in normal tissue functions are strictly regulated by a series of complicated zymogen activation processes and inhibition by protein tissue inhibitors for matrix metalloproteinases (TIMPs). Excessive MMP activity, when the regulation process fails, has been implicated in cancer growth, tumor metastasis, angiogenesis in tumors, arthritis and connective tissue diseases, cardiovascular disease, inflammation, autoimmune diseases, respiratory diseases, and neurological disorders.

Increased levels of activity for the human gelatinases MMP-2 and MMP-9 have been implicated in several metabolic processes, for example, cancer, tumor metastasis, angiogenesis in tumors, arthritis and connective tissue diseases, cardiovascular disease, inflammation, autoimmune diseases, respiratory diseases, and neurological disorders. Gelatinases are also of particular importance for both female ovulation and implantation of zygotes in the womb (for example, see U.S. Pat. No. 6,703,415). As a result, selective inhibitors of MMPs are highly sought.

Several competitive inhibitors of MMPs are currently known. These inhibitors of MMPs take advantage of chelation to the active site zinc for inhibition of activity. Because of this general property, these competitive inhibitors for MMPs are often toxic to the host, which has been a major impediment in their clinical use.

Accordingly, there is a current need for new inhibitors of MMPs. Such inhibitors would be useful to treat or prevent cancer, tumor metastasis, angiogenesis in tumors, contraception, arthritis and connective tissue diseases, cardiovascular disease, inflammation, autoimmune diseases, respiratory diseases, or neurological disorders. Also needed are inhibitors that exhibit selectivity for one or more specific MMPs. Such inhibitors will preferably not include negative long-term side-effects.

SUMMARY OF THE INVENTION

The present invention relates to compounds of formulas I-IX, compositions that include compounds of formulas I-IX, methods of their preparation, and methods of their use. The pharmaceutical composition can include other therapeutic agents that are compatible with the compound of the invention. The compounds can be used in medical therapy, for example to treat cancer, angiogenesis, cardiovascular disease, neurological disease, eye disease, inflammation, autoimmune disease, and for regulating contraception, and other conditions that are affected by the regulation of MMPs.

BRIEF DESCRIPTION OF THE DRAWINGS

Embodiments of the invention may be best understood by referring to the following detailed description and the accompanying drawings which illustrate certain embodiments.

In FIG. 4, compounds 3, 5, and 7 refer to compounds 2.3, 2.5, and 2.7 of Example 2, respectively.

In FIG. 7, inhibitor 3 refers to compound 2.3 of Example 2.

DETAILED DESCRIPTION

Figure 1:
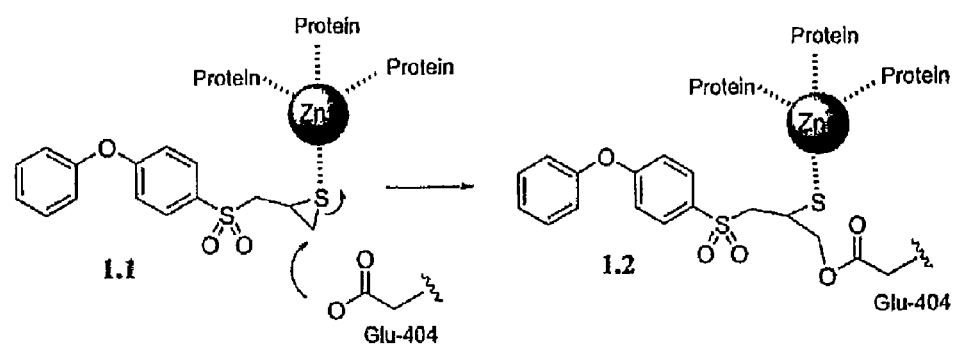
FIG. 1 is a schematic illustration wherein a coordinated thiirane moiety is predisposed to nucleophilic attack by the active site glutamate (Glu-404 in MMP-2) in MMP enzymes, a process that leads to covalent modification of the enzyme and the attendant loss of activity.

Reference will now be made in detail to certain embodiments of the invention, examples of which are illustrated in the accompanying structures, formulas, and Examples. While the invention will be described in conjunction with the enumerated claims, it will be understood that they are not intended to limit the invention to those claims. On the contrary, the invention is intended to cover all alternatives, modifications, and equivalents, which may be included within the scope of the present invention as defined by the claims.

The present invention relates to compounds of formulas I-IX, compositions that include compounds of formulas I-IX, methods of their preparation, and methods of their use. When describing the compounds and methods, the following terms have the following meanings, unless otherwise indicated.

Definitions

References in the specification to "one embodiment", "an embodiment", "an example embodiment", etc., indicate that the embodiment described may include a particular feature, structure, or characteristic, but every embodiment may not necessarily include that particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

"Substituted" is intended to indicate that one or more hydrogens on a group indicated in the expression using "substituted" is replaced with a selection from the indicated group(s), provided that the indicated atom's normal valency is not exceeded, and that the substitution results in a stable compound. Suitable indicated groups include, e.g., alkyl, alkenyl, alkylidenyl, alkenylidenyl, alkoxy, aryloxy, halo, haloalkyl, hydroxy, hydroxyalkyl, aryl, heteroaryl, heterocycle, cycloalkyl, alkanoyl, alkoxycarbonyl, aroyl, acyloxy, aroyloxy, amino, imino, alkylamino, acylamino, nitro, trifluoromethyl, trifluoromethoxy, carboxy, carboxyalkyl, keto, thioxo, alkylthio, alkylsulfinyl, alkylsulfonyl, cyano, acetamido, acetoxy, acetyl, benzamido, benzenesulfinyl, benzenesulfonamido, benzenesulfonyl, benzenesulfonylamino, benzoyl, benzoylamino, benzoyloxy, benzyl, benzyloxy, benzyloxycarbonyl, benzylthio, carbamoyl, carbamate, isocyanato, sulfamoyl, sulfmamoyl, sulfmo, sulfo, sulfoamino, thiosulfo, NR$^x$R$^y$ and/or COOR$^x$, wherein each R$^x$ and R$^y$ are independently H, alkyl, alkenyl, aryl, heteroaryl, heterocycle, cycloalkyl or hydroxy. As would be readily understood by one skilled in the art, when a substituent is keto (i.e., =O) or thioxo (i.e., =S), or the like, then two hydrogen atoms on the substituted atom are replaced.

As used herein, the terms "optional" or "optionally" mean that the subsequently described event or condition may but need not occur, and that the description includes instances where the event or condition occurs and instances in which it does not. For example, "optionally substituted" means that the named substituent may be present but need not be present, and the description includes situations where the named substituent is included and situations where the named substituent is not included.

Specific values described for radicals, substituents, and ranges, as well as specific embodiments of the invention described herein, are for illustration only; they do not exclude other defined values or other values within defined ranges, as would be recognized by one skilled in the art.

As used herein, the term "alkyl" refers to a branched, unbranched, or cyclic hydrocarbon having, for example, from 1 to 12 carbon atoms, and often 1 to 6 carbon atoms. Examples include, but are not limited to, methyl (Me, —CH$_3$), ethyl (Et, —CH$_2$CH$_3$), 1-propyl (n-Pr, n-propyl, —CH$_2$CH$_2$CH$_3$), 2-propyl (i-Pr, i-propyl, —CH(CH$_3$)$_2$), 1-butyl (n-Bu, n-butyl, —CH$_2$CH$_2$CH$_2$CH$_3$), 2-methyl-1-propyl (1-Bu, i-butyl, —CH$_2$CH(CH$_3$)$_2$), 2-butyl (s-Bu, s-butyl, —CH(CH$_3$)CH$_2$CH$_3$), 2-methyl-2-propyl (t-Bu, t-butyl, —C(CH$_3$)$_3$), 1-pentyl (n-pentyl, —CH$_2$CH$_2$CH$_2$CH$_2$CH$_3$), 2-pentyl (—CH(CH$_3$)CH$_2$CH$_2$CH$_3$), 3-pentyl (—CH (CH$_2$CH$_3$)$_2$), 2-methyl-2-butyl (—C(CH$_3$)$_2$CH$_2$CH$_3$), 3-methyl-2-butyl (—CH(CH$_3$)CH(CH$_3$)$_2$), 3-methyl-1-butyl (—CH$_2$CH$_2$CH(CH$_3$)$_2$), 2-methyl-1-butyl (—CH$_2$CH(CH$_3$) CH$_2$CH$_3$), 1-hexyl (—CH$_2$CH$_2$CH$_2$CH$_2$CH$_2$CH$_3$), 2-hexyl (—CH(CH$_3$)CH$_2$CH$_2$CH$_2$CH$_3$), 3-hexyl (—CH(CH$_2$CH$_3$) (CH$_2$CH$_2$CH$_3$)), 2-methyl-2-pentyl (—C(CH$_3$)$_2$ CH$_2$CH$_2$CH$_3$), 3-methyl-2-pentyl (—CH(CH$_3$)CH(CH$_3$) CH$_2$CH$_3$), 4-methyl-2-pentyl (—CH(CH$_3$)CH$_2$CH(CH$_3$)$_2$), 3-methyl-3-pentyl (—C(CH$_3$)(CH$_2$CH$_3$)$_2$), 2-methyl-3-pentyl (—CH(CH$_2$CH$_3$)CH(CH$_3$)$_2$), 2,3-dimethyl-2-butyl (—C (CH$_3$)$_2$CH(CH$_3$)$_2$), and 3,3-dimethyl-2-butyl (—CH(CH$_3$)C (CH$_3$)$_3$, hexyl, octyl, decyl, or dodecyl. The alkyl can be unsubstituted or substituted. The alkyl can also be optionally partially or fully unsaturated. As such, the recitation of an alkyl group includes both alkenyl and alkynyl groups. The alkyl can be a monovalent hydrocarbon radical, as described and exemplified above, or it can be a divalent hydrocarbon radical (i.e., alkylene).

The alkyl can optionally be substituted with one or more alkyl, alkenyl, alkylidenyl, alkenylidenyl, alkoxy, halo, haloalkyl, hydroxy, hydroxyalkyl, aryl, heteroaryl, heterocycle, cycloalkyl, alkanoyl, alkoxycarbonyl, amino, imino, alkylamino, acylamino, nitro, trifluoromethyl, trifluoromethoxy, carboxy, carboxyalkyl, keto, thioxo, alkylthio, alkylsulfinyl, alkylsulfonyl, cyano, acetamido, acetoxy, acetyl, benzamido, benzenesulfinyl, benzenesulfonamido, benzenesulfonyl, benzenesulfonylamino, benzoyl, benzoylamino, benzoyloxy, benzyl, benzyloxy, benzyloxycarbonyl, benzylthio, carbamoyl, carbamate, isocyannato, sulfamoyl, sulfinamoyl, sulfino, sulfo, sulfoamino, thiosulfo, NR$^x$R$^y$ and/or COOR$^x$, wherein each R$^x$ and R$^y$ are independently H, alkyl, alkenyl, aryl, heteroaryl, heterocycle, cycloalkyl or hydroxy. The alkyl can optionally be interrupted with one or more non-peroxide oxy (—O—), thio (—S—), imino (—N (H)—), methylene dioxy (—OCH$_2$O—), carbonyl (—C(=O)—), carboxy (—C(=O)O—), carbonyldioxy (—OC(=O)O—), carboxylato (—OC(=O)—), imine (C=NH), sulfinyl (SO) or sulfonyl (SO$_2$) groups.

The term "alkenyl" refers to a C$_2$-C$_{12}$ hydrocarbon containing normal, secondary, tertiary or cyclic carbon atoms with at least one site of unsaturation, i.e. a carbon-carbon, sp2 double bond. Examples include, but are not limited to: ethylene or vinyl (—CH=CH$_2$), allyl (—CH$_2$CH=CH$_2$), cyclopentenyl (—C$_5$H$_7$), and 5-hexenyl (—CH$_2$CH$_2$CH$_2$CH=CH$_2$). The alkenyl can be a movalent hydrocarbon radical, as described and exemplified above, or it can be a divalent hydrocarbon radical (i.e., alkenylene). An alkenyl group can be substituted as described for alkyl groups above.

The term "alkynyl" refers to a monoradical branched or unbranched hydrocarbon chain, having a point of complete unsaturation (i.e. a carbon-carbon, sp triple bond). In one embodiment, the alkynyl group can have from 2 to 10 carbon atoms, or 2 to 6 carbon atoms. In another embodiment, the alkynyl group can have from 2 to 4 carbon atoms. This term is exemplified by groups such as ethynyl, 1-propynyl, 2-propynyl, 1-butynyl, 2-butynyl, 3-butynyl, 1-hexynyl, 2-hexynyl, 3-hexynyl, 1-octynyl, and the like. The alkynyl can be unsubstituted or substituted, as described above for alkyl groups.

The term "cycloalkyl" refers to cyclic alkyl groups of from 3 to 20 carbon atoms having a single cyclic ring or multiple condensed rings. Such cycloalkyl groups include, by way of example, single ring structures such as cyclopropyl, cyclobutyl, cyclopentyl, cyclooctyl, and the like, or multiple ring structures such as adamantanyl, and the like. The cycloalkyl can optionally be partially unsaturated, thereby providing a cycloalkenyl. The cycloalkyl group can be monovalent or divalent, and can be optionally substituted as described above for alkyl groups.

The term "alkoxy" refers to the group alkyl-O—, where alkyl is as defined herein. Preferred alkoxy groups include, e.g., methoxy, ethoxy, n-propoxy, iso-propoxy, n-butoxy, tert-butoxy, sec-butoxy, n-pentoxy, n-hexoxy, 1,2-dimethylbutoxy, and the like. Alkoxy groups can optionally be substituted as described above for alkyl groups.

As used herein, "aryl" refers to an aromatic hydrocarbon group derived from the removal of one hydrogen atom from a single carbon atom of a parent aromatic ring system. The radical can be at a saturated or unsaturated carbon atom of the parent ring system. The aryl group itself can have from 6 to 18 carbon atoms (excluding substituents). The aryl group can have a single ring (e.g., phenyl) or multiple condensed (fused) rings, wherein at least one ring is aromatic (e.g., naphthyl, dihydrophenanthrenyl, fluorenyl, or anthryl). Typical aryl groups include, but are not limited to, radicals derived from benzene, naphthalene, anthracene, biphenyl, and the like. The aryl can be unsubstituted or optionally substituted, as described above for alkyl groups.

The term "halo" refers to fluoro, chloro, bromo, and iodo. Similarly, the term "halogen" refers to fluorine, chlorine, bromine, and iodine.

The term "haloalkyl" refers to alkyl as defined herein substituted by 1 or more halo groups as defined herein, which may be the same or different. In one embodiment, the haloalkyl can be substituted with 1, 2, 3, 4, or 5 halo groups. In another embodiment, the haloalkyl can by substituted with 1, 2, or 3 halo groups. The term haloalkyl also include perfluoro-alkyl groups. Representative haloalkyl groups include, by way of example, trifluoromethyl, 3-fluorododecyl, 12,12,12-trifluorododecyl, 2-bromooctyl, 3-bromo-6-chloroheptyl, 1H,1H-perfluorooctyl, and the like.

The term "heteroaryl" is defined herein as a monocyclic, bicyclic, or tricyclic ring system containing one, two, or three aromatic rings and containing at least one nitrogen, oxygen, or sulfur atom in an aromatic ring, and which can be unsubstituted or substituted, for example, with one or more, and in particular one to three, substituents, as described above in the definition of "substituted". Examples of heteroaryl groups include, but are not limited to, 2H-pyrrolyl, 3H-indolyl, 4H-quinolizinyl, acridinyl, benzo[b]thienyl, benzothiazolyl, β-carbolinyl, carbazolyl, chromenyl, cinnolinyl, dibenzo[b, d]furanyl, furazanyl, furyl, imidazolyl, imidizolyl, indazolyl, indolisinyl, indolyl, isobenzofuranyl, isoindolyl, isoquinolyl, isothiazolyl, isoxazolyl, naphthyridinyl, oxazolyl, perimidinyl, phenanthridinyl, phenanthrolinyl, phenarsazinyl, phenazinyl, phenothiazinyl, phenoxathiinyl, phenoxazinyl, phthalazinyl, pteridinyl, purinyl, pyranyl, pyrazinyl, pyrazolyl, pyridazinyl, pyridyl, pyrimidinyl, pyrimidinyl, pyrrolyl, quinazolinyl, quinolyl, quinoxalinyl, thiadiazolyl, thianthrenyl, thiazolyl, thienyl, triazolyl, tetrazolyl, and xanthenyl. In one embodiment the term "heteroaryl" denotes a monocyclic aromatic ring containing five or six ring atoms containing carbon and 1, 2, 3, or 4 heteroatoms independently selected from non-peroxide oxygen, sulfur, and N(Z) wherein Z is absent or is H, O, allyl, aryl, or (C$_1$-C$_6$)alkylaryl. In another embodiment heteroaryl denotes an ortho-fused bicyclic heterocycle of about eight to ten ring atoms derived therefrom, particularly a benz-derivative or one derived by fusing a propylene, trimethylene, or tetramethylene diradical thereto.

The term "heterocycle" refers to a saturated or partially unsaturated ring system, containing at least one heteroatom selected from the group oxygen, nitrogen, and sulfur, and optionally substituted with one or more groups as defined herein under the term "substituted". A heterocycle can be a monocyclic, bicyclic, or tricyclic group containing one or more heteroatoms. A heterocycle group also can contain an oxo group (=O) attached to the ring. Non-limiting examples of heterocycle groups include 1,3-dihydrobenzofuran, 1,3-dioxolane, 1,4-dioxane, 1,4-dithiane, 2H-pyran, 2-pyrazoline, 4H-pyran, chromanyl, imidazolidinyl, imidazolinyl, indolinyl, isochromanyl, isoindolinyl, morpholine, piperazinyl, piperidine, piperidyl, pyrazolidine, pyrazolidinyl, pyrazolinyl, pyrrolidine, pyrroline, quinuclidine, and thiomorpholine. Other heterocycles include those described by Paquette in *Principles of Modern Heterocyclic Chemistry* (W. A. Benjamin, New York, 1968), particularly Chapters 1, 3, 4, 6, 7, and 9; and in *The Chemistry of Heterocyclic Compounds. A Series of Monographs*" (John Wiley & Sons, New York, 1950 to present), in particular Volumes 13, 14, 16, 19, and 28; and *J. Am. Chem. Soc.* 1960, 82, 5566.

The term "alkanoyl" or "acyl" refers to —C(=O)R, wherein R is an alkyl group as previously defined.

The term "aroyl" refers to —C(=O)Ar, wherein Ar is an aryl group as previously defined.

The term "alkoxycarbonyl" refers to —C(=O)OR, wherein R is an alkyl group as previously defined.

The term "acyloxy" refers to —O—C(=O)R, wherein R is an alkyl group as previously defined. Examples of acyloxy groups include, but are not limited to, acetoxy, propanoyloxy, butanoyloxy, and pentanoyloxy. Any allyl group as defined above can be used to form an acyloxy group.

The term "amino" refers to —NH$_2$. The amino group can be optionally substituted as defined herein for the term "substituted". The term "alkylamino" refers to —NR$_2$, wherein at least one R is alkyl and the second R is alkyl or hydrogen. The term "acylamino" refers to N(R)C(=O)R, wherein each R is independently hydrogen, alkyl, or aryl.

As to any of the above groups, which contain one or more substituents, it is understood, of course, that such groups do not contain any substitution or substitution patterns that are sterically impractical and/or synthetically non-feasible. In addition, the compounds of this invention include all stereochemical isomers arising from the substitution of these compounds.

One diastereomer of a compound disclosed herein may display superior properties or activity compared with another. When required, separation of the racemic material can be achieved by HPLC using a chiral column or by a resolution using a resolving agent such as camphonic chloride as described by Thomas J. Tucker, et al., *J. Med. Chem.* 1994, 37, 2437-2444. A chiral compound may also be directly synthesized using a chiral catalyst or a chiral ligand, e.g., as described by Mark A. Huffman, et al., *J. Org. Chem.* 1995, 60, 1590-1594.

Selected substituents within the compounds described herein are present to a recursive degree. In this context, "recursive substituent" means that a substituent may recite another instance of itself. Because of the recursive nature of such substituents, theoretically, a large number may be present in any given claim. One of ordinary skill in the art of medicinal chemistry and organic chemistry understands that the total number of such substituents is reasonably limited by the desired properties of the compound intended. Such properties include, by of example and not limitation, physical properties such as molecular weight, solubility or log P, application properties such as activity against the intended target, and practical properties such as ease of synthesis.

Recursive substituents are an intended aspect of the invention. One of ordinary skill in the art of medicinal and organic chemistry understands the versatility of such substituents. To the degree that recursive substituents are present in an claim of the invention, the total number will be determined as set forth above.

"Stable compound" and "stable structure" are meant to indicate a compound that is sufficiently robust to survive isolation to a useful degree of purity from a reaction mixture, and formulation into an efficacious therapeutic agent. Only stable compounds are contemplated herein.

The phrase "pharmaceutically acceptable" is employed herein to refer to those compounds, materials, compositions, and/or dosage forms which are, within the scope of sound medical judgment, suitable for use in contact with the tissues of human beings or animals without excessive toxicity, irritation, allergic response, or other problems or complications commensurate with a reasonable benefit/risk ratio.

As used herein, "pharmaceutically acceptable salts" refer to compounds described herein, wherein the parent compound is modified by making acid or base salts thereof. Examples of pharmaceutically acceptable salts include, but are not limited to, mineral or organic acid salts of basic residues such as amines, and alkali or organic salts of acidic residues such as carboxylic acids; and the like. The pharmaceutically acceptable salts include conventional non-toxic salts or quaternary ammonium salts of the parent compound formed, for example, from inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

The pharmaceutically acceptable salts of the compounds described herein can be synthesized from the parent compound, which contains a basic or acidic moiety, by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences*, 17th ed., Mack Publishing Company, Easton, Pa., (1985), 1418, the disclosure of which is incorporated herein by reference.

As used herein, "treating" or "treat" includes preventing a pathologic condition from occurring (e.g. prophylaxis); inhibiting the pathologic condition or arresting its development; relieving a subject of the pathologic condition; and/or diminishing symptoms associated with the pathologic condition. "Treat," "treating" or "treatment" includes treating, reversing, preventing, ameliorating, or inhibiting an injury or disease-related condition or a symptom of an injury or disease-related condition.

As used herein, "contacting" refers to the act of touching, making contact, or of bringing into immediate proximity.

The term "therapeutically effective amount" or "effective amount" is intended to include an amount of a compound described herein, or an amount of the combination of compounds described herein, e.g., to treat or prevent a disease or disorder, or to treat the symptoms of a disease or disorder, typically in a host. The combination of compounds is preferably a synergistic combination. Synergy, as described for example by Chou and Talalay (*Adv. Enzyme Regul.*, 1984, 22, 27), occurs when the effect of the compounds when administered in combination is greater than the additive effect of the compounds when administered alone as a single agent. In general, a synergistic effect is most clearly demonstrated at suboptimal concentrations of the compounds. Synergy can be in terms of lower cytotoxicity, increased activity, or some other beneficial effect of the combination compared with the individual components.

As used herein, a "therapeutic agent" is a compound that has biological activity against any of tumor metastasis, angiogenesis in tumors, cancer, arthritis and connective tissue diseases, cardiovascular disease, inflammation, autoimmune diseases, respiratory diseases, or neurological disorders. The therapeutic agent can be administered to a patient with a compound of formulas I-IX without losing its therapeutic activity. Suitable therapeutic agents include, e.g., anti-inflammatory agents, antibiotics, anti-viral agents, anticoagulants, α-adrenergic agonists, β-adrenergic agonists, analgesics, antineoplasts, adjuncts, androgen inhibitors, antibiotic derivatives, antiestrogens, antimetabolites, cytotoxic agents, hormones, immunomodulators, nitrogen mustard derivatives and steroids. Other therapeutic agents that can be used in conjunction with the compounds of the invention are disclosed in the *Physicians' Desk Reference*, 59th Ed.; Thompson PDR: Montvale, N.J. (2005).

A "subject" can be a vertebrate, preferably a mammal, more preferably a human. Mammals include, but are not limited to, humans, farm animals, sport animals, and companion animals.

The term "protecting group" refers to any group which, when bound to a hydroxyl, nitrogen, or other heteroatom prevents undesired reactions from occurring at this group and which can be removed by conventional chemical or enzymatic steps to reestablish the hydroxyl group. The particular removable blocking group employed is not critical and preferred removable hydroxyl blocking groups include conventional substituents such as, for example, allyl, benzyl, acetyl, chloroacetyl, thiobenzyl, benzylidine, phenacyl, methyl methoxy, silyl ethers (e.g., trimethylsilyl (TMS), t-butyl-diphenylsilyl (TBDPS), or t-butyldimethylsilyl (TBS)) and any other group that can be introduced chemically onto a hydroxyl functionality and later selectively removed either by chemical or enzymatic methods in mild conditions compatible with the nature of the product.

A large number of protecting groups and corresponding chemical cleavage reactions are described in *Protective Groups in Organic Synthesis*, Theodora W. Greene (John Wiley & Sons, Inc., New York, 1991, *ISBN* 0-471-62301-6) ("Greene", which is incorporated herein by reference in its entirety). Included therein are nitrogen protecting groups, for example, amide-forming groups. In particular, see Chapter 1, Protecting Groups: An Overview, pages 1-20, Chapter 2, Hydroxyl Protecting Groups, pages 21-94, Chapter 4, Carboxyl Protecting Groups, pages 118-154, and Chapter 5, Carbonyl Protecting Groups, pages 155-184. See also Kocienski, Philip J.; *Protecting Groups* (Georg Thieme Verlag Stuttgart, New York, 1994), which is incorporated herein by reference in its entirety. Some specific protecting groups that can be employed in conjunction with the methods of the invention are discussed below.

Typical nitrogen protecting groups described in Greene (pages 14-118) include benzyl ethers, silyl ethers, esters including sulfonic acid esters, carbonates, sulfates, and sulfonates. For example:
  substituted methyl ethers;
  substituted ethyl ethers;
  p-chlorophenyl, p-methoxyphenyl, 2,4-dinitrophenyl, benzyl;
  substituted benzyl ethers (p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2- and 4-picolyl, diphenylmethyl, 5-dibenzosuberyl, triphenylmethyl, p-methoxyphenyldiphenylmethyl, di(p-methoxyphenyl)phenylmethyl, tri(p-methoxyphenyl)methyl, 1,3-benzodithiolan-2-yl, benzisothiazolyl S,S-dioxido);
  silyl ethers (silyloxy groups) (trimethylsilyl, triethylsilyl, triisopropylsilyl, dimethylisopropylsilyl, diethylisopropylsilyl, dimethylthexylsilyl, t-butyldimethylsilyl, t-butyldiphenylsilyl, tribenzylsilyl, tri-p-xylylsilyl, triphenylsilyl, diphenylmethylsilyl, t-butylmethoxyphenylsilyl);
  esters (formate, benzoylformate, acetate, choroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), pivaloate, adamantoate, crotonate, 4-methoxycrotonate, benzoate, p-phenylbenzoate, 2,4,6-trimethylbenzoate (mesitoate));
  carbonates (methyl, 9-fluorenylmethyl, ethyl, 2,2,2-trichloroethyl, 2-(trimethylsilyl)ethyl, 2-(phenylsulfonyl)ethyl, 2-(triphenylphosphonio)ethyl, isobutyl, vinyl, allyl, p-nitrophenyl, benzyl, p-methoxybenzyl, 3,4-dimethoxybenzyl, o-nitrobenzyl, p-nitrobenzyl, S-benzyl thiocarbonate, 4-ethoxy-1-naphthyl, methyl dithiocarbonate);
  groups with assisted cleavage (2-iodobenzoate, 4-azidobutyrate, 4-nitro-4-methylpentanoate, o-(dibromomethyl) benzoate, 2-formylbenzenesulfonate, 2-(methylthiomethoxy)ethyl carbonate, 4-(methylthiomethoxy) butyrate,
  miscellaneous esters (2,6-dichloro-4-methylphenoxyacetate, 2,6-dichloro-4-(1,1,3,3 tetramethylbutyl)phenoxyacetate, 2,4-bis(1,1-dimethylpropyl)phenoxyacetate, chlorodiphenylacetate, isobutyrate, monosuccinate, (E)-2-methyl-2-butenoate (tigloate), o-(methoxycarbonyl)benzoate, p-poly-benzoate, α-naphthoate, nitrate, alkyl N,N,N',N'-tetramethylphosphorodiamidate, n-phenylcarbamate, borate, 2,4-dinitrophenylsulfenate); and
  sulfonates (sulfate, methanesulfonate (mesylate), benzylsulfonate, tosylate, triflate).

Compounds of the Invention

The present invention provides compounds of formulas I-IX, compositions that include such compounds, methods of their preparation, and methods of their use. Specifically, the invention provides a compound of formula I:

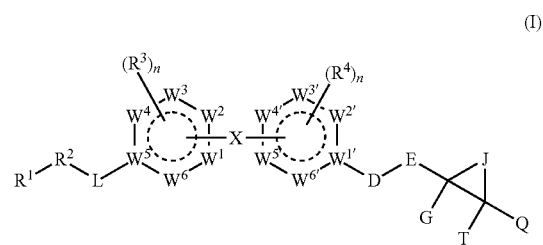

(I)

wherein $R^1$ is $(C_1-C_6)$alkyl, halo$(C_1-C_6)$alkyl, $(C_1-C_6)$alkoxy, aryl$(C_1-C_6)$alkyl, heteroaryl$(C_1-C_6)$alkyl, aryl$(C_1-C_6)$alkoxy, heteroaryl$(C_1-C_6)$alkoxy, aryl, heteroaryl, hydroxy, $SR^5$, $NR^5R^5$, or absent;

$R^2$ is $CH_2$, carbonyl, $SO_2$, or OH;

L is $CH_2$, $NR^5$, or O;

$W^1$-$W^6$ are each independently C, N, O, S, or absent, and form a 5 or 6 membered aryl, heterocycle, or heteroaryl ring;

$W^{1'}$-$W^{6'}$ are each independently C, N, O, S, or absent, and form a 5 or 6 membered aryl, heterocycle, or heteroaryl ring;

the dashed circles within the rings formed by $W^1$-$W^6$ and $W^{1'}$-$W^{6'}$ denote optional double bonds of the rings formed by $W^1$-$W^6$ and $W^{1'}$-$W^{6'}$;

$R^3$ and $R^4$ are each independently hydroxy, $(C_1-C_6)$alkyl, $(C_1-C_6)$alkoxy, $(C_1-C_6)$alkanoyl, $(C_1-C_6)$alkanoyloxy, aryl, heteroaryl, carboxy, cyano, nitro, halo, trifluoromethyl, trifluoromethoxy, $SR^5$, $SO_2N(R_5)_2$, $NR^5R^5$, or $COOR^5$;

each n is independently 0 to 4;

each $R^5$ is independently H, $(C_1-C_6)$alkyl, $(C_1-C_6)$alkanoyl, $(C_6-C_{10})$aroyl, aryl, aryl$(C_1-C_6)$alkyl, heteroaryl, heteroaryl$(C_1-C_6)$alkyl, or a nitrogen protecting group;

X is O, S, SO, $SO_2$, $CH_2$—O, $CH_2$—S, $CH_2$—$NR^5$, NR, carbonyl, or a direct bond;

D is S, SO, $SO_2$, P(O)OH, P(O)O$(C_1-C_6)$alkyl, P(O$(C_1-C_6)$alkyl)$_2$, C=N—OH, or carbonyl;

E is a direct bond, $(C_1-C_6)$allyl, $(C_3-C_8)$cycloalkyl, $(C_2-C_6)$alkenyl, $(C_2-C_6)$alkynyl, or $(C_3-C_8)$heterocycle;

J is S, O, or $NR^5$;

G, T, and Q are each independently H, $(C_1-C_6)$alkyl, or cyano;

any alkyl, amino, aryl, heteroaryl, or cycloalkyl is optionally substituted with 1 to about 5 $(C_1-C_6)$alkyl, $(C_1-C_6)$alkoxy, aryl, heteroaryl, aryl$(C_1-C_6)$alkyl, heteroaryl$(C_1-C_6)$alkyl, nitro, halo, amino, or hydroxy groups;

or a pharmaceutically acceptable salt thereof;

provided that when L is $CH_2$ or O, and $R^2$ is $CH_2$, $R^1$ is not $(C_1-C_6)$alkyl;

when L is O and $R^2$ is carbonyl, $R^1$ is not $(C_1-C_6)$alkyl; and when L is NR, $R^2$ is $CH_2$.

The invention also provides a compound of formula II:

(II)

wherein $R^1$ is H, $(C_1-C_6)$alkyl, halo$(C_1-C_6)$alkyl, $(C_1-C_6)$alkoxy, $(C_1-C_6)$alkanoyl, $(C_1-C_6)$alkanoyloxy, aryl$(C_1-C_6)$alkyl, heteroaryl$(C_1-C_6)$alkyl, aryl$(C_1-C_6)$alkoxy, heteroaryl$(C_1-C_6)$ alkoxy, aryl, heteroaryl, hydroxy, nitro, cyano, halo, trifluoromethyl, trifluoromethoxy, $SR^5$, $NR^5R^5$, or $CO_2R^5$;

$R^2$ is $CH_2$, carbonyl, $SO_2$, or a direct bond;

L is $CH_2$, NR, O, S, SO, $SO_2$, or a direct bond;

$W^1$-$W^6$ are each independently C, N, O, S, or absent, and form a 5 or 6 membered aryl, heterocycle, or heteroaryl ring;

$W^{1'}$-$W^{6'}$ are each independently C, N, O, S, or absent, and form a 5 or 6 membered aryl, heterocycle, or heteroaryl ring;

the dashed circles within the rings formed by $W^1$-$W^6$ and $W^{1'}$-$W^{6'}$ denote optional double bonds of the rings formed by $W^1$-$W^6$ and $W^{1'}$-$W^{6'}$;

$R^3$ and $R^4$ are each independently hydroxy, $(C_1-C_6)$allyl, $(C_1-C_6)$alkoxy, $(C_1-C_6)$alkanoyl, $(C_1-C_6)$alkanoyloxy, aryl, heteroaryl, carboxy, cyano, nitro, halo, trifluoromethyl, trifluoromethoxy, $SR^5$, $SO_2N(R_5)_2$, $NR^5R^5$, or $COOR^5$;

each n is independently 0 to 4;

each $R^5$ is independently H, $(C_1-C_6)$alkyl, $(C_1-C_6)$alkanoyl, $(C_6-C_{10})$aroyl, aryl, aryl$(C_1-C_6)$alkyl, heteroaryl, heteroaryl$(C_1-C_6)$alkyl, or a nitrogen protecting group;

X is $CH_2$—O, $CH_2$—$NR^5$, $CH_2$—S, or carbonyl;

D is S, SO, $SO_2$, P(O)OH, P(O)O$(C_1-C_6)$alkyl, P(O$(C_1-C_6)$alkyl)$_2$, C=N—OH, or carbonyl;

E is a direct bond, $(C_1-C_6)$alkyl, $(C_3-C_8)$cycloalkyl, $(C_2-C_6)$alkenyl, $(C_2-C_6)$alkynyl, or $(C_3-C_8)$heterocycle;

J is S, O, or $NR^5$;

G, T, and Q are each independently H, $(C_1-C_6)$alkyl, or cyano;

any alkyl, amino, aryl, heteroaryl, or cycloalkyl is optionally substituted with 1 to about 5 $(C_1-C_6)$alkyl, $(C_1-C_6)$alkenyl, $(C_1-C_6)$alkynyl, $(C_1-C_6)$alkoxy, aryl, heteroaryl, aryl$(C_1-C_6)$alkyl, heteroaryl$(C_1-C_6)$alkyl, nitro, halo, amino, or hydroxy groups;

or a pharmaceutically acceptable salt thereof.

The invention also provides a compound of formula III:

(III)

wherein $R^1$ is H, $(C_1-C_6)$alkyl, halo$(C_1-C_6)$alkyl, $(C_1-C_6)$alkoxy, $(C_1-C_6)$alkanoyl, $(C_1-C_6)$alkanoyloxy, aryl$(C_1-C_6)$alkyl, heteroaryl$(C_1-C_6)$alkyl, aryl$(C_1-C_6)$alkoxy, heteroaryl$(C_1-C_6)$ alkoxy, aryl, heteroaryl, hydroxy, nitro, cyano, halo, trifluoromethyl, trifluoromethoxy, $SR^5$, $NR^5R^5$, or $CO_2R^5$;

$R^2$ is $CH_2$, carbonyl, $SO_2$, or a direct bond;

L is $CH_2$, NR, O, S, SO, $SO_2$, or a direct bond;

$W^1$-$W^6$ are each independently C, N, O, S, or absent, and form a 5 or 6 membered aryl, heterocycle, or heteroaryl ring;

$W^{1'}$-$W^{6'}$ are each independently C, N, O, S, or absent, and form a 5 or 6 membered aryl, heterocycle, or heteroaryl ring;

the dashed circles within the rings formed by $W^1$-$W^6$ and $W^{1'}$-$W^{6'}$ denote optional double bonds of the rings formed by $W^1$-$W^6$ and $W^{1'}$-$W^{6'}$;

$R^3$ and $R^4$ are each independently hydroxy, $(C_1-C_6)$alkyl, $(C_1-C_6)$alkoxy, $(C_1-C_6)$alkanoyl, $(C_1-C_6)$alkanoyloxy, aryl, heteroaryl, carboxy, cyano, nitro, halo, trifluoromethyl, trifluoromethoxy, $SR_5$, $SO_2N(R_5)_2$, $NR_5R_5$, or $COOR^5$;

each n is independently 0 to 4;

each $R^5$ is independently H, $(C_1-C_6)$alkyl, $(C_1-C_6)$alkanoyl, $(C_6-C_{10})$aroyl, aryl, aryl$(C_1-C_6)$alkyl, heteroaryl, heteroaryl$(C_1-C_6)$alkyl, or a nitrogen protecting group;

X is O, S, SO, $SO_2$, $CH_2$—O, $CH_2$—$NR^5$, $CH_2$—S, $N(R^6)$, carbonyl, or a direct bond;

D is P(O)OH, P(O)O$(C_1-C_6)$alkyl, P(O$(C_1-C_6)$alkyl)$_2$, C=N—OH, or carbonyl;

E is a direct bond, $(C_1-C_6)$alkyl, $(C_3-C_8)$cycloalkyl, $(C_2-C_6)$alkenyl, $(C_2-C_6)$alkynyl, or $(C_3-C_8)$heterocycle;

J is S, O, or $NR^5$;

G, T, and Q are each independently H, $(C_1-C_6)$alkyl, or cyano;

any alkyl, amino, aryl, heteroaryl, or cycloalkyl is optionally substituted with 1 to about 5 $(C_1-C_6)$alkyl, $(C_1-C_6)$alkenyl, $(C_1-C_6)$alkynyl, $(C_1-C_6)$alkoxy, aryl, heteroaryl, aryl$(C_1-C_6)$alkyl, heteroaryl$(C_1-C_6)$allyl, nitro, halo, amino, or hydroxy groups;

or a pharmaceutically acceptable salt thereof.

The invention also provides a compound of formula IV:

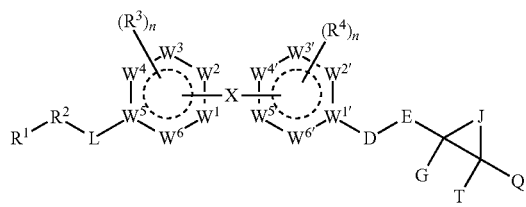

(IV)

wherein $R^1$ is H, $(C_1-C_6)$alkyl, halo$(C_1-C_6)$alkyl, $(C_1-C_6)$alkoxy, $(C_1-C_6)$alkanoyl, $(C_1-C_6)$alkanoyloxy, aryl$(C_1-C_6)$alkyl, heteroaryl$(C_1-C_6)$alkyl, aryl$(C_1-C_6)$alkoxy, heteroaryl$(C_1-C_6)$alkoxy, aryl, heteroaryl, hydroxy, nitro, cyano, halo, trifluoromethyl, trifluoromethoxy, $SR^5$, $NR^5R^5$, or $CO_2R^5$;

$R^2$ is $CH_2$, carbonyl, $SO_2$, or a direct bond;

L is $CH_2$, NR, O, S, SO, $SO_2$, or a direct bond;

$W^1-W^6$ are each independently C, N, O, S, or absent, and form a 5 or 6 membered aryl, heterocycle, or heteroaryl ring;

$W^{1'}-W^{6'}$ are each independently C, N, O, S, or absent, and form a 5 or 6 membered aryl, heterocycle, or heteroaryl ring;

the dashed circles within the rings formed by $W^1-W^6$ and $W^{1'}-W^{6'}$ denote optional double bonds of the rings formed by $W^1-W^6$ and $W^{1'}-W^{6'}$;

$R^3$ and $R^4$ are each independently hydroxy, $(C_1-C_6)$alkyl, $(C_1-C_6)$alkoxy, $(C_1-C_6)$alkanoyl, $(C_1-C_6)$alkanoyloxy, aryl, heteroaryl, carboxy, cyano, nitro, halo, trifluoromethyl, trifluoromethoxy, $SR^5$, $SO_2N(R_5)_2$, $NR^5R^5$, or $COOR^5$;

each n is independently 0 to 4;

each $R^5$ is independently H, $(C_1-C_6)$alkyl, $(C_1-C_6)$alkanoyl, $(C_6-C_{10})$aroyl, aryl, aryl$(C_1-C_6)$alkyl, heteroaryl, heteroaryl$(C_1-C_6)$alkyl, or a nitrogen protecting group;

X is $NR^6$;

$R^6$ is $(C_1-C_6)$alkanoyl, $(C_6-C_{10})$aroyl, aryl, aryl$(C_1-C_6)$alkyl, heteroaryl, heteroaryl$(C_1-C_6)$alkyl, or a nitrogen protecting group;

D is S, SO, $SO_2$, P(O)OH, P(O)O$(C_1-C_6)$alkyl, P(O$(C_1-C_6)$alkyl$)_2$, C=N—OH, or carbonyl;

E is a direct bond, $(C_1-C_6)$alkyl, $(C_3-C_8)$cycloalkyl, $(C_2-C_6)$alkenyl, $(C_2-C_6)$alkynyl, or $(C_3-C_8)$heterocycle;

J is S, O, or $NR^5$;

G, T, and Q are each independently H, $(C_1-C_6)$alkyl, or cyano;

any alkyl, amino, aryl, heteroaryl, or cycloalkyl is optionally substituted with 1 to about 5 $(C_1-C_6)$alkyl, $(C_1-C_6)$alkenyl, $(C_1-C_6)$alkynyl, $(C_1-C_6)$alkoxy, aryl, heteroaryl, aryl$(C_1-C_6)$alkyl, heteroaryl$(C_1-C_6)$alkyl, nitro, halo, amino, or hydroxy groups;

or a pharmaceutically acceptable salt thereof.

The invention also provides a compound of formula V:

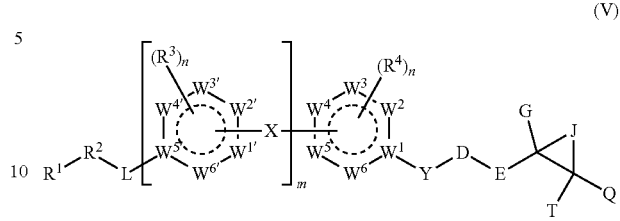

(V)

wherein $R^1$ is H, $(C_1-C_6)$alkyl, halo$(C_1-C_6)$alkyl, $(C_1-C_6)$alkoxy, $(C_1-C_6)$alkanoyl, $(C_1-C_6)$alkanoyloxy, aryl$(C_1-C_6)$alkyl, heteroaryl$(C_1-C_6)$alkyl, aryl$(C_1-C_6)$alkoxy, heteroaryl$(C_1-C_6)$alkoxy, aryl, heteroaryl, heterocycle, hydroxy, nitro, cyano, halo, trifluoromethyl, trifluoromethoxy, $SR^5$, $NR^5R^5$, or $CO_2R^5$;

$R^2$ is $CH_2$, carbonyl, $SO_2$, or a direct bond;

L is $CH_2$, $NR^5$, O, S, SO, $SO_2$, or a direct bond;

$W^1-W^6$ are each independently C, N, O, S, or absent, and form a 5 or 6 membered aryl, heterocycle, or heteroaryl ring;

$W^{1'}-W^{6'}$ are each independently C, N, O, S, or absent, and form a 5 or 6 membered aryl, heterocycle, or heteroaryl ring;

the dashed circles within the rings formed by $W^1-W^6$ and $W^{1'}-W^{6'}$ denote optional double bonds of the rings formed by $W^1-W^6$ and $W^{1'}-W^{6'}$;

$R^3$ and $R^4$ are each independently hydroxy, $(C_1-C_6)$alkyl, $(C_1-C_6)$alkoxy, $(C_1-C_6)$alkanoyl, $(C_1-C_6)$alkanoyloxy, aryl, heteroaryl, carboxy, cyano, nitro, halo, trifluoromethyl, trifluoromethoxy, $SR^5$, $SO_2N(R^5)_2$, $NR^5R^5$, or $COOR^5$;

each n is independently 0 to 4;

m is 0 or 1;

each $R^5$ is independently H, $(C_1-C_6)$alkyl, $(C_1-C_6)$alkanoyl, $(C_6-C_{10})$aroyl, aryl, aryl$(C_1-C_6)$alkyl, heteroaryl, heteroaryl$(C_1-C_6)$alkyl, or a nitrogen protecting group;

X is O, S, SO, $SO_2$, $CH_2$—O, $NR^1$, carbonyl, or a direct bond;

Y is O or $NR^5$;

D is S, SO, $SO_2$, P(O)OH, P(O)O$(C_1-C_6)$alkyl, P(O$(C_1-C_6)$alkyl$)_2$, C=N—OH, or carbonyl;

E is a direct bond, $(C_1-C_6)$alkyl, $(C_3-C_8)$cycloalkyl, $(C_2-C_6)$alkenyl, $(C_2-C_6)$alkynyl, or $(C_3-C_8)$heterocycle;

J is S, O, or $NR^5$;

G, T, and Q are each independently H, $(C_1-C_6)$alkyl, or cyano;

any alkyl, amino, aryl, heteroaryl, or cycloalkyl is optionally substituted with 1 to about 5 $(C_1-C_6)$alkyl, $(C_1-C_6)$alkenyl, $(C_1-C_6)$alkynyl, $(C_1-C_6)$alkoxy, aryl, heteroaryl, aryl$(C_1-C_6)$alkyl, heteroaryl$(C_1-C_6)$alkyl, nitro, halo, amino, or hydroxy groups;

or a pharmaceutically acceptable salt thereof.

The invention also provides a compound of formula VI:

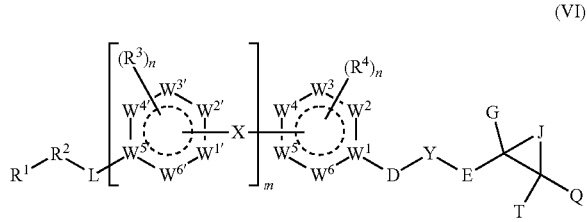

(VI)

wherein

R$^1$ is H, (C$_1$-C$_6$)alkyl, halo(C$_1$-C$_6$)alkyl, (C$_1$-C$_6$)alkoxy, (C$_1$-C$_6$)alkanoyl, (C$_1$-C$_6$)alkanoyloxy, aryl(C$_1$-C$_6$)alkyl, heteroaryl(C$_1$-C$_6$)alkyl, aryl(C$_1$-C$_6$)alkoxy, heteroaryl(C$_1$-C$_6$)alkoxy, aryl, heteroaryl, heterocycle, hydroxy, nitro, cyano, halo, trifluoromethyl, trifluoromethoxy, SR$^5$, NR$^5$R$^5$, or CO$_2$R$^5$;

R$^1$ is CH$_2$, carbonyl, SO$_2$, or a direct bond;

L is CH$_2$, NR$^5$, O, S, SO, SO$_2$, or a direct bond;

W$^1$-W$^6$ are each independently C, N, O, S, or absent, and form a 5 or 6 membered aryl, heterocycle, or heteroaryl ring;

W$^{1'}$-W$^{6'}$ are each independently C, N, O, S, or absent, and form a 5 or 6 membered aryl, heterocycle, or heteroaryl ring;

the dashed circles within the rings formed by W$^1$-W$^6$ and W$^{1'}$-W$^{6'}$ denote optional double bonds of the rings formed by W$^1$-W$^6$ and W$^{1'}$-W$^{6'}$;

R$^3$ and R$^4$ are each independently hydroxy, (C$_1$-C$_6$)alkyl, (C$_1$-C$_6$)alkoxy, (C$_1$-C$_6$)alkanoyl, (C$_1$-C$_6$)alkanoyloxy, aryl, heteroaryl, carboxy, cyano, nitro, halo, trifluoromethyl, trifluoromethoxy, SR$^5$, SO$_2$N(R$_5$)$_2$, NR$^5$R$^5$, or COOR$^5$;

each n is independently 0 to 4;

m is 0 or 1;

each R$^5$ is independently H, (C$_1$-C$_6$)alkyl, (C$_1$-C$_6$)alkanoyl, (C$_6$-C$_{10}$)aroyl, aryl, aryl(C$_1$-C$_6$)alkyl, heteroaryl, heteroaryl(C$_1$-C$_6$)alkyl, or a nitrogen protecting group;

X is O, S, SO, SO$_2$, CH$_2$—O, NR$^5$, carbonyl, or a direct bond;

Y is O or NR$^5$;

D is S, SO, SO$_2$, P(O)OH, P(O)O(C$_1$-C$_6$)alkyl, P(O(C$_1$-C$_6$)alkyl)$_2$, C=N—OH, or carbonyl;

E is a direct bond, (C$_1$-C$_6$)alkyl, (C$_3$-C$_8$)cycloalkyl, (C$_2$-C$_6$)alkenyl, (C$_2$-C$_6$)alkynyl, or (C$_3$-C$_8$)heterocycle;

J is S, O, or NR$^5$;

G, T, and Q are each independently H, (C$_1$-C$_6$)alkyl, or cyano;

any alkyl, amino, aryl, heteroaryl, or cycloalkyl is optionally substituted with 1 to about 5 (C$_1$-C$_6$)alkyl, (C$_1$-C$_6$)alkenyl, (C$_1$-C$_6$)alkynyl, (C$_1$-C$_6$)alkoxy, aryl, heteroaryl, aryl (C$_1$-C$_6$)alkyl, heteroaryl(C$_1$-C$_6$)alkyl, nitro, halo, amino, or hydroxy groups;

or a pharmaceutically acceptable salt thereof.

The invention also provides a compound of formula VII:

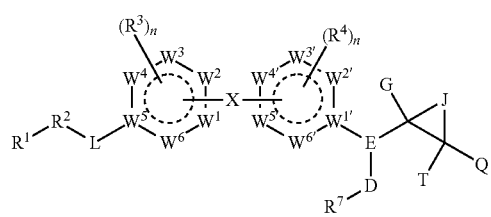

(VII)

wherein

R$^1$ is H, (C$_1$-C$_6$)alkyl, halo(C$_1$-C$_6$)alkyl, (C$_1$-C$_6$)alkoxy, (C$_1$-C$_6$)alkanoyl, (C$_1$-C$_6$)alkanoyloxy, aryl(C$_1$-C$_6$)alkyl, heteroaryl(C$_1$-C$_6$)alkyl, aryl(C$_1$-C$_6$)alkoxy, heteroaryl(C$_1$-C$_6$)alkoxy, aryl, heteroaryl, heterocycle, hydroxy, nitro, cyano, halo, trifluoromethyl, trifluoromethoxy, SR$^5$, NR$^5$R$^5$, or CO$_2$R$^5$;

R$^2$ is CH$_2$, carbonyl, SO$_2$, or a direct bond;

L is CH$_2$, NR$^5$, O, S, SO, SO$_2$, or a direct bond;

W$^1$-W$^6$ are each independently C, N, O, S, or absent, and form a 5 or 6 membered aryl, heterocycle, or heteroaryl ring;

W$^{1'}$-W$^{6'}$ are each independently C, N, O, S, or absent, and form a 5 or 6 membered aryl, heterocycle, or heteroaryl ring;

the dashed circles within the rings formed by W$^1$-W$^6$ and W$^{1'}$-W$^{6'}$ denote optional double bonds of the rings formed by W$^1$-W$^6$ and W$^{1'}$-W$^{6'}$;

R$^3$ and R$^4$ are each independently hydroxy, (C$_1$-C$_6$)alkyl, (C$_1$-C$_6$)alkoxy, (C$_1$-C$_6$)alkanoyl, (C$_1$-C$_6$)alkanoyloxy, aryl, heteroaryl, carboxy, cyano, nitro, halo, trifluoromethyl, trifluoromethoxy, SR$^5$, SO$_2$N(R)$_2$, NR$^5$R$^5$, or COOR$^5$;

each n is independently 0 to 4;

m is 0 or 1;

each R$^5$ is independently H, (C$_1$-C$_6$)alkyl, (C$_1$-C$_6$)alkanoyl, (C$_6$-C$_{10}$)aroyl, aryl, aryl(C$_1$-C$_6$)alkyl, heteroaryl, heteroaryl(C$_1$-C$_6$)allyl, or a nitrogen protecting group;

X is O, S, SO, SO$_2$, CH$_2$—O, NR$^5$, carbonyl, or a direct bond;

D is S, SO, SO$_2$, P(O)OH, P(O)O(C$_1$-C$_6$)alkyl, P(O(C$_1$-C$_6$)alkyl)$_2$, C=N—OH, or carbonyl;

R$^7$ is H, hydroxy, (C$_1$-C$_6$)allyl, (C$_2$-C$_6$)alkenyl, (C$_2$-C$_6$)alkynyl, halo(C$_1$-C$_6$)alkyl, (C$_1$-C$_6$)alkoxy, aryl(C$_1$-C$_6$)alkyl, heteroaryl(C$_1$-C$_6$)alkyl, aryl(C$_1$-C$_6$)alkoxy, heteroaryl(C$_1$-C$_6$)alkoxy, aryl, heteroaryl, heterocycle, halo, trifluoromethyl, trifluoromethoxy, NR$^5$R$^5$, or CO$_2$R$^5$;

E is (C$_1$-C$_6$)alkyl, (C$_3$-C$_8$)cycloalkyl, (C$_2$-C$_6$)alkenyl, (C$_2$-C$_6$)alkynyl, or (C$_3$-C$_9$)heterocycle;

J is S, O, or NR$^5$;

G, T, and Q are each independently H, (C$_1$-C$_6$)alkyl, or cyano;

any alkyl, amino, aryl, heteroaryl, or cycloalkyl is optionally substituted with 1 to about 5 (C$_1$-C$_6$)alkyl, (C$_1$-C$_6$)alkenyl, (C$_1$-C$_6$)alkynyl, (C$_1$-C$_6$)alkoxy, aryl, heteroaryl, aryl (C$_1$-C$_6$)alkyl, heteroalyl(C$_1$-C$_6$)alkyl, nitro, halo, amino, or hydroxy groups;

or a pharmaceutically acceptable salt thereof.

The invention also provides a compound of formula VIII:

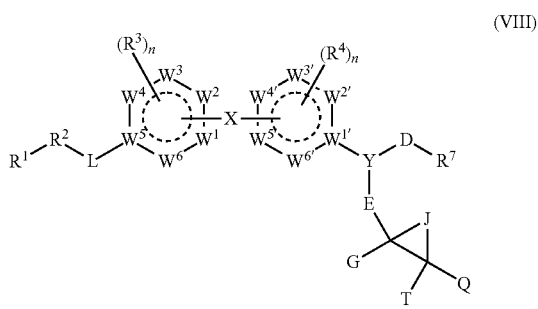

(VIII)

wherein

R$^1$ is H, (C$_1$-C$_6$)alkyl, (C$_2$-C$_6$)alkenyl, (C$_2$-C$_6$)alkynyl, halo(C$_1$-C$_6$)alkyl, (C$_1$-C$_6$)alkoxy, (C$_1$-C$_6$)alkanoyl, (C$_1$-C$_6$)alkanoyloxy, aryl(C$_1$-C$_6$)alkyl, heteroaryl(C$_1$-C$_6$)alkyl, aryl (C$_1$-C$_6$)alkoxy, heteroaryl(C$_1$-C$_6$)alkoxy, aryl, heteroaryl, heterocycle, hydroxy, nitro, cyano, halo, trifluoromethyl, trifluoromethoxy, SR$^5$, NR$^5$R$^5$, or CO$_2$R$^5$;

R$^2$ is CH$_2$, carbonyl, SO$_2$, or a direct bond;

L is CH$_2$, NR, O, S, SO, SO$_2$, or a direct bond;

W$^1$-W$^6$ are each independently C, N, O, S, or absent, and form a 5 or 6 membered aryl, heterocycle, or heteroaryl ring;

W$^{1'}$-W$^{6'}$ are each independently C, N, O, S, or absent, and form a 5 or 6 membered aryl, heterocycle, or heteroaryl ring;

the dashed circles within the rings formed by W$^1$-W$^6$ and W$^{1'}$-W$^{6'}$ denote optional double bonds of the rings formed by W$^1$-W$^6$ and W$^{1'}$-W$^{6'}$;

R³ and R⁴ are each independently hydroxy, $(C_1$-$C_6)$alkyl, $(C_1$-$C_6)$alkoxy, $(C_1$-$C_6)$alkanoyl, $(C_1$-$C_6)$alkanoyloxy, aryl, heteroaryl, carboxy, cyano, nitro, halo, trifluoromethyl, trifluoromethoxy, $SR^5$, $SO_2N(R_5)_2$, $NR^5R^5$, or $COOR^5$;

each n is independently 0 to 4;

m is 0 or 1;

each $R^5$ is independently H, $(C_1$-$C_6)$alkyl, $(C_1$-$C_6)$alkanoyl, $(C_6$-$C_{10})$aroyl, aryl, aryl$(C_1$-$C_6)$alkyl, heteroaryl, heteroaryl$(C_1$-$C_6)$alkyl, or a nitrogen protecting group;

X is O, S, SO, $SO_2$, $CH_2$—O, $NR^5$, carbonyl, or a direct bond;

Y is $C(R^5)$ or N;

D is S, SO, $SO_2$, P(O)OH, P(O)O$(C_1$-$C_6)$alkyl, P(O$(C_1$-$C_6)$alkyl$)_2$, C=N—OH, or carbonyl;

$R^7$ is H, hydroxy, $(C_1$-$C_6)$alkyl, $(C_2$-$C_6)$alkenyl, $(C_2$-$C_6)$alkynyl, halo$(C_1$-$C_6)$alkyl, $(C_1$-$C_6)$alkoxy, aryl$(C_1$-$C_6)$alkyl, heteroaryl$(C_1$-$C_6)$alkyl, aryl$(C_1$-$C_6)$alkoxy, heteroaryl$(C_1$-$C_6)$alkoxy, aryl, heteroaryl, heterocycle, halo, trifluoromethyl, trifluoromethoxy, $NR^5R^5$, or $CO_2R^5$;

E is a direct bond, $(C_1$-$C_6)$alkyl, $(C_3$-$C_8)$cycloalkyl, $(C_2$-$C_6)$alkenyl, $(C_2$-$C_6)$alkynyl, or $(C_3$-$C_8)$heterocycle;

J is S, O, or $NR^5$;

G, T, and Q are each independently H, $(C_1$-$C_6)$alkyl, or cyano;

any alkyl, amino, aryl, heteroaryl, or cycloalkyl is optionally substituted with 1 to about 5 $(C_1$-$C_6)$alkyl, $(C_1$-$C_6)$alkenyl, $(C_1$-$C_6)$alkynyl, $(C_1$-$C_6)$alkoxy, aryl, heteroaryl, aryl$(C_1$-$C_6)$alkyl, heteroaryl$(C_1$-$C_6)$alkyl, nitro, halo, amino, or hydroxy groups;

or a pharmaceutically acceptable salt thereof.

The invention also provides a compound of formula IX:

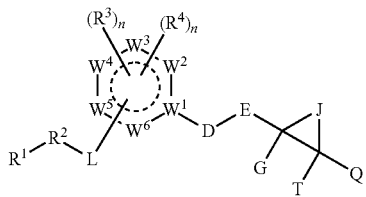

(IX)

wherein $R^1$ is H, $(C_1$-$C_6)$alkyl, halo$(C_1$-$C_6)$alkyl, $(C_1$-$C_6)$alkoxy, $(C_1$-$C_6)$alkanoyl, $(C_1$-$C_6)$alkanoyloxy, aryl$(C_1$-$C_6)$alkyl, heteroaryl$(C_1$-$C_6)$alkyl, aryl$(C_1$-$C_6)$alkoxy, heteroaryl$(C_1$-$C_6)$alkoxy, aryl, heteroaryl, hydroxy, nitro, cyano, halo, trifluoromethyl, trifluoromethoxy, $SR^5$, $NR^5R^5$, or $CO_2R^5$;

$R^2$ is $CH_2$, carbonyl, $SO_2$, or a direct bond;

L is $CH_2$, NR, O, S, SO, $SO_2$, or a direct bond;

$W^1$-$W^6$ are each independently C, N, O, S, or absent, and form a 5 or 6 membered aryl, heterocycle, or heteroaryl ring;

the dashed circles within the rings formed by $W^1$-$W^6$ denote optional double bonds of the ring formed by $W^1$-$W^6$;

each n is independently 0 to 4 and the sum of n groups is not greater than 4;

each $R^3$ and $R^4$ are independently hydroxy, $(C_1$-$C_6)$alkyl, $(C_1$-$C_6)$alkoxy, $(C_1$-$C_6)$alkanoyl, $(C_1$-$C_6)$alkanoyloxy, aryl, heteroaryl, carboxy, cyano, nitro, halo, trifluoromethyl, trifluoromethoxy, $SR^5$, $SO_2N(R_5)_2$, $NR^5R^5$, or $COOR^5$;

or each n is 1 and $R^3$ and $R^4$ together form an ortho-fused aryl, heteroaryl, carbocycle, or heterocycle attached to two of $W^2$-$W^6$;

each $R^5$ is independently H, $(C_1$-$C_6)$alkyl, $(C_1$-$C_6)$alkanoyl, $(C_6$-$C_{10})$aroyl, aryl, aryl$(C_1$-$C_6)$alkyl, heteroaryl, heteroaryl$(C_1$-$C_6)$alkyl, or a nitrogen protecting group;

D is S, SO, $SO_2$, P(O)OH, P(O)O$(C_1$-$C_6)$alkyl, P(O$(C_1$-$C_6)$alkyl$)_2$, C=N—OH, carbonyl, or absent;

E is a direct bond, $(C_1$-$C_6)$alkyl, $(C_3$-$C_8)$cycloalkyl, $(C_2$-$C_6)$alkenyl, $(C_2$-$C_6)$alkynyl, or $(C_3$-$C_8)$heterocycle;

J is S, O, or $NR^5$;

G, T, and Q are each independently H, $(C_1$-$C_6)$alkyl, or cyano;

any alkyl, amino, aryl, heteroaryl, heterocycle, carbocycle, or cycloalkyl is optionally substituted with 1 to about 5 $(C_1$-$C_6)$alkyl, $(C_1$-$C_6)$alkenyl, $(C_1$-$C_6)$alkynyl, $(C_1$-$C_6)$alkoxy, aryl, heteroaryl, aryl$(C_1$-$C_6)$alkyl, heteroaryl$(C_1$-$C_6)$alkyl, nitro, halo, amino, or hydroxy groups;

or a pharmaceutically acceptable salt thereof.

The following definitions apply to compounds of each of formulas I-IX, unless otherwise noted.

One value of $R^1$ is $(C_1$-$C_6)$alkyl. A specific value of $R^1$ is methyl. $R^1$ can also be ethyl, n-propyl, iso-propyl, or sec-butyl.

Another value for $R^1$ is $(C_1$-$C_6)$alkoxy. $R^1$ can also be methoxy or hydroxy.

Another value for $R^1$ is heteroaryl$(C_1$-$C_6)$alkoxy. Specific values of R include pyridylmethyloxy, furanylmethyloxy, and thiophenylmethyloxy.

Another value for $R^1$ is halo$(C_1$-$C_6)$alkyl. A specific value of $R^1$ is bromopentyl.

Another value for $R^1$ is aryl$(C_1$-$C_6)$allyl. A specific value of $R^1$ is benzyl.

Another value for $R^1$ is aryl. A specific value of $R^1$ is phenyl.

The group $R^1$ can be aryl substituted with 1 to about 5 $(C_1$-$C_6)$alkyl, $(C_1$-$C_6)$alkoxy, aryl, heteroaryl, aryl$(C_1$-$C_6)$alkyl, heteroaryl$(C_1$-$C_6)$alkyl, nitro, halo, amino, or hydroxy groups. Specifically, $R^1$ can be aryl substituted with methyl, methoxy, iso-propyl, nitro, halo, amino, or hydroxy.

Another value for $R^1$ is $NR^5R^5$. In one embodiment, each $R^5$ can independently be H or $(C_1$-$C_6)$alkyl. One specific value of $R^1$ is diethylamino.

In one embodiment, $R^1$ is absent and $R^2$ is OH.

For the compounds of any one of formulas II-IX, a specific value for $R^1$ is H. In formulas II-IX, $R^2$ and L can both be absent. In certain specific embodiments of formulas II-IX, $R^1$ is H and $R^2$ and L are both absent.

One value for $R^2$ is $CH_2$. Another value for $R^2$ is carbonyl. A further value for $R^2$ is $SO_2$.

One value for L is $CH_2$. Another value for L is $NR^5$. Specific values for L include $NR^5$ wherein $R^5$ is H, $(C_1$-$C_6)$alkyl, or a nitrogen protecting group. Another specific value for L is O.

The rings formed by $W^1$-$W^6$ can form a phenyl ring. The rings formed by $W^1$-$W^6$ can also form a 6-membered heteroaryl ring, such a pyridyl ring. The rings formed by $W^1$-$W^6$ can also form a 5-membered heteroaryl ring. Examples of such 5-membered heteroaryl rings include imidazole, thiazole, triazole, tetrazole, furan, and thiophene rings.

For the compounds of any of formulas I-VIII, the rings formed by $W^{1'}$-$W^{6'}$ can form a phenyl ring. The rings formed by $W^{1'}$-$W^{6'}$ can also form a 6-membered heteroaryl ring, such a pyridyl ring. The rings formed by $W^{1'}$-$W^{6'}$ can also form a 5-membered heteroaryl ring. Examples of such 5-membered heteroaryl rings include imidazole, thiazole, triazole, tetrazole, furan, and thiophene rings.

The dashed circles within the ring formed by $W^1$-$W^6$ can be two or three conjugated double bonds. For the compounds of any of formulas I-VIII, the dashed circles within the ring formed by $W^{1'}$-$W^{6'}$ can also be two or three conjugated double bonds.

The value $R^3$ can be absent (i.e., the value of n is 0). In certain embodiments, values for $R^3$ include hydroxy, halo, amino, or combinations thereof. $R^3$ can also be hydroxyphenyl or halophenyl. In yet another embodiment, $R^3$ can be $SO_2N(R_5)_2$. In one embodiment, each $R^5$ of $R^3$ is H.

The value $R^4$ can be absent (i.e., the value of n is 0). In certain embodiments, values for $R^4$ include hydroxy, halo, amino, or combinations thereof. $R^4$ can also be hydroxyphenyl or halophenyl. In yet another embodiment, $R^4$ can be $SO_2N(R_5)_2$. In one embodiment, each $R^5$ of $R^4$ is H.

For the compounds of any of formulas I, III, and V-IX, X can be O. Other specific values for X include S, SO, $SO_2$, $CH_2$—O, $CH_2$—S, NR, $CH_2$—$NR^5$, carbonyl, and a direct bond.

The attachment of the groups $CH_2$—O, $CH_2$—S, and $CH_2$—NR is 'reversible', i.e., the methylene group can be attached to either ring of formulas I, III, and V-IX. For example, the methylene group can be attached to the ring formed by $W^1$-$W^6$ or the ring formed by $W^{1'}$-$W^{6'}$. Accordingly, the heteroatom of the recited group would then be attached to the other ring.

For the compounds of any of formulas I, III, and V-IX, when X is $NR^5$, $R^5$ can be H. In other embodiments, $R^5$ can be $(C_1$-$C_6)$alkyl, for example, methyl. In another embodiment, $R^5$ can be aryl, for example, phenyl. In yet another embodiment, $R^5$ can be aryl($C_1$-$C_6$)alkyl, for example, benzyl. In another embodiment, $R^5$ can be a heteroaryl($C_1$-$C_6$)alkyl, such as pyridylmethyl, imidazolylmethyl, thiazolylmethyl, triazolylmethyl, tetrazolylmethyl, furanylmethyl, or thiophenylmethyl. In yet another embodiment, $R^5$ can be a nitrogen protecting group.

For the compounds of any of formulas I, III, and V-IX, when X is $CH_2$—$NR^5$, $R^5$ can be H. In other embodiments, $R^5$ can be $(C_1$-$C_6)$alkyl, for example, methyl. In another embodiment, $R^5$ can be aryl, for example, phenyl. In yet another embodiment, $R^5$ can be aryl($C_1$-$C_6$)alkyl, for example, benzyl. In another embodiment, $R^5$ can be a heteroaryl($C_1$-$C_6$)alkyl, such as pyridylmethyl, imidazolylmethyl, thiazolylmethyl, triazolylmethyl, tetrazolylmethyl, furanylmethyl, or thiophenylmethyl. In yet another embodiment, $R^5$ can be a nitrogen protecting group.

For the compounds of any of formulas I-II and IV-IX, one specific value of D is S. Another specific value of D is SO. Yet another specific value of D is $SO_2$.

For the compounds of any of formulas I-IX, D can be P(O)OH, P(O)O($C_1$-$C_6$)alkyl, for example, P(O)OCH$_3$, or P(O($C_1$-$C_6$)alkyl)$_2$, for example, P(OCH$_3$)$_2$. In another embodiment, D can be C=N—OH. In yet another embodiment, D can be carbonyl.

The variable E can be a direct bond. E can also be $(C_1$-$C_6)$alkyl, for example, $CH_2$. In another embodiment, B can be $(C_3$-$C_8)$cycloalkyl, such as cyclohexyl, or a geminally-substituted cyclohexyl. E can also be $(C_2$-$C_6)$alkenyl, for example, 2-butenyl. Another value for E is $(C_2$-$C_6)$alkynyl. In a specific embodiment, E can be 2-butynyl. In other embodiments, E can be $(C_3$-$C_8)$heterocycle, for example, piperidynyl. The piperidynyl can be an N-substituted piperidynyl linked to both its neighboring groups at the 4-position.

The variable J can be S, O, or $NR^5$. In one embodiment, J is $NR^5$ and $R^5$ is H. In another embodiment, J can be $NR^5$ and $R^5$ can be $(C_1$-$C_6)$alkyl, for example, methyl. In another embodiment, J can be $NR^5$ and $R^5$ can be $(C_1$-$C_6)$alkanoyl, such as acetyl (—C(=O)CH$_3$). In yet another embodiment, J can be $NR^5$ and $R^5$ can be $(C_6$-$C_{10})$aroyl, for example, benzoyl; aryl, for example, phenyl; aryl($C_1$-$C_6$)alkyl, for example, benzyl; heteroaryl, for example, imidazolyl, thiazolyl, triazolyl, tetrazolyl, furanyl, thiophenyl, or pyridinyl; heteroaryl($C_1$-$C_6$)alkyl, for example, imidazolylmethyl, thiazolylmethyl, triazolylmethyl, tetrazolylmethyl, furanylmethyl, thiophenylmethyl, or pyridinylmethyl; or a nitrogen protecting group.

The variable G can be H. Another value for G is $(C_1$-$C_6)$ alkyl, for example, methyl. Yet another value for G is cyano.

The variable T can be H. Another value for T is $(C_1$-$C_6)$ alkyl, for example, methyl. Yet another value for T is cyano.

The variable Q can be H. Another value for Q is $(C_1$-$C_6)$ alkyl, for example, methyl. Yet another value for Q is cyano.

In one embodiment, G, T, and Q are each H.

For the compounds of formulas IV, X can be $NR^6$, wherein $R^6$ is $(C_1$-$C_6)$alkanoyl. In a specific embodiment, $R^6$ is acetyl. $R^6$ can also be $(C_6$-$C_{10})$aroyl, for example, benzoyl; aryl, for example, phenyl; aryl($C_1$-$C_6$)alkyl, for example, benzyl; heteroaryl, for example, pyridyl, imidazolyl, thiazolyl, triazolyl, tetrazolyl, furanyl, or thiophenyl; heteroaryl($C_1$-$C_6$)alkyl, for example, pyridylmethyl, imidazolylmethyl, thiazolylmethyl, triazolylmethyl, tetrazolylmethyl, furanylmethyl, or thiophenylmethyl; or a nitrogen protecting group.

For the compounds of formulas V or VI, the value of m can be 0. In other embodiments, the value of m can be 1.

For the compounds of formulas V or VI, Y can be O. In other embodiments, Y can be $NR^5$. In one embodiment, Y is $NR^5$, and $R^5$ is H. In other embodiments, Y can be $NR^5$, and $R^5$ can be $(C_1$-$C_6)$alkyl, for example, methyl; $(C_1$-$C_6)$ alkanoyl, for example, acetyl; $(C_6$-$C_{10})$aroyl, for example, benzoyl; aryl, for example, phenyl; aryl($C_1$-$C_6$)alkyl, for example, benzyl; heteroaryl, for example, pyridyl, imidazolyl, thiazolyl, triazolyl, tetrazolyl, furanyl, or thiophenyl; heteroaryl($C_1$-$C_6$)alkyl, for example, pyridylmethyl, imidazolylmethyl, thiazolylmethyl, triazolylmethyl, tetrazolylmethyl, furanylmethyl, or thiophenylmethyl; or a nitrogen protecting group.

For the compounds of formulas VII and VIII, $R^7$ can be H. $R^7$ can also be hydroxy. Another value for $R^7$ is $(C_1$-$C_6)$alkyl, for example, methyl. Another value for $R^7$ is $(C_2$-$C_6)$alkenyl, for example, propenyl. Another value for $R^7$ is $(C_2$-$C_6)$alkynyl, for example, propynyl. Another value for $R^7$ is halo($C_1$-$C_6$)alkyl, for example, bromopentyl. Another value for $R^7$ is $(C_1$-$C_6)$alkoxy, for example, methoxy. Another value for $R^7$ is aryl($C_1$-$C_6$)allyl, for example, benzyl. Another value for $R^7$ is heteroaryl($C_1$-$C_6$)alkyl, for example, pyridylmethyl, imidazolylmethyl, thiazolylmethyl, triazolylmethyl, tetrazolylmethyl, furanylmethyl, or thiophenylmethyl. Another value for $R^7$ is aryl($C_1$-$C_6$)alkoxy, for example, benzyloxy. Another value for $R^7$ is heteroaryl($C_1$-$C_6$)alkoxy, pyridylmethyloxy. Another value for $R^7$ is aryl, for example, phenyl. Another value for $R^7$ is heteroaryl, for example, pyridyl, imidazolyl, thiazolyl, triazolyl, tetrazolyl, furanyl, or thiophenyl. Another value for $R^7$ is heterocycle, for example, piperidinyl.

For the compounds of formulas VII and VIII, $R^7$ can also be halo, for example, fluoro, chloro, bromo, or iodo. Yet another value for 17 is trifluoromethyl. Another value for $R^7$ is trifluoromethoxy. Another value for $R^7$ is $NR^5R^5$, wherein each $R^5$ is H. Another value for $R^7$ is $NR^5R^5$, wherein each $R^5$ is $(C_1$-$C_6)$alkyl. Another value for $R^7$ is $NR^5R^5$, wherein each $R^5$ is methyl. Another value for $R^7$ is $NR^5R^5$, wherein one $R^5$ is H and the other $R^5$ of $R^7$ is a nitrogen protecting group. Another value for $R^7$ is $CO_2R^5$. Another value for $R^7$ is $CO_2R^5$, wherein $R^5$ is H. Another value for $R^7$ is $CO_2R^5$, wherein $R^5$ is $(C_1$-$C_6)$alkyl. Another value for $R^7$ is $CO_2R^5$, wherein $R^5$ is methyl. Another value for $R^7$ is $CO_2R^5$, wherein $R^5$ is aryl. Yet another value for $R^7$ is $CO_2R^5$, wherein $R^5$ is phenyl.

For the compounds of formula VIII, Y can be N or C($R^5$). In one embodiment, Y is N. In another embodiment, Y is $C(R^5)$. In one specific embodiment, Y is $C(R^5)$, wherein $R^5$ is H. In another embodiment, Y is $C(R^5)$, wherein $R^5$ is $(C_1-C_6)$ alkyl. In one specific embodiment, Y is $C(R^5)$, wherein $R^5$ is methyl.

For the compounds of formula IX, each n can be 1 and $R^3$ and $R^4$ together can form an ortho-fused furanyl group. In another embodiment, each n is 1 and $R^3$ and $R^4$ together form an ortho-fused 1,2,3,4-tetrahydrobenzofuranyl group.

Methods of Use and Medical Indications

The invention also provides a pharmaceutical composition that includes a compound of any of formulas I-IX, or a pharmaceutically acceptable salt thereof, and a pharmaceutically acceptable carrier. The pharmaceutical composition can also include other therapeutic agents that are compatible with the compound of the invention.

The invention also provides a compound of any of formulas I-IX, for use in medical therapy. The medical therapy can be for the treatment of cancer, angiogenesis, cardiovascular disease, neurological disease, inflammation, eye disease, autoimmune disease, for regulating contraception, or other conditions that are affected by the regulation of MMPs.

The cancer can be pancreatic cancer, gastric cancer, lung cancer, colorectal cancer, prostate cancer, renal cell cancer, basal cell cancer, breast cancer, bone cancer, brain cancer, lymphoma, leukemia, melanoma, myeloma and other hematological cancers, and the like. The cancer can be primary, metastatic, or both. The treatment of cancer using a compound of the invention can affect angiogenesis.

The cardiovascular disease can be stroke, aneurysm, ischemia or reperfusion injury.

The neurological disease can be one that arises from at least one of painful neuropathy, neuropathic pain, diabetic neuropathy, drug dependence, drug withdrawal, depression, anxiety, movement disorders, tardive dyskinesia, cerebral infections that disrupt the blood-brain barrier, meningitis, stroke, hypoglycemia, cardiac arrest, spinal cord trauma, head trauma, and perinatal hypoxia. The neurological disease can also be a neurodegenerative disorder. The neurological disease can be epilepsy, Alzheimer's disease, Huntington's disease, Parkinson's disease, multiple sclerosis, or amyotrophic lateral sclerosis, as well as Alexander disease, Alper's disease, Ataxia telangiectasia, Batten disease (also known as Spielmeyer-Vogt-Sjogren-Batten disease), Canavan disease, Cockayne syndrome, Corticobasal degeneration, Creutzfeldt-Jakob disease, Kennedy's disease, Krabbe disease, lewy body dementia, Machado-Joseph disease (Spinocerebellar ataxia type 3), Multiple System Atrophy, Pelizaeus-Merzbacher disease, Pick's disease, primary lateral sclerosis, Refsum's disease, Sandhoff disease, Schilder's disease, spinocerebellar ataxia (multiple types with varying characteristics), spinal muscular atrophy, Steele-Richardson-Olszewski disease, or tabes dorsalis.

The compounds of the invention can be used to treat conditions of the eye, including corneal wounds, glaucoma, dry eye disease, and macula degeneration. The compounds can also be used to treat eye conditions that involve, are caused by, are effected by, or are exacerbated by MMP-9.

The compounds of the invention can be used to treat inflammation, wherein the inflammation involves connective tissue, airway tissue, or central nervous system tissue. The inflammation can be acute asthma, chronic asthma, allergic asthma, or chronic obstructive pulmonary disease. In one embodiment, the inflammation is arthritis.

The compounds of the invention can be used to effect contraception, wherein the contraception occurs by inhibition of implantation.

The compounds of the invention can be used in medical therapy, wherein the medical therapy is treatment of a skin disease.

The compounds of the invention can also be used in imaging, wherein the inhibitor can be modified to be detectable by imaging techniques; for pre- and post-operative treatments for removal of tumors; and in combination with any other chemotherapeutic modalities (biological and non-biological).

The invention also provides the use of a compound of any of formulas I-IX, to prepare a medicament for treatment of cancer, angiogenesis, cardiovascular disease, neurological disease, inflammation, autoimmune disease, or contraception. The medicaments can also be used to treat any of the diseases or conditions discussed above.

The invention further provides a method to treat a disease comprising contacting a cell with a compound of formulas I-IX, wherein the compound is effective to inhibit a matrix metalloproteinase. The invention also provides a method to treat a subject in need thereof, comprising administering to the subject an effective amount of a matrix metalloproteinase inhibitor of a compound of formulas I-IX. The matrix metalloproteinase can be a gelatinase, collagenase, stromelysin, membrane-type My, or matrilysin. The matrix metalloproteinase can be, for example, MMP-2, MMP-9, or MMP-14. The matrix metalloproteinase can be a human matrix metalloproteinase.

The matrix metalloproteinase inhibitor can be administered to the subject in a pharmaceutically acceptable excipient. The subject can be an animal, for example, a mammal. The subject can be a human. The methods employing the compound of formulas I-IX can be used to treat any of the diseases or conditions discussed above.

A compound of formulas I-IX, or a pharmaceutically acceptable salt thereof, can be administered to a mammal (e.g., human) in conjunction with a chemotherapeutic agent, or a pharmaceutically acceptable salt thereof. Accordingly, a compound of formulas I-IX can be administered in conjunction with a chemotherapeutic agent to treat a disease, a tumor, or cancer.

According to one embodiment of the invention, the matrix metalloproteinase can be contacted with the compound, e.g., a compound of any one of formulas I-IX, in vitro. Alternatively, the matrix metalloproteinase can be contacted with the compound, e.g., a compound of any one of formulas I-IX, in vivo.

An important aspect of the invention is that a compound of formulas I-IX can be selective for a particular matrix metalloproteinase over other matrix metalloproteinases. This selectivity can provide a significant benefit to treating the diseases and conditions discussed above because of the reduced dosage required for a given treatment.

Methods of Making the Compounds of the Invention.

Processes for preparing compounds of formulas I-IX and processes for preparing intermediates useful for preparing compounds of formulas I-IX are provided as further embodiments of the invention. Intermediates useful for preparing compounds of formulas I-IX are also provided as further embodiments of the invention.

The compounds described herein can be prepared by any of the applicable techniques of organic synthesis. Many such techniques are well known in the art. However, many of the known techniques are elaborated in *Compendium of Organic Synthetic Methods* (John Wiley & Sons, New York) Vol. 1, Ian T. Harrison and Shuyen Harrison (1971); Vol. 2, Ian T. Harrison and Shuyen Harrison (1974); Vol. 3, Louis S. Hegedus and Leroy Wade (1977); Vol. 4, Leroy G. Wade Jr., (1980);

Vol. 5, Leroy G. Wade Jr. (1984); and Vol. 6, Michael B. Smith; as well as March, J., *Advanced Organic Chemistry*, 3rd Edition, John Wiley & Sons, New York (1985); *Comprehensive Organic Synthesis. Selectivity Strategy & Efficiency in Modern Organic Chemistry, In 9 Volumes*, Barry M. Trost, Editor-in-Chief, Pergamon Press, New York (1993); *Advanced Organic Chemistry Part B: Reactions and Synthesis*, 4th Ed.; Carey and Sundberg; Kluwer Academic/Plenum Publishers: New York (2001); *Advanced Organic Chemistry Reactions, Mechanisms, and Structure*, 2nd Edition, March, McGraw Hill (1977); *Protecting Groups in Organic Synthesis*, 2nd Edition, Greene, T. W., and Wutz, P. G. M., John Wiley & Sons, New York (1991); and *Comprehensive Organic Transformations*, 2nd Edition, Larock, R. C., John Wiley & Sons, New York (1999).

As would be recognized by one skilled in the art, numerous modifications and variations of the present invention are possible in light of the above teachings. It is therefore to be understood that within the scope of the appended claims, the invention may be practiced otherwise than as specifically described herein.

Specific ranges, values, and embodiments provided herein are for illustrative purposes only and do not otherwise limit the scope of the invention, as defined by the claims.

Pharmaceutical Formulations:

The compounds described herein can be administered as the parent compound, a pro-drug of the parent compound, or an active metabolite of the parent compound.

The compounds of this invention can be formulated with conventional carriers and excipients, which can be selected in accord with ordinary practice. Tablets will contain excipients, glidants, fillers, binders and the like. Aqueous formulations are prepared in sterile form, and when intended for delivery by other than oral administration generally will be isotonic. All formulations will optionally contain excipients such as those set forth in the *Handbook of Pharmaceutical Excipients*, 5$^{th}$ Ed.; Rowe, Sheskey, and Owen, Eds.; American Pharmacists Association; Pharmaceutical Press: Washington, D.C., 2006. Excipients include ascorbic acid and other antioxidants, chelating agents such as EDTA, carbohydrates such as dextrin, hydroxyalkylcellulose, hydroxyalkylmethyl-cellulose, stearic acid and the like. The pH of the formulations ranges from about 3 to about 11, but is ordinarily about 7 to 10.

While it is possible for the active ingredients to be administered alone it may be preferable to present them as pharmaceutical formulations. The formulations, both for veterinary and for human use, include at least one active ingredient, as described herein, together with one or more acceptable carriers therefor, and optionally other therapeutic ingredients. The carrier(s) must be "acceptable" in the sense of being compatible with the other ingredients of the formulation and physiologically innocuous to the recipient thereof.

The formulations include those suitable for the foregoing administration routes. The formulations may conveniently be presented in unit dosage form and may be prepared by any of the methods well known in the art of pharmacy. Techniques and formulations generally are found in *Remington's Pharmaceutical Sciences*, Mack Publishing Company, Easton, Pa., (1985). Such methods include the step of bringing into association the active ingredient with the carrier which constitutes one or more accessory ingredients. In general the formulations are prepared by uniformly and intimately bringing into association the active ingredient with liquid carriers or finely divided solid carriers or both, and then, if necessary, shaping the product.

Formulations of the present invention suitable for oral administration may be presented as discrete units such as capsules, cachets or tablets each containing a predetermined amount of the active ingredient; as a powder or granules; as a solution or a suspension in an aqueous or non-aqueous liquid; or as an oil-in-water liquid emulsion or a water-in-oil liquid emulsion. The active ingredient may also be administered as a bolus, electuary or paste.

A tablet is made by compression or molding, optionally with one or more accessory ingredients. Compressed tablets may be prepared by compressing in a suitable machine the active ingredient in a free-flowing form such as a powder or granules, optionally mixed with a binder, lubricant, inert diluent, preservative, surface active or dispersing agent. Molded tablets may be made by molding in a suitable machine a mixture of the powdered active ingredient moistened with an inert liquid diluent. The tablets may optionally be coated or scored and optionally are formulated so as to provide slow or controlled release of the active ingredient therefrom.

For administration to the eye or other external tissues e.g., mouth and skin, the formulations are preferably applied as a topical ointment or cream containing the active ingredient(s) in an amount of, for example, 0.075 to 20% w/w (including active ingredient(s) in a range between 0.1% and 20% in increments of 0.1% w/w such as 0.6% w/w, 0.7% w/w, etc.), preferably 0.2 to 15% w/w and most preferably 0.5 to 10% w/w. When formulated in an ointment, the active ingredients may be employed with either a paraffinic or a water-miscible ointment base. Alternatively, the active ingredients may be formulated in a cream with an oil-in-water cream base.

If desired, the aqueous phase of the cream base may include, for example, at least 30% w/w of a polyhydric alcohol, i.e. an alcohol having two or more hydroxyl groups such as propylene glycol, butane 1,3-diol, mannitol, sorbitol, glycerol and polyethylene glycol (including PEG 400) and mixtures thereof. The topical formulations may desirably include a compound which enhances absorption or penetration of the active ingredient through the skin or other affected areas. Examples of such dermal penetration enhancers include dimethyl sulfoxide and related analogs.

The oily phase of the emulsions of this invention may be constituted from known ingredients in a known manner. While the phase may comprise merely an emulsifier (otherwise known as an emulgent), it desirably comprises a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make up the so-called emulsifying wax, and the wax together with the oil and fat make up the so-called emulsifying ointment base which forms the oily dispersed phase of the cream formulations.

Emulgents and emulsion stabilizers suitable for use in the formulation of the invention include Tween® 60, Span® 80, cetostearyl alcohol, benzyl alcohol, myristyl alcohol, glyceryl mono-stearate and sodium lauryl sulfate.

The choice of suitable oils or fats for the formulation is based on achieving the desired cosmetic properties. The cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used, the last three being preferred esters. These may be used alone or in combination depending on the properties required. Alternatively, high melting point lipids such as white soft paraffin and/or liquid paraffin or other mineral oils are used.

Pharmaceutical formulations according to the present invention comprise one or more compounds of the invention together with one or more pharmaceutically acceptable carriers or excipients and optionally other therapeutic agents. Pharmaceutical formulations containing the active ingredient may be in any form suitable for the intended method of administration. When used for oral use for example, tablets, troches, lozenges, aqueous or oil suspensions, dispersible powders or granules, emulsions, hard or soft capsules, syrups or elixirs may be prepared. Compositions intended for oral use may be prepared according to any method known to the art for the manufacture of pharmaceutical compositions and such compositions may contain one or more agents including sweetening agents, flavoring agents, coloring agents and preserving agents, in order to provide a palatable preparation.

Tablets containing the active ingredient in admixture with non-toxic pharmaceutically acceptable excipient which are suitable for manufacture of tablets are acceptable. These excipients may be, for example, inert diluents, such as calcium or sodium carbonate, lactose, lactose monohydrate, croscarmellose sodium, povidone, calcium or sodium phosphate; granulating and disintegrating agents, such as maize starch, or alginic acid; binding agents, such as cellulose, microcrystalline cellulose, starch, gelatin or acacia; and lubricating agents, such as magnesium stearate, stearic acid or talc. Tablets may be uncoated or may be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax may be employed.

Formulations for oral use may be also presented as hard gelatin capsules where the active ingredient is mixed with an inert solid diluent, for example calcium phosphate or kaolin, or as soft gelatin capsules wherein the active ingredient is mixed with water or an oil medium, such as peanut oil, liquid paraffin or olive oil.

Aqueous suspensions of the invention contain the active materials in admixture with excipients suitable for the manufacture of aqueous suspensions. Such excipients include a suspending agent, such as sodium carboxymethylcellulose, methylcellulose, hydroxypropyl methylcelluose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycetanol), a condensation product of ethylene oxide with a partial ester derived from a fatty acid and a hexitol anhydride (e.g., polyoxyethylene sorbitan monooleate). The aqueous suspension may also contain one or more preservatives such as ethyl or n-propyl p-hydroxy-benzoate, one or more coloring agents, one or more flavoring agents and one or more sweetening agents, such as sucrose or saccharin.

Oil suspensions may be formulated by suspending the active ingredient in a vegetable oil, such as arachis oil, olive oil, sesame oil or coconut oil, or in a mineral oil such as liquid paraffin. The oral suspensions may contain a thickening agent, such as beeswax, hard paraffin or cetyl alcohol. Sweetening agents, such as those set forth above, and flavoring agents may be added to provide a palatable oral preparation. These compositions may be preserved by the addition of an antioxidant such as ascorbic acid.

Dispersible powders and granules of the invention suitable for preparation of an aqueous suspension by the addition of water provide the active ingredient in admixture with a dispersing or wetting agent, a suspending agent, and one or more preservatives. Suitable dispersing or wetting agents and suspending agents are exemplified by those disclosed above. Additional excipients, for example sweetening, flavoring and coloring agents, may also be present.

The pharmaceutical compositions of the invention may also be in the form of oil-in-water emulsions. The oily phase may be a vegetable oil, such as olive oil or arachis oil, a mineral oil, such as liquid paraffin, or a mixture of these. Suitable emulsifying agents include naturally-occurring gums, such as gum acacia and gum tragacanth, naturally occurring phosphatides, such as soybean lecithin, esters or partial esters derived from fatty acids and hexitol anhydrides, such as sorbitan monooleate, and condensation products of these partial esters with ethylene oxide, such as polyoxyethylene sorbitan monooleate. The emulsion may also contain sweetening and flavoring agents. Syrups and elixirs may be formulated with sweetening agents, such as glycerol, sorbitol or sucrose. Such formulations may also contain a demulcent, a preservative, a flavoring or a coloring agent.

The pharmaceutical compositions of the invention may be in the form of a sterile injectable preparation, such as a sterile injectable aqueous or oleaginous suspension. This suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent, such as a solution in 1,3-butane-diol or prepared as a lyophilized powder. Among the acceptable vehicles and solvents that may be employed are water, Ringer's solution and isotonic sodium chloride solution. In addition, sterile fixed oils may conventionally be employed as a solvent or suspending medium. For this purpose any bland fixed oil may be employed including synthetic mono- or diglycerides. In addition, fatty acids such as oleic acid may likewise be used in the preparation of injectables.

The amount of active ingredient that may be combined with the carrier material to produce a single dosage form will vary depending upon the host treated and the particular mode of administration. For example, a time-release formulation intended for oral administration to humans may contain approximately 1 to 1000 mg of active material compounded with an appropriate and convenient amount of carrier material which may vary from about 5 to about 95% of the total compositions (weight:weight). The pharmaceutical composition can be prepared to provide easily measurable amounts for administration. For example, an aqueous solution intended for intravenous infusion may contain from about 3 to 500 µg of the active ingredient per milliliter of solution in order that infusion of a suitable volume at a rate of about 30 mL/hour can occur.

Formulations suitable for administration to the eye include eye drops wherein the active ingredient is dissolved or suspended in a suitable carrier, especially an aqueous solvent for the active ingredient. The active ingredient is preferably present in such formulations in a concentration of 0.5 to 20%, advantageously 0.5 to 10% particularly about 1.5% w/w.

Formulations suitable for topical administration in the mouth include lozenges comprising the active ingredient in a flavored basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

Formulations for rectal administration may be presented as a suppository with a suitable base comprising for example cocoa butter or a salicylate.

Formulations suitable for intrapulmonary or nasal administration have a particle size for example in the range of 0.1 to 500 microns (including particle sizes in a range between 0.1 and 500 microns in increments microns such as 0.5, 1, 30 microns, 35 microns, etc.), which is administered by rapid inhalation through the nasal passage or by inhalation through the mouth so as to reach the alveolar sacs. Suitable formulations include aqueous or oily solutions of the active ingredient. Formulations suitable for aerosol or dry powder administration may be prepared according to conventional methods and may be delivered with other therapeutic agents such as compounds heretofore used in the treatment or prophylaxis of a given condition.

Formulations suitable for vaginal administration may be presented as pessaries, tampons, creams, gels, pastes, foams or spray formulations containing in addition to the active ingredient such carriers as are known in the art to be appropriate.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents.

The formulations are presented in unit-dose or multi-dose containers, for example sealed ampoules and vials, and may be stored in a freeze-dried (lyophilized) condition requiring only the addition of the sterile liquid carrier, for example water for injection, immediately prior to use. Extemporaneous injection solutions and suspensions are prepared from sterile powders, granules and tablets of the kind previously described. Preferred unit dosage formulations are those containing a daily dose or unit daily sub-dose, as herein above recited, or an appropriate fraction thereof, of the active ingredient.

It should be understood that in addition to the ingredients particularly mentioned above the formulations of this invention may include other agents conventional in the art having regard to the type of formulation in question, for example those suitable for oral administration may include flavoring agents.

The invention further provides veterinary compositions comprising at least one active ingredient as above defined together with a veterinary carrier therefor.

Veterinary carriers are materials useful for the purpose of administering the composition and may be solid, liquid or gaseous materials which are otherwise inert or acceptable in the veterinary art and are compatible with the active ingredient. These veterinary compositions may be administered orally, parenterally or by any other desired route.

Compounds of the invention can also be formulated to provide controlled release of the active ingredient to allow less frequent dosing or to improve the pharmacokinetic or toxicity profile of the active ingredient. Accordingly, the invention also provided compositions comprising one or more compounds of the invention formulated for sustained or controlled release.

Effective dose of active ingredient depends at least on the nature of the condition being treated, toxicity, whether the compound is being used prophylactically (lower doses), the method of delivery, and the pharmaceutical formulation, and will be determined by the clinician using conventional dose escalation studies. It can be expected to be from about 0.0001 to about 100 mg/kg body weight per day. Typically, from about 0.01 to about 10 mg/kg body weight per day. More typically, from about 0.01 to about 5 mg/kg body weight per day. More typically, from about 0.05 to about 0.5 mg/kg body weight per day. For example, the daily candidate dose for an adult human of approximately 70 kg body weight will range from 1 mg to 1000 mg, preferably between 5 mg and 500 mg, and may take the form of single or multiple doses.

One or more compounds of the invention (herein referred to as the active ingredients) are administered by any route appropriate to the condition to be treated. Suitable routes include oral, rectal, nasal, topical (including buccal and sublingual), vaginal and parenteral (including subcutaneous, intramuscular, intravenous, intradermal, intrathecal and epidural), and the like. It will be appreciated that the preferred route may vary with for example the condition of the recipient.

Mechanism of Action of Compounds of the Invention

A specific group of the compounds of the present invention, that can be activated by zinc for nucleophilic substitution and that can form a covalent bond with a nucleophile of the matrix metalloproteinase, includes a thiirane ring. Another specific group of the compounds of the present invention, that can be activated by zinc for nucleophilic substitution and that can form a covalent bond with a nucleophile of the matrix metalloproteinase, includes an oxirane ring. In addition, a specific nucleophile of the matrix metalloproteinase which can form a covalent bond with the group of the compounds of the present invention (e.g., thiirane or oxirane) is located at the amino acid residue corresponding to residue 404 of the matrix metalloproteinase, wherein the numbering is based on the active site general base for gelatinase A, which is observed in other MMPs. More specifically, the nucleophile is a carboxy (i.e., $COO^-$) oxygen atom located at amino acid residue corresponding to residue 404 of the matrix metalloproteinase, wherein the numbering is based on the active site general base for gelatinase A, which is observed in other MMPs. See, FIG. 1.

Pharmaceutical Kits

Pharmaceutical kits useful in the present invention, which include a therapeutically effective amount of a pharmaceutical composition that includes a compound of component (a) and one or more compounds of component (b), in one or more sterile containers, are also within the ambit of the present invention. Sterilization of the container may be carried out using conventional sterilization methodology well known to those skilled in the art. Component (a) and component (b) may be in the same sterile container or in separate sterile containers. The sterile containers or materials may include separate containers, or one or more multi-part containers, as desired. Component (a) and component (b), may be separate, or physically combined into a single dosage form or unit as described above.

Such kits may further include, if desired, one or more of various conventional pharmaceutical kit components, such as for example, one or more pharmaceutically acceptable carriers, additional vials for mixing the components, etc., as will be readily apparent to those skilled in the art. Instructions, either as inserts or as labels, indicating quantities of the components to be administered, guidelines for administration, and/or guidelines for mixing the components, may also be included in the kit.

EXAMPLES

Several methods for the preparation of compounds of formulas I-IX are provided in the Examples hereinbelow. These methods are intended to illustrate the nature of such compounds and preparations and are not intended to limit the scope of the compounds and applicable synthetic methods of the invention.

Some abbreviations used herein include the following: Ac, acetyl; mCPBA, 3-chloroperoxybenzoic acid; DMF, N,N-dimethylformamide; Me, methyl; Ms, methanesulfonyl; THF, tetrahydrofuran; MMP, matrix metalloproteinase; DMEM, Dulbecco's modified Eagle's medium; DMSO, dimethyl sulfoxide ($Me_2SO$); PBS, phosphate buffer saline; FBS, fetal bovine serum.

Example 1

Design, Synthesis, and Evaluation of a Mechanism-Based Inhibitor for Gelatinase A The first mechanism-based inhibitor for MMPs have been previously described (J. Am. Chem. Soc. 2000, 122, 6799-6800), which in chemistry mediated by the active site zinc ion selectively and covalently inhibits MMP-2, MMP-3 and MMP-9. Computational analyses indicated that this selectivity in inhibition of MMPs could be improved by design of new variants of the inhibitor class. The syntheses of methyl 2-(4-{4-[(2-thiiranylpropyl) sulfonyl]phenoxy}phenyl)-acetate (1.3) and 2-(4-{4-[(2-thiiranylpropyl) sulfonyl]phenoxy}phenyl)acetic acid (1.4) are reported herein. The results of this Example show that compound 1.3 serves as a mechanism-based inhibitor exclusively for MMP-2. This molecule should prove useful in delineating the functions of MMP-2 in biological systems.

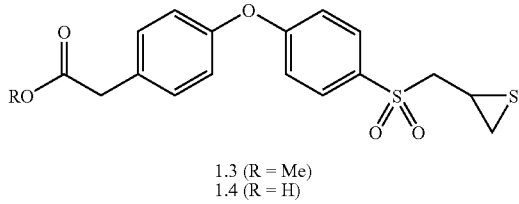

1.3 (R = Me)
1.4 (R = H)

Matrix metalloproteinases (MMPs) are zinc-dependent endopeptidases with important pathological and physiological functions (Massova, I.; Kotra, L. P.; Fridman, R.; Mobashery, S. Matrix Metalloproteases: Structures, Evolution and Diversification, FASEB J 1998, 12, 1075; see also Can. J. Physiol. Pharmacol. 1999, 77, 465-480; J. Clin. Oncol. 2000, 18, 1135-1149; Cell 2000, 100, 57-70; Nature Rev. 2002, 2, 563-572; Nature Rev. 2002, 2, 727-739; Nature Rev. 2002, 3, 1-6; Nature Rev. 2003, 3, 401-410; Nature Med. 2003, 9, 822-823; Nature Med. 2003, 9, 999-1000).

A total of 26 MMPs are known. Their unregulated and uncontrolled activities have been associated with a number of disease processes, including neurological disorders, arthritis, cardiovascular diseases and cancer, neurological disorders, and others. Inhibition of MMPs as a means to intervention of disease is highly sought (Nature Rev. 2002, 1, 415-426; Current Opinion Chem. Biol. 1999, 3, 500-509; Chem. Rev. 1999, 99, 2735-2776; Curr., Med. Chem. 2001, 8, 425-474; and Lee, M.; Fridman, R.; Mobashery, S. Chem. Soc. Rev. 2004, 33, 401-409). With very few exceptions, the known inhibitors of MMPs are broad-spectrum molecules, designed to chelate the active-site zinc ions of these enzymes. This broad breadth of activity has been problematic in clinical trials of MMP inhibitors, as the molecules tend to show serious side effects (Egeblad and Werb, Nature Rev. Cancer 2002, 2, 161-174; Coussens et al. Science 2002, 295, 2387-2392).

This Example is an investigation into selective inhibition of gelatinases, MMP-2 and MMP-9 (also known as gelatinases A and B, respectively). The excessive and unregulated activities of these two enzymes have been indicated in a number of cancer metastases (J. Surg. Res. 2003, 110, 383-392; Breast Cancer Res Treat 2003, 77, 145-155; Biochim. Biophys. Acta. 2004, 1705, 69-89; Gynecol. Oncol. 2004, 94, 699-704; Eur. J. Surg. Oncol. 2004, 30, 560-4; and Mod. Pathol. 2004, 17, 496-502).

Mobashery and co-workers disclosed for the first time a novel strategy in mechanism-based inhibition of MMP by a thiirane-containing inhibitor, where the thiirane sulfur first coordinates with the active-site zinc ion (J. Am. Chem. Soc. 2000, 122, 6799-6800). The coordinated thiirane predisposes it to nucleophilic attack by the active site glutamate (Glu-404 in MMP-2) in these enzymes, a process that leads to covalent modification of the enzyme and the attendant loss of activity. This process is depicted in FIG. 1 for a known member (compound 1.1) of this class of inhibitors (1.1→1.2).

Figure 2:
FIG. 2 illustrates a stereoview of compound 1.3 bound to the active site of MMP-2. A Connolly solvent-accessible surface is constructed in the active site (shown in green), while the protein is rendered in purple. Compound 1.3, along with the active site Glu-404 and the three histidines that are coordinated to the catalytic zinc are shown in capped-stick representation, colored according to atom types (yellow, red, blue, and white for S, O, N, and C, respectively). The zinc ion is shown as an orange sphere. The white arrow points to the S1' pocket. The side chain hydroxyl of Thr428 is expected to hydrogen bond (2.8 Å) to the ester carbonyl of compound 1.3. The methyl group of compound 1.3 is located near Leu399, Leu420, and Phe431, resulting in favorable hydrophobic interactions that would likely contribute to the overall binding affinity.

Inhibitor 1.1 underwent the chemistry shown in FIG. 1 with three MMPs: MMP-2, MMP-3 and MMP-9. The goal of the experiments disclosed herein is to develop inhibitors of this class that show an even narrower spectrum of inhibition than that exhibited by compound 1.1. Specific interactions at the bottom of the deep S1' pocket of MMP-2 and MMP-9 were identified that could be exploited with a structural variant of inhibitor 1.1 to enhance selectivity toward gelatinases (FIG. 2). Two such molecules, 1.3 and 1.4, were designed by computational analyses. The syntheses of these molecules are reported herein. Furthermore, that compound 1.3 shows the pattern of slow-binding inhibition that leads to covalent chemistry only with MMP-2 is documented.

The syntheses of compounds 1.3 and 1.4 were accomplished according to Scheme 1 below. An N,N-dimethyl glycine-promoted Ullmann coupling reaction between the commercially available aryl bromide 1.5 and phenol 1.7, which was in turn prepared from 4-hydroxythiophenol (1.6) by chemoselective allylation, proceeded smoothly to give 1.8 in 65% yield. Oxidation of the sulfur and olefin moieties in 1.8 was achieved by the use of an excess of m-CPBA (12 equiv.) to afford oxirane 1.9 in 92% yield, which was treated with thiourea to provide thiirane 1.3 in 77% yield.

Attempts at hydrolysis of the methyl ester of 1.3 to the corresponding carboxylic acid 1.4 under various basic conditions were unsuccessful, probably due to the deprotonation of the acidic α-position to the sulfonyl moiety, followed by β-elimination of the thiolate. The method of Mascaretti with the use of $(Bu_3Sn)_2O$ in toluene at 80° C. was found to be most effective for this conversion. Under these conditions, methyl ester 1.3 was converted to the corresponding tin ester, which was subsequently hydrolyzed on $C_{18}$-reverse phase silica gel to afford the desired carboxylic acid 1.4 in 65% yield (with an attendant 12% recovery of 1.3).

Scheme 1

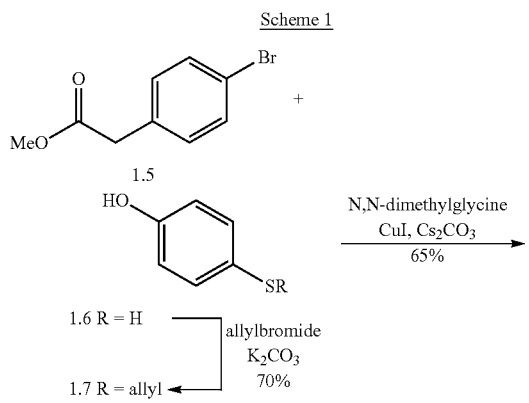

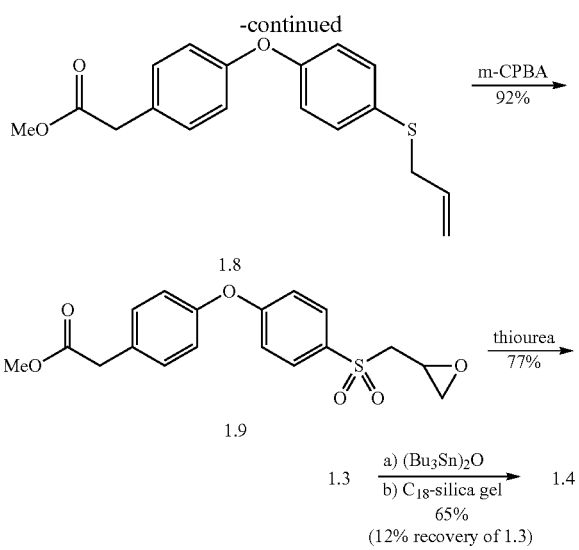

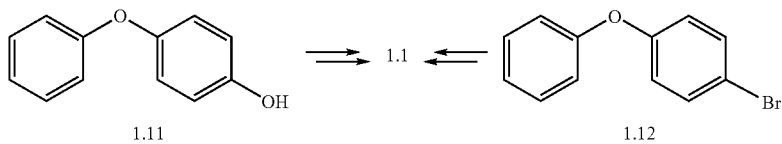

The synthetic route to compounds 1.3 and 1.4 is different than those reported for inhibitor 1.1. (*J. Am. Chem. Soc.* 2000, 122, 6799-6800; *J. Org. Chem.* 2004, 69, 3572-3573.) Syntheses of 1.1 began from the commercially available diphenyl ethers 1.11 or 1.12 illustrated below. The synthetic route of Scheme 1 allows more flexibility in creating structural diversity in the two ring systems and should find more general applicability for entries into this molecular class of versatile enzyme inhibitors.

Compounds 1.3 and 1.4 were evaluated with a representative set of MMPs. As shown in Table 1, compound 1.4 inhibits MMP-2 with a K; of 460 iiM. Whereas compound 1.3 exhibits dissociation constants for MMP-2 and -9 in the low nanomolar levels, it behaves as a slow-binding inhibitor that leads to mechanism-based inhibition only with MMP-2. Therefore, compound 1.3 is a selective and potent mechanism-based inhibitor of MMP-2 (gelatinase A). Both compounds are merely poor competitive inhibitors (micromolar) of the other MMP that were tested. Hence, high selectivity in inhibition of MMP-2 has been achieved.

TABLE 1

Kinetic Parameters for Competitive Inhibition of MMPs by the Synthetic Inhibitors

| | $K_i$ (nM) | |
|---|---|---|
| | 1.3 | 1.4 |
| MMP-2 | 50 ± 14[a] | 460 ± 30 |
| MMP-9 | 40 ± 2 | (4.1 ± 0.2) × $10^3$ |
| MMP-14$_{cat}$ | 590 ± 70 | (5.3 ± 0.3) × $10^4$ |
| MMP-1 | (1.1 ± 0.2) × $10^4$ | (4.5 ± 0.9) × $10^3$ |
| MMP-3 | (8.7 ± 0.5) × $10^3$ | (5.4 ± 1.0) × $10^5$ |
| MMP-7 | 1.3 × $10^4$ | (2.5 ± 0.1) × $10^5$ |

[a]Parameters for slow-binding component of inhibition: $k_{on}$ = (1.2 ± 0.3) □ $10^4$ $M^{-1}s^{-1}$, $k_{off}$ = (6.2 ± 0.7) × $10^{-4}$ $s^{-1}$.

Superimposition of the X-ray structures for MMP-2 and MMP-9 reveals some important differences (*J. Biol. Chem.* 2003, 278, 51646-51653). Midway through the S1' loop, an arginine residue is present in MMP-9, as opposed to a threonine in MMP-2. The pocket of MMP-9 appears to be more constricted than that of MMP-2, as the backbone of the S1' loop of MMP-9 is about 2-3 Å inward. This could potentially lead to unfavorable steric interaction for the methyl moiety of compound 1.3 in MMP-9.

Methods: Enzyme kinetics were performed as previously described (*J. Am. Chem. Soc.* 2000, 122, 6799-6800).

Experimental Procedures and Data for Compounds of Example 1

4-(Allylthio)phenol (1.7). To a stirred solution of 4-hydroxythiophenol (1.6) (4.30 g, 34.1 mmol) in DMF (25 mL) were added $K_2CO_3$ (4.71 g, 34.1 mmol) and allyl bromide (3.09 mL, 34.1 mmol) at ice-water temperature, and the mixture was stirred for 15 minutes, prior to stirring overnight at room temperature. After the addition of 1 M aqueous HCl, the mixture was extracted with ether (3×). The combined organic layer was washed with water and brine, dried over $MgSO_4$, and concentrated under reduced pressure. The resultant residue was purified by silica gel column chromatography (ethyl acetate/hexane=1/10 to 1/6) to give 1.7 (5.74 g, 70%) as a white semi-solid. The $^1H$ and $^{13}C$ NMR spectra and mass spectrum were identical to the reported values (*Tetrahedron* 1994, 50, 10321-10330).

Methyl 2-{4-[4-(Allylthio)phenoxy]phenyl}acetate (1.8). A mixture of 1.5 (1.51 g, 6.59 mmol), 7 (1.64 g, 9.88.mmol), $Cs_2CO_3$ (4.30 g, 13.2 mmol), N, N-dimethylglycine hydrochloride salt (276 mg, 1.98 mmol), CuI (125 mg, 0.659 mmol), and degassed 1,4-dioxane (14 mL) was heated at 90° C. for 22 hours under a nitrogen atmosphere. After dilution with water, the mixture was extracted with ethyl acetate. The combined organic layer was washed with water and brine, dried over $Na_2SO_4$, and concentrated under reduced pressure. The resultant residue was purified by silica gel column chromatography (ethyl acetate/hexane=1/12) to give 1.8 (1.35 g, 65%) as a pale yellow semi-solid. $^1H$ NMR (300 MHz, $CDCl_3$): δ 3.49 (d, 2H, J=7.2 Hz), 3.61 (s, 2H), 3.71 (s, 3H), 5.03-5.10 (m, 2H), 5.86 (m, 1H), 6.91-6.97 (m, 4H), 7.23-7.26 (m, 2H), 7.32-7.35 (m, 2H); $^{13}C$ NMR (125 MHz, $CDCl_3$): δ 38.5, 40.3, 52.1, 117.5, 119.0, 119.1, 129.0, 129.3, 130.6, 132.9, 133.7, 156.0, 156.3, 172.0; HRMS (FAB) calcd for $C_{18}H_{18}O_3S$ ($M^+$) 314.0977, found 314.0986.

Methyl 2-(4-{4-[(2-Oxiranylpropyl)sulfonyl] phenoxy}phenyl)-acetate (1.9). To a stirred solution of 1.8 (500 mg, 1.59 mmol) in $CH_2Cl_2$ (20 mL) was added m-CPBA (ca. 70%, 4.7 g, 19.1 mmol) at ice-water temperature, and the mixture was subsequently stirred at room temperature for eight days. With ice-cooling, the reaction was quenched with a saturated $Na_2S_2O_3$ solution, followed by saturated $NaHCO_3$ solution, and the mixture was extracted with ethyl acetate (3×). The combined organic layer was washed with saturated $Na_2S_2O_3$ solution, saturated $NaHCO_3$ solution, water and brine, dried over $Na_2SO_4$, and concentrated under reduced pressure. The resultant residue was purified by silica gel column chromatography (ethyl acetate/hexane=1/2 to 2/3) to give 1.9 (528 mg, 92%) as a colorless oil. $^1$H NMR (500 MHz, $CDCl_3$): δ 2.47 (dd, 1H, J=5.0, 2.0 Hz), 2.82 (m, 1H), 3.26-3.33 (m, 3H), 3.65 (s, 2H), 3.72 (s, 3H), 7.03-7.05 (m, 2H), 7.08-7.10 (m, 2H), 7.32-7.34 (m, 2H), 7.86-7.88 (m, 2H); $^{13}$C NMR (125 MHz, $CDCl_3$): δ 40.3, 45.8, 52.1, 59.6, 117.6, 120.6, 130.5, 130.9, 131.1, 132.4, 153.8, 162.8, 171.8; HRMS (FAB) calcd for $C_8H_{18}O_6S$ ($M^+$) 362.0824, found 362.0829.

Methyl 2-(4-{4-[(2-Thiiranylpropyl)sulfonyl] phenoxy}phenyl)-acetate (1.3). To a stirred solution of 1.9 (500 mg, 1.38 mmol) in MeOH—$CH_2Cl_2$ (10:1, 11 mL) was added thiourea (262 mg, 3.45 mmol) at room temperature, and the mixture was stirred overnight. After concentration under reduced pressure, the residue was dissolved in ethyl ether. The ethyl ether solution was washed with water and brine, dried over $MgSO_4$, and concentrated under reduced pressure. The residue was purified by silica gel column chromatography (ethyl acetate/hexane=2/5) to give 1.3 (400 mg, 77%) as a colorless oil. $^1$H NMR (500 MHz, $CDCl_3$): δ 2.15 (dd, 1H, J=5.5, 2.0 Hz), 2.53 (dd, 1H, J=6.5, 2.0 Hz), 3.05 (m, 1H), 3.17 (dd, 1H, J=14.5, 7.0 Hz), 3.51 (dd, 1H, J=14.5, 5.5 Hz), 3.65 (s, 2H), 3.72 (s, 3H), 7.03-7.05 (m, 2H), 7.08-7.10 (m, 2H), 7.33-7.34 (m, 2H), 7.85-7.86 (m, 2H); $^{13}$C NMR (125 MHz, $CDCl_3$): δ 24.2, 26.0, 40.3, 52.1, 62.6, 117.7, 120.5, 130.7, 130.9, 131.1, 131.9, 153.8, 162.8, 171.8; HRMS (FAB) calcd for $C_{18}H_{19}O_5S_2$ ($M+H^+$) 379.0674, found 379.0645.

2-(4-{4-[(2-Thiiranylpropyl)sulfonyl]phenoxy}phenyl) acetic acid (1.4). To a stirred solution of 3 (312 mg, 0.83 mmol) in toluene (11 mL) was added bis(tributyltin)oxide (1.05 mL, 2.06 mmol) at room temperature, and the mixture was stirred at 80° C. for 12 hours. The solution was cooled to room temperature and was concentrated to dryness under reduced pressure. The residue was dissolved in acetonitrile, and the solution was washed with hexane (3×) and concentrated under reduced pressure to leave the crude tin ester 1.10 (532 mg) as a pale-yellow oil. Subsequently, 1.10 was passed through a $C_{18}$-reverse phase silica gel pad (ODS silica gel 20 g, washed with water, 1:2 water/acetonitrile and acetonitrile) to afford a mixture of 1.3 and 1.4, which was purified by silica gel column chromatography (chloroform/methanol=30/1 to 10/1) to give 1.4 (195 mg, 65%) as a white solid with the recovery of some of 1.3 (38 mg, 12%). Compound 1.10: $^1$H NMR (300 MHz, $CDCl_3$): δ 0.90 (t, 9H, J=7.2 Hz), 1.23-1.38 (m, 12H), 1.54-1.64 (m, 6H), 2.16 (dd, 1H, J=5.4, 1.8 Hz), 2.54 (dd, 1H, J=6.0, 1.8 Hz), 3.07 (m, 1H), 3.15 (dd, 1H, J=13.8, 7.8 Hz), 3.54 (dd, 1H, J=13.8, 5.1 Hz), 3.64 (s, 2H), 7.03 (m, 2H), 7.08 (m, 2H), 7.35 (m, 2H), 7.86 (m, 2H); Mass (FAB): m/z 655 ($M+H^+$); Rf value=0.3 (chloroform/methanol=10/1). Compound 1.4: mp 133-134° C.; $^1$H NMR (500 MHz, $CDCl_3$): δ 2.16 (d, 1H, J=4.0 Hz), 2.54 (d, 1H, J=5.5 Hz), 3.06 (m, 1H), 3.19 (dd, 1H, J=14.0, 8.0 Hz), 3.52 (dd, 1H, J=14.0, 6.0 Hz), 3.68 (s, 2H), 7.05 (br d, 2H, J=8.5 Hz), 7.10 (br d, 2H, J=8.5 Hz), 7.35 (br d, 2H, J=8.5 Hz), 7.86 (br d, 2H, J=8.5 Hz); $^{13}$C NMR (125 MHz, $CDCl_3$): δ 24.2, 26.0, 40.2, 62.6, 117.8, 120.5, 130.2, 130.7, 131.3, 132.0, 154.1, 162.7, 177.1; HRMS (FAB) calcd for $C_{17}H_{17}O_5S_2$ ($M+H^+$) 365.0517, found 365.0495; Rf value=0.2 (chloroform/methanol=10/1).

Computational Procedures. The X-ray structure of MMP-2 provided the Cartesian coordinates for the molecular docking study (RCSB code 1 QIB). The Sybyl program (Tripos Inc., St. Louis, Mo.) was used for the manipulation and visualization of all structures and for the protonation of the bound ligand. AM1-BCC charges were computed for the ligand using the antechamber module from the AMBER 7 suite of programs (Case et al., AMBER 7 ed.; University of California: San Francisco, 2002). The ligand was docked into the active site of MMP-2 using a Lamarekian genetic algorithm as implemented in the AutoDock 3.04 program (Morris et al. *J. Comp. Chem.* 1998, 19, 1639-1662). Parameters for the docking runs were similar to those used previously (Morris et al. *J. Comp. Chem.* 1998, 19, 1639-1662), except for the following differences: the quaternion step, the translation step, and the torsion step were set to 0.2, 5, and 5, respectively. The number of evaluations was increased to $2.5 \times 10^7$ from 250,000 and the ligand was fully flexible during the docking runs.

Example 2

Potent Mechanism-Based Inhibitors For Matrix Metalloproteinases

Matrix metalloproteinases (MMPs) are zinc-dependent endopeptidases that play important roles in physiological and pathological conditions. Both gelatinases (MMP-2 and MMP-9) and membrane-type 1 MMP (MMP-14) are important targets for inhibition since their roles in various diseases, including cancer, have been well established. This Example describes a set of mechanism-based inhibitors that show high selectivity to gelatinases and MMP-14 (inhibitor 2.3) and to only MMP-2 (inhibitors 2.5 and 2.7). These molecules bind to the active sites of these enzymes, initiating a slow-binding profile for the onset of inhibition, which leads to covalent enzyme modification. The full kinetic analysis for the inhibitors is reported. These are nanomolar inhibitors ($K_i$) for the formation of the non-covalent enzyme-inhibitor complexes. The onset of slow-binding inhibition is rapid ($k_{on}$ of $10^2$ to $10^4$ $M^{-1}s^{-1}$) and the reversal of the process is slow ($k_{off}$ of $10^{-3}$ to $10^{-4}$ $s^{-1}$). However, with the onset of covalent chemistry with the best of these inhibitors (e.g., inhibitor 2.3), very little recovery of activity (<10%) was seen over 48 hours of dialysis. We previously reported that broad-spectrum MMP inhibitors like GM6001 (hydroxamate inhibitor) enhance MT1-MMP-dependent activation of pro-MMP-2 in the presence of TIMP-2. Herein, we show that inhibitor 2.3, in contrast to GM6001, had no effect on pro-MMP-2 activation by MT1-MMP. Furthermore, inhibitor 2.3 reduced tumor cell migration and invasion in vitro. These results show that these new inhibitors are promising candidates for selective inhibition of MMPs in animal models of relevant human diseases.

Extracellular proteolysis is an essential aspect of both physiological and pathological processes. Several enzyme families have been implicated in extracellular proteolysis, of which the matrix metalloproteinases (MMPs) constitute an important group. The MMPs are zinc-dependent endopeptidases that play key roles in embryonic development, neurological processes, wound healing, angiogenesis, arthritis, cardiovascular diseases and cancer, just to mention a few. In cancer, for instance, MMPs are implicated at all stages of tumor progression, including tumor growth, angiogenesis, and metastasis (Egeblad and Werb, (2002) *Nat Rev Cancer* 2, 161-174). Two MMPs, gelatinases A and B (MMP-2 and MMP-9, respectively), are highly expressed in human cancer and a direct relationship between cancer progression and gelatinase expression and activity has been well established in many studies (McCawley and Matrisian, (2000) *Mol Med Today* 6, 149-156). As tumors manifest high levels of gelatinase activity, inhibitors specific for the gelatinases are highly sought.

In the past eight years there have been numerous approaches aimed at targeting MMP activities in tumors and several clinical trials were carried out to test the efficacy of various inhibitors. Unfortunately, the results of these trials were disappointing due to the lack of an objective clinical response and undesired side effects. Many reasons have been postulated for these effects but at the core of the problem remains the issue of inhibitor selectivity (Pavlaki, M. and Zucker, S. (2003) *Cancer Metastasis Rev* 22, 177-203; Coussens, L. M., Fingleton, B., and Matrisian, L. M. (2002) *Science* 295, 2387-2392). Indeed, virtually all MMP inhibitors tested so far have been broad-spectrum inhibitors, designed around chelation of the active site zinc ion (Skiles et al. (2004) *Curr Med Chem* 11, 2911-2977) and their spectrum of inhibition includes, in addition to MMPs, other metalloenzymes. Because targeting gelatinases remains to be of great promise in cancer therapy (Matrisian et al. (2003) *Cancer Res* 63, 6105-6109), efforts aimed at developing better and selective gelatinase inhibitors continue.

Figure 3:
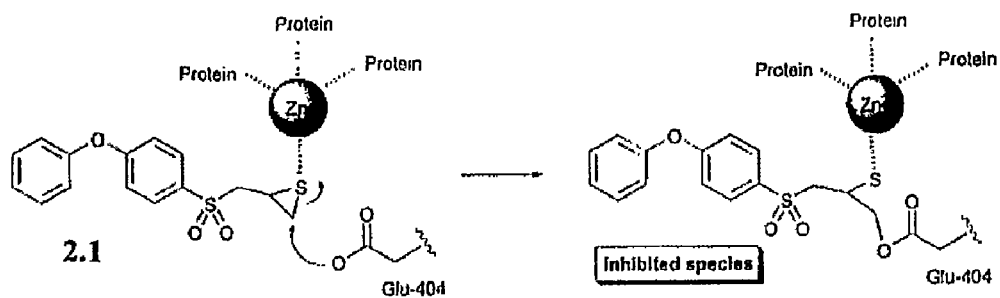
FIG. 3 illustrates a schematic depiction of the mechanism of action of inhibitor 2.1. (A) Coordination of the thiirane with the zinc ion is a prerequisite for the inhibition process. (B) Stereoview of the computational model for the non-covalent binding of inhibitor 2.1 in the active site of MMP-2. The active site of the enzyme is depicted as a Connolly surface in green. The active site zinc ion is depicted as an orange sphere, with the three coordinating histidine residues depicted in capped sticks. Inhibitor 2.1 (in capped sticks and colored according to atom types) is shown coordinated to the active site zinc ion via the thiirane sulfur. The loop that constitutes the $S_1'$ subsite of the enzyme is drawn as a tube in purple, so the terminal phenyl group of the inhibitor is visible. The site of structure elaboration in arriving at molecules 2.2-2.7 is indicated by the white arrow.
Figure 3:
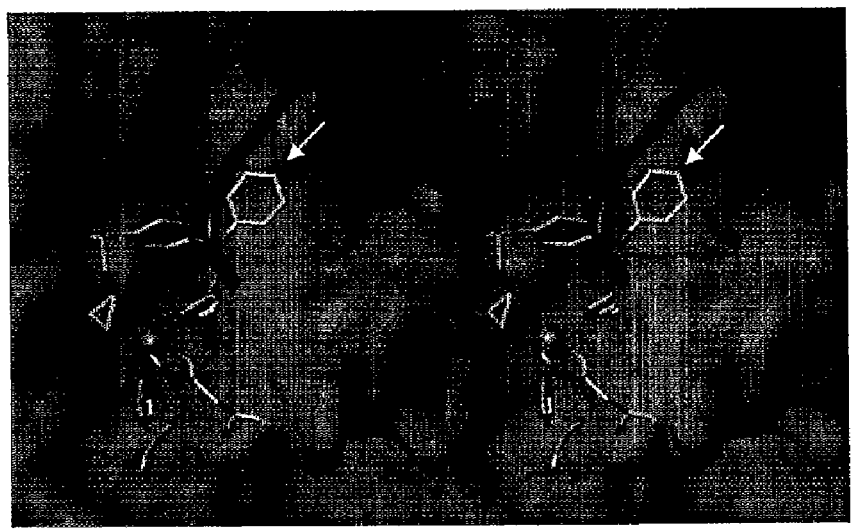

A mere handful of selective inhibitors for MMPs have been reported in the literature (for a review see: Brown, S., Meroueh, S. O., Fridman, R., and Mobashery, S. (2004) *Curr Top Med Chem* 4, 1227-1238). The design and properties of inhibitor 2.1 (Scheme 2) has been previously described. Inhibitor 2.1 is a selective mechanism-based inhibitor for gelatinases. This compound binds to the active sites of MMP-2 and MMP-9 with the thiirane moiety coordinating with the zinc ion. This coordination to the active site metal ion activates the thiirane ring for opening by the nucleophilic attack of the active site glutamate in these enzymes (FIG. 3a). A unique property of this inhibitor is that on binding to the active site zinc ion a pattern of slow-binding for inhibition sets in, leading to a rapid process for the on-set of inhibition with an attendant slow process for recovery from slow-binding at the non-covalent stage of inhibition. This non-covalent inhibited species leads to covalent inhibition by modification of the glutamate.

Scheme 2

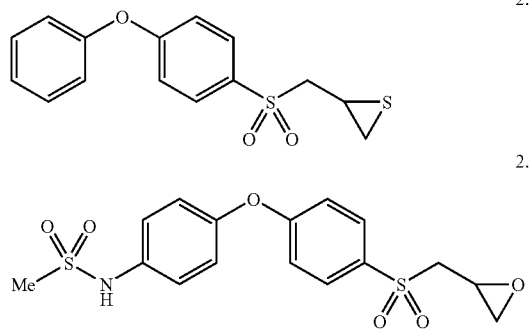

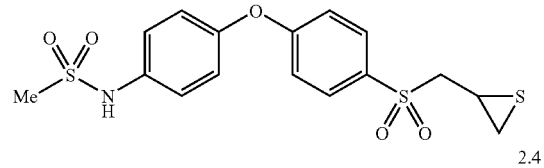

2.3

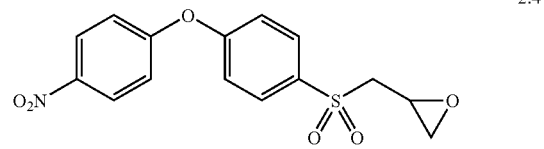

2.4

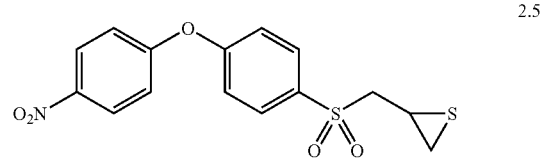

2.5

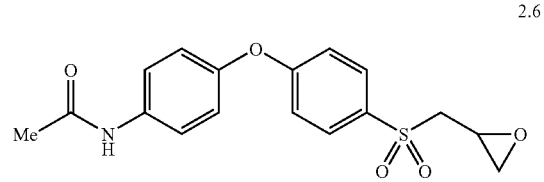

2.6

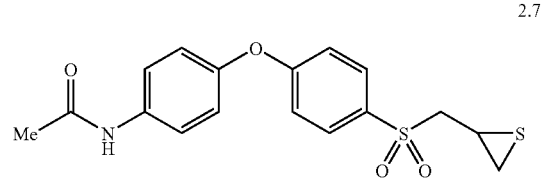

2.7

The synthetic procedures for compounds 2.1-2.7 are given in the Experimental Procedures section below.

Inhibitor 2.1, the prototype of this type of novel mechanism-based inhibitor for gelatinases, is showing promise in mouse models for diseases involving gelatinases (Gu, Z., Cui, J., Brown, S., Fridman, R., Mobashery, S., Strongin, A. Y., and Lipton, S. A. (2005) *J. Neurosci.* 25, 6401-6408; Kruger, A., Arlt, M. J., Gerg, M., Kopitz, C., Bernardo, M. M., Chang, M., Mobashery, S., and Fridman, R. (2005) *Cancer Res.* 65, 3523-3526). The poor solubility of this inhibitor in aqueous medium, however, is a limitation of the molecule. The compounds designed and described in this Example provide increased aqueous solubility over inhibitor 2.1. Furthermore, the concept behind the inhibitor design in targeting other MMPs has been explored in this Example.

A computational model of the inhibitor bound in the active site of MMP-2 within the constraints of the data from X-ray absorption spectroscopy has been generated; see FIG. 2B; (Klcifeld, O., Kotra, L. P., Gervasi, D. C., Brown, S., Bernardo, M. M., Fridman, R., Mobashery, S., and Sagi, I. (2001) *J. Biol. Chem.* 276, 17125-17131). This model for inhibition of inhibitor 2.1 led the way in exploration of the next generation of this type of M inhibitor. The possibility for specific electrostatic interactions near the terminal phenyl group in inhibitor 2.1 bound to the active site of MMP-2 was anticipated for judiciously designed chemical functionalities into the molecular template of compound 2.1.

Three new functional groups are introduced in MMP inhibitors in this Example, the methylsulfonamide (compounds 2.2 and 2.3), the nitro (compounds 2.4 and 2.5) and the acetamide (compounds 2.6 and 2.7), at the terminal phenyl ring system to exploit these electrostatic interactions (Scheme 52). It was expected that these molecules would improve the solubility in aqueous solutions, while exhibiting high selectivity in inhibition toward gelatinases and the membrane-anchored MMP, MT1-MMP (MMP-14), which all share a deep S1' binding site. As will be described herein, these expectations have been borne out, making these inhibitors valuable tools in studies of the functions of MMPs in disease processes. Furthermore, oxirane variants of these molecules (compounds 2.2, 2.4, and 2.6) have been prepared. The fact that the oxirane variants are either poor inhibitors or demonstrate no observable inhibitory properties toward MMPs underscore the importance of the thiirane group for this inhibitor class.

Experimental Procedures:

Synthesis—$^1$H and $^{13}$C NMR spectra were recorded on either a Varian UnityPlus 300 MHz or a Varian INOVA 500 MHz spectrometer. Chemical shifts are reported in ppm from tetramethylsilane on the δ scale. Mass spectra were recorded on a JEOL JMS-AX505HA and a Finnigan-MAT 8430 high-resolution magnetic sector mass spectrometers. For silica gel column chromatography, EMD Silica gel 60 was employed. Thin-layer chromatography was performed with Whatman 0.25 mm silica gel 60-F plates. All other reagents were purchased from Aldrich Chemical Company, Lancaster or Across Organics.

4-(Allylthio)phenol. To a stirred solution of 4-hydroxythiophenol (4.30 g, 34.1 mmol) in DMF (25 ml) were added $K_2CO_3$ (4.71 g, 34.1 mmol) and allyl bromide (3.09 ml, 34.1 mmol) at ice-water temperature, and the mixture was stirred for 15 minutes, prior to stirring overnight at room temperature. After the addition of 1 M aqueous HCl, the mixture was extracted with ether (3×). The combined organic layer was washed with water and brine, dried over $MgSO_4$, and concentrated under reduced pressure. The resultant residue was purified by silica gel column chromatography (ethyl acetate/hexane, 1/10 to 1/6) to give 2.9 (5.74 g, 70%) as a white semi-solid. The $^1$H and $^{13}$C NMR spectra and mass spectrum were identical to the reported values (Goux, C., Lhoste, P., and Sinou, D. (1994) *Tetrahedron* 50, 10321-10330).

1-Allylthio-4-(4-nitrophenoxy)benzene. To a stirred solution of 2.9 (3.46 g, 20.8 mmol) in DMF (100 ml) were added cesium carbonate (10.2 g, 31.2 mmol) and 1-fluoro-4-nitrobenzene (2.10) (2.94 g, 20.8 mmol) at room temperature, and the mixture was stirred at the same temperature for 2 days. After dilution with water, the mixture was extracted into hexane (3×). The combined organic layer was washed with water and brine, dried over $Na_2SO_4$, and concentrated under reduced pressure to give 2.11 (5.32 g, 89%) as a pale yellow oil. $^1$H NMR (300 MHz, $CDCl_3$): δ 3.55 (dt, 2H, J=6.9, 1.2 Hz), 5.10 (dt, 1H, J=10.2, 1.2 Hz), 5.13 (dt, 1H, J=17.1, 1.2 Hz), 5.88 (ddt, 1H, J=17.1, 10.2, 6.9 Hz), 6.98-7.04 (m, 4H), 7.38-7.43 (m, 2H), 8.18-8.22 (m, 2H); $^{13}$C NMR (125 MHz, $CDCl_3$): δ 37.8, 117.1, 117.9, 120.9, 126.0, 132.3, 132.5, 133.4, 142.7, 153.4, 163.1; HRMS (FAB) calcd for $C_{15}H_{13}NO_3S$ ($M^+$) 287.0616, found 287.0593.

1-Allylthio-4-[4-(methanesulfonamido)phenoxy]benzene. To a stirred solution of 2.11 (636 mg, 2.21 mmol) in THF (22 ml) were added acetic acid (2.54 ml, 44.2 mmol) and zinc powder (5.80 g, 88.4 mmol) at room temperature, and the suspension was stirred for 30 min (an exothermic reaction). After dilution with ethyl acetate, the mixture was filtered through Celite. The filtrate was washed with saturated $NaHCO_3$ and brine, dried over $Na_2SO_4$, and concentrated under reduced pressure to give a crude 2.12 (577 mg) as an orange oil, which was employed in the next reaction without purification.

To a stirred solution of 2.12 (577 mg) in $CH_2Cl_2$ (10 ml) were added pyridine (894 μL, 11.1 mmol) and methanesulfonyl chloride (205 μL, 2.65 mmol) at ice-water temperature. After 15 min, the mixture was warmed to room temperature and the stirring was continued for an additional 2 h. Subsequent to the addition of saturated $NaHCO_3$, the mixture was extracted with ethyl acetate (3×). The combined organic layer was washed with 1 M aqueous HCl, saturated $NaHCO_3$ solution and brine, dried over $Na_2SO_4$, and concentrated under reduced pressure. The resultant residue was purified by silica gel column chromatography ($CH_2Cl_2$) to give 2.13 (662 mg, 89% from 2.11) as a pale red solid. Compound 2.12: $^1$H NMR (300 MHz, $CDCl_3$): δ 3.45 (br.d, 2H, J=7.2 Hz), 3.59 (br.s, 2H), 5.01-5.06 (m, 2H), 5.84 (ddt, 1H, J=17.1, 9.6, 6.9 Hz), 6.66-6.70 (m, 2H), 6.83-6.88 (m, 4H), 7.29-7.32 (m, 2H). Compound 2.13: $^1$H NMR (300 MHz, $CDCl_3$): δ 3.01 (s, 3H), 3.50 (dt, 2H, J=7.2, 1.2 Hz), 5.04-5.11 (m, 2H), 5.86 (ddt, 1H, J=16.8, 10.2, 6.9 Hz), 6.67 (br.s, 1H), 6.90-6.95 (m, 2H), 6.96-7.01 (m, 2H), 7.20-7.26 (m, 2H), 7.32-7.37 (m, 2H); $^{13}$C NMR (75 MHz, $CDCl_3$): □ 38.4, 39.3, 117.5, 119.3, 119.9, 123.8, 130.2, 132.0, 132.9, 133.8, 155.2, 156.1; HRMS (FAB) calcd for $C_{16}H_{17}NO_3S_2$ (NO 335.0650, found 335.0639.

4-(4-Acetamidophenory)-1-allylthiobenzene. To a stirred solution of 2.12 (794 mg), which was prepared from 2.11 (830 mg, 2.89 mmol) in the same manner as described for compound 2.13, in $CH_2Cl_2$ (15 ml) were added pyridine (500 mL, 6.18 mmol) and acetic anhydride (292 μL, 3.09 mmol) at ice-water temperature, and the mixture was stirred at the same temperature for 1 h. Subsequent to the addition of saturated $NaHCO_3$, the mixture was extracted with ethyl acetate (3×). The combined organic layer was washed with 1 M aqueous HCl, saturated $NaHCO_3$ solution and brine, dried over $Na_2SO_4$, and concentrated under reduced pressure. The resultant residue was purified by silica gel column chromatography (ethyl acetate/$CH_2Cl_2$=1/8) to give 2.14 (782 mg, 99% from 2.11) as a white solid. $^1$H NMR (500 MHz, $CDCl_3$): δ 2.17 (s, 3H), 3.47 (d, 2H, J=7.0 Hz), 5.04-5.07 (m, 2H), 5.85 (ddt, 1H, J=17.0, 10.0, 7.0 Hz), 6.87-6.90 (m, 2H), 6.94-6.97 (m, 2H), 7.31-7.35 (m, 2H), 7.44-7.47 (m, 2H), 7.54 (br.s, 1H); $^{13}$C NMR (75 MHz, $CDCl_3$): δ 24.4, 38.5, 117.5, 118.7, 119.6, 121.7, 129.0, 132.9, 133.6, 133.7, 153.1, 156.7, 168.4; HRMS (FAB) calcd for $C_{17}H_{17}NO_2S$ ($M^+$) 299.0980, found 299.0980.

{4-[4-(Methanesulfonamido)phenoxy]phenylsulfonyl}methyloxirane. To a stirred solution of 2.13 (544 mg, 1.62 mmol) in $CH_2Cl_2$ (20 ml) was added mCPBA (4.2 g, 17.05 mmol) at ice-water temperature, and the mixture was stirred at room temperature for 9 days. With ice-cooling, the reaction was quenched with saturated $Na_2S_2O_3$ and saturated $NaHCO_3$ solutions, and the mixture was extracted with ethyl acetate (3×). The combined organic layer was washed with saturated $Na_2S_2O_3$ solution, saturated $NaHCO_3$ solution, water and brine, dried over $Na_2SO_4$, and concentrated under reduced pressure. The resultant residue was purified by silica gel column chromatography (ethyl acetate/hexane=3/2) to give 2.2 (386 mg, 62%) as a white solid. $^1$H NMR (300 MHz, $CDCl_3$): δ 2.49 (dd, 1H, J=5.1, 1.8 Hz), 2.83 (m, 1H), 3.06 (s, 3H), 3.27-3.36 (m, 3H), 6.77 (br.s, 1H), 7.08-7.11 (m, 4H), 7.28-7.33 (m, 2H), 7.88-7.93 (m, 2H); $^{13}$C NMR (125 MHz, acetone-$d_6$): δ 39.4, 45.9, 46.6, 59.9, 118.3, 122.3, 123.6, 131.6, 134.6, 136.5, 152.7, 163.5; HRMS (FAB) calcd for $C_{16}H_{17}NO_6S_2$ ($M^+$) 383.0497, found 383.0496.

[4-(4-Nitrophenoxy)phenylsulfoyl]methyloxirane. This material was prepared in the same manner as described for 2.2, with the exception that 2.11 was used in place of 2.13. The crude material was purified by silica gel column chromatography (ethyl acetate/hexane, 2/3) to give 2.4 (56%) as a pale yellow solid. $^1$H NMR (500 MHz, CDCl$_3$): δ 2.51 (dd, 1H, J=4.5, 2.5 Hz), 2.83 (t, 1H, J=4.5 Hz), 3.28 (dd, 1H, J=14.0, 7.0 Hz), 3.35 (m, 1H), 3.41 (dd, 1H, J=14.0, 4.0 Hz), 7.16-7.17 (m, 2H), 7.23-7.25 (m, 2H), 7.99-8.01 (m, 2H), 8.28-8.30 (m, 2H); $^{13}$C NMR (125 MHz, CDCl$_3$): δ 45.7, 45.8, 59.6, 119.1, 119.6, 126.2, 131.0, 134.9, 144.0, 160.2, 160.8; HRMS (FAB) calcd for C$_{15}$H$_{14}$NO$_6$S (M+H$^+$) 336.0542, found 336.0545.

[4-(4-Acetamidophenoxy)phenylsulfonyl]methyloxirane. This material was prepared in the same manner as described for 2.2, with the exception that 2.14 was used in place of 2.13. The crude material was purified by silica gel column chromatography (ethyl acetate/hexane=3/1) to give 2.6 (34%) as a white semi-solid. $^1$H NMR (300 MHz, CDCl$_3$): δ 2.20 (s, 3H), 2.48 (dd, 1H, J=4.5, 1.5 Hz), 2.82 (m, 1H), 3.26-3.34 (m, 3H), 7.03-7.08 (m, 4H), 7.41 (br.s, 1H), 7.55-7.58 (m, 2H), 7.85-7.88 (m, 2H); $^{13}$C NMR (75 MHz, CDCl$_3$): δ 24.1, 45.7, 45.8, 59.8, 117.6, 120.8, 122.0, 130.4, 133.0, 135.4, 151.1, 163.0, 168.5; HRMS (FAB) calcd for C$_{17}$H$_{18}$NO$_5$S (M+H$^+$) 348.0906, found 348.0913.

{4-[4-(Methanesulfonamido)phenoxy]phenylsulfonyl}methylthiirane.

To a stirred solution of 2.2 (82 mg, 0.21 mmol) in MeOH-THF (3:1, 2 ml) was added thiourea (41 mg, 0.53 mmol) at room temperature, and the mixture was stirred overnight at the same temperature. After concentration under reduced pressure, the residue was dissolved into ethyl acetate. The ethyl acetate solution was washed with water and brine, dried over Na$_2$SO$_4$, and concentrated under reduced pressure. The residue was purified by silica gel column chromatography (ethyl acetate/hexane, 1/1) to give 2.3 (67 mg, 77%) as a white solid. $^1$H NMR (300 MHz, CDCl$_3$): δ 2.17 (dd, 1H, J=5.1, 1.8 Hz), 2.55 (dd, 1H, J=6.3, 1.2 Hz), 3.06 (s, 3H), 3.07 (m, 1H), 3.22 (dd, 1H, J=14.1, 7.8 Hz), 3.50 (dd, 1H, J 14.1, 5.7 Hz), 6.72 (br.s, 1H), 7.08-7.12 (m, 4H), 7.30-7.33 (m, 2H), 7.87-7.91 (m, 2H); $^{13}$C NMR (125 MHz, acetone-d$_6$): δ 24.4, 27.2, 39.3, 62.6, 118.4, 122.3, 123.6, 131.9, 133.9, 136.4, 152.7, 163.6; HRMS (FAB) calcd for C$_{16}$H$_{17}$NO$_5$S$_3$ (M$^+$) 399.0269, found 399.0268.

[4-(4-Nitrophenoxy)phenylsulfonyl]methylthiirane. This material was prepared in the same manner as described for 2.3, with the exception that 2.4 was used in place of 2.2. The crude material was purified by silica gel column chromatography (ethyl acetate/hexane, 1/3) to give 5 (79%) as a pale yellow solid. $^1$H NMR (500 MHz, CDCl$_3$): δ 2.20 (dd, 1H, J=5.5, 2.0 Hz), 2.58 (dd, 1H, J=6.0, 2.0 Hz), 3.10 (m, 1H), 3.31 (dd, 1H, J=14.0, 7.5 Hz), 3.52 (dd, 1H, J=14.0, 6.5 Hz), 7.15-7.18 (m, 2H), 7.23-7.26 (m, 2H), 7.97-8.00 (m, 2H), 8.28-8.31 (m, 2H); $^{13}$C NMR (125 MHz, CDCl$_3$): □ 24.0, 26.0, 62.5, 119.1, 119.8, 126.2, 131.2, 134.4, 160.3, 160.8; $^{13}$C NMR (125 MHz, acetone-d$_6$): δ 24.5, 27.2, 62.6, 120.2, 121.0, 127.1, 132.3, 136.2, 145.0, 161.1, 162.4; HRMS (FAB) calcd for C$_{15}$H$_{14}$NO$_5$S$_2$ (M+H$^+$) 352.0313, found 352.0297.

[4-(4-Acetamidophenoxy)phenylsulfonyl]methylthiirane. This material was prepared in the same manner as described for 2.3, with the exception that 2.6 was used in place of 2.2. The crude material was purified by silica gel column chromatography (ethyl acetate/hexane, 3/2 to 2/1) to give 7 (76%) as a white solid. $^1$H NMR (300 MHz, CDCl$_3$): δ 2.16 (dd, 1H, J=5.1, 1.8 Hz), 2.20 (s, 3H), 2.54 (dd, 1H, J=6.3, 1.5 Hz), 3.06 (m, 1H), 3.19 (dd, 1H, J=14.1, 7.8 Hz), 3.52 (dd, 1H, J=14.1, 5.7 Hz), 7.03-7.08 (m, 4H), 7.52 (br.s, 1H), 7.56-7.59 (m, 2H), 7.84-7.87 (m, 2H); $^{13}$C NMR (125 MHz, CDCl$_3$): δ 24.1, 24.4, 26.0, 62.6, 117.4, 121.0, 121.8, 130.7, 131.6, 135.2, 150.7, 163.1, 168.6; HRMS (FAB) calcd for C$_{17}$H$_{18}$NO$_4$S$_2$ (M+H) 364.0677, found 364.0651.

Assessment of Inhibitor Solubility—Aliquots (10 µL) of the solutions of the thiirane compounds 2.1, 2.3, 2.5, and 2.7 in DMSO (e.g., 10 mM, 12 mM, 14 mM and higher concentrations) were added to 990 µL of buffer R [50 mM HEPES (pH 7.5), 0.15 M NaCl, 5 mM CaCl$_2$, 0.01% Brij-35, 1% DMSO] at 37° C. Each mixture was inspected for clarity (or turbidity) to calculate the approximate upper limit of solubility.

Enzymatic Activity Assays—Enzymatic activity was monitored with synthetic peptide, fluorescence-quenched substrates from Peptides International, Inc. (Louisville, Ky.). The activities of MMP-2, MMP-9, MMP-7 and MMP-14 were monitored with MOCAcPLGLA$_2$pr(Dnp)AR-NH$_2$ at excitation and emission wavelengths of 328 and 393 nm, respectively, in buffer R MOCAcRPKPVE(Nva)WRK(Dnp)NH$_2$ was the fluorogenic substrate used to measure MMP-3 at 325 and 393 nm, in buffer R. MMP-1 was assayed with (Dnp)P(Cha)GC(Me)HAK(NMa)NH$_2$ at 340 and 440 nm, in a buffer consisting of 50 mM Tris (pH 7.6), 200 mM NaCl, 5 mM CaCl$_2$, 20 mM ZnSO$_4$, 0.05% Brij.35. Less than 10% substrate hydrolysis was monitored (Knight, C. G. (1995) *Methods Enzymol* 248, 18-34).

Fluorescence was measured using a Photon Technology International (PTI) spectrofluorometer, equipped with Radio-Master™ and FeliX™ hardware and software, respectively. The excitation and emission band passes were 1 and 3 nm, respectively. An integration time of 4 seconds was used for data acquisition. The assays were carried out at 25° C. and the cuvette holder was kept at the same temperature. Quartz or disposable acrylic micro or semi-micro cuvettes from Sarstedt (Newton, N. C.) and Perfector Scientific (Atascadero, Calif.), respectively, were used.

Enzyme Inhibition Studies—Slow-binding enzyme inhibition was monitored continuously for 20-60 min, by adding the enzyme (0.5-1 nM) to a solution of buffer R containing the appropriate fluorogenic substrate and increasing concentrations of the inhibitor (final volume 2 ml) in acrylic cuvettes with stifling. The progress curves were non-linear least squares fitted to Equation 1 (Muller-Steffner et al. (1992) *J Biol Chem* 267, 9606-9611):

$$F = v_s t + (v_o - v_s)(1 - \exp(-kt))/k + F_o \tag{Eq. 1}$$

where $v_o$ represents the initial rate, $v_s$ the steady state rate, k the apparent first-order rate constant characterizing the formation of the steady-state enzyme-inhibitor complex, and F$_o$ the initial fluorescence, using the program Scientist (MicroMath Scientific Software, Salt Lake City, Utah). Association and dissociation rate constants (k$_{on}$ and k$_{off}$, respectively) were obtained from the slope and intercept, respectively, of plots of the apparent first-order rate constant k versus the inhibitor concentration according to Equation 2:

$$k = k_{off} + k_{on}[I]/(1 + [S]/K_m) \tag{Eq. 2}$$

describing a one-step association mechanism (Scheme 3),

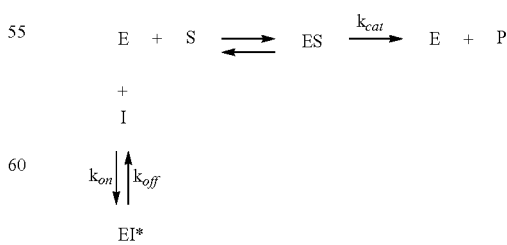

where S is the fluorogenic peptide substrate used and the EI* is the product of slow-binding inhibition. The expression for k$_m$ includes the requisite conformational change necessary for the formation of EI*. The $K_m$ values used for the reaction of MMP-2, MMP-9 and MMP-14 with the fluorogenic substrate MOCAcPLGLA$_2$pr(Dnp)AR-NH$_2$ were 2.46±0.34, 3.06±0.74 (Olson, M. W., Gervasi, D. C., Mobashery, S., and Fridman, R. (1997) *J Biol Chem* 272, 29975-29983) and 6.9±0.6 µM (Toth, M., Bernardo, M. M., Gervasi, D. C., Soloway, P. D., Wang, Z., Bigg, H. F., Overall, C. M., DeClerck, Y. A., Tschesche, H., Chem., M. L., Brown, S., Mobashery, S., and Fridman, R. (2000) *J Biol Chem* 275, 41415-41423), respectively. The inhibition constant, $K_i$, was given by $k_{off}/k_{on}$. Alternatively, $K_i$ values were obtained by plotting $(v_o-v_s)/v_s$ versus the inhibitor concentration, according to Equation 3:

$$(v_o-v_s)/v_s = [I](K_i(1+[S]/K_m)) \quad \text{(Eq. 3)}$$

For analysis of simple linear competitive inhibition, reaction mixtures containing the enzyme (~1 nM) and increasing concentrations of the inhibitor, in buffer R (final volume 1 mL), were incubated for ~16 hours, at 25° C. in semi-micro acrylic cuvettes. The remaining enzymatic activity was measured with the appropriate synthetic peptide fluorogenic substrate for 5-10 minutes. The initial velocities for the reaction of the enzyme with the substrate were determined by linear regression analysis of the fluorescence versus time traces using FeliX™. These initial rates were fitted to Equation 4 (Segel, I. H. *Enzyme Kinetics*, John Wiley & Sons, Inc.: New York (1975)):

$$v_i/v_o = (K_m+[S])/(K_m(1+[I]/K_i)+[S])) \quad \text{(Eq. 4)}$$

where $v_i$ and $v_o$ represent the initial velocity in the presence and absence of inhibitor, respectively, using the program Scientist.

Equilibrium Dialysis—Mixtures of enzyme (10 nM) in the presence and absence of inhibitor (1 mM) were incubated at room temperature for ~3 hours. The remaining enzyme activity was measured with the appropriate fluorogenic substrate, as described above. Part of the reaction mixture (~150 µL) was dialyzed in either dialysis tubing (Invitrogen) or in a 0.1-0.5 mL capacity Slide-A-Lyzer® dialysis cassette (Pierce), against buffer R (3×1 L) containing no DMSO, at room temperature, for >4 hour periods prior to change of buffer to allow for equilibration, over a 48 hour period. The remaining of the inhibition mixture was left on a rotator, at room temperature, over the same period of time. Both the dialyzed and non-dialyzed solutions were tested for MMP activity using the proper fluorogenic substrate. Enzyme activity was expressed in percentage relative to that in the absence of inhibitor.

Cell Culture—Human HeLa S3 cells were obtained from the American Type Culture Collection (ATTC, Manassas, Va.) (CCL-2.2) and grown in suspension in MEM Spinner (Quality Biologicals, Inc., Gaithersburg, Md.) supplemented with 5% horse serum. Nonmalignant, monkey kidney epithelial cells, BS-C-1 (CCL-26), and human fibrosarcoma cells, HT1080 (CCL-2.2), were obtained from ATCC and cultured in Dulbecco's modified Eagle's medium (DMEM, Invitrogen, Carlsbad, Calif.), supplemented with 10% fetal bovine serum (FBS) and antibiotics.

Recombinant Vaccinia Viruses—Recombinant vaccinia viruses encoding for T7 RNA polymerase (vTF7-3) or pro-MMP-2 (vT7-72), pro-MMP-9 (vT7-92), MT1-MMP (vTF-MT1), TIMP-1 (vTF-TEVT-1) and TIMP-2 (vSC59-T2) were produced by homologous recombination as previously described (Fuerst, T. R., Earl, P. L., and Moss, B. (1987) *Mol Cell Biol* 7, 2538-2544).

Recombinant Proteins, Enzymes and Inhibitors—Human recombinant pro-MMP-2 and pro-MMP-9, TIMP-1 and TIMP-2 were expressed in HeLa S3 cells infected with the corresponding recombinant vaccinia viruses and purified to homogeneity from the media as previously described (Olson, M. W., Gervasi, D. C., Mobashery, S., and Fridman, R. (1997) *J Biol Chem* 272, 29975-29983). Pro-MMP-2 and pro-MMP-9 were activated by incubation with 1 mM p-aminophenylmercuric acetate (APMA) for ~2 hours at 37° C. as previously described (Olson, M. W., Gervasi, D. C., Mobashery, S., and Fridman, R. (1997) *J Biol Chem* 272, 29975-29983). APMA was dialyzed out in collagenase buffer (50 mM Tris-HCl (pH 7.5) 5 mM CaCl$_2$, 150 mM NaCl and 0.02% Brij-35).

Human recombinant active MMP-1, and MMP-7 were from R&D Systems (Minneapolis, Minn.) and Chemicon International (Temecula, Calif.), respectively, and the recombinant catalytic domains of human MMP-3 and MMP-14 were from CalBiochem (San Diego, Calif.). Active enzyme concentration was determined by active-site titration with solutions of either TIMP-1 or TIMP-2 with known concentration. The hydroxamate-based MMP inhibitor BB-94 was synthesized in the Mobashery laboratory and GM6001 (hydroxamate inhibitor) was purchased from Chemicon. Stock solutions of BB-94, GM6001, and compounds 2.2-2.7 were prepared in DMSO in the mM concentration range.

Pro-MMP-2 Activation on Cells—Confluent BS-C-1 cells in 12-well plates, were co-infected with v-TF7-3 and vTF-MT1 viruses for 45 min, in infection medium (DMEM supplemented with 2.5% PBS and antibiotics), at 37° C., as described by Hernandez-Barrantes et al. ((2000) *J Biol Chem* 275, 12080-12089). The infection medium was removed and the cells were incubated overnight with serum-free DMEM supplemented with L-glutamine and antibiotics containing increasing concentrations (0-5 µM) of the synthetic MMP inhibitors (MMPIs). The cells were washed twice with phosphate buffer saline (PBS), and incubated for 6 hours with serum-free DMEM containing pro-MMP-2 (10 nM). The cells were rinsed twice with cold PBS and lysed with cold lysis buffer (25 mM Tris-HCl (pH 7.5), 1% IGEPAL CA-630, 100 mM NaCl) containing protease inhibitors (1 pellet of Complete Mini, EDTA-free protease inhibitor mixture from Roche Diagnostics/10 mL of buffer). The lysates were then subjected to gelatin zymography to monitor pro-MMP-2 activation and to immunoblot analysis to detect MT1-MMP expression and processing.

Gelatin Zymography and Immunoblot Analysis—Gelatin zymography was performed using 10% Tris-glycine SDS-polyacrylamide gels, containing 0.1% gelatin, as previously described (Toth, M., Gervasi, D. C., and Fridman, R. (1997) *Cancer Res.* 57, 3159-3167). The samples for immunoblot analysis were subjected to reducing SDS-PAGE followed by transfer to nitrocellulose membranes. MT1-MMP was probed with rabbit polyclonal antibody 815 to MT1-MMP, from Chemicon.

Migration and Invasion Assays—For migration assays, HT1080 cells were cultured in 6-well plates in complete media until they reached confluence. Prior to the migration assay, the cells were treated with serum-free media containing mitomycin C (25 µg/mL), in the presence and absence of concanavalin A (ConA) (20 µg/mL, 30 minutes) to induce pro-MMP-2 activation (Gervasi, D. C., Raz, A., Dehem, M., Yang, M., Kurkinen, M., and Fridman, R. (1996) *Biochem Biophys Res Commun* 228, 530-538). Scratch wounds were then carefully made in the confluent monolayer using a disposable plastic pipette tip. After gentle rinsing twice with PBS to remove detached cells, serum-free media containing increasing concentrations of inhibitor 2.3 were added, and the cells were incubated at 37° C. for various times. Photographs were taken using an Olympus Model DF 12-2 camera connected to a Nikon TMS-F microscope at 10× magnification, at the indicated time points. The extent of wound closure in the presence or absence of inhibitor was quantified by measuring the width of the wound with a ruler using an amplified PowerPoint figure.

Tumor cell invasion was carried out in 8-µm pore Transwell inserts (Becton Dickinson, Boston, Mass.) coated with 50 µg Matrigel per filter. HT1080 cells suspended in serum-free DMEM containing 0.1% bovine serum albumin (BSA) and various doses of inhibitor 2.3 (0.1-10 μM) or 1% DMSO (vehicle) were seeded (2×10⁵ cells/insert) on the Matrigel-coated inserts. The lower compartment was filled with DMEM containing 5% FBS. After an 18 h-incubation at 37° C. in a humidified atmosphere with 5% $CO_2$, the upper surface of the membrane in each insert was wiped off with a cotton swab to remove all of the non invading cells. The cells that migrated to the lower side of the Matrigel-coated filter were fixed and stained with Diff-Quik® (Dade Behring Inc., Newark, Del.), and counted under a microscope in three different fields. Each treatment was assayed in quadruplicate.

Chemosensitivity Assay—Cell viability after exposure of the cells to the inhibitors was assessed by 2-(4-iodophenyl)-3-(4-nitrophenyl)-5-(2,4-disulfophenyl)-2H-tetrazolium, monosodium salt (WST-1, Roche Diagnostics Gmbh, Mannheim, Germany) staining. Briefly, HT1080 cells (2×10⁴ cells/well) were seeded in 96-well culture plates in complete medium. After overnight culture, the medium was replaced with serum and phenol-free media containing 0.1% BSA and supplemented with or without inhibitor 2.3 (0-10 μM final concentrations). Control medium was supplemented with 1% DMSO. After 18 hours incubation, WST-1 (10 μL/well) was added and the difference in absorbance at 450 and 655 (reference filter) nm was measured using a Bio-Rad Benchmark microplate reader. Data were collected using the Microplate Manager software. The absorbance of blank wells containing control media but no cells (typically <5%) was subtracted. Each treatment was assayed in quadruplicate.

Results And Discussion:

Design and synthesis of MMP inhibitors—The computational model for binding of inhibitor 2.1 to the active site of M-2 is shown in FIG. 3B. The site for substitution at the para position of the terminal phenyl ring of the inhibitor is indicated by an arrow. Scheme 4 illustrates the synthetic route to oxiranes 2.2, 2.4 and 2.6, and thiiranes 2.3, 2.5 and 2.7.

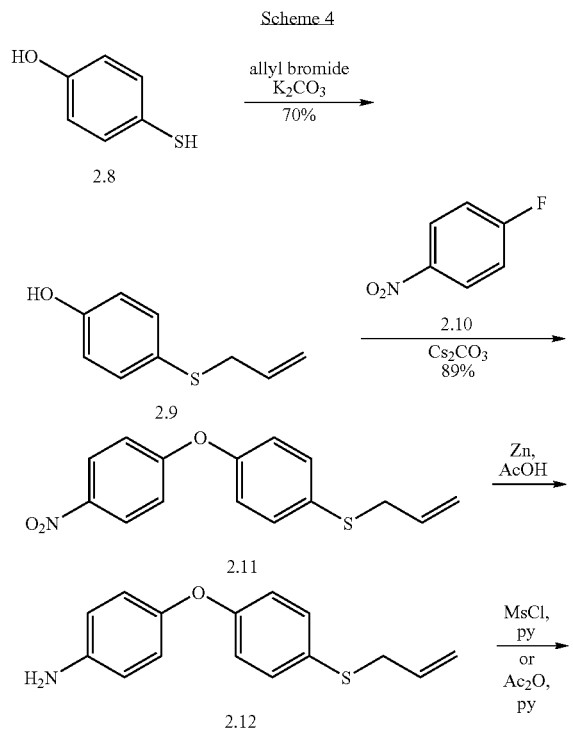

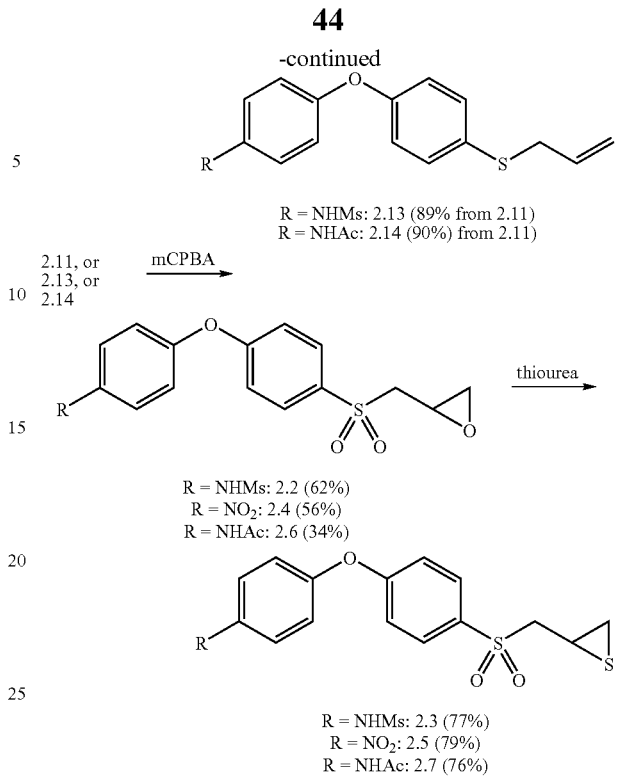

Chemoselective allylation of commercially available 4-hydroxythiophenol (2.8) provided phenol 2.9 (Goux et al. *Tetrahedron* 1994, 50, 10321-10330) in 70% yield, which was subsequently coupled with 1-fluoro-4-nitrobenzene (2.10) in the presence of cesium carbonate to afford the diphenyl ether 2.11 in 89% yield. The nitro group of 2.11 was reduced over elemental zinc and the resulting amine 2.12 was treated with methanesulfonyl chloride or acetic anhydride to give the corresponding amides 2.13 and 2.14, respectively, in high yields. Oxidation of 2.13, 2.11 and 2.14 to their corresponding oxiranes 2.2, 2.4 and 2.6 required excess of mCPBA (10-12 equiv.) and took long reaction time (9-10 days) due to the low reactivity of the olefin moieties; the isolated yields of the oxiranes were moderate (34-62%).

Finally, the conversion of compounds 2.2, 2.4 and 2.6 to the corresponding thiiranes 2.3, 2.5 and 2.7 was accomplished by the treatment with thiourea in good yields. Compounds 2.3 and 2.7 had improved solubility in aqueous solution compared to the prototypic inhibitor 2.1. Solubility was investigated in 50 mM HEPES (pH 7.5), 0.15 M NaCl, 5 mM $CaCl_2$, 0.01% Brij-35, 1% DMSO, which was the buffer that we used for all the kinetic experiments (see below). The maximal solubility for the samples were 2.1: 80 μM; 2.3: 340 μM; 2.5: 60 μM; 2.7: 540 μM.

Enzyme inhibition kinetics—The mechanism of action of this class of MMP inhibitors stipulates that the thiirane sulfur would coordinate with the active-site zinc ion (FIG. 2). Consistent with this expectation, the three synthetic thiiranes of this study (compounds 2.3, 2.5 and 2.7) are excellent inhibitors of gelatinases (and of MT1-MMP in the case of inhibitor 2.3) (Table 2), whereas the corresponding oxiranes (compounds 2.2, 2.4 and 2.6) are either poor inhibitors or not inhibitory at all toward all the tested MMPs (Table 3). For Table 2, the enzymes (0.5-1 nM) were added to a solution of the proper synthetic fluorogenic substrate and increasing concentrations of the inhibitor in buffer R. Substrate hydrolysis was monitored for up to 30 minutes. The kinetic parameters were evaluated as described above. For Table 2, the enzymes (0.5-1 nM) were incubated with increasing concentrations of inhibitor in buffer R. The remaining activity was measured with the appropriate synthetic fluorogenic substrate. The kinetic parameters for rapid, competitive inhibition were evaluated as described above.

TABLE 2

Kinetic parameters for MMP inhibition by compounds 2.3, 2.5, and 2.7

| Enzyme | $k_{on}$ $M^{-1}s^{-1}$ | $k_{off}$ $s^{-1}$ | $K_i$ µM |
|---|---|---|---|
| Compound 2.3 | | | |
| MMP-2 | $(2.1 \pm 0.5) \times 10^4$ | $(3.5 \pm 1.6) \times 10^{-4}$ | $0.016 \pm 0.09$ |
| MMP-9 | $(4.9 \pm 0.2) \times 10^3$ | $(9.0 \pm 2.0) \times 10^{-4}$ | $0.18 \pm 0.05$ |
| MMP-14 | $(6.9 \pm 0.8) \times 10^2$ | $(6.4 \pm 0.5) \times 10^{-4}$ | $0.9 \pm 0.1$ |
| MMP-7 | | | $295 \pm 10$ |
| MMP-3 | | | $3.6 \pm 0.2$ |
| MMP-1 | | | NI[a] up to 25 µM |
| Compound 2.5 | | | |
| MMP-2 | $(1.9 \pm 0.6) \times 10^3$ | $(1.3 \pm 0.2) \times 10^{-3}$ | $0.7 \pm 0.2$ |
| MMP-9 | | | $1.0 \pm 0.1$ |
| MMP-14 | | | $4.9 \pm 0.3$ |
| MMP-7 | | | $153 \pm 16$ |
| MMP-3 | | | $131 \pm 9$ |
| MMP-1 | | | $67 \pm 18$ |
| Compound 2.7 | | | |
| MMP-2 | $(1.2 \pm 0.3) \times 10^4$ | $(1.3 \pm 0.3) \times 10^{-3}$ | $0.11 \pm 0.04$ |
| MMP-9 | | | $0.13 \pm 0.01$ |
| MMP-14 | | | $0.68 \pm 0.05$ |
| MMP-7 | | | $39 \pm 3$ |
| MMP-3 | | | $12.2 \pm 0.9$ |
| MMP-1 | | | $5.4 \pm 0.4$ |

[a]NI: not inhibiting

TABLE 3

Kinetic parameters for MMP inhibition by compounds 2.2, 2.4, and 2.6

| Enzyme | $K_i$ µM |
|---|---|
| Compound 2.2 | |
| MMP-2 | $2.4 \pm 0.5$ |
| MMP-9 | NI[a] up to 26 µM |
| MMP-14 | NI up to 170 µM |
| MMP-7 | $379 \pm 29$ |
| MMP-3 | NI up to 170 µM |
| MMP-1 | $45 \pm 9$ |
| Compound 2.4 | |
| MMP-2 | $13 \pm 1$ |
| MMP-9 | $25 \pm 5$ |
| MMP-14 | $76 \pm 13$ |
| MMP-7 | $130 \pm 15$ |
| MMP-3 | NI up to 190 µM |
| MMP-1 | NI up to 298 µM |
| Compound 2.6 | |
| MMP-2 | $0.84 \pm 0.03$ |
| MMP-9 | $34 \pm 3$ |
| MMP-14 | NI up to 230 µM |
| MMP-7 | NI up to 184 µM |
| MMP-3 | NI up to 188 µM |
| MMP-1 | NI up to 154 µM |

[a]NI: not inhibiting

Figure 4:
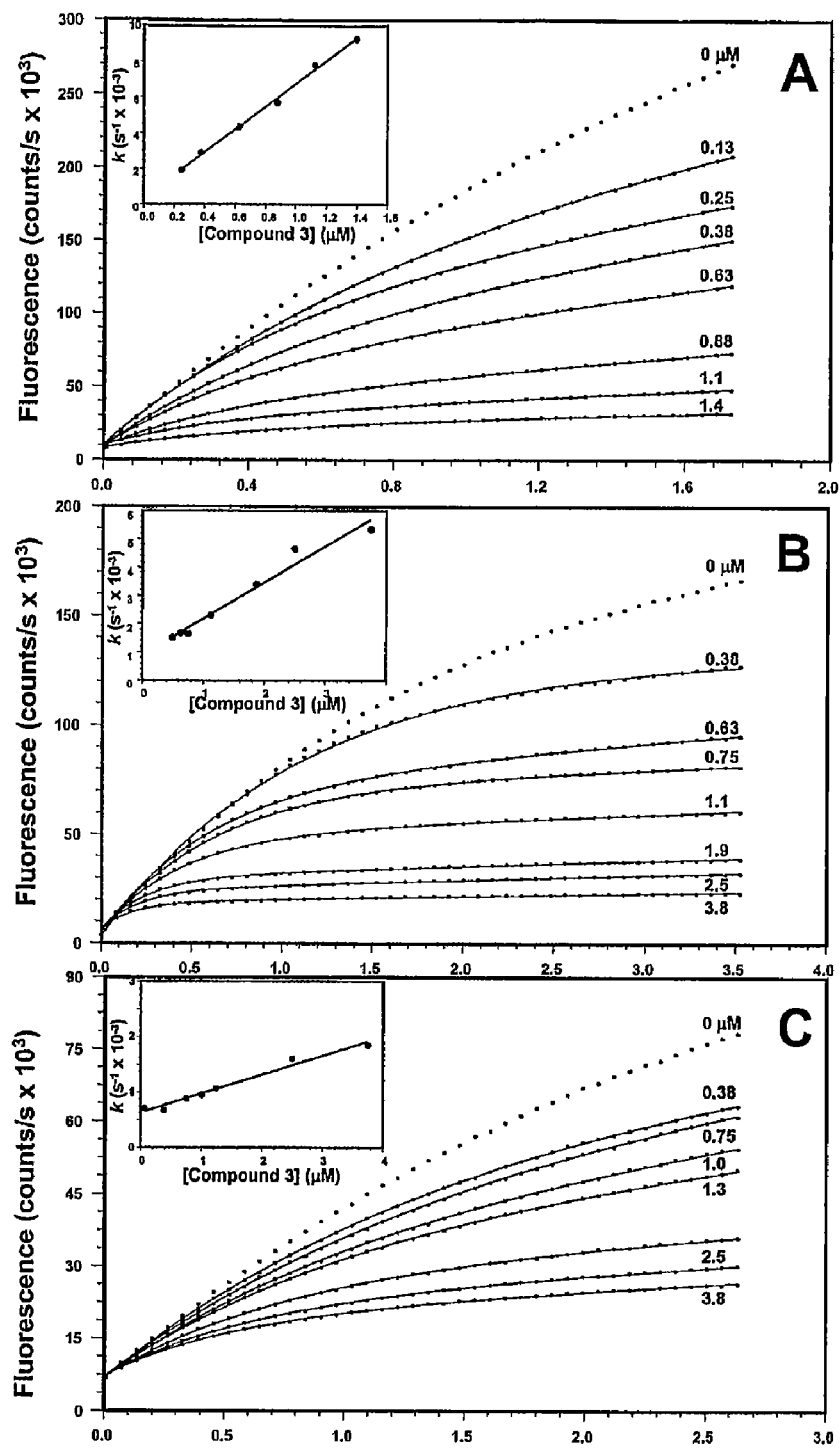
FIG. 4 illustrates slow-binding MMP inhibition by synthetic inhibitors of Example 2. Progress curves were obtained by monitoring the fluorescence of the synthetic substrate MOCAcPLGLA$_2$pr(Dnp)AR-NH$_2$ (7 μM) in solutions of buffer R containing 0.5-1 nM of MMP-2 (A), MMP-9 (B) and MMP-14$_{cat}$ (C) and inhibitor 2.3, as described under the Experimental Procedures section of Example 2. Inhibition of MMP-2 (0.5-1 nM) activity by compounds 2.5 (D) and 2.7 (E), under the same conditions. The lines represent nonlinear least-squares fits of the data to Equation 1, using the program Scientist. Insets, nonlinear least squares fits of the apparent rate constant k variation with inhibitor concentration to Equation 2, describing a one-step association mechanism.

In slow-binding inhibition, on binding of the inhibitor to the enzyme, the complex undergoes a requisite conformational change that is not readily predisposed for the reversal of the inhibition (Duggleby et al. (1982) *Biochemistry* 21, 3364-3370; Morrison et al. *Adv. Enzymol. Relat. Areas Mol. Biol.* 61, 201-301; and Szedlacsek and Duggleby (1995) *Methods Enzymol.* 249, 144-180). The slow-binding inhibitor shows a unique profile for the onset of inhibition that is discerned by non-linear progress curves. Slow-binding behavior was seen for inhibitor 2.3 (with MMP-2, MMP-9, and MMP-14), for inhibitor 2.5 (only with MMP-2), and for inhibitor 2.7 (only with MMP-2) (FIG. 4).

The second-order rate constants for the onset of slow-binding inhibition ($k_{on}$) are rapid ($10^2$ to $10^4$ $M^{-1}s^{-1}$) and the first-order rate constants for the reversal of the process from the non-covalent enzyme-inhibitor complexes ($k_{off}$) are slow ($10^{-4}$ to 10-35-1; e.g., the $t_{1/2}$ for reversal for inhibitor 2.3 with MMP-2 and MMP-9 are 34 minutes and 13 minutes, respectively). The dissociation constants for the non-covalent complexes ($K_i$) that result from slow-binding inhibition are computed from the ratios of $k_{off}/k_{on}$. Compounds 2.3, 2.5, and 2.7 are clearly selective for gelatinases, with 2.3 showing the slow-binding behavior with MMP-14 as well. The $K_i$ values of the slow-binding component for inhibition by 2.3 (16±9 nM, 180±50 nM, 0.9±0.1 µM for MMP-2, MMP-9 and MMP-14, respectively), 2.5 (700±200 nM for MMP-2), and 2.7 (110±40 nM for MMP-2) are listed in Table 2.

It is noteworthy that the inhibition profiles for inhibitors 2.1, 2.3, 2.5, and 2.7 as mechanism-based inhibitors are different from one another, despite the similar structural template for the class. Briefly, inhibitor 2.1 can inhibit both MMP-2 and MMP-9 (the gelatinases), inhibitor 2.3 inhibits the gelatinases plus MMP-14, and most interestingly, inhibitors 2.5 and 2.7 are mechanism-based inhibitors only for MMP-2. Furthermore, these are nanomolar inhibitors for their targeted enzymes and exhibit comparable values for the $k_{on}$ and $k_{off}$ parameters for the slow-binding components of their kinetics.

Covalent vs. non-covalent inhibition of MMPs—The thiirane class of MMP inhibitors was designed to be covalent enzyme inhibitors. On formation of the non-covalent enzyme-inhibitor complex, the ubiquitous active site glutamates of MMPs ($Glu^{404}$ for MMP-2, for example) were expected to be covalently modified by the inhibitor with the requisite thiirane ring opening (FIG. 2). The kinetics of inhibition indicate two components, a non-covalent stage (slow-binding) and a subsequent stage that may be attributed to the covalent modification of the active site glutamate, as will be outlined.

The covalent component of inhibition results in modification of the glutamate as an ester on its side chain carboxylate. The earlier X-ray absorption spectroscopy analysis with inhibitor 2.1 (Kleifeld et al. (2001) *J Biol Chem* 276, 17125-17131) had provided evidence for the covalent bond formation, in that on the onset of inhibition the method revealed the formation of a thiolate from the thiirane of the inhibitor (ring opening), coordinated to the active site zinc ion.

Whereas a slow-binding step need not necessarily be a prerequisite for covalent chemistry, both the mechanism-based process leading to covalent enzyme modification and the slow-binding behavior produce time-dependence for the loss of activity seen with these inhibitors (FIG. 4). Our experience with inhibitor 2.1 had shown that slow-binding led to covalent chemistry, with a longevity for the final inhibited species substantially exceeding the duration that would have been anticipated from four times the $t_{1/2}$ for recovery of activity from the slow-binding component of inhibition (in other words, four half-lives leading to an anticipated 94% recovered of activity due to the non-covalent component). This is the case with inhibitors 2.3, 2.5, and 2.7 as well.

Figure 5:
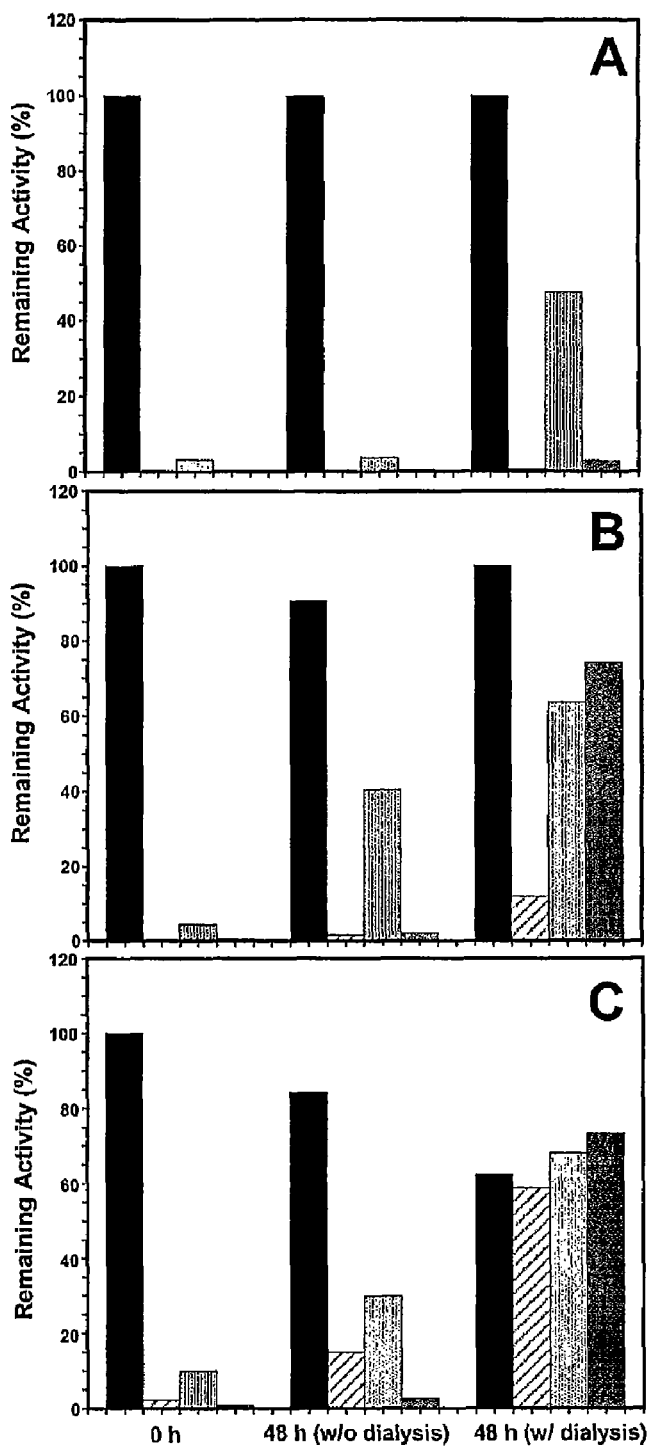
FIG. 5 illustrates equilibrium dialysis of MMP:inhibitor complexes. MMP-2 (A), MMP-9 (B) and MMP-14 (C) (10 nM each) were incubated in the absence (■) and presence of either compound 2.3 (▨), 2.5 (▨) and 2.7 (▨) (1 mM each), in buffer R, for 3 hours, at room temperature. The remaining MMP activity was monitored with MOCAcPLGLA$_2$pr(Dnp) AR-NH$_2$ (0 hours). Part of the reaction mixtures was subjected to extensive dialysis against buffer R, containing no dimethyl sulfoxide, as described under "Experimental Procedures" of Example 2, and the remaining solution was placed on a rotator. After 48 hours, the enzymatic activity in both the non-dialyzed (48 hours w/o dialysis) and dialyzed (48 hours w/dialysis) solutions was measured with the aforementioned fluorogenic substrate.

The slowest $t_{1/2}$ calculated for recovery of activity from the non-covalent slow-binding species for the best inhibition (compound 2.3 with MMP-2) is 34 minutes. Yet, a mere 1% of activity recovery was seen for MMP-2 inhibited by inhibitor 2.3 after 48 hours of dialysis. Four half-lives for recovery from inhibition (94% anticipated recovered activity) with this inhibitor and MMP-2 should be achieved in just under 2.5 hours (136 minutes), were it merely the slow-binding event that accounted for MMP-2 inhibition. This is clearly not the case and the inhibited enzyme is more stable than the $k_{off}$ (from which $t_{1/2}$ is evaluated) indicates. The results of dialyses for inhibitors 2.3, 2.5, and 2.7 are given in FIG. 5.

Having documented above that mere slow-binding behavior cannot be responsible for the observed complete inhibition, an explanation was sought as to why any recovery of activity should be seen, if covalent chemistry is involved. The answer is that stability of covalent bonds is relative. Esters are among the least stable covalent bonds in aqueous solution (Westheimer, F. H. (1987) *Science* 235, 1173-1178). This bond would undergo hydrolysis, resulting in recovery of activity. The process accelerates when there is a more significant exposure of the ester bond to water, conditions that can arise when the protein is denatured.

Matrix-assisted laser desorption time-of-flight mass spectrometry (MALDI-TOF MS) analysis, performed on an Applied Biosystems Voyager-DE STR (Framingham, Mass.) at the Harvard Microchemistry and Proteomics Analysis Facility (Cambridge, Mass.), was attempted on samples containing MMP-2 (10 µM) in the presence and absence of inhibitor 2.3 to detect a shift in molecular mass consistent with a complex of active MMP-2 (~62 kDa) with the inhibitor. However, after several attempts with different conditions we failed to detect a 400 Da addition in molecular mass to the 62-kDa peak. The difficulty is that at this high end of mass detection the signals are broadened and the identification of the small incremental increase due to the mass of the inhibitor was not possible within the resolution of the instrument.

Effect of Gelatinase Inhibitors on pro-MMP-2 Activation by MT1-MMP—MT1-MMP has been identified as the physiological activator of pro-MMP-2 (Strongin et al. (1993) *J Biol Chem* 268, 14033-14039). This reaction is regulated at multiple levels and its rate is significantly enhanced by TOIP-2, which, by binding active MT1-MMP, acts as a "receptor" for pro-MMP-2 on the cell surface (Westheimer, F. H. (1987) *Science* 235, 1173-1178). The binding of pro-MMP-2 to the MT1-MMP/TIMP-2 complex, facilitates the first pro-MMP-2 cleavage by a neighboring TIMP-2-free MT1-MMP molecule (Strongin et al. (1995) *J Biol Chem* 270, 5331-5338). Pro-MMP-2 activation requires a second autolytic cleavage (Will et al. (1996) *J Biol Chem* 271, 17119-17123), leading to full activation.

It has been shown previously that broad-spectrum synthetic MMP inhibitors, e.g. marimastat, enhance pro-MMP-2 activation by MT1-MMP in the presence of TIMP-2 (Toth et al. (2000) *J Biol Chem* 275, 41415-41423), a process that appears to involve stabilization of mature MT1-MMP at the cell surface by the MMP inhibitor. This enhancing effect on pro-MMP-2 activation was not observed when the cells were exposed to inhibitor 2.1, which exhibits lower affinity towards MT1-MMP, a feature of its selectivity for inhibition of gelatinases.

Figure 6:
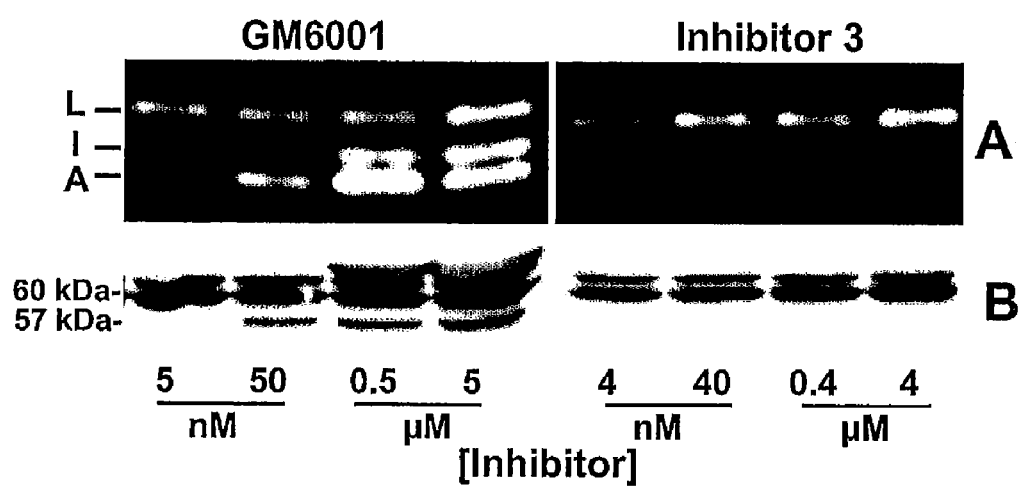
FIG. 6 illustrates that GM6001 (hydroxamate inhibitor), but not inhibitor 2.3, enhances MT1-MMP-dependent pro-MMP-2 activation by BS-C-1 cells. BS-C-1 cells, co-infected to express MT1-MMP, as described under the Experimental Procedures of Example 2, were incubated for 16 hours with serum-free DMEM medium containing the indicated inhibitor concentrations. After rinsing, the cells were incubated for 5 hours with serum-free DMEM supplemented with recombinant pro-MMP-2 (10 nM). (A) The media were collected and analyzed by gelatin zymography. L, I and A refer to the latent, intermediate and active forms of MMP-2, respectively. (B) The cells were lysed and the lysates were subjected to immunoblot analysis using the anti-MT1-MMP polyclonal antibody 815. The 60- and 57-kDa forms represent pro- and active MT1-MMP, respectively.

Therefore, it was proposed that non-specific targeting of MT1-MMP by broad-spectrum MMP inhibitors might, under certain conditions, elicit a counterproductive effect by enhancing the activity of the MT1-MMP/gelatinase A axis (Bernardo, M. M., Brown, S., Li, Z. H., Fridman, R., and Mobashery, S. (2002) *J Biol Chem* 277, 11201-11207). Because inhibitor 2.3 is also selective for the gelatinases, it was postulated that it might behave like inhibitor 2.1 in a cellular system of pro-MMP-2 activation by MT1-MMP in the presence of TIMP-2. To this end, BS-C-1 cells, which express low levels of endogenous TIMP-2, were infected to express MT1-MMP, and incubated with pro-MMP-2 in the presence of either GM6001, a broad-spectrum MMP inhibitor or inhibitor 2.3, as described by Toth and co-workers ((2000) *J Biol Chem* 275, 41415-41423). Pro-MMP-2 activation was followed by gelatin zymography. As shown in FIG. 6a, exposure of the MT1-MMP-expressing cells to as little as 40 nM GM6001, induced pro-MMP-2 activation, as determined by the appearance of the active form. Higher inhibitor concentrations further enhanced pro-MMP-2 activation, under these conditions.

Of note, this enhancing effect of broad-spectrum MMP inhibitors such as GM6001 requires the endogenous TIMP-2, as have shown previously shown by Toth and co-workers ((2000) *J Biol Chem* 275, 41415-41423). Consistently, GM6001 caused a dose-dependent accumulation of active MT1-MMP (57 kDa) (FIG. 6B). In contrast, when the cells were incubated with inhibitor 2.3 (up to 4 µM), pro-MMP-2 activation was not observed. Also, the accumulation of active MT1-MMP was not observed with inhibitor 2.3, consistent with its reduced affinity for this protease when compared to MMP-2 (Table 2).

Although inhibitor 2.3 is also a mechanism-based inhibitor for MT1-MMP, its lower affinity relative to MMP-2 is likely to preclude this inhibitor to influence pro-MMP-2 activation under these conditions. It is also possible that covalent inhibition of MT1-MMP, as opposed to a reversible inhibition, alters the availability of the active site of MT1-MMP for TIMP-2 binding, a prerequisite for pro-MMP-2 activation ((2000) *J Biol Chem* 275, 41415-41423). Although more studies are required, these results suggest that the concept behind inhibitor 2.3 is a promising framework from which to further develop more effective and selective MT1-MMP inhibitors, a key protease in tumor cell invasion. Nevertheless, these studies further demonstrate the selectivity of inhibitor 2.3 in a live cellular system and lend credit to the hypothesis that selectivity, rather than affinity, may be key to the successful therapeutic application of synthetic MMP inhibitors.

Figure 7:
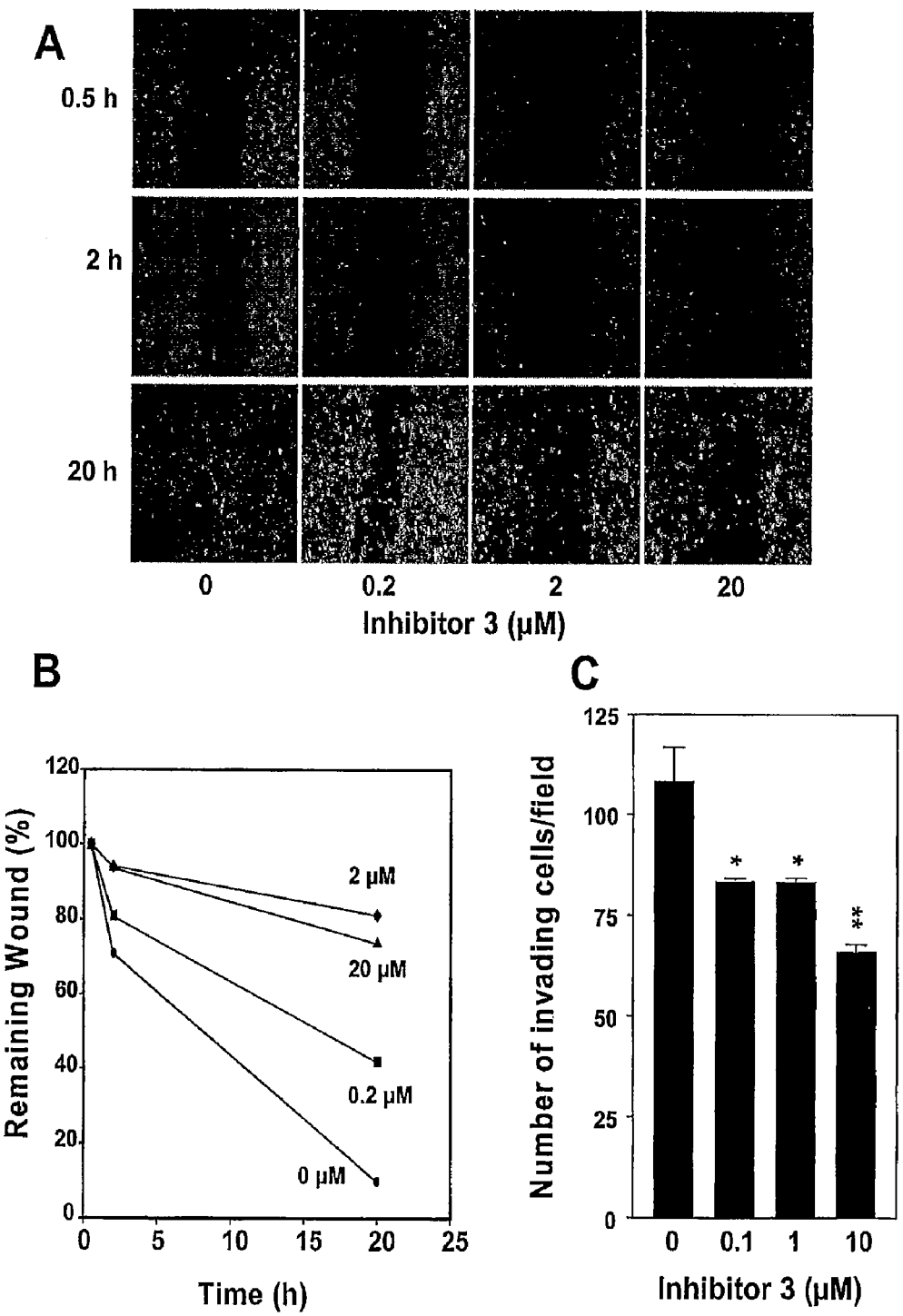
FIG. 7 illustrates inhibition of HT1080 cell motility and invasion by inhibitor 2.3. A-B: Confluent cultures of HT1080 cells in 6-well plates were treated with mitomycin C (25 μg/ml) in serum-free DMEM media for 30 minutes. Scratch wounds were made on the monolayers and the wounded cultures were then incubated with serum-free DMEM supplemented without or with various amounts of inhibitor 2.3 (0-20 μM) for up to 20 hours. At each time period, the cultures were photographed (A) and the width of the scratch wound was measured as described under the Experimental Procedures section of Example 2. (C): HT1080 cells were seeded in 8-μm pore Transwell filters coated with Matrigel (50 μg/filter) in the presence or absence of inhibitor 2.3 (0.1-10 μM). The number of cells that invaded to the lower side of the filter was counted in three representative fields. Each value represents the mean±SE of four independent determinations. * $P<0.05$, and * $P<0.001$ when tested against the control using Tukey-Kramer Multiple Comparisons Test (P=0.004 by ANOVA).
Figure 8:
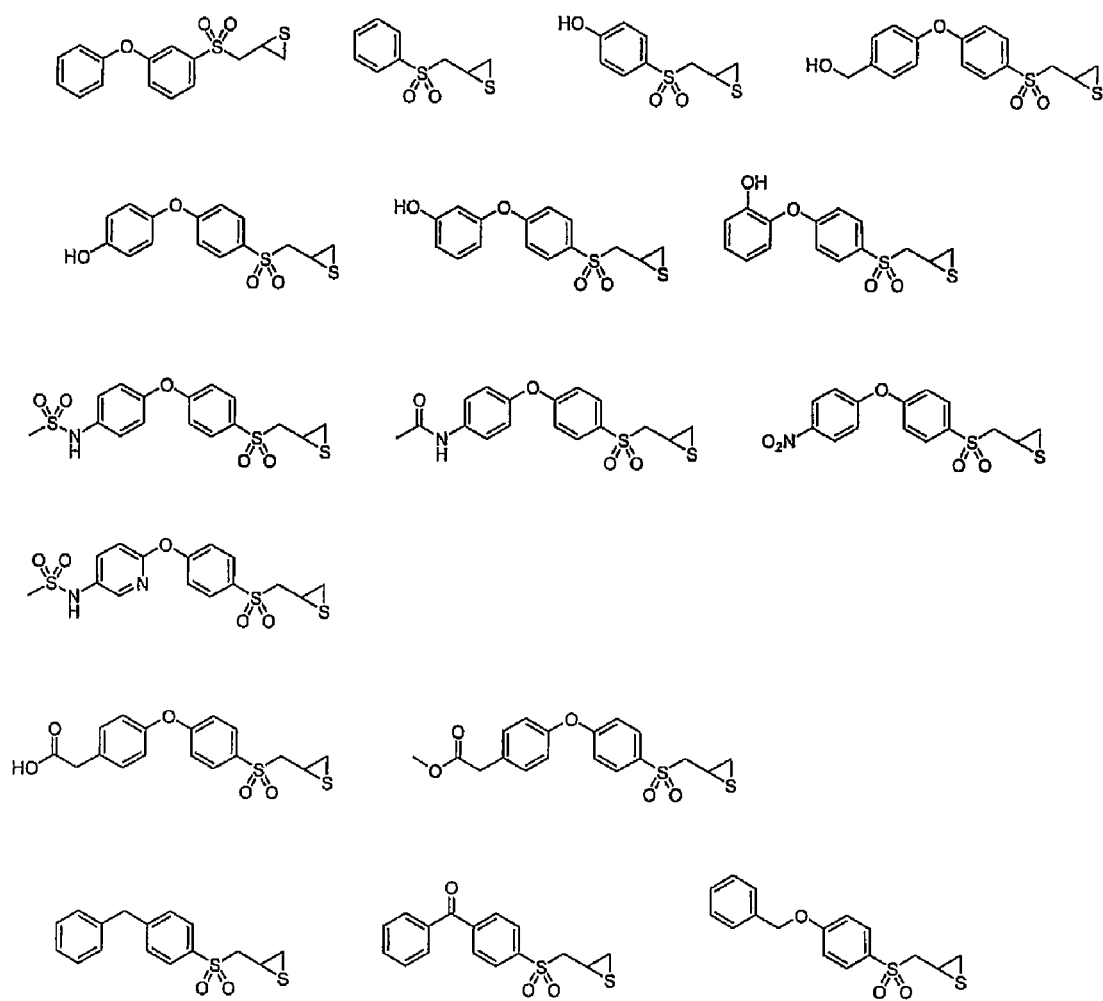
FIG. 8 illustrates specific compounds according to various embodiments of the invention. These compounds have been prepared according to the methods described herein.

Inhibitor 2.3 inhibits HT1080 cell migration and invasion—It is well established that tumor cell migration and invasion depend on gelatinase activity. Therefore, we wished to evaluate the effect of inhibitor 2.3, which is selective for the gelatinases, on the migration and invasion of HT1080 cells, as described above. Cell migration was monitored under conditions of pro-MMP-2 activation, which was achieved by ConA treatment, and inhibition of cell proliferation. As shown in FIGS. 7A and B, exposure of HT1080 cells to various doses (0-20 µM) of inhibitor 2.3 significantly inhibited (80% at 2 µM) their migration in a scratch wound assay when compared to untreated cells. Likewise, the ability of HT1080 cells to invade Matrigel-coated filters was significantly reduced by inhibitor 2.3 and as little as 100 nM of inhibitor caused >25% inhibition of HT1080 cell invasion (FIG. 7C).

These effects of inhibitor 2.3 could not be ascribed to cytotoxicity as no evidence of cell toxicity was detected when HT1080 cells were exposed to inhibitor 2.3 up to concentrations of 10 µM, as determined using the WST-1 chemosensitivity assay (data not shown). Given the high selectivity exhibited by this compound towards MMP-2 relative to other MMPs (Table 2), the slower migration in the presence of 200 nM of inhibitor 2.3, a concentration too low to inhibit other MMs including MT1-MMP, suggests that the observed effect was most likely due to MMP-2 inhibition. These results further demonstrate the ability of inhibitor 2.3 to act as a selective gelatinase inhibitor in cellular systems and to alter MMP-dependent processes. The new characteristics of inhibitor 2.3 and its high selectivity make this inhibitor an excellent candidate for future in vivo testing in relevant human disease models in mice.

The thiirane class of mechanism-based inhibitors was conceived, designed and prepared by us for the first time in our pursuit of selectivity in inhibition of MMPs of importance to several disease processes. We have revealed in the present report that inhibitor 2.3 targets MMP-2, -9, and -14, whereas inhibitors 2.5 and 2.7 are inhibitory only toward MMP-2. The activities for these new inhibitors provide a unique opportunity in investigations of the roles of these MMPs in various disease processes.

Example 3

Synthetic Approach to Aromatic Sulfonylmethylthiiranes

A general strategy for the synthesis of aromatic sulfonylmethylthiiranes and their derivatives is described below (Scheme 5-9). The compounds explicitly depicted in the schemes of Example 3 have been synthesized and their compound data is provided in the Experimental Section following Scheme 29.

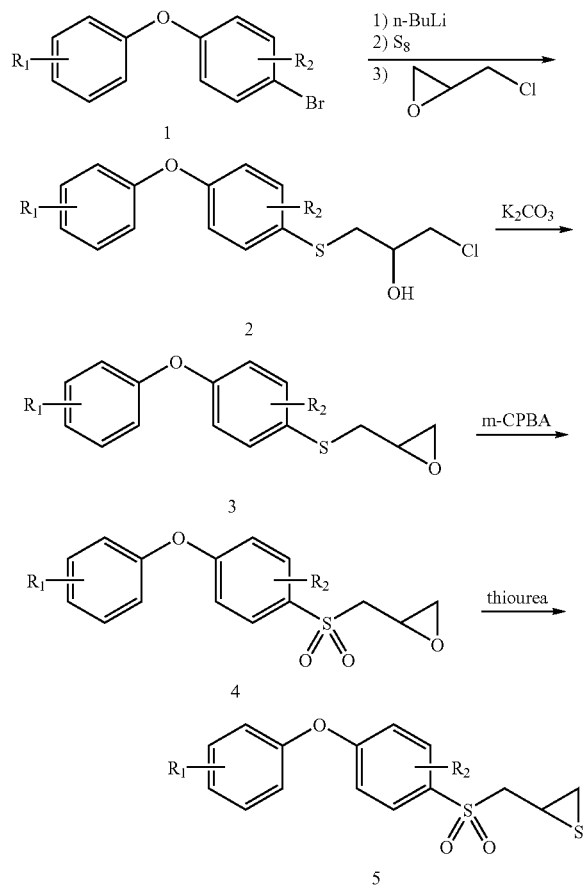

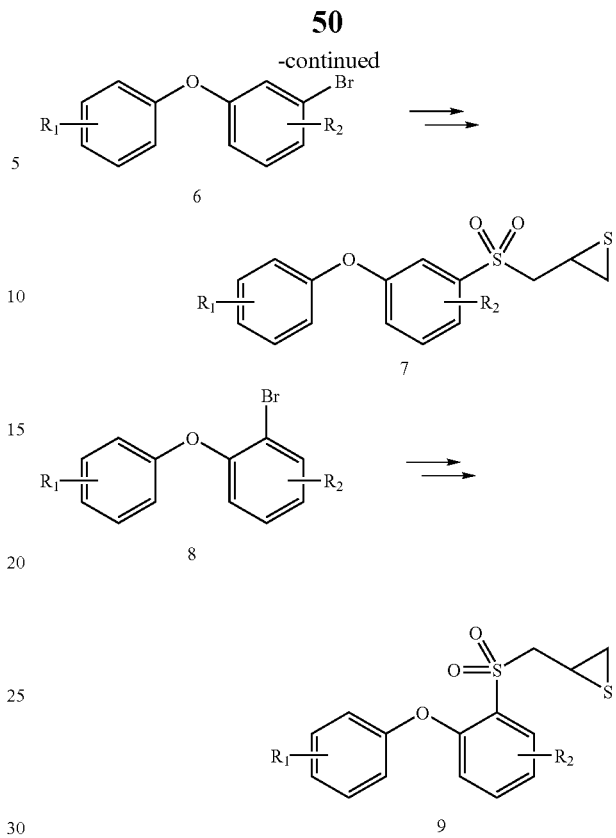

A suitable synthetic sequence to afford phenoxyphenylsulfonylmethyl-thiirane 5 is outlined in Scheme 5 (see Lee et al. Org. Lett. 2005, 7, 4463-4465; Lim, Brown, and Mobashery, J. Org. Chem. 2004, 69, 3572-3573). Synthesis commenced with a commercially available bromide, which was lithiated with n-BuLi, was then converted to the thiolate. The thiolate was alkylated with epichlorohydrin to result in compound 2. The hydrochloride moiety in compound 2 was transformed to an epoxide ring, followed by sulfide oxidation by use of m-CPBA. The resulting epoxide 4 was converted to thiirane 5 using thiourea. When ortho- or meta-bromide are used instead of para bromide 1, corresponding sulfonylmethylthiiranes 7 or 9 can be obtained by the same sequence illustrated in Scheme 5.

The thiolate, which was generated by treatment of n-BuLi and sulfur, is a very useful intermediate because it can be reacted with other electrophiles, such as allylbromide and acetyl chloride, yielding compounds 10 and 11 (see Schemes 6 and 7), which can be ultimately converted to epoxide 4, a precursor of thiirane 5 (Scheme 6). Allylthio-4-phenoxybenzene derivative 10 can be converted directly to sulfonylmethyloxirane 4 by m-CPBA. While this method cannot be applied in some cases, dihydroxylation (J. Am. Chem. Soc. 1997, 119, 311-325) serves as an alternative route to sulfonylmethyloxirane 4. Diols 12 and 13 can be converted to the epoxide either via tosylation (Heterocycles 1990, 31, 1555-1562) or Mitsunobu reaction (Synthesis 1983, 116-117). The sulfide can be oxidized to the sulfone before or after formation of the epoxide. The second alkylation product thioacetate 11 can directly give 3 by treatment with epichlorohydrin. When allyl bromide or glycidol are reacted with compound 11, compounds 10 and 12 can be obtained.

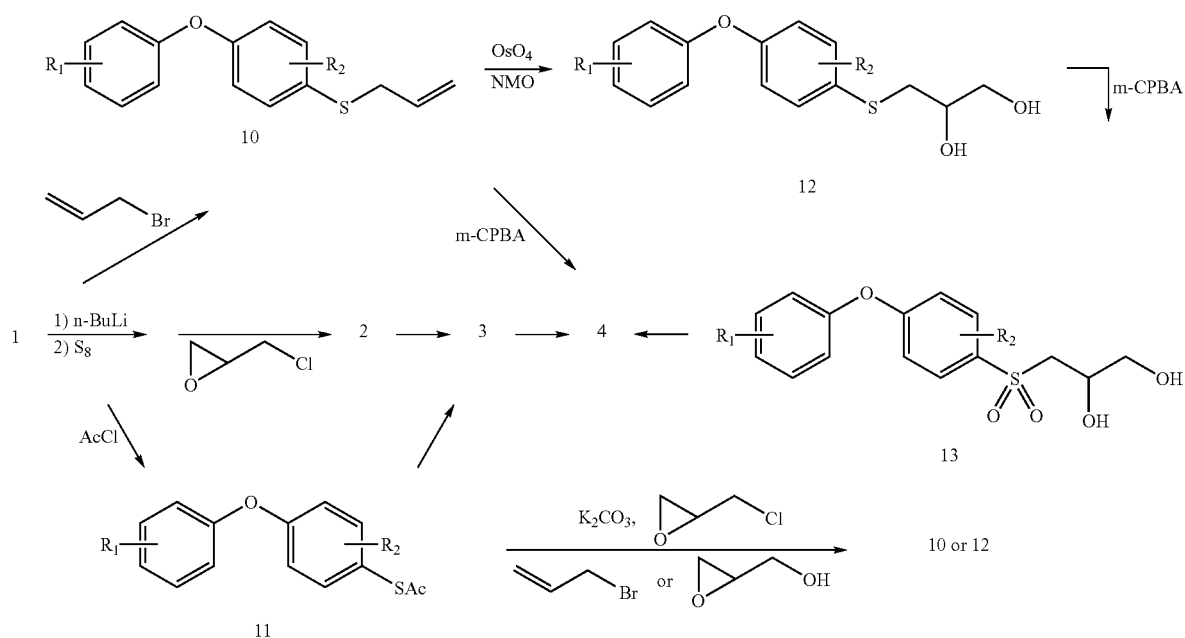

Scheme 6.

Aromatic amines or nitro compounds can be used to prepare compound 11 by the route in Scheme 7. Nitro compound 13 was reduced in the presence of Pd/C and $H_2$, or $SnCl_2$ or Zn in the presence of AcOH, to provide amine 14. Aromatic amine 14 was then diazotized using isoamyl nitrite and reacted with potassium thioacetate to yield aromatic thioacetate 11 (*Synthesis* 2003, 1225-1230). The resulting thioacetate 11 was then converted to compound 5, by the route described in Scheme 6.

Scheme 7.

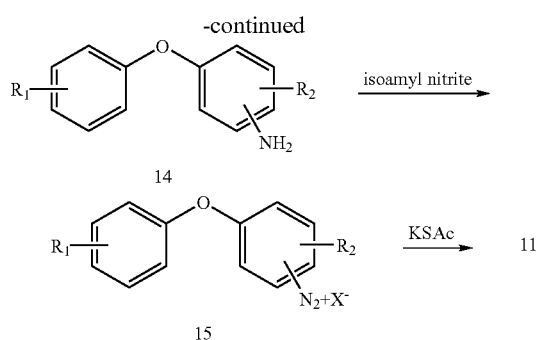

When aromatic bromide or amine are not commercially available, phenolic ethers can be prepares by several methods, as illustrated in Scheme 8.

Scheme 8.

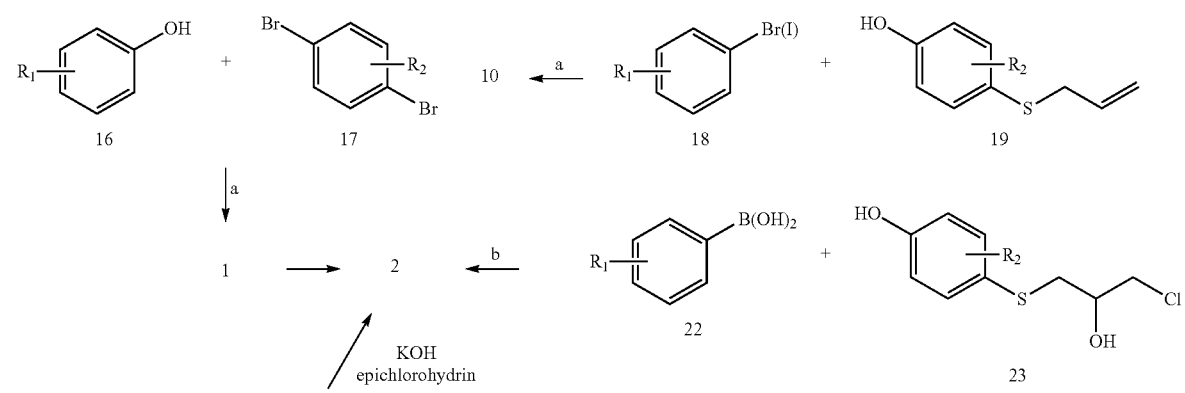

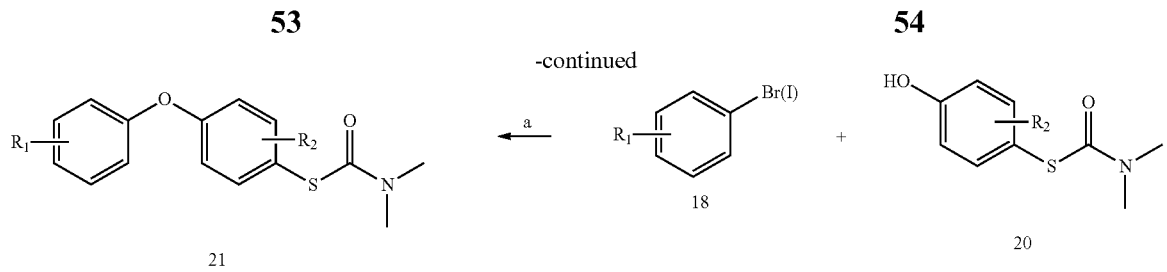

a. CuI (I), N,N-dimethylglycine HCl salt, Cs₂CO₃;
b. Cu(OAc)₂, Et₃N, 4 Å molecular seives Phenolic ethers can be constructed by copper catalyzed reactions. One method is by Ullmann condensation between aromatic halides and phenol. Another method is by using aromatic boronic acid and phenol.

Phenoxyphenyl bromide was constructed by a N,N-dimethylglycine promoted Ullmann coupling reaction (*Org. Lett.* 2003, 5, 3799-3802) between phenol 16 and dibromobenzene 17 in the presence of copper (I) iodide. When substituted thiophenols are used, we can make thiol incorporated phenol ether, which obviates the step to introduce sulfur atom to the molecule. When allylthiophenol 19 is reacted with aromatic halide 18, compound 10 can be made. When dimethyl-thiocarbamic acid S-(4-phenoxyphenyl) ester 20 is reacted with aromatic halide 18, compound 21 can be formed, which was then hydrolyzed to give free thiol under basic condition and then alkylated with epichlorohydrin in the presence of potassium carbonate.

Phenoxyphenyl ring can be formed by the reaction of aromatic boronic acid 22, which was reacted with phenol 23 in the presence of copper acetate. Copper-mediated arylation of phenol using boronic acid was previously reported by Chan and Evans (*Tetrahedron Lett.* 1998, 39, 2933-2936; and *Tetrahedron Lett.* 1998, 39, 2937-2940, respectively).

Some activated halides such as compounds 24-26 do not need copper catalyst. Compounds 24-26 were smoothly transformed to phenol ether in the presence of base such as cesium carbonate, potassium carbonate or sodium hydroxide (Scheme 9).

Scheme 9.

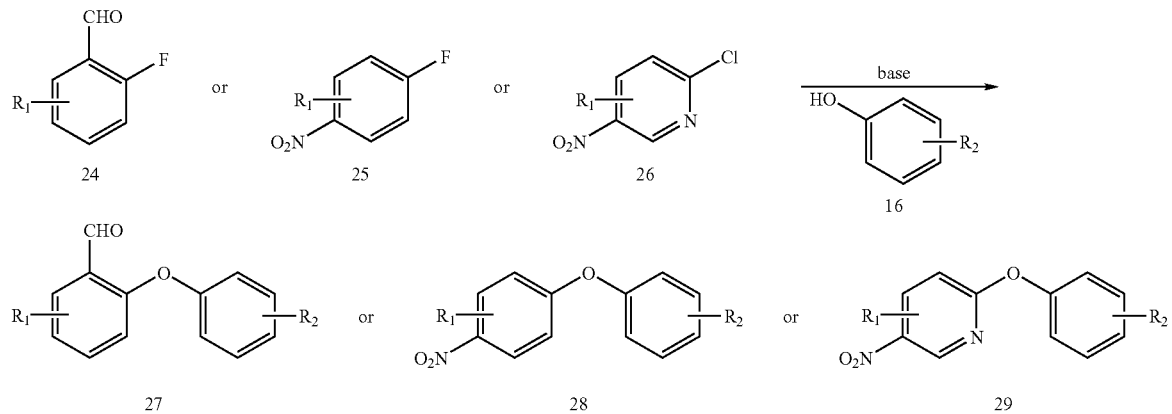

Compounds with functional groups such as amino (30) and hydroxyl (33) groups are useful because they can easily react with many different electrophiles, such as alkylbromides, acid chlorides, and sulfonyl chlorides (Scheme 10). Carboxylic acid 36 is also useful in this sense for its reactivity with alcohols or amines to afford esters 37 or amide compounds 38.

Scheme 10.

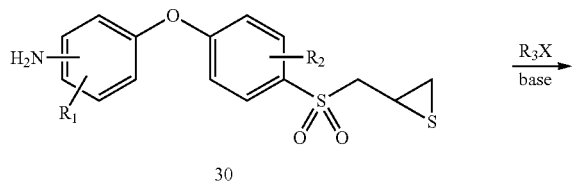

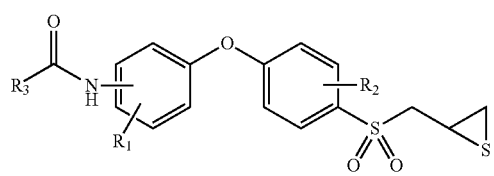

31

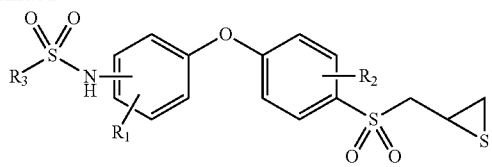

32

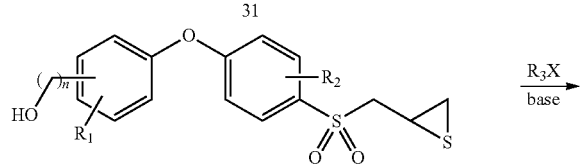

33

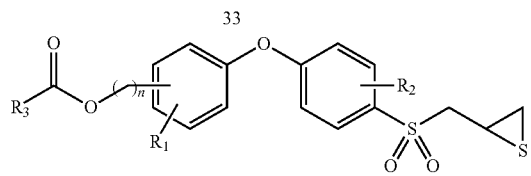

34

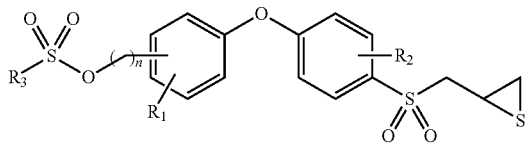

35

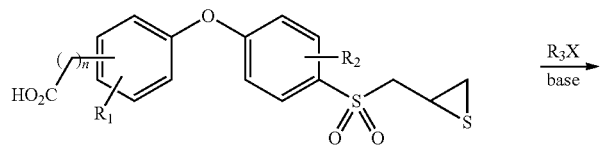

36

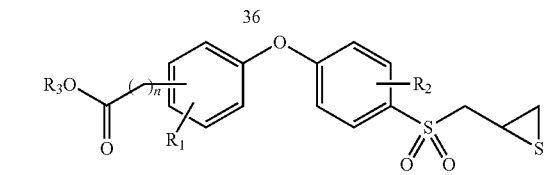

37

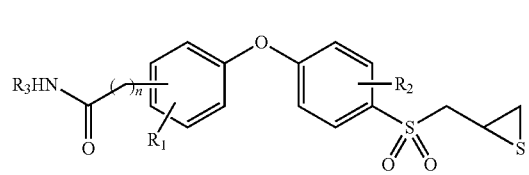

38 p-Aminophenylphenoxy derivatives were synthesized according to Scheme 11. 4-amino group was introduced by use of nitrobenzene fluoride 39. This activated substrate was reacted with allylthiophenol 19 in the presence of cesium carbonate to yield 1-allylthio-4-(4-nitrophenyl)benzene 40, which was then reduced to amine in the presence of zinc. Compound 42 was reacted with several electrophiles, followed by m-CPBA oxidation and thiirane formation reaction to afford compound 42.

Scheme 11.

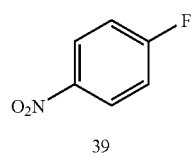

39

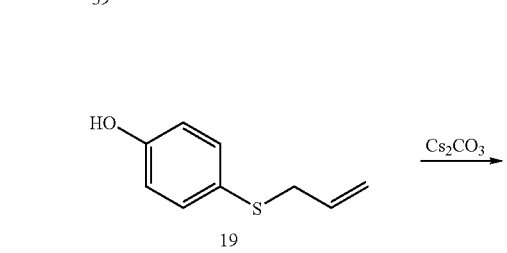

19

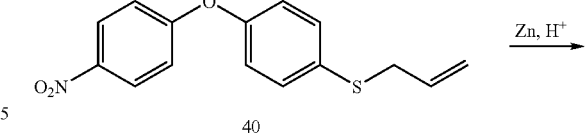

40

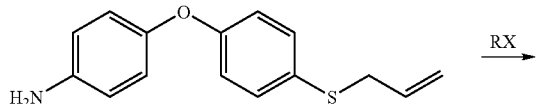

41

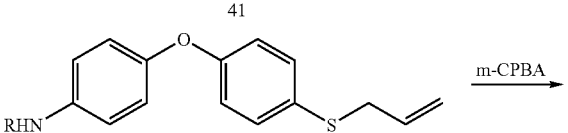

42

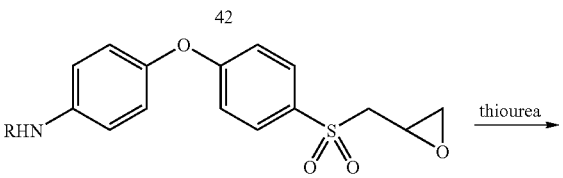

43

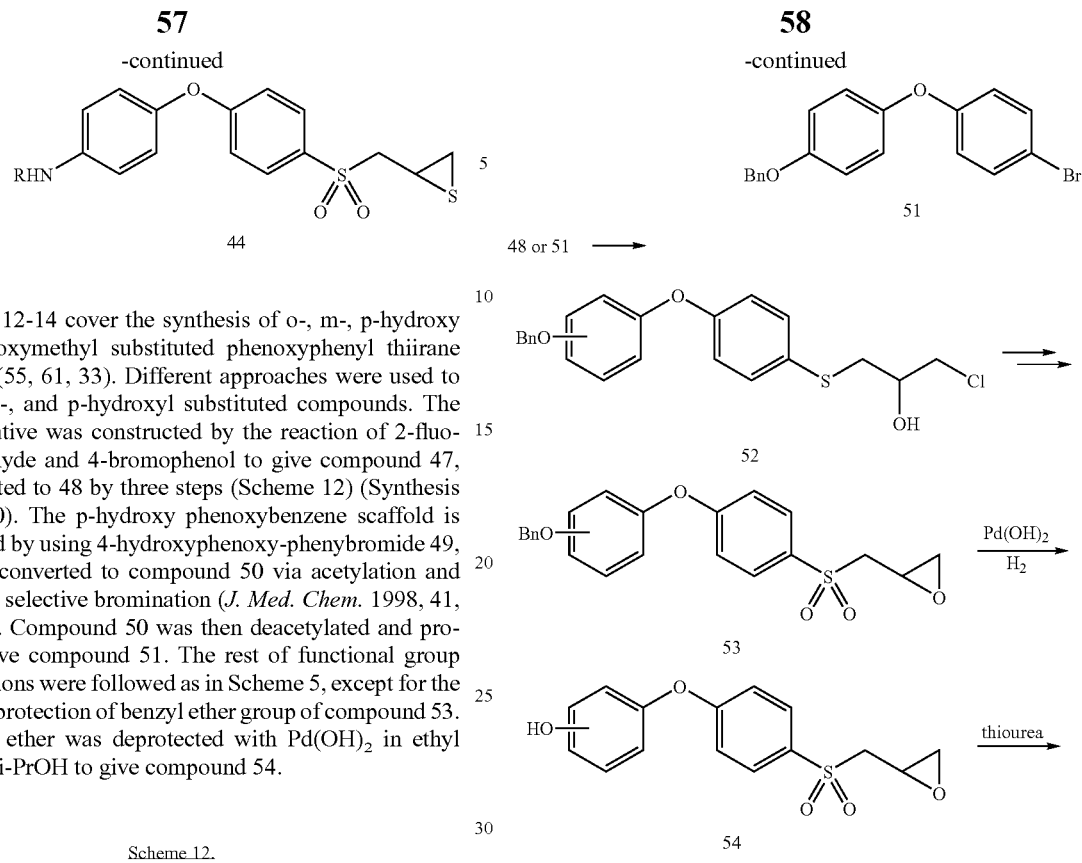

Schemes 12-14 cover the synthesis of o-, m-, p-hydroxy and p-hydroxymethyl substituted phenoxyphenyl thiirane derivatives (55, 61, 33). Different approaches were used to make o-, m-, and p-hydroxyl substituted compounds. The ortho derivative was constructed by the reaction of 2-fluorobenzaldehyde and 4-bromophenol to give compound 47, then converted to 48 by three steps (Scheme 12) (Synthesis 1995, 28-30). The p-hydroxy phenoxybenzene scaffold is incorporated by using 4-hydroxyphenoxy-phenybromide 49, which was converted to compound 50 via acetylation and followed by selective bromination (*J. Med. Chem.* 1998, 41, 1540-1554). Compound 50 was then deacetylated and protected to give compound 51. The rest of functional group transformations were followed as in Scheme 5, except for the selective deprotection of benzyl ether group of compound 53. The benzyl ether was deprotected with Pd(OH)$_2$ in ethyl acetate and i-PrOH to give compound 54.

Meta Substituted scaffold was constructed by Ullmann condensation between 3-benzyloxyiodobenzene and compound 20 to afford compound 57 (Scheme 13) (see *Org. Lett.* 2003, 5, 3799-3802). Compound 57 was then hydrolyzed to give free thiol 58 and then alkylated with epichlorohydrin in the presence of potassium carbonate. Functional group transformation from compound 58 to compound 61 was followed in Scheme 6.

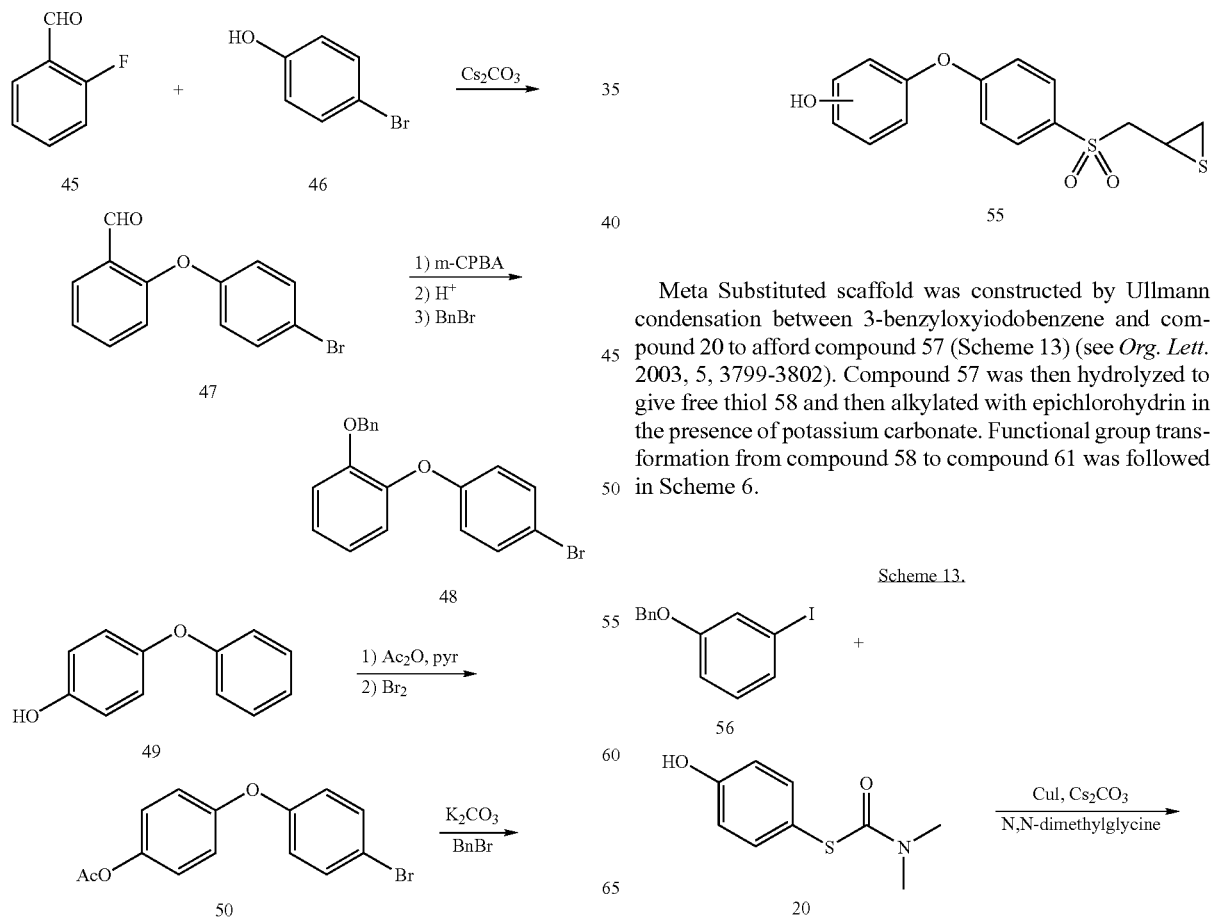

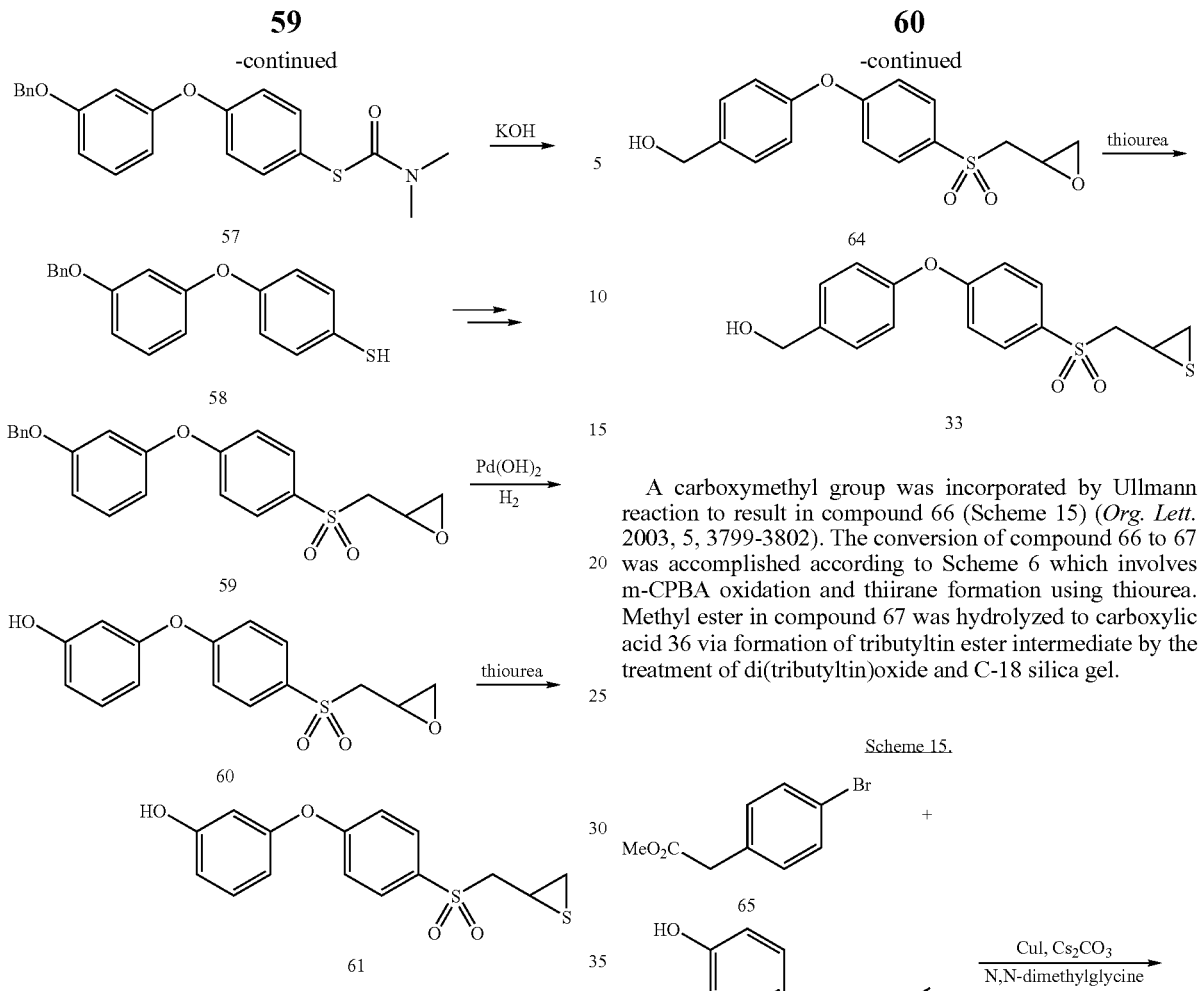

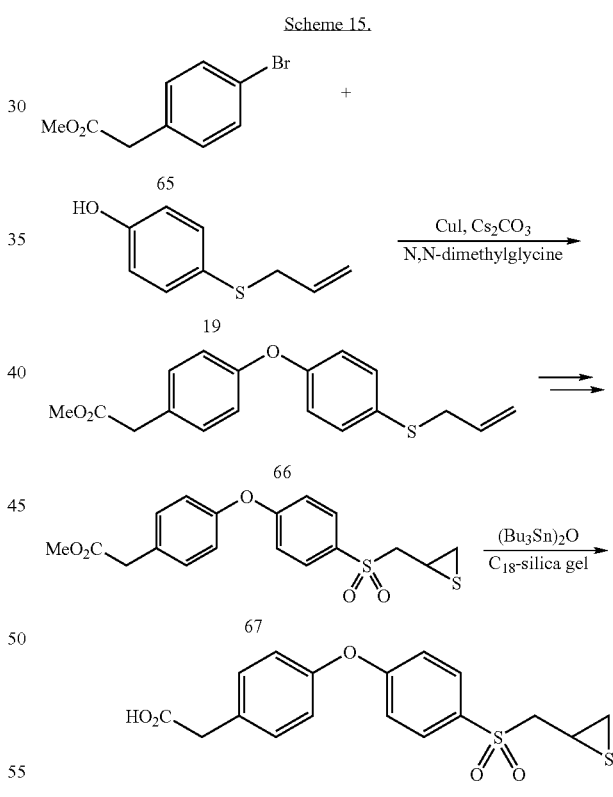

A carboxymethyl group was incorporated by Ullmann reaction to result in compound 66 (Scheme 15) (*Org. Lett.* 2003, 5, 3799-3802). The conversion of compound 66 to 67 was accomplished according to Scheme 6 which involves m-CPBA oxidation and thiirane formation using thiourea. Methyl ester in compound 67 was hydrolyzed to carboxylic acid 36 via formation of tributyltin ester intermediate by the treatment of di(tributyltin)oxide and C-18 silica gel.

Hydroxymethyl group was introduced by Suzuki type reaction between hydroxyphenyl boronic acid 62 and compound 19 (Scheme 14) (*Tetrahedron Lett.* 1998, 39, 2933-2936; *Tetrahedron Lett.* 1998, 39, 2937-2940). The resulting compound 63 was converted to compound 33 by the same route in Scheme 5.

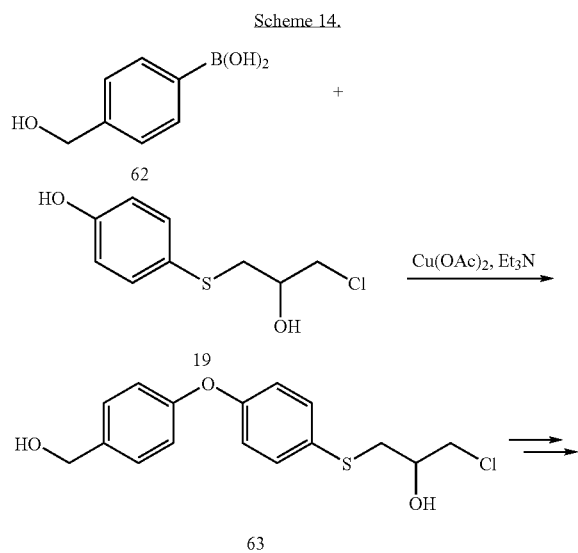

The possibility of introducing different bridges between two benzene rings instead of an oxygen bridge was investigated (Scheme 16). For these compounds, aromatic amines 68, 71, and 74 served as the initial starting materials, which were diazotized and then converted to the corresponding thioesters (69, 72, 75) (see *Synthesis* 1998, 1171-1175 and *Synthesis* 2003, 1225-1230). The remainder of the synthetic route from the thioacetate to sulfonylmethylthiirane was followed as in Scheme 6.

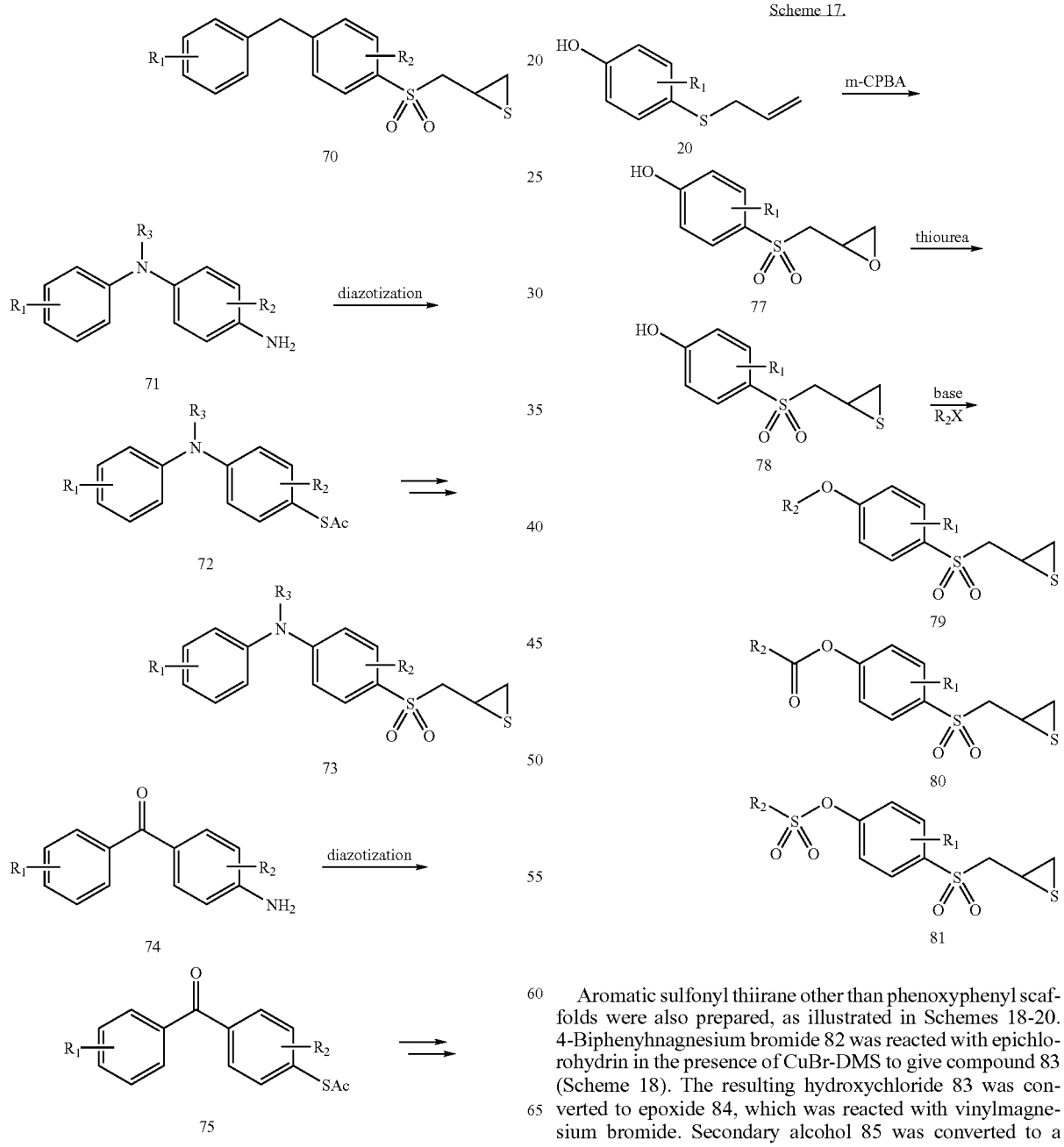

When 4-thiiranylmethanesulfonylphenol 78 was reacted with alkylhalides, acid chlorides, or sulfonyl chlorides, different bridged molecules such as compounds 79-81 were obtained (Scheme 17).

Aromatic sulfonyl thiirane other than phenoxyphenyl scaffolds were also prepared, as illustrated in Schemes 18-20. 4-Biphenyhnagnesium bromide 82 was reacted with epichlorohydrin in the presence of CuBr-DMS to give compound 83 (Scheme 18). The resulting hydroxychloride 83 was converted to epoxide 84, which was reacted with vinylmagnesium bromide. Secondary alcohol 85 was converted to a mesylate. The mesylate was then displaced placed by thioacetate, which was hydrolyzed and alkylated to afford thiol ether 87. The conversion of the alkene moiety of 87 to thiirane 88 was same as outlined in Scheme 6, which involves oxidation and thiirane ring formation.

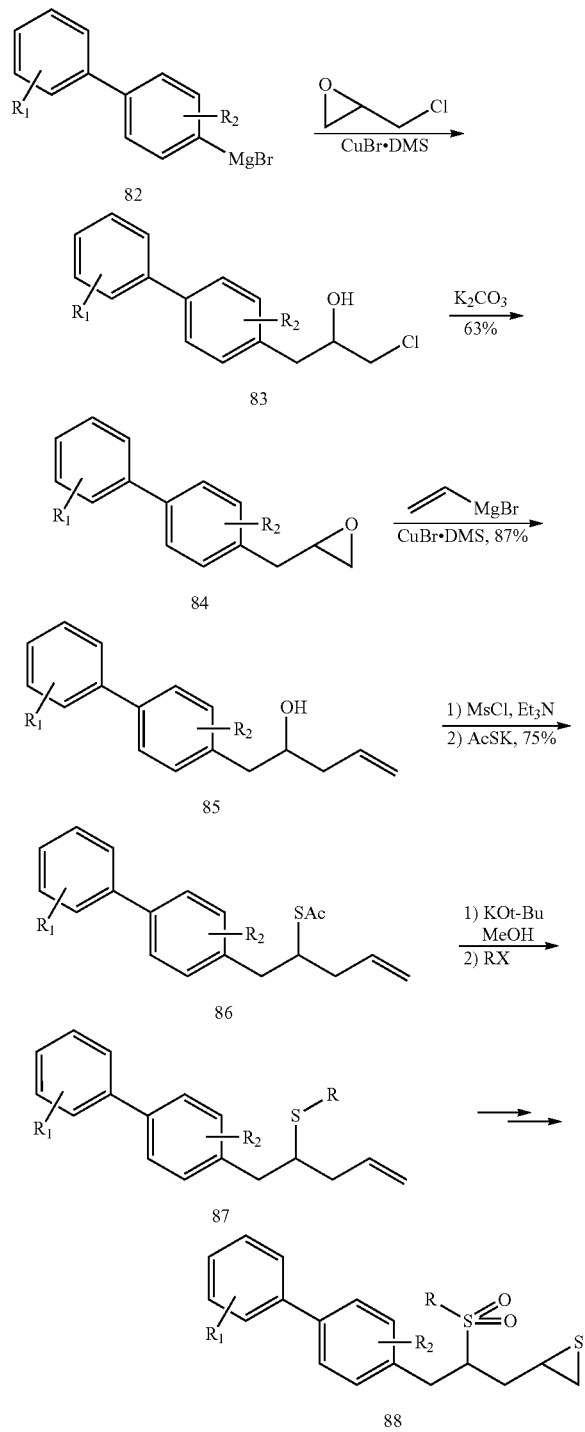

Scheme 18.

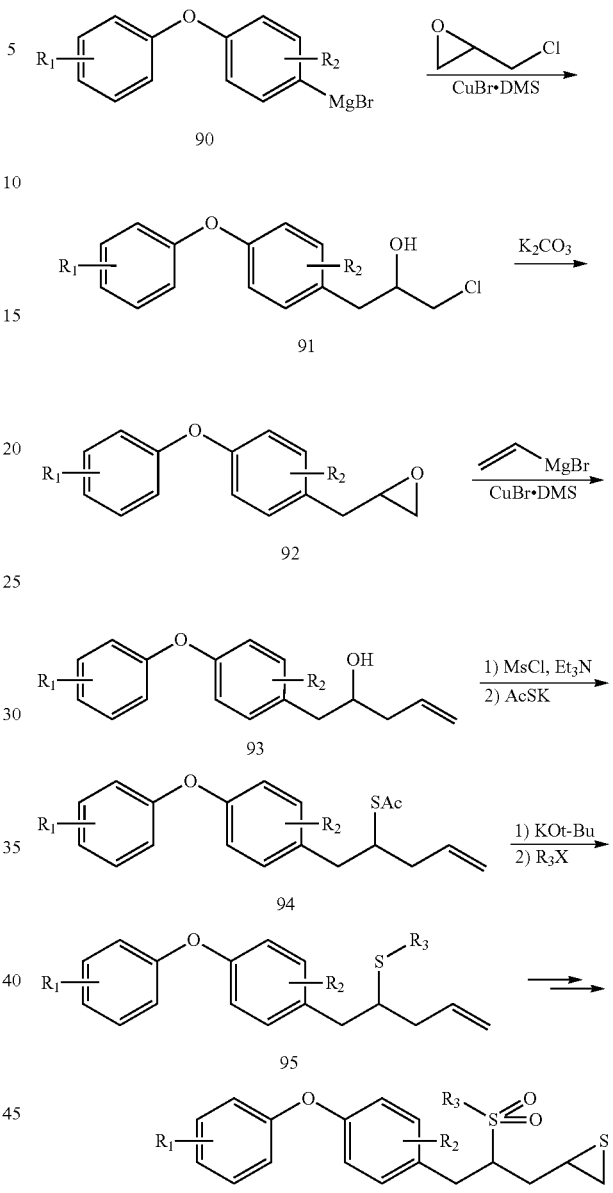

Scheme 19.

When phenoxyphenyl magnesiumbromide 90 is used instead of biphenylmagnesium bromide 82, compound 96 can be obtained (Scheme 19). The remainder of synthetic route is similar to that of Scheme 14.

1,3,5-Substituted benzene was chosen since it contains three positions to be functionalized (Scheme 20). Synthesis commences from bromination of 2-amino-5-nitrophenol 97 using N-bromosuccinimide (J. Am. Chem. Soc. 1997, 119, 311-325). Deamination of compound 98 afforded construction of 1,3,5-substituted benzene scaffold. The resulting phenol 99 was alkylated with halides. Suzuki coupling of compound 100 with aromatic boronic acid 18 in the presence of tetrakis(triphenylphosphine)palladium catalyst resulted in biphenyl derivative 101 (J. Med. Chem. 1997, 40, 437-448). Nitro group in compound 101 was reduced to corresponding amine 102 by catalytic hydrogenation. Conversion of thioacetate 103 to 104 followed the method as described for Scheme 6.

Scheme 20.

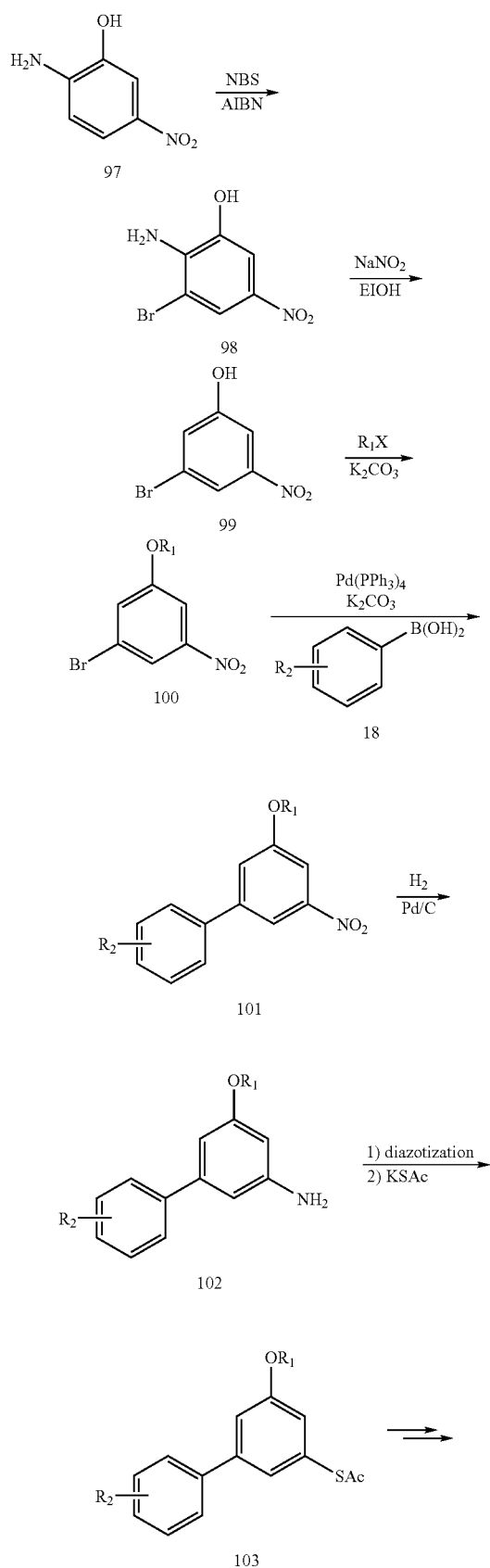

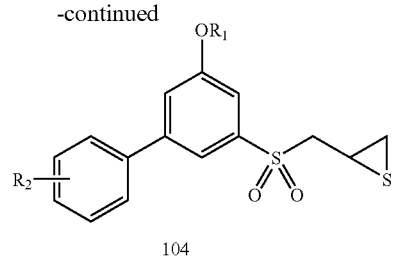

Sulfonamide and phosphoamide groups were introduced instead of sulfonyl group (Scheme 21-24). Sulfonamide was formed by the reaction of phenoxyaniline 14 and allylsulfonyl chloride to yield compound 105 (Scheme 21). After alkylation of amine in 105, double bond was converted to diol 106, which was converted to sulfonylmethylthiirane 107 by the similar method outlined in Scheme 6.

Scheme 21.

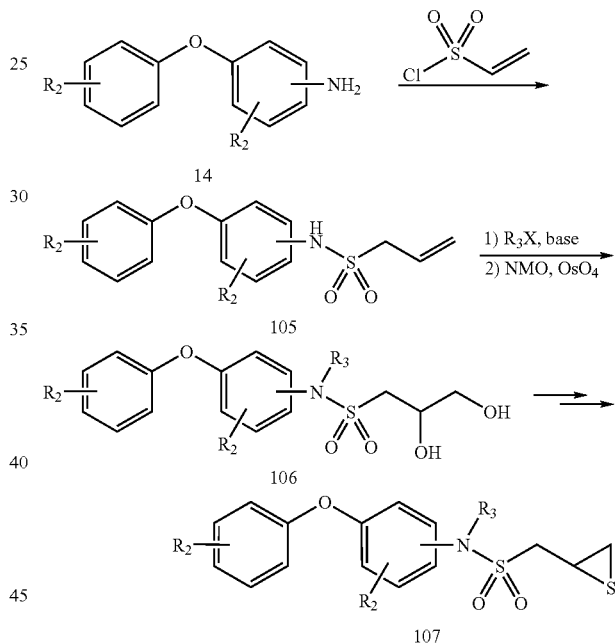

A phosphonamide can be a good surrogate of sulfonamide because they share the same tetrahedral geometry. Phosphonamide 110 was formed by using phenoxyphenylamine 14 and allylphosphonic acid chloride methyl ester instead of allylsulfonyl chloride to result in compound 108 (Scheme 22). The rest of synthetic conversion was followed by the same method outlined Scheme 21.

Scheme 22.

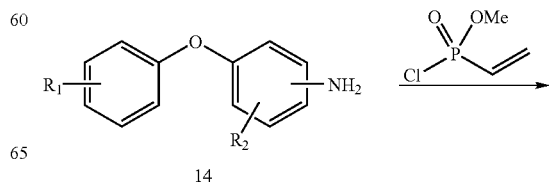

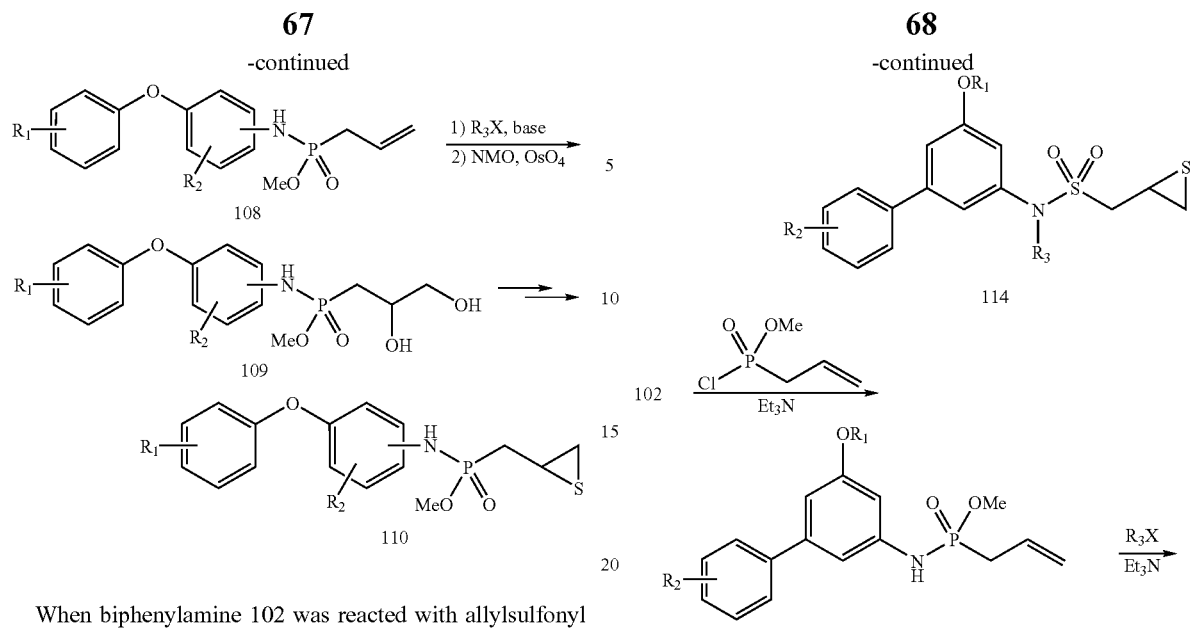

When biphenylamine 102 was reacted with allylsulfonyl chloride or allylphosphonic acid chloride methyl ester, compounds III and 115 were formed, respectively (Scheme 23). Those compounds were converted to corresponding sulfonamide thiirane 114 and phosphonanide thiirane 118 via corresponding diol intermediates 113 and 117.

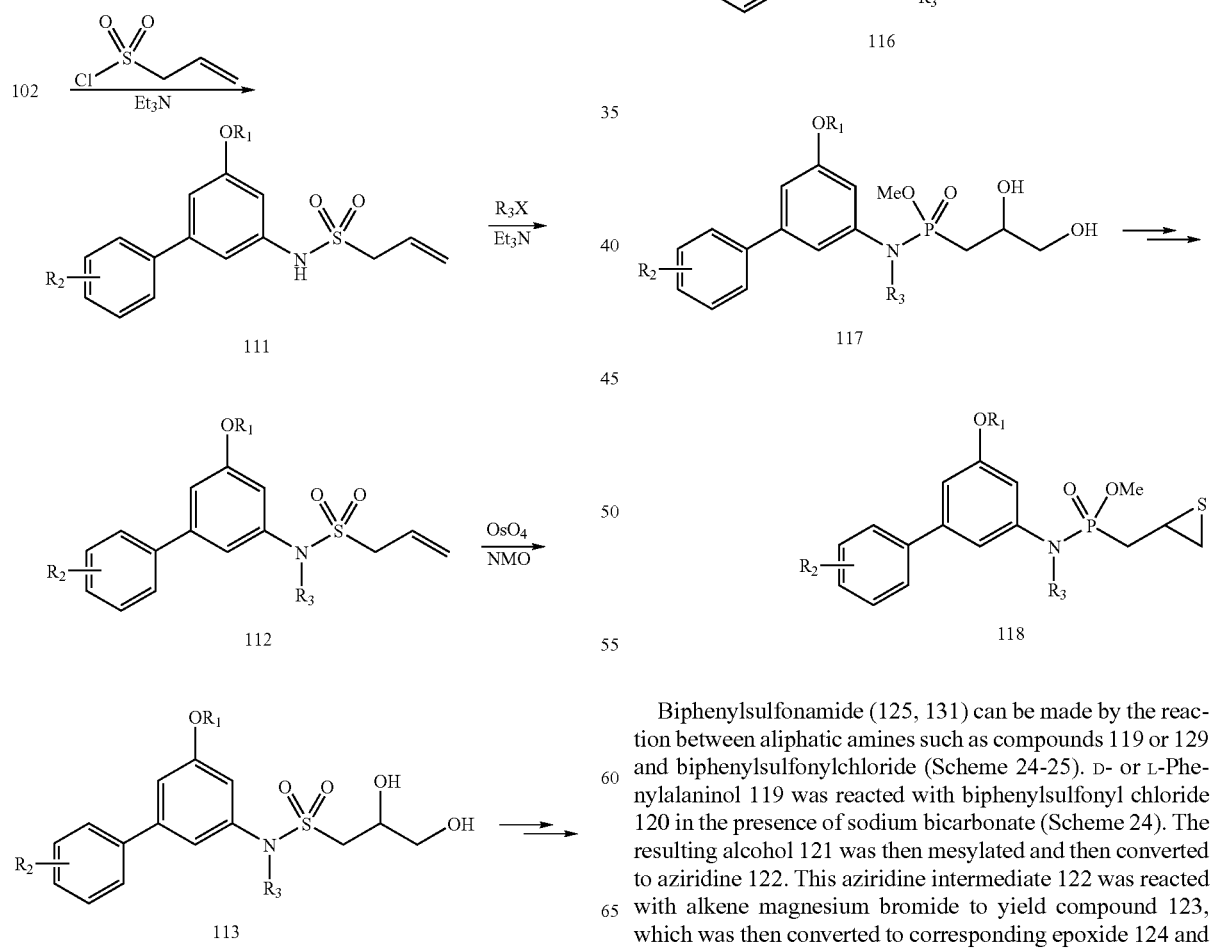

Biphenylsulfonamide (125, 131) can be made by the reaction between aliphatic amines such as compounds 119 or 129 and biphenylsulfonylchloride (Scheme 24-25). D- or L-Phenylalaninol 119 was reacted with biphenylsulfonyl chloride 120 in the presence of sodium bicarbonate (Scheme 24). The resulting alcohol 121 was then mesylated and then converted to aziridine 122. This aziridine intermediate 122 was reacted with alkene magnesium bromide to yield compound 123, which was then converted to corresponding epoxide 124 and thiirane 125.

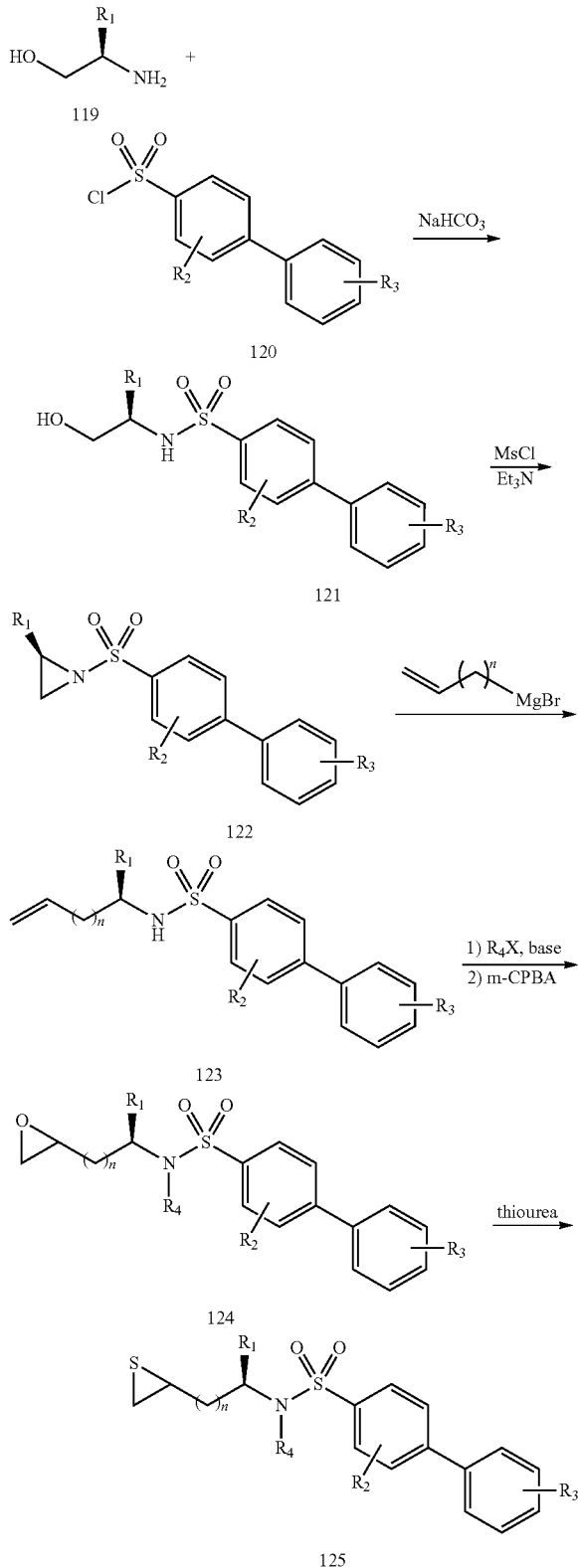

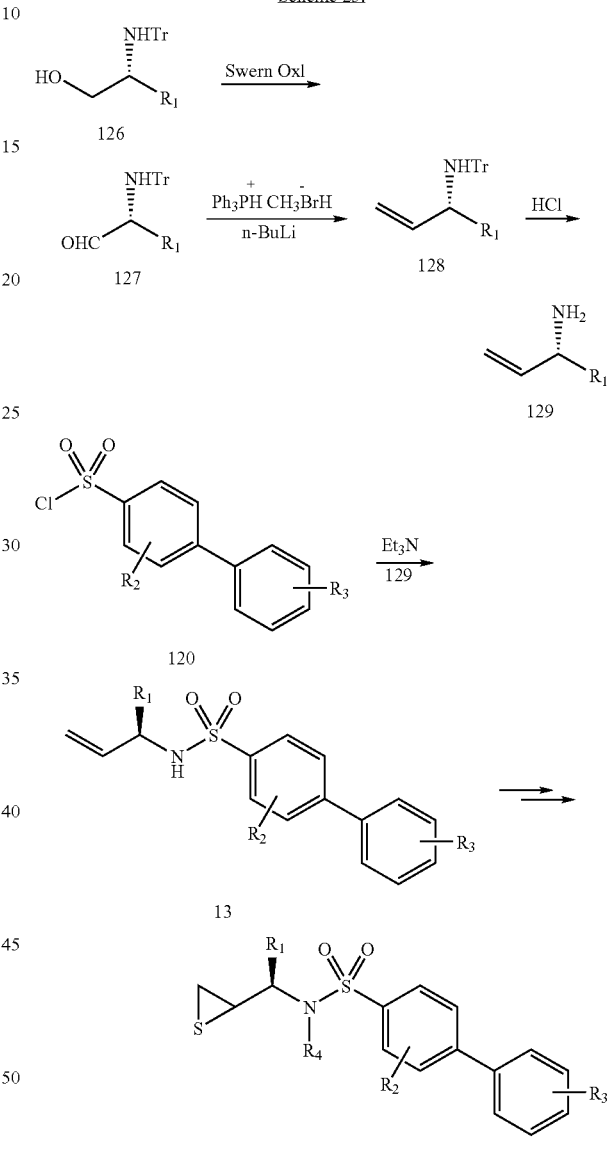

Trityl-protected D- or L-phenylalaminol 126 was oxidized under Swern oxidation condition (Scheme 25). The resulting aldehyde 127 was reacted with triphenylphosphonium methylbromide in the presence of n-BuLi. The trityl group in resultant Wittig product 128 was then removed in acidic condition to afford free amine 129, which was then reacted with biphenylsulfonyl chloride 120. Conversion of compound 130 to compound 131 was followed by the method illustrated in Scheme 24.

Ketones and oximes were considered to be surrogates of the sulfonyl group (Schemes 26-28). Phenoxyphenylmagnesium bromide was reacted with alkene aldehyde to result in secondary alcohol 133, which was the oxidized to ketone 134 (Scheme 26). The double bond in compound 134 was converted to epoxide 135 via hydrobromination. Epoxide 135 then converted to thiirane using thiourea. Ketone 136 was transformed to oxime 137 in the presence of hydroxylamine hydrochloride and sodium acetate.

Scheme 26.

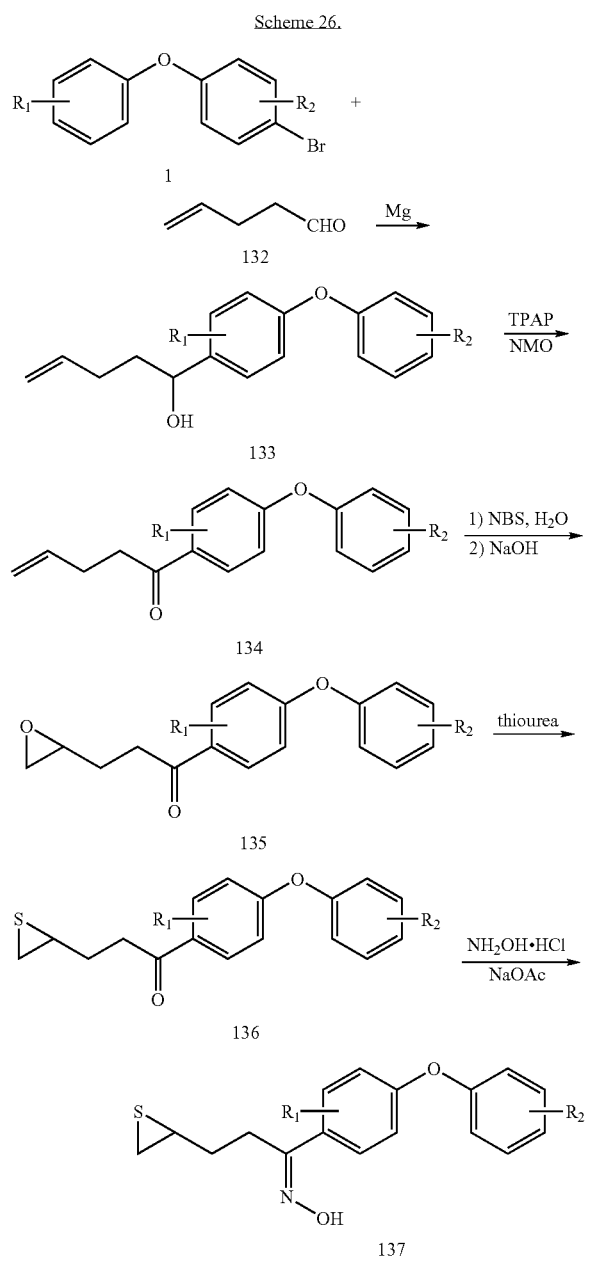

Phenoxybenzaldehyde 138 was reacted with allylmagnesium chloride to give compound 139 (Scheme 27). The rest of the functional group conversion to compound 143 is similar in Scheme 26, except oxidation to ketone was done after double bond oxidation and thiirane formation.

Scheme 27.

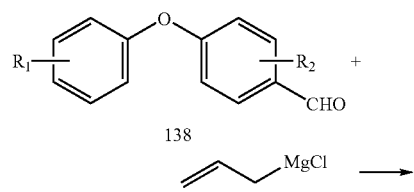

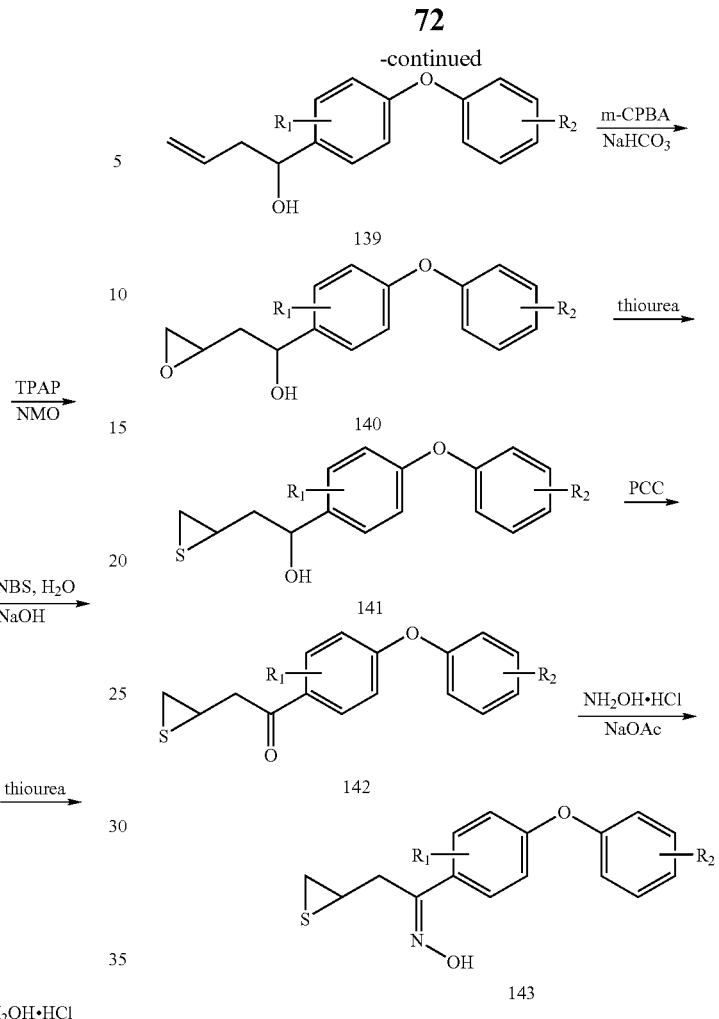

Tetrahydro-dibenzofurane moiety was investigated as a surrogate of phenoxyphenyl group. The synthesis of compound 153 is outlined in Scheme 28. Tetrahydrodibenzofuran derivative 149, which was obtained from phenol and cyclohexene oxide according to literature procedures (J. Am. Chem. Soc. 1935, 57, 2095-2099; Bull. Soc. Chim. Fr. 1956, 1817-1822), was converted 150 under Negishi's conditions (Tetrahedron Lett. 1979, 20, 845-848). Epoxidation of 150 was achieved via bromohydrin intermediates and the resulting oxirane 151 was treated with thiourea to give thiirane 152. Finally, the conversion of 152 to oxime 153 was carried out by the $NH_2OH.HCl/AcONa$ (Tetrahedron Lett. 1989, 30, 3471-3472; Chem. Pharm. Bull. 2003, 51, 138-151; Tetrahedron 1968, 24, 3347-3360).

Aromatic pyrrol group was also designed as an aromatic scaffold (158-159). Substituted benzaldehyde 154 and ethyl cyanoacetate were subjected to Knoevenagel condensation in the presence of catalytic amount of piperidine to give α,β-unsaturated cyanoester 155, followed by a tandem Michael addition-decarboxylation involving potassium cyanide. The resulting disuccinonitrile 156 was reduced to form pyrrole 157 using Dibal-H according to the method reported by Babler et al. (Tetrahedron Lett. 1984, 25, 1659-1660). Pyrrole 157 was deprotonated with sodium hydride and reacted with several electrophiles which containing oxirane (Synlett 1998, 1411-1413; and Mueller, A. C., Shokal, E. C., (Shell Development Co.), US, 1957). Conversion of oxirane to thiirane was done under standard thiourea condition.

Scheme 28.

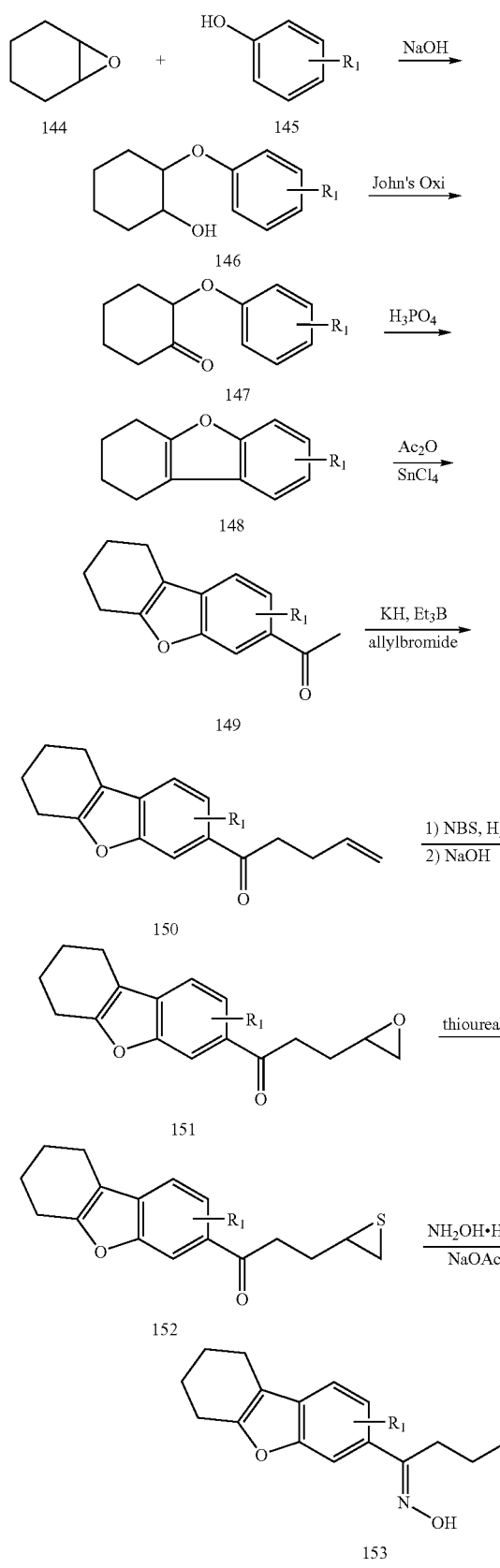

Scheme 29.

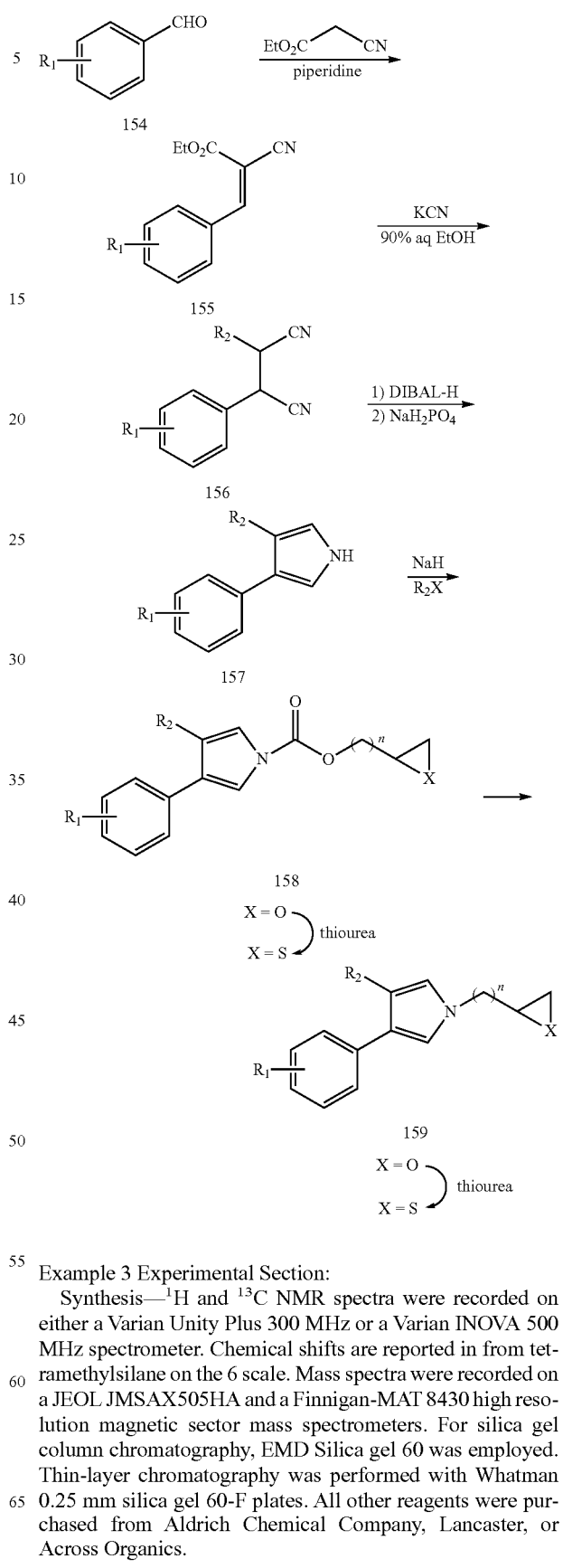

Example 3 Experimental Section:

Synthesis—$^1$H and $^{13}$C NMR spectra were recorded on either a Varian Unity Plus 300 MHz or a Varian INOVA 500 MHz spectrometer. Chemical shifts are reported in from tetramethylsilane on the 6 scale. Mass spectra were recorded on a JEOL JMSAX505HA and a Finnigan-MAT 8430 high resolution magnetic sector mass spectrometers. For silica gel column chromatography, EMD Silica gel 60 was employed. Thin-layer chromatography was performed with Whatman 0.25 mm silica gel 60-F plates. All other reagents were purchased from Aldrich Chemical Company, Lancaster, or Across Organics.

Compounds of Scheme 5.

Compound 2a ($R_1=R_2=H$). n-BuLi (10.7 mL, 2.5 M in hexane) was added to a solution of 4-bromophenyl phenyl ether (4.7 mL, 26.8 mmol) in anhydrous THF (120 mL) with vigorous stirring at −78° C. After stirring for 30 minutes, sulfur (0.86 g, 26.8 mmol) was added to the reaction mixture. The mixture was stirred for 0.5 hours, while temperature was raised to 0° C. After cooled down to −78° C., epichlorohydrin (2.2 mL, 28.1 mmol) was added dropwise to the reaction mixture. Stirring was continued for 1 hour, while temperature was raised to −20° C. The reaction was quenched by the addition of a saturated solution of ammonium chloride. The mixture was extracted with EtOAc and the organic layer was washed with water, dried ($MgSO_4$), and filtered. The solvent was evaporated under reduced pressure, and the residue was purified by column chromatography to afford the desired product (6.70 g, 85%). When allyl bromide or acetyl chloride were used instead of epichlorohydrin for this reaction, compound 10a or 11a were obtained; $^1$H NMR (500 MHz, $CDCl_3$) δ 7.4 (d, J=8.4 Hz, 2H), 7.4 (dd, J=8.4, 7.6 Hz, 2H), 7.1 (t, J=7.4 Hz, 1H), 7.0 (d, J=7.6 Hz, 2H), 7.0 (d, J=8.6 Hz, 2H), 3.9 (m, 1H, CHOH), 3.7 (m, 2H, $CH_2Cl$), 3.1 (ddd, J=42.5, 14.0 Hz, 5.6 Hz, 2H, $SCH_2CH$), 2.8 (brs, 1H, OH); $^{13}$C NMR (125 MHz, $CDCl_3$) δ 157.2, 156.7, 133.2, 130.0, 128.0, 123.9, 119.4, 119.3, 69.6, 48.1, 39.7; HRMS calcd for $C_{15}H_{15}ClO_2S$ ($M^+$) 294.0481, found 294.0465.

Compound 3a ($R_1=R_2=H$). Potassium carbonate (2.81 g, 20.4 mmol) was added to a solution of compound 2a (3.00 g, 10.2 mmol) in a 1:2 mixture of methanol and acetonitrile (100 mL) in ice-water bath with vigorous stirring. After 10 minutes, ice-water bath was removed and stirring was continued for 1 hour at room temperature and was filtered through a small layer of silica gel. The filtrate was concentrated under reduced pressure, and the residue was purified by column chromatography to afford the desired product (2.49 g, 95%) as an oil; $^1$H NMR (500 MHz, $CDCl_3$) δ 7.4 (d, J=8.9 Hz, 2H), 7.4 (t, J=8.0 Hz, 2H), 7.1 (t, J=7.4 Hz, 1H), 7.0 (d, J=8.6 Hz, 2H), 7.0 (d, J=8.8 Hz, 2H), 3.2 (m, 1H), 3.1 (dd, J=14.2, 5.2 Hz, 1H), 2.9 (dd, J=14.0, 6.0 Hz, 1H), 2.8 (t, J=4.8 Hz, 1H), 2.5 (dd, J=5.0, 2.6 Hz, 1H); $^{13}$C NMR (125 MHz, $CDCl_3$) δ 157.0, 156.7, 133.5, 129.9, 128.7, 123.8, 119.3, 119.2, 51.2, 47.4, 38.0; HRMS calcd for $C_{15}H_{14}O_2S$ ($M^+$) 258.0715, found 258.0729.

Compound 4a ($R_1=R_2=H$). To a solution of compound 3a (2.00 g, 7.74 mmol) in dichloromethane (20 mL) was added a solution of m-chloroperoxybenzoic acid (3.47 g, 15.5 mmol, 77%) in ice-water bath. After 10 minutes, the suspension was filtered, and the filtrate was diluted with EtOAc and washed with 10% aqueous sodium thiosulfate, followed by saturated sodium bicarbonate and brine. The organic layer was dried over magnesium sulfate and was concentrated. The product was purified by silica gel chromatography to yield the title compound as an oil (1.96 g, 87%); $^1$H NMR (500 MHz, $CDCl_3$) δ 7.9 (d, J=8.8 Hz, 2H), 7.4 (dd, J=8.4, 7.4 Hz, 2H), 7.2 (t, J=6.9 Hz, 1H), 7.1 (d, J=8.6 Hz, 4H), 3.3 (m, 3H), 2.8 (m, 1H), 2.5 (dd, J=5.2, 4.2 Hz, 1H); $^{13}$C NMR (125 MHz, $CDCl_3$) δ 163.0, 154.8, 132.5, 130.6, 130.4, 125.4, 120.6, 117.7, 59.7, 46.0, 46.0; HRMS calcd for $C_{15}H_{14}O_4S$ ($M^+$) 290.0613, found 290.0630.

Compound 5a ($R_1=R_2=H$). Thiourea (0.52 g, 6.89 mmol) was added to a solution of compound 4a (1.00 g, 3.44 mmol) in methanol (10 mL). The reaction mixture was stirred at room temperature overnight. The solvent was removed under reduced pressure. The residue was partitioned between ethyl ether and water, the organic layer was washed with water and brine, dried ($MgSO_4$), and the suspension was filtered. Evaporation of solvent gave the crude product, which was purified by column chromatography. The desired product was crystallized as white needles from 1-butanol (0.89 g, 84%); $^1$H NMR (500 MHz, $CDCl_3$) δ 7.9 (d, J=8.6 Hz, 2H), 7.5 (t, J=7.8 Hz, 2H), 7.3 (t, J=7.2 Hz, 1H), 7.1 (d, J=8.6 Hz, 4H), 3.6 (dd, J=14.2, 5.6 Hz, 1H), 3.2 (dd, J=14.2, 7.8 Hz, 1H), 3.1 (m, 1H), 2.6 (dd, J=6.0, 1.4 Hz, 1H), 2.2 (dd, J=5.2, 1.6 Hz, 1H); $^{13}$C NMR (125 MHz, $CDCl_3$) δ 163.1, 154.9, 132.0, 130.9, 125.5, 120.6, 117.9, 62.8, 26.3, 24.4; HRMS calcd for $C_{15}H_{14}O_3S_2$ ($M^+$) 306.0384, found 306.0396.

Compounds of Scheme 6.

Compound 4a (from compound 10a). Compound 10a (2.40 g, 10.0 mmol) was dissolved in m-CPBA (11.5 g, 50.0 mmol, 77% max) in ice-water bath and stirred for 7 days. The resulting suspension was filtered and filtrate was diluted with EtOAc and washed with 10% aqueous sodium thiosulfate, followed by saturated sodium bicarbonate and brine. The organic layer was dried over magnesium sulfate and was concentrated. The product was purified by silica gel chromatography to yield the title compound as an oil (2.50 g, 87%).

Compound 12a ($R_1=R_2=H$). A mixture of compound 10a (0.27 g, 1.1 mmol) and N-methylmorpholine N-oxide (0.25 g, 2.1 mmol) in acetone-water (30 mL, 4:1) was treated with osmium tetraoxide (0.3 mL, 47 μmol, 4% aqueous solution) and the resultant solution was stirred at room temperature overnight under dark. Sodium sulfite (0.1 g) was added and the resulting mixture was stirred for an additional 1 hour. After filtration through a small layer of silica gel, the filtrate was evaporated and the residue was purified by column chromatography on silica gel to give the title compound (0.26 g, 85%); $^1$H NMR (300 MHz, $CDCl_3$): δ 7.4 (d, J=8.4 Hz, 2H), 7.4 (dd, J=8.4, 7.6 Hz, 2H), 7.1 (t, J=7.4 Hz, 1H), 7.0 (d, J=7.6 Hz, 2H), 7.0 (d, J=8.6 Hz, 2H), 3.83 (brs, 1H), 3.51-3.68 (m, 2H), 3.15-3.25 (m, 2H); $^{13}$C NMR (75 MHz, $CDCl_3$): δ 157.2, 156.7, 133.2, 130.0, 128.0, 123.9, 119.4, 119.3, 69.6, 48.1, 39.7.

Compound 13a ($R_1=R_2=H$). Compound 12a was oxidized to compound 13a by the same procedure for the preparation of compound 4a from compound 3a.

Compound 4a (from compound 13a). Conversion of diol to oxirane was done by two methods. The first method is using Mitsunobu condition. The second is via the formation of tosylated intermediate. A mixture of compound 13a (163 mg, 530 μmol), triphenylphosphine (142 mg, 530 μmol), and diethylazodicarboxylate (90 μL, 530 μmol) was refluxed for 4 hours in anhydrous benzene (10 mL) and the volatile was evaporated. The residue was purified by column chromatography on silica gel to afford the title compound (98.5 mg, 64%).

The second procedure involving formation of a tosylated intermediate: A mixture of compound 13a (163 mg, 530 μmol) and tosyl chloride (111 mg, 583 μmol) in $CH_2Cl_2$ (2 mL) was treated with pyridine (138 μL, 1.75 mmol) and the resulting mixture was stirred overnight in ice-water bath. The reaction mixture was washed with water several times and volatile was concentrated. The crude product was used for the next step without further purification was dissolved in anhydrous THF (2 mL) and cooled down in ice-water bath. To this reaction mixture, NaH (35 mg, 875 μmol, 60% in oil) was added and the resulting mixture was stirred for 10 minutes and filtered through a small layer of silica gel and washed with THF. The combined filtrate was evaporated under reduced pressure and the resulting crude product was purified by column chromatography to afford the desired product as colorless oil (115 mg, 75%).

Compound 3a (from compound 11a). Compound 11a (0.61 g, 2.5 mmol) was stirred at room temperature for 0.5 hours in the presence of $K_2CO_3$ (1.38 g, 20 mmol) in 1:1 mixture of MeOH:acetonitrile (10 mL). Epibromohydrin (0.8 mL, 10.0 mmol) was added dropwise to the reaction mixture and the resulting solution was stirred at room temperature for additional 1 hour. The reaction mixture was filtered and the filtrate was evaporated. The residue was purified by column chromatography on silica gel to afford the desired product (0.56 g, 87%). When allyl bromide or glycidol were used for this reaction instead of epichlorohydrin, compound 10a or 12a were obtained in similar yield.

Compounds of Scheme 7.

Compound 11b (from compound 14a, $R_1=R_2=H$, 3-amino). A solution of o-benzenedisulfonimide (2.63 g, 12 mmol) in glacial acetic acid (40 mL) was slowly added, over a period of 10 minutes, to a solution of 3-phenoxyaniline (1.85 g, 10 mmol) in acetic acid (20 mL) in an ice bath. Isoamylnitrite (1.5 mL, 11 mmol) was added dropwise to the reaction mixture over 10 min and the resulting mixture was stirred for 0.5 hours at the same temperature. Addition of diethyl ether to the reaction mixture resulted in diazonium salt as an orange powder, which was filtered and washed with cold diethyl ether. Potassium thioacetate (0.98 g, 10 mmol) in acetonitrile (10 mL) was added to the crude diazonium salt (2.0 g) in anhydrous acetonitrile (10 mL) and the resulting suspension was stirred at room temperature for 2 hours. The reaction mixture was filtered and the filtrate was evaporated. The residue was purified by column chromatography on silica gel to afford the desired product (0.97 g, 40%); $^1$H NMR (500 MHz, CDCl$_3$): δ 2.45 (s, 3H), 7.09-7.22 (m, 6H), 7.38-7.44 (m, 3H); $^{13}$C NMR (125 MHz, CDCl$_3$): δ 30.3, 119.4, 119.8, 123.9, 124.4, 129.1, 130.4, 156.7, 157.9; HRMS (FAB) calcd for C$_{14}$H$_2$O$_2$S (M$^+$) 244.0558, found 244.0556.

Compound 3b (from compound 11b, $R_1=R_2=H$, 2-amino). Compound 11b (0.61 g, 2.5 mmol) was stirred at room temperature for 0.5 hours in the presence of K$_2$CO$_3$ (1.38 g, 10 mmol) in 1:1 mixture of MeOH: acetonitrile (10 mL). Epibromohydrin (0.8 mL, 10.0 mmol) was added dropwise to the reaction mixture and the resulting solution was stirred at room temperature for additional 1 hour. The reaction mixture was filtered and the filtrate was evaporated. The residue was purified by column chromatography on silica gel to afford the desired product (0.56 g, 87%); $^1$H NMR (500 MHz, CDCl$_3$): δ 2.57 (dd, 1H, J=2.2, 4.7 Hz), 2.81 (t, 1H, J=4.2 Hz), 2.98 (q, 1H, J=7.8 Hz), 3.16-3.20 (m, 2H), 6.88 (dd, 1H, J=2.5, 7.9 Hz), 7.04-7.09 (m, 3H), 7.16 (t, 2H, J=7.4 Hz), 7.28 (t, 1H, J=-7.8 Hz), 7.38 (t, 2H, J=7.8 Hz); $^{13}$C NMR (125 MHz, CDCl$_3$): δ 36.3, 47.6, 51.0, 117.0, 119.3, 119.8, 123.8, 124.4, 130.0, 130.3, 137.4, 156.8, 157.9; HRMS (FAB) calcd for C$_{15}$H$_{14}$O$_2$S (M$^+$) 258.0715, found 258.0713.

Conversion from compound 3b to compounds 4b, and 5b was followed by the same method as described in Scheme 5.

Compound 4b ($R_1=R_2=H$, 2-amino). $^1$H NMR (500 MHz, CDCl$_3$): δ 2.49 (dd, 1H, J=1.0, 5.0 Hz), 2.84 (dd, 1H, J=3.7, 4.7 Hz), 3.26-3.37 (m, 3H), 7.08 (dd, 1H, J=1.2, 8.7 Hz), 7.22 (t, 1H, J=7.4 Hz), 7.32 (m, 1H), 7.42 (dd, 2H, J=7.4, 8.4 Hz), 7.56 (m, 2H), 7.68 (dt, 1H, J=1.0, 8.4 Hz); $^{13}$C NMR (125 MHz, CDCl$_3$): δ 45.9, 46.1, 59.6, 117.7, 119.8, 122.5, 124.0, 124.9, 130.4, 131.0, 140.8, 155.9, 158.6; HRMS (FAB) calcd for C$_{15}$H$_{14}$O$_4$S (M$^+$) 290.0613, found 290.0603.

Compound 5b ($R_1=R_2=H$, 2-amino). $^1$H NMR (500 MHz, CDCl$_3$): δ 2.14 (dd, 1H, J=1.7, 5.2 Hz), 2.51 (dd, 1H, J=1.7, 6.2 Hz), 3.03 (m, 1H), 3.18 (dd, 1H, J=7.7, 14.1 Hz), 3.51 (dd, 1H, J=5.4, 14.3 Hz), 7.05 (dd, 1H, J=1.0, 8.9 Hz), 7.19 (t, 1H, J=7.4 Hz), 7.29, 7.31 (2dd, 1H, J=1.0, 2.5 Hz), 7.39 (dd, 2H, J=7.4, 8.4 Hz), 7.52-7.55 (m, 2H), 7.64 (dt, 1H, J=1.5, 7.9 Hz); $^{13}$C NMR (125 MHz, CDCl$_3$): δ 24.3, 20.0, 62.4, 117.7, 119.8, 122.6, 123.9, 124.8, 130.3, 131.0, 140.2, 155.7, 158.6; HRMS (FAB) calcd for C$_{15}$H$_{15}$O$_3$S$_2$ (MH$^+$) 307.0463, found 307.0474.

Compounds of Scheme 8.

Compound 1b ($R_1=H$, $R_2=d4$, from compound 16a and 17a). The procedure was adapted from that reported by Ma et al. (*Org. Lett.* 2003, 5, 3799-3802). A mixture of 1,4-dibromobenzene-d$_4$ (17a, 2.50 g, 10.4 mmol), phenol (16a, 1.47 g, 15.6 mmol), Cs$_2$CO$_3$ (6.80 g, 20.9 mmol), N,N-dimethylglycine hydrochloride salt (0.44 g, 3.15 mmol), CuI (0.20 mg, 1.05 mmol) in degassed 1,4-dioxane (20 mL) was heated at 90° C. for 22 hours under a nitrogen atmosphere. After dilution with water, the mixture was extracted with ethyl acetate. The combined organic layer was washed with water and brine, dried over anhydrous MgSO$_4$, and concentrated under reduced pressure. The resultant residue was purified by column chromatography to give the desired product as colorless oil (2.00 g, 76%). $^1$H NMR (500 MHz, CDCl$_3$) δ 7.06 (d, J=7.9 Hz, 2H), 7.18 (t, J=7.6 Hz, 1H), 7.39 (t, J=7.2 Hz, 2H); $^{13}$C NMR (126 MHz, CDCl$_3$) δ 115.5, 119.2, 120.2 (t, J=25.5 Hz), 123.9, 130.1, 132.4 (t, J=25.5 Hz), 156.7, 156.9; HRMS calcd for C$_{12}$H$_5$D$_4$BrO (M$^+$) 252.0088, found 252.0072.

Conversion from compound 1b to compounds 2c-5c was followed by the same method as described in Scheme 5.

Compound 2c ($R_1=H$, $R_2=d4$) $^1$H NMR (500 MHz, CDCl$_3$) δ 3.03 (dd, J=13.8, 7.2 Hz, 1H), 3.12 (dd, J=14.1, 5.5 Hz, 1H), 3.64-3.74 (m, 2H), 3.88-3.94 (m, 1H), 7.03 (d, J=7.6 Hz, 2H), 7.15 (t, J=7.2 Hz, 1H), 7.36 (t, J=8.6, 7.6 Hz, 2H); $^{13}$C NMR (126 MHz, CDCl$_3$) δ 39.8, 48.2, 69.6, 119.1 (t, J=25.5 Hz), 119.4, 124.0, 127.7, 130.1, 132.9 (t, J=25.5, 23.9 Hz), 156.7, 157.3; HRMS calcd for C$_{15}$H$_{11}$D$_4$ClO$_2$S (M$^+$) 298.0732, found 298.0737.

Compound 3c ($R_1=H$, $R_2=d4$). $^1$H NMR (500 MHz, CDCl$_3$) δ 2.49 (dd, J=4.1, 1.4 Hz, 1H), 2.82-2.86 (m, 1H), 3.28-3.36 (m, 3H), 7.11 (dd, J=8.6, 0.7 Hz, 2H), 7.27 (t, J=7.6 Hz, 1H), 7.45 (t, J=8.3, 7.6 Hz, 2H); $^{13}$C NMR (126 MHz, CDCl$_3$) δ 38.2, 47.6, 51.3, 119.0 (t, J=25.7 Hz), 119.3, 123.9, 128.5, 130.0, 133.2 (t, J=23.9 Hz), 156.8, 157.1 (m); HRMS calcd for C$_{15}$H$_{10}$D$_4$O$_2$S (M$^+$) 262.0966, found 262.0949.

Compound 4c ($R_1=H$, $R_2=d4$). $^1$H NMR (500 MHz, CDCl$_3$) δ 2.50 (dd, J=4.1, 1.4 Hz, 1H), 2.84 (dd, J=3.8, 2.4 Hz, 1H), 3.26-3.37 (m, 3H), 7.11 (d, J=8.6 Hz, 2H), 7.27 (t, J=7.4 Hz, 1H), 7.45 (t, J=7.9 Hz, 2H); $^{13}$C NMR (126 MHz, CDCl$_3$) δ 46.0, 46.1, 59.8, 117.4 (t, J=25.5 Hz), 120.7, 125.4, 130.3 (t, J=25.5 Hz), 130.4, 132.4, 154.9, 163.0; HRMS calcd for C$_{15}$H$_{10}$D$_4$O$_4$S (M$^+$) 294.0864, found 294.0869.

Compound 5c ($R_1=H$, $R_2=d4$). $^1$H NMR (500 MHz, CDCl$_3$) δ 2.17 (dd, J=5.2, 1.7 Hz, 13H), 2.54 (dd, J=6.2, 1.7 Hz, 1H), 3.04-3.10 (m, 1H), 3.18 (dd, J=14.5, 7.9 Hz, 1H), 3.53 (dd, J=14.1, 5.9 Hz, 1H), 7.10 (d, J=7.6 Hz, 2H), 7.25 (t, J=6.9 Hz, 1H), 7.44 (t, J=7.9 Hz, 2H); $^{13}$C NMR (126 MHz, CDCl$_3$) δ24.4, 26.3, 62.8, 117.5 (t, J=24.7 Hz), 120.6, 125.4, 125.4, 130.5 (t, J=25.5 Hz), 130.5, 131.9, 154.9, 163.0; HRMS calcd for C$_{15}$H$_{11}$D$_4$O$_3$S$_2$ M+H$^+$) 311.0714, found 311.0700.

Compound 19a ($R_2=H$). To a stirred solution of 4-hydroxythiophenol (6) (4.30 g, 34.1 mmol) in DMF (25 mL) were added K$_2$CO$_3$ (4.71 g, 34.1 mmol) and allyl bromide (3.09 mL, 34.1 mmol) at ice-water temperature, and the mixture was stirred for 15 minutes, prior to stirring overnight at room temperature. After the addition of 1 M aqueous HCl, the mixture was extracted with ether (3×). The combined organic layer was washed with water and brine, dried over MgSO$_4$, and concentrated under reduced pressure. The resultant residue was purified by silica gel column chromatography (ethyl acetate/hexane=1/10 to 1/6) to give the product (5.74 g, 70%) as a white semi-solid.

Compound 10b ($R_1$=p-$CH_2CO_2Et$, $R_2$=H). A mixture of 18a (1.51 g, 6.59 mmol), 19a (1.64 g, 9.88 mmol), $Cs_2CO_3$ (4.30 g, 13.2 mmol), N,N-dimethylglycine hydrochloride salt (276 mg, 1.98 mmol), CuI (125 mg, 0.659 mmol) and degassed 1,4-dioxane (14 mL) was heated at 90° C. for 22 hours under a nitrogen atmosphere. After dilution with water, the mixture was extracted with ethyl acetate. The combined organic layer was washed with water and brine, dried over $Na_2SO_4$, and concentrated under reduced pressure. The resultant residue was purified by silica gel column chromatography (ethyl acetate/hexane=1/12) to give the product (1.35 g, 65%) as a pale yellow semi-solid. $^1$H NMR (300 MHz, $CDCl_3$): δ 3.49 (d, 2H, J=7.2 Hz), 3.61 (s, 2H), 3.71 (s, 3H), 5.03-5.10 (m, 2H), 5.86 (m, 1H), 6.91-6.97 (m, 4H), 7.23-7.26 (m, 2H), 7.32-7.35 (m, 2H); $^{13}$C NMR (125 MHz, $CDCl_3$): δ38.5, 40.3, 52.1, 117.5, 119.0, 119.1, 129.0, 129.3, 130.6, 132.9, 133.7, 156.0, 156.3, 172.0; HRMS (FAB) calcd for $C_{18}H_{18}O_3S$ ($M^+$) 314.0977, found 314.0986.

Compound 20a ($R_2$=H). Synthesis of compound 20a was accomplished by the same method for the preparation of compound 19a using dimethylcarbamoyl chloride instead of allyl bromide.

Compound 21a ($R_1$=3-benzyloxy, $R_2$=1). Synthesis of compound 21a was accomplished by the same method for the preparation of compound 10b using compound 20a and 1-benzyloxy-3-iodobenzene (18b). $^1$H NMR (500 MHz, $CDCl_3$) δ 3.09 (d, J=23.3 Hz, 6H), 5.06-5.08 (m, 2H), 6.70 (dd, J=8.2, 2.4 Hz, 1H), 6.75 (t, J=2.2 Hz, 1H), 6.82 (dd, J=8.4, 2.4 Hz, 1H), 7.05 (d, J=9.0 Hz, 2H), 7.28 (t, J=8.2 Hz, 1H), 7.34-7.51 (m, 7H); $^{13}$C NMR (126 MHz, $CDCl_3$) δ 36.9, 70.1, 106.4, 110.6, 111.9, 118.9, 127.6, 128.1, 128.6, 130.3, 136.7, 137.5, 157.5, 158.4, 160.1, 167.2.

Compound 3d ($R_1$=3-benzyloxy, $R_2$=H, from compound 21a). Compound 21a (4.30 g, 11.3 mmol) was added to methanolic KOH (6.26 g, 88.2 mol) in MeOH (80 mL) and then refluxed for 3 hours. The solvent was removed under reduced pressure and the residue was diluted with methylene chloride/2 N HCl. The aqueous layer was extracted with methylene chloride and the combined organic layer was washed with water and brine, dried over anhydrous $MgSO_4$, and concentrated under reduced pressure. The resultant residue was dissolved in acetonitrile/MeOH (2:1, 60 mL) and $K_2CO_3$ (2.95 g, 21.4 mmol) was added. After 0.5 hours, epichlorohydrin (1.67 mL, 21.4 mmol) was added to the reaction mixture and was stirred at room temperature for 1 hour and was filtered through a layer of silica gel. The filtrate was evaporated under reduced pressure and the residue was purified by column chromatography to give compound 3d as colorless oil (3.00 g, 73%). $^1$H NMR (500 MHz, $CDCl_3$) δ 3.09 (d, J=24.1 Hz, 6H), 5.04-5.08 (m, 2H), 6.69 (dd, J=7.2, 3.1 Hz, 1H), 6.74 (t, J=2.4 Hz, 1H), 6.81 (dd, J=8.3, 2.4 Hz, 1H), 7.04 (d, J=9.0 Hz, 2H), 7.28 (t, J=8.3 Hz, 1H), 7.34-7.50 (m, 7H); $^{13}$C NMR (126 MHz, $CDCl_3$) δ 70.2, 106.4, 110.6, 112.0, 118.9, 122.4, 127.6, 128.1, 128.7, 130.4, 136.7, 137.5, 157.5, 158.4, 160.2, 167.2.

Compound 23a ($R_2$=H). Synthesis of compound 23a was accomplished by the same method for the preparation of compound 19a using epichlorohydrin instead of allyl bromide. $^1$H NMR (500 MHz, $CDCl_3$) δ 2.95 (dd, J=13.8, 7.2 Hz, 1H), 3.03 (dd, J=13.8, 5.5 Hz, 1H), 3.25 (br.s., 1H), 3.66 (ddd, J=21.4, 11.0, 4.1 Hz, 2H), 3.87 (m, 1H), 6.79 (d, J=8.3 Hz, 2H), 7.22 (br.s., 1H), 7.31 (d, J=8.3 Hz, 2H); $^{13}$C NMR (126 MHz, $CDCl_3$) δ 40.3, 48.0, 69.6, 116.4, 124.0, 134.3, 156.4, 172.2; HRS calcd for $C_9H_{11}ClO_2S$ ($M^+$) 218.0168, found 218.0172.

Compound 2e ($R_2$=d5, $R_2$=H, from compound 22a and compound 23a). The procedure was adapted from that reported by Evan et al. (*Tetrahedron Lett.* 1998, 39, 2937-2940). A mixture of compound 23a (0.86 g, 3.93 mmol), $Cu(OAc)_2$ (0.72 g, 3.96 mmol), phenyl-$d_5$ boronic acid (22a, 1.00 g, 7.87 mmol), and powdered 4 Å molecular sieves was stirred in $CH_2Cl_2$ and triethylamine (1.10 mL, 7.89 mmol) was added. After stirring for 18 hours at room temperature, the resulting slurry was filtered through a layer of Celite and the filtrate was concentrated under reduced pressure. The residue was purified by column chromatography to give the desired product (0.85 g, 72%). $^1$H NMR (500 MHz, $CDCl_3$) δ 2.95 (br.s., 1H), 3.09 (ddd, J=42.0, 14.1, 5.5 Hz, 2H), 3.71 (ddd, J=17.2, 11.0, 4.5 Hz, 2H), 3.94 (m, 1H), 6.98 (d, J=9.0 Hz, 2H), 7.43 (d, J=9.0 Hz, 2H); $^{13}$C NMR (126 MHz, $CDCl_3$) δ 39.6, 48.1, 69.6, 118.9 (t, J=24.7 Hz), 119.4, 123.4 (t, J=24.7 Hz), 128.0, 129.5 (t, J=23.9 Hz), 133.2, 156.6, 157.2; HRMS calcd for $C_{15}H_{10}D_5ClO_2S$ ($M^+$) 299.0795, found 299.0988.

Conversion from compound 2e to compounds 3e-5e was followed by the same method as described in Scheme 5.

Compound 3e ($R_2$=d5, $R_2$=H). $^1$H NMR (500 MHz, $CDCl_3$) δ 2.50 (dd, J=4.8, 2.8 Hz, 1H), 2.79 (td, J=8.6, 0.7 Hz, 1H), 2.89 (dd, J=13.8, 5.9 Hz, 1H), 3.12 (dd, J=13.8, 5.2 Hz, 1H), 3.16-3.21 (m, 1H), 6.96 (d, J=9.0 Hz, 2H), 7.45 (d, J=9.0 Hz, 2H); $^{13}$C NMR (126 MHz, $CDCl_3$) δ 38.1, 47.6, 51.3, 118.9 (t, J=25.5 Hz), 119.3, 123.3 (t, J=23.9 Hz), 128.7, 129.5 (t, J=24.0 Hz), 133.6, 156.7, 157.2; HRMS calcd for $C_{15}H_9D_5O_2S$ ($M^+$) 263.1028, found 263.1035.

Compound 4e ($R_2$=d5, $R_2$=H). $^1$H NMR (500 MHz, $CDCl_3$) δ 2.48 (dd, J=4.8, 2.1 Hz, 1H), 2.81-2.84 (m, 1H), 3.24-3.36 (m, 3H), 7.09 (d, J=9.0 Hz, 2H), 7.89 (d, J=9.0 Hz, 2H); $^{13}$C NMR (126 MHz, $CDCl_3$) δ 45.7, 45.8, 59.5, 117.6, 120.0 (t, J=24.7 Hz), 124.7 (t, J=23.9 Hz), 129.7 (t, J=24.7 Hz), 130.5, 132.4, 154.6, 162.7; HRMS calcd for $C_{15}H_9D_5O_4S$ ($M^+$) 295.0926, found 295.0929.

Compound 5e ($R_2$-$d_5$, $R_2$=H). $^1$H NMR (500 MHz, $CDCl_3$) δ 2.16 (dd, J=5.2, 1.7 Hz, 1H), 2.54 (dd, J=6.2, 1.4 Hz, 1H), 3.03-3.10 (m, 1H), 3.18 (dd, J=14.1, 7.9 Hz, 1H), 3.53 (dd, J=14.1, 5.5 Hz, 1H), 7.10 (d, J=9.0 Hz, 2H), 7.87 (d, J=9.0 Hz, 2H); $^{13}$C NMR (126 MHz, $CDCl_3$) δ 24.4, 26.3, 62.8, 117.9, 120.2 (t, J=23.9 Hz), 124.9 (t, J=25.0 Hz), 129.9 (t, J=24.7 Hz), 130.9, 132.0, 154.8, 163.1; HRMS calcd for $C_{15}H_{10}D_5O_3S_2$ ($M+H^+$) 312.0773, found 312.0796.

Compounds of Scheme 9.

Compound 28a ($R_2$=p-$NO_2$, Rz=allylthio). To a stirred solution of 19a (3.46 g, 20.8 mmol) in DMF (100 ml) were added cesium carbonate (10.2 g, 31.2 mmol) and 1-fluoro-4-nitrobenzene (25a) (2.94 g, 20.8 mmol) at room temperature, and the mixture was stirred at the same temperature for 2 days. After dilution with water, the mixture was extracted into hexane (3×). The combined organic layer was washed with water and brine, dried over $Na_2SO_4$, and concentrated under reduced pressure to give 28a (5.32 g, 89%) as a pale yellow oil. $^1$H NMR (300 MHz, $CDCl_3$): δ 3.55 (dt, 2H, J=6.9, 1.2 Hz), 5.10 (dt, 1H, J=10.2, 1.2 Hz), 5.13 (dt, 1H, J=17.1, 1.2 Hz), 5.88 (ddt, 1H, J=17.1, 10.2, 6.9 Hz), 6.98-7.04 (m, 4H), 7.38-7.43 (m, 2H), 8.18-8.22 (m, 2H); $^{13}$C NMR (125 MHz, $CDCl_3$): δ 37.8, 117.1, 117.9, 120.9, 126.0, 132.3, 132.5, 133.4, 142.7, 153.4, 163.1; HRMS (FAB) calcd for $C_{16}H_{17}NO_3S_2$ ($M^+$) 287.0616, found 287.0593.

Compound 29a ($R_2$=p-$NO_2$, $R_2$=dimethylthiocarbamyl). Preparation of compound 29 was accomplished by the method for the synthesis of compound 28a using 2-chloro-5-nitropyridine (26a) and compound 20a. $^1$H NMR (500 MHz, $CDCl_3$) δ 3.12 (d, J=33.3 Hz, 6H), 7.06 (d, J=9.0 Hz, 1H), 7.19 (d, J=8.6 Hz, 2H), 7.58 (d, J=8.6 Hz, 2H), 8.10 (m, 1H), 8.49 (d, J=1.4 Hz, 1H), 9.04 (d, J=1.4 Hz, 6H); $^{13}$C NMR (126 MHz, $CDCl_3$) δ 37.2, 111.7, 122.2, 125.7, 126.4, 135.2, 137.5, 145.1, 153.7, 166.7 (s); HRMS calcd for $C_{25}H_{30}N_5O_6S$ (M+H$^+$) 528.1917, found 528.1920.

Compounds of Scheme 10.

Compound 34a ($R_1=R_2=H$, $R_3=Me$, n=1,4-carbonyloxy). A mixture of compound 33a (100 mg, 310 μmol) and pyridine (50 μL, 620 μmol) in $CH_2Cl_2$ (1 mL) in ice-water bath was added acetic anhydride (32 μL, 340 μmol) and the resulting solution was stirred for 1 hour. The reaction mixture washed with water and the volatile was concentrated and the crude product was purified by column chromatography. $^1$H NMR (500 MHz, CDCl$_3$) δ 2.15 (dd, J=4.8, 1.4 Hz, 1H), 2.31 (s, 3H), 2.52 (d, J=6.2 Hz, 1H), 3.05 (m, 1H), 3.18 (dd, J=14.3, 7.8 Hz, 1H), 3.51 (dd, J=14.3, 5.7 Hz, 1H), 7.07-7.16 (m, 6H), 7.86 (d, J=9.0 Hz, 2H); $^{13}$C NMR (126 MHz, CDCl$_3$) δ21.2, 24.3, 26.2, 62.7, 117.8, 121.4, 123.5, 130.9, 132.2, 147.7, 152.3, 162.8, 169.5.

Compounds 34b-34h were prepared in the same manner as described for 34a, with the exception corresponding acid chlorides or anhydrides was used in place of acetic anhydride.

Compound 34b ($R_1=R_2=H$, $R_3=$t-Bu, n=1,4-carbonyloxy). $^1$H NMR (500 MHz, CDCl$_3$) δ 1.40 (s, 9H), 2.17 (dd, J=5.2, 1.7 Hz, 1H), 2.55 (dd, J=6.2, 1.7 Hz, 1H), 3.08 (m, 1H), 3.19 (dd, J=14.3, 7.8 Hz, 1H), 3.53 (dd, J=14.1, 5.5 Hz, 1H), 7.09-7.14 (m, 6H), 7.87 (d, J=9.0 Hz, 2H); $^{13}$C NMR (126 MHz, CDCl$_3$) δ 24.4, 26.3, 27.3, 39.3, 62.8, 117.8, 121.5, 123.5, 130.9, 132.2, 148.2, 152.1, 163.1, 177.3.

Compound 34c ($R_1=R_2=H$, $R_3=$Ph, n=1,4-carbonyloxy). $^1$H NMR (500 MHz, CDCl$_3$) δ 2.17 (dd, J=5.2, 1.7 Hz, 1H), 2.54 (dd, J=4.5, 1.7 Hz, 1H), 3.04-3.09 (m, 1H), 3.20 (dd, J=14.3, 7.8 Hz, 1H), 3.53 (dd, J=14.3, 5.7 Hz, 1H), 7.15 (t, J=8.6 Hz, 4H), 7.29 (d, J=9.0 Hz, 2H), 7.53 (t, J=7.8 Hz, 2H), 7.66 (t, J=7.6 Hz, 1H), 7.89 (d, J=9.0 Hz, 2H), 8.22 (d, J=7.2 Hz, 2H); $^{13}$C NMR (126 MHz, CDCl$_3$) δ 24.4, 26.2, 62.7, 117.8, 121.5, 123.7, 128.8, 129.3, 130.3, 130.9, 132.3, 134.0, 148.0, 152.4, 162.9, 165.3.

Compound 34d ($R_1=R_2=H$, $R_3=CH_2Ph$, n–1,4-carbonyloxy). $^1$H NMR (500 MHz, CDCl$_3$) δ 2.17 (m, 1H), 2.48 (s, 2H), 2.55 (t, J=6.0 Hz, 1H), 3.08 (m, 1H), 3.19 (m, 1H), 3.52 (m, 1H), 3.89 (s, 1H), 7.09 (t, J=8.6 Hz, 2H), 7.12-7.17 (m, 3H), 7.26-7.35 (m, 3H), 7.37-7.42 (m, 2H), 7.88 (ddd, J=11.8, 8.9, 2.8 Hz, 2H), 8.11 (d, J=7.9 Hz, 1H).

Compound 34e ($R_1=R_2=H$, $R_3=CH_{12}(CH_2)_9Br$, n=1,4-carbonyloxy). $^1$H NMR (500 MHz, CDCl$_3$) δ 1.57 (m, 2H), 1.78 (m, 2H), 1.92 (m, 2H), 2.14 (dd, J=5.2, 1.7 Hz, 1H), 2.52 (d, J=6.2 Hz, 1H), 2.59 (t, J=7.4 Hz, 3H), 3.04 (m, 1H), 3.18 (dd, J=14.1, 7.9 Hz, 1H), 3.43 (t, J=6.5 Hz, 3H), 3.50 (dd, J=14.3, 5.7 Hz, 1H), 7.07-7.11 (m, 4H), 7.12-7.15 (m, 2H), 7.86 (d, J=9.0 Hz, 2H); $^{13}$C NMR (126 MHz, CDCl$_3$) δ 24.1, 24.3, 26.2, 27.6, 32.4, 33.6, 34.1, 62.7, 117.8, 121.4, 123.4, 130.9, 132.2, 147.7, 152.2, 162.9, 172.0.

Compound 34f ($R_1=R_2=H$, $R_3=$4-methylphenyl, n=1,4-carbonyloxy). $^1$H NMR (500 MHz, CDCl$_3$) δ 2.18 (d, J=4.1 Hz, 1H), 2.47 (s, 3H), 2.56 (d, J=5.9 Hz, 1H), 3.08 (m, 1H), 3.19 (dd, J=14.1, 7.6 Hz, 1H), 3.54 (dd, J=14.1, 5.5 Hz, 1H), 7.15 (dd, J=8.8, 5.0 Hz, 4H), 7.30 (dd, J=23.1, 7.9 Hz, 4H), 7.89 (d, J=9.0 Hz, 2H), 8.11 (d, J=8.3 Hz, 2H); $^{13}$C NMR (126 MHz, CDCl$_3$) δ 22.0, 24.4, 26.3, 62.8, 117.9, 121.6, 123.8, 126.6, 129.6, 130.4, 131.0, 132.3, 144.9, 148.1, 152.3, 163.1, 165.4.

Compound 34g ($R_1=R_{21}=H$, $R_3=$4-nitrophenyl, n=1,4-carbonyloxy). $^1$H NMR (500 MHz, CDCl$_3$) δ2.18 (dd, J=5.0, 1.9 Hz, 1H), 2.56 (d, J=6.2 Hz, 1H), 3.08 (m, 1H), 3.22 (dd, J=14.3, 7.8 Hz, 1H), 3.53 (dd, J=14.5, 5.9 Hz, 1H), 7.17 (dd, J=14.8, 9.0 Hz, 4H), 7.32 (d, J=9.0 Hz, 1H), 7.91 (d, J=9.0 Hz, 2H), 8.34-8.43 (m, 4H); $^{13}$C NMR (126 MHz, CDCl$_3$) δ24.4, 26.3, 62.8, 118.1, 121.7, 123.5, 124.0, 124.4, 131.1, 131.5, 131.9, 132.6, 134.8, 147.5, 151.2, 152.9, 162.8, 163.5.

Compound 34h ($R_1=R_2=H$, $R_3=$4-methoxyphenyl, n=1, 4-carbonyloxy). $^1$H NMR (500 MHz, CDCl$_3$) δ 2.18 (dd, J=5.2, 1.7 Hz, 1H), 2.56 (dd, J=6.2, 1.0 Hz, 1H), 3.08 (m, 1H), 3.19 (dd, J=14.3, 7.8 Hz, 1H), 3.54 (dd, J=14.3, 5.7 Hz, 1H), 3.92 (s, 3H), 7.01 (d, J=9.0 Hz, 2H), 7.15 (dd, J=9.0, 3.8 Hz, 4H), 7.28 (d, J=9.0 Hz, 2H), 7.89 (d, J=9.0 Hz, 2H), 8.17 (d, J=9.0 Hz, 2H); $^{13}$C NMR (126 MHz, CDCl$_3$) δ 24.4, 26.3, 55.8, 62.8, 114.1, 117.9, 121.6, 121.6, 123.8, 131.0, 132.3, 132.5, 148.2, 152.3, 163.1, 164.3, 165.1.

Compound 35a ($R_1=R_2=H$, $R_3=Me$, n=1,4-sulfonyloxy). A mixture of compound 33a (100 mg, 310 μmol) and Et$_3$N (86 μL, 620 mmol) in $CH_2Cl_2$ (1 mL) in ice-water bath was added acetic anhydride (26 μL, 340 μmol) and the resulting solution was stirred for 1 hour. The reaction mixture washed with water and the volatile was concentrated and the crude product was purified by column chromatography. $^1$H NMR (500 MHz, CDCl$_3$) δ 2.13 (dd, J=5.2, 1.7 Hz, 1H), 2.51 (d, J=6.2 Hz, 1H), 3.03 (m, 1H), 3.18 (s, 3H), 3.22 (dd, J=14.1, 7.6 Hz, 1H), 3.47 (dd, J=14.3, 6.0 Hz, 1H), 7.10 (dd, J=9.0, 2.8 Hz, 4H), 7.32 (d, J=9.3 Hz, 2H), 7.87 (d, J=9.0 Hz, 2H); $^{13}$C NMR (126 MHz, CDCl$_3$) δ 24.2, 26.1, 37.5, 62.5, 118.2, 121.6, 124.0, 130.9, 132.6, 145.6, 153.8, 162.1.

Compounds 35b-35g were prepared in the same manner as described for 35a, with the exception corresponding sulfonyl chlorides was used in place of mesylehloride.

Compound 35b ($R_1=R_2=H$, $R_3=$n-Pr, n=1,4-sulfonyloxy). $^1$H NMR (300 MHz, CDCl$_3$) δ 1.14 (t, J=7.5 Hz, 3H), 2.03 (m, 2H), 2.16 (dd, J=5.0, 1.7 Hz, 1H), 2.53 (dd, J=6.1, 1.7 Hz, 1H), 3.06 (m, 1H), 3.25 (m, 3H), 3.50 (dd, J=14.4, 5.8 Hz, 1H), 7.13 (d, J=8.8 Hz, 4H), 7.33 (d, J=8.8 Hz, 2H), 7.89 (d, J=8.6 Hz, 2H); $^{13}$C NMR (75 MHz, CDCl$_3$) δ 12.9, 17.4, 24.2, 26.2, 52.2, 62.5, 118.1, 121.6, 124.1, 130.9, 132.6, 145.6, 153.6, 162.3.

Compound 35c (R=$R_2=H$, $R_3=$i-Pr, n=1,4-sulfonyloxy). $^1$H NMR (300 MHz, CDCl$_3$) δ 1.56 (d, J=6.6 Hz, 6H), 2.14 (dd, J=5.2, 1.7 Hz, 1H), 2.52 (d, J=6.1 Hz, 1H), 3.06 (m, 1H), 3.22 (dd, J=14.1, 7.5 Hz, 1H), 3.50 (m, 2H), 7.10 (d, J=8.6 Hz, 4H), 7.31 (d, J=9.1 Hz, 2H), 7.87 (d, J=8.6 Hz, 2H); $^{13}$C NMR (75 MHz, CDCl$_3$) δ 16.8, 24.2, 26.1, 52.7, 62.5, 118.0, 121.5, 124.0, 130.9, 132.5, 145.5, 153.4, 162.3.

Compound 35d ($R_1=R_2=H$, $R_3=$Ph, n=1,4-sulfonyloxy). 39-phenylsulfonyl $^1$H NMR (500 MHz, CDCl$_3$) δ 2.16 (dd, J=5.0, 1.6 Hz, 1H), 2.53 (dd, J=6.2, 1.4 Hz, 1H), 3.05 (m, 1H), 3.22 (dd, J=14.1, 7.6 Hz, 1H), 3.49 (dd, J=14.5, 5.9 Hz, 1H), 6.98-7.05 (m, 4H), 7.07 (d, J=9.0 Hz, 2H), 7.56 (t, J=7.9 Hz, 2H), 7.69 (t, J=7.6 Hz, 1H), 7.87 (dd, J=8.6, 6.5 Hz, 4H); $^{13}$C NMR (126 MHz, CDCl$_3$) δ 24.3, 26.2, 62.7, 118.2, 121.3, 124.4, 128.6, 129.4, 131.0, 132.8, 134.6, 135.2, 146.2, 153.7, 162.3.

Compound 35e ($R_1=R_2=H$, $R_3=$4-methylphenyl, u=1,4-sulfonyloxy). $^1$H NMR (500 MHz, CDCl$_3$) δ 2.15 (dd, J=5.2, 1.7 Hz, 1H), 2.46 (s, 3H), 2.53 (d, J=6.2 Hz, 1H), 3.06 (m, 11:1), 3.22 (dd, J=14.5, 7.6 Hz, 1H), 3.48 (m, 1H), 7.01 (d, J=12.1 Hz, 4H), 7.07 (d, J=9.0 Hz, 2H), 7.34 (d, J=8.3 Hz, 2H), 7.73 (d, J=7.9 Hz, 2H), 7.88 (d, J=8.6 Hz, 2H); $^{13}$C NMR (126 MHz, CDCl$_3$) δ 22.8, 24.3, 26.2, 62.7, 118.2, 121.3, 124.4, 128.7, 130.0, 131.0, 132.3, 132.8, 145.8, 146.4, 153.6, 162.4.

Compound 35f ($R_1=R_2=H$, $R_3=$4-methoxyphenyl, n=1, 4-sulfonyloxy). $^1$H NMR (500 MHz, CDCl$_3$) δ 2.14 (d, J=5.2 Hz, 1H), 2.52 (d, J=6.2 Hz, 1H), 3.04 (m, 1H), 3.21 (dd, J=14.5, 7.6 Hz, 1H), 3.48 (dd, J=14.1, 5.9 Hz, 1H), 3.88 (s, 3H), 7.00 (dd, J=11.4, 9.6 Hz, 6H), 7.06 (d, J=8.6 Hz, 2H), 7.75 (d, J=8.6 Hz, 2H), 7.87 (d, J=8.6 Hz, 2H); $^{13}$C NMR (126

MHz, CDCl$_3$) δ 24.3, 26.2, 55.9, 62.6, 114.5, 118.1, 121.3, 124.4, 124.4, 126.3, 130.9, 131.0, 132.7, 146.3, 153.5, 162.3, 164.4.

Compound 35g (R$_1$=R$_2$=H, R$_3$=2,4,6-trimethylphenyl, n=1,4-sulfonyloxy). $^1$H NMR (500 MHz, CDCl$_3$) δ 1.21 (d, J=6.9 Hz, 12H), 1.27 (d, J=7.2 Hz, 6H), 2.15 (dd, J=5.2, 1.4 Hz, 1H), 2.53 (m, 1H), 2.94 (m, 1H), 3.05 (m, 1H), 3.21 (dd, J=14.1, 7.6 Hz, 1H), 3.49 (dd, J=14.5, 5.9 Hz, 1H), 4.08 (m, 1H), 7.01-7.06 (m, 6H), 7.21-7.23 (m, 2H), 7.86 (d, J=9.0 Hz, 2H); $^{13}$C NMR (126 MHz, CDCl$_3$) δ 23.7, 24.3, 24.7, 26.2, 29.9, 34.4, 62.7, 117.9, 121.5, 124.1, 124.6, 129.4, 130.9, 132.6, 146.3, 151.4, 153.5, 154.7, 162.5.

Compound 37b (R$_1$=R$_2$=H, R$_3$=i-Bu, n=1,4-carboxymethyl). To s stirred solution of 36a (50 mg, 0.14 mmol), EDC (53 mg, 0.28 mmol), DMAP (1.3 mg, 0.01 mmol) in CH$_2$Cl$_2$ (5 ml) was added iso-butanol (0.013 mml, 10.43 mg, 0.14 mmol) and the mixture was stirred at room temperature for 2 hours. The solution was concentrated under reduced pressure. The residue was dissolved in ethyl acetate, washed with 10% citric acid solution, saturated NaHCO$_3$-solution, water and brine, dried over MgSO$_4$ and concentrated under reduced pressure. The residue was purified by silica gel column chromatography (hexane/ethyl acetate=2/1) to give 37b as a colorless oil (35 mg, 0.08 mmol, 60%). $^1$H-NMR (300 MHz, CDCl$_3$, TMS): δ 0.92 (d, 6H, J=6.7 Hz), 1.94 (sep, 1H, J=6.7 Hz), 2.17 (dd, 1H, J=5.1, 1.8 Hz), 2.55 (dd, 1H, J=6.3, 1.7 Hz), 3.07 (m, 1H), 3.18 (dd, 1H, J=14.0, 7.8 Hz), 3.53 (dd, 1H, J=13.9, 5.4 Hz), 3.66 (s, 2H), 3.91 (d, 2H, J=6.6 Hz), 7.07 (m, 4H), 7.35 (m, 2H), 7.87 (m, 2H). $^{13}$C—N (500 MHz, CDCl$_3$, TMS): δ 19.0, 24.3, 26.1, 27.7, 40.7, 62.7, 71.1, 117.4, 120.6, 130.7 (d), 131.2 (d), 131.3, 131.9, 153.7, 162.9, 171.4 MS (FAB) m/z 420.1046 (calcd for C$_{21}$H$_{24}$O$_5$S$_2$ [M]$^+$ 420.1065) TLC R$_f$=0.54 (1:1 hexanes/EtOAc)

Compounds 37c-37g were prepared in the same manner as described for compound 37b with the exception of corresponding alcohol was used instead of isobutanol.

Compound 37c (R$_1$=R$_2$=H, R$_3$=4-chlorobenzyl, n=1,4-carboxymethyl). $^1$H-NMR (300 MHz, CDCl$_3$, TMS): δ 2.16 (dd, 1H, 5.1, 1.7 Hz), 2.54 (dd, 1H, 6, 1.4 Hz), 3.06 (m, 1H), 3.18 (dd, 1H, 14.1, 7.8 Hz), 3.52 (dd, 1H, 13.8, 5.4 Hz), 3.69 (s, 2H), 5.12 (s, 2H), 7.06 (m, 4H), 7.29 (m, 6H), 7.86 (m, 2H) $^{13}$C-NMR (500 MHz, CDCl$_3$, TMS): δ 24.3, 26.1, 40.5, 62.7, 66.0, 117.4, 117.8, 120.6, 128.8, 129.6, 130.7, 130.8, 131.2 (d), 132.0, 134.2, 153.9, 162.8, 171.1 MS (FAB) m/z 489.0576 (calcd for C$_{24}$H$_{22}$ClO$_5$ [M+H]$^+$ 489.0597) TLC R$_f$=0.53 (1:1 hexanes/EtOAc)

Compound 37d (R$_1$=R$_2$=H, R$_3$=thiophen-2-yl, n=1,4-carboxymethyl). $^1$H-NMR (500 MHz, acetone, TMS): δ 2.18 (dd, 1H, J=5.0, 1.4 Hz), 2.55 (dd, H, 6.0, 1.3 Hz), 3.06 (m, 1H), 3.40 (dd, 1H, 14.5, 7.3 Hz), 3.59 (dd, 1H, 14.5, 6.1 Hz), 3.74 (s, 2H), 5.33 (s, 2H), 7.01 (m, 1H), 7.14 (m, 5H), 7.41 (m, 2H), 7.48 (m, 1H), 7.94 (m, 2H) $^{13}$C-NMR (500 MHz, CDCl$_3$, TMS): δ 24.3, 26.1, 40.4, 61.1, 62.7, 117.4, 117.7, 120.6, 126.9, 127.0, 128.3, 130.7, 130.8 (d), 131.2 (d), 131.9, 137.6, 153.9, 162.9, 171.1 MS (FAB)—(measurement was not possible) TLC R$_f$=0.53 (1:1 hexanes/EtOAc)

Compound 37e (R$_1$=R$_2$=H, R$_3$=pyridin-2-yl)methyl, n=1,4-carboxymethyl). $^1$H-NMR (300 MHz, CDCl$_3$, TMS): δ 2.17 (dd, 1H, J=5.1, 1.7 Hz), 2.54 (dd, 1H, J=6.0, 1.4 Hz), 3.07 (m, 1H), 3.19 (dd, 1H, J=13.8, 7.8 Hz), 3.53 (dd, 1H, J=14.1, 5.4 Hz), 3.78 (s, 1H), 5.30 (s, 1H), 7.08 (m, 4H), 7.32 (m, 4H), 7.72 (d of t, 1H, J=7.8, 1.5 Hz), 7.87 (m, 2H), 8.62 (d, 1H, J=4.9 Hz), $^{13}$C-NMR (500 MHz, CDCl$_3$, TMS): δ 24.3, 26.1, 40.4, 62.6, 67.3, 117.4, 117.8, 120.6, 121.9, 123.1, 130.8 (t), 131.3 (d), 132.0, 136.9, 149.5, 153.9, 155.4, 162.9, 171.1 MS (FAB) m/z 456.0943 (calcd for C$_{23}$H$_{22}$O$_5$NS$_2$ [M+H]$^+$ 456.0939) TLC R$_f$=0.19 (1:1 hexanes/EtOAc)

Compound 37f (R$_1$=R$_2$=H, R$_3$= pyridin-3-yl)methyl, n=1,4-carboxymethyl). $^1$H-NMR (500 MHz, acetone, TMS): δ 2.18 (dd, 1H, J=5.0, 1.4 Hz), 2.55 (dd, 1H, J=6.5, 1.2 Hz), 3.06 (quinett t,t, 1H, J=6.2, 1.1 Hz), 3.41 (dd, 1H, J=14.5, 7.3 Hz), 3.59 (dd, 1H, J-14.5, 6.1 Hz), 3.79 (s, 2H), 5.21 (s, 2H), 7.15 (m, 4H), 7.37 (ddd, 1H, J=5.0, 8.0, 0.8 Hz), 7.43 (m, 2H), 7.77 (m, 1H), 7.95 (m, 2H), 8.54 (dd, 1H, J=4.5, 1.6 Hz), 8.59 (d, 1H, J=1.8 Hz) $^{13}$C-NMR (500 MHz, CDCl$_3$, TMS): δ 24.3, 26.1, 40.4, 62.6, 64.2, 117.5, 117.8, 120.6, 123.6, 130.5, 130.8 (d), 131.2 (d), 132.0, 136.2, 149.4, 149.5, 154.0, 162.8, 171.1 MS (FAB) m/z 456.0961 (calcd for C$_{23}$H$_{22}$O$_5$NS$_2$ [M+H]$^+$ 456.0939) TLC R$_f$=0.14 (1:1 hexanes/EtOAc)

Compound 37g (R$_1$=R$_2$=H, R$_3$=benzyl, n=1; 4-carboxymethyl). $^1$H-NMR (300 MHz, CDCl$_3$, TMS): δ 2.17 (dd, 1H, J=5.1, 1.7 Hz), 2.55 (dd, 1H, J=6.0, 1.1 Hz), 3.07 (m, 1H), 3.19 (dd, 1H, I=14.1, 7.9 Hz), 3.53 (dd, 1H, J 14.1, 5.4 Hz), 3.71 (s, 1H), 5.17 (s, 1H), 7.08 (m, 4H), 7.35 (m, 61), 7.87 (m, 2H) $^{13}$C-NMR (500 MHz, CDCl$_3$, TMS): δ 24.2, 26.1, 40.6, 62.7, 66.8, 117.7, 120.6, 128.2, 128.4, 128.6, 130.7, 130.8, 130.9, 131.2, 132.0, 135.7, 153.9, 162.9, 171.2 MS (FAB) m/z 455.0989 (calcd for C$_{24}$H$_{23}$O$_5$S$_2$ [M+H]$^+$ 455.0987) TLC R$_f$=0.53 (1:1 hexanes/EtOAc)

Compound 37h (R$_1$=R$_2$=H, R$_3$=perfluorophenyl, n=1,4-carboxymethyl). To a stirred solution of 36a (521 mg, 1.43 mmol), EDC (548 mg, 2.86 mmol), DMAP (12 mg, 0.1 mmol) in CH$_2$Cl$_2$ (30 ml) was added pentafluorophenol (PfP) (263 mg, 1.43 mmol) and the mixture was stirred overnight at room temperature. The solution was concentrated under reduced pressure. The residue was dissolved in ethyl acetate, washed with 10% citric acid solution, saturated NaHCO$_3$-solution, water and brine, dried over MgSO$_4$ and concentrated under reduced pressure to give the crude PfP-ester (636 mg). The crude material was used for the next step.

Compound 38a (R$_1$=R$_2$=H, R$_3$=diethyl, n=1,4-acetamide). To a stirred solution of 37h (54 mg, 0.10 mmol) in CH$_2$Cl$_2$ (5 ml) is added diethylamine (14.6 mg, 0.10 mmol) and the mixture is stirred overnight at room temperature. The solution was concentrated under reduced pressure. The residue was dissolved in ethyl acetate, washed with 10% citric acid solution, saturated NaHCO$_3$ solution, water and brine, dried over MgSO$_4$ and concentrated under reduced pressure. The residue was purified by silica gel column chromatography (hexane/ethyl acetate=1/2) to give 38a (23 mg, 0.055 mmol, 55%) as a colorless oil. $^1$H-NMR (500 MHz, CDCl$_3$, TMS): δ 1.14 (t, 3H, J=7.1 Hz), 1.16 (t, 3H, J=7.1 Hz) 2.16 (dd, 1H, J=5.0, 1.8 Hz), 2.54 (dd, 1H, J=6.0, 1.1 Hz), 3.06 (m, 1H), 3.17 (dd, 1H, 14.0, 7.9 Hz), 3.36 (q, 2H, J=7.1 Hz), 3.41 (q, 2H, J=7.1 Hz), 3.52 (dd, 1H, J=14.0, 5.5 Hz), 3.71 (s, 2H), 7.06 (m, 4H), 7.31 (m, 2H), 7.85 (m, 2H) $^{13}$C-NMR (500 MHz, CDCl$_3$, TMS): δ 13.0, 14.4, 24.3, 26.1, 39.8, 40.4, 42.4, 62.6, 117.3, 117.6, 120.6, 130.7 (d), 130.8 (d), 131.8, 132.7, 153.4, 163.0, 169.8 MS (FAB) m/z 420.1306 (calcd for C$_{21}$H$_{26}$O$_4$NS$_2$ [M+H]$^+$ 420.1303) TLC R$_f$=0.30 (1:2 hexanes/EtOAc)

Compounds 38b-38e were prepared in the same manner as described for compound 38a with the exception of corresponding amine was used instead of diethylamine.

Compound 38b (R$_1$=R$_2$=H, R$_3$=benzyl, n=1,4-acetamide). $^1$H-NMR (300 MHz, CDCl$_3$, TMS): δ 2.17 (dd, 1H, J=5.1, 1.8 Hz), 2.55 (dd, 1H, J=6.0, 1.7 Hz), 3.07 (m, 1H), 3.19 (dd, 1H, J=14.0, 7.8 Hz), 3.52 (dd, 1H, J=14.1, 5.7 Hz), 3.63 (s, 2H), 4.46 (d, 2H, J=5.7 Hz), 5.80 (m, 1H), 7.08 (m, 4H), 7.29 (m, 7H), 7.87 (m, 2H) $^{13}$C-NMR (500 MHz, CDCl$_3$, TMS): δ 24.2, 26.1, 43.0, 43.8, 62.6, 117.5, 117.8, 117.9, 120.8, 127.7, 128.8, 130.8 (d), 131.2 (d), 131.8, 132.1, 138.0, 154.1, 162.7, 170.4 MS (FAB) m/z 454.1162 (calcd for $C_{24}H_{24}O_4NS_2$ [M+2H]$^+$ 454.1147) TLC $R_f$=0.30 (1:1 hexanes/EtOAc)

Compound 38c ($R_1=R_2=H$, $R_3$=(furan-2-yl)methyl, n=1,4-acetamide). $^1$H-NMR (300 MHz, CDCl$_3$) δ 2.17 (dd, 1H, J=4.8, 1.8 Hz), 2.55 (dd, 1H, J=6.0, 1.7 Hz), 3.07 (m, 1H), 3.20 (dd, 1H, J=13.8, 7.7 Hz), 3.52 (dd, 1H, J=14.1, 5.6 Hz), 3.61 (s, 2H), 4.45 (d, 2H, J=5.6 Hz), 5.80 (m, 1H), 6.20 (d, 1H, J=3.3 Hz), 6.32 (m, 1H), 7.09 (m, 4H), 7.33 (m, 3H), 7.87 (m, 2H) $^{13}$C-NMR (500 MHz, CDCl$_3$, TMS): δ 24.2, 26.1, 36.7, 42.8, 62.7, 107.5, 110.4, 117.5, 117.8, 120.8, 130.8 (d), 131.2 (d), 131.6, 132.1, 142.3, 150.9, 154.1, 162.7, 170.3 MS (FAB) m/z 444.0920 (calcd for $C_{22}H_{22}O_5NS_2$ [M+2H]$^+$ 444.0939) TLC $R_f$=0.32 (1:1 hexanes/EtOAc)

Compound 38d ($R_1=R_2=H$, $R_3$=(pyridin-2-yl)methyl, n=1,4-acetamide). $^1$H-NMR (500 MHz, CDCl$_3$): δ 2.16 (dd 1H, J=5.0, 1.8 Hz), 2.54 (dd 1H, J=6.0, 1.5 Hz), 3.06 (m, 1H), 3.18 (dd, 1H, J=14.5, 7.8 Hz), 3.52 (dd, 1H, J=14.5, 5.6 Hz), 3.66 (s, 2H), 4.59 (d, 2H, J=5.0 Hz), 7.07 (m, 4H), 7.32 (m, 4H), 7.80 (m, 3H), 8.51 (d, 1H, J=5.0 Hz) $^{13}$C-NMR (500 MHz, CDCl$_3$): δ 24.2, 26.1, 42.8, 44.1, 62.7, 117.4, 117.8 (d), 120.8, 122.8, 122.9, 130.8, 131.3 (d), 131.9 (d), 137.9, 148.0, 153.9, 155.7, 162.9, 170.8 MS (FAB) m/z 455.1100 (calcd for $C_{23}H_{23}O_4N_2S_2$ [M+2H]$^+$) TLC $R_f$=0.42 (30:1 CH$_2$Cl$_2$/MeOH).

Compound 38e ($R_1=R_2=H$, $R_3$=(pyridin-3-yl)methyl, n=1,4-acetamide). $^1$H-NMR (500 MHz, CDCl$_3$): δ 2.16 (dd, 1H, J=5.0, 1.7 Hz), 2.54 (dd, 1H, J=6.0, 1.8 Hz), 3.06 (m, 1H), 3.19 (dd, 1H, J=14.5, 7.7 Hz), 3.50 (dd, 1H, J=14.0, 5.7 Hz), 3.63 (s, 2H), 4.46 (d, 2H, J=6.06 Hz), 5.98 (m, 1H), 7.07 (m, 4H), 7.30 (m, 3H), 7.60 (m, 1H), 7.83 (m, 2H), 8.47 (d, 1H, J=2.1 Hz), 8.51 (dd, 1H, J=5.0, 1.5 Hz) $^{13}$C-NMR (500 MHz, CDCl$_3$): δ 24.2, 26.1, 41.2, 42.8, 62.6, 117.6, 117.9 (d), 120.8, 123.7, 130.8 (d), 131.2 (d), 131.5, 132.2, 133.9, 135.7, 148.8, 154.2, 162.6, 170.7 MS (FAB) m/z 455.1101 (calcd for $C_{23}H_{23}O_4N_2S_2$ [M+2H]$^+$ 455.1099) TLC $R_f$=0.40 (30:1 CH$_2$Cl$_2$/MeOH).

Compounds of Scheme 11.

Compound 40=compound 28a ($R_2$=p-NO$_2$, $R_2$=allylthio).

Compound 42a (R=SO$_2$CH$_3$). To a stirred solution of 40 (636 mg, 2.21 mmol) in THF (22 mL) were added acetic acid (2.54 mL, 44.2 mmol) and zinc powder (5.80 g, 88.4 mmol) at room temperature, and the suspension was stirred for 30 minutes (an exothermic reaction). After dilution with ethyl acetate, the mixture was filtered through Celite. The filtrate was washed with saturated NaHCO$_3$ and brine, dried over Na$_2$SO$_4$, and concentrated under reduced pressure to give a crude 41 (577 mg) as an orange oil, which was employed in the next reaction without purification. To a stirred solution of 41 (577 mg) in CH$_2$Cl$_2$ (10 ml) were added pyridine (894 μL, 11.1 mmol) and methanesulfonyl chloride (205 μL, 2.65 mmol) at ice-water temperature. After 15 minutes, the mixture was warmed to room temperature and the stirring was continued for an additional 2 hours. Subsequent to the addition of saturated NaHCO$_3$, the mixture was extracted with ethyl acetate (3×). The combined organic layer was washed with 1 M aqueous HCl, saturated NaHCO$_3$ solution and brine, dried over Na$_2$SO$_4$, and concentrated under reduced pressure.

The resultant residue was purified by silica gel column chromatography (CH$_2$Cl$_2$) to give 42a (662 mg, 89% from 40) as a pale red solid. Compound 41: $^1$H NMR (300 MHz, CDCl$_3$): δ 3.45 (br.d, 2H, J=7.2 Hz), 3.59 (br.s, 2H), 5.01-5.06 (m, 2H), 5.84 (ddt, 1H, J=17.1, 9.6, 6.9 Hz), 6.66-6.70 (m, 2H), 6.83-6.88 (m, 4H), 7.29-7.32 (m, 2H). Compound 42: 1H MR (300 MHz, CDCl$_3$): δ 3.01 (s, 3H), 3.50 (dt, 2H, J=7.2, 1.2 Hz), 5.04-5.11 (m, 2H), 5.86 (ddt, 1H, J=16.8, 10.2, 6.9 Hz), 6.67 (br.s, 1H), 6.90-6.95 (m, 2H), 6.96-7.01 (m, 2H), 7.20-7.26 (m, 2H), 7.32-7.37 (m, 2H); $^{13}$C NMR (75 MHz, CDCl$_3$): δ 38.4, 39.3, 117.5, 119.3, 119.9, 123.8, 130.2, 132.0, 132.9, 133.8, 155.2, 156.1; HRMS (FAB) calcd for $C_{16}H_{17}NO_3S_2$ (M$^+$) 335.0650, found 335.0639.

Compound 42b (R=COCH$_3$). To a stirred solution of 41 (794 mg), which was prepared from 40 (830 mg, 2.89 mmol) in the same manner as described for compound 42, in CH$_2$Cl$_2$ (15 ml) were added pyridine (500 μL, 6.18 mmol) and acetic anhydride (292 μL, 3.09 mmol) at ice-water temperature, and the mixture was stirred at the same temperature for 1 hour. Subsequent to the addition of saturated NaHCO$_3$, the mixture was extracted with ethyl acetate (3×). The combined organic layer was washed with 1 M aqueous HCl, saturated NaHCO$_3$ solution and brine, dried over Na$_2$SO$_4$, and concentrated under reduced pressure.

The resultant residue was purified by silica gel column chromatography (ethyl acetate/CH$_2$Cl$_2$=1/8) to give 42b (782 mg, 99% from 40) as a white solid. $^1$H NMR (500 MHz, CDCl$_3$): δ 2.17 (s, 3H), 3.47 (d, 2H, J=7.0 Hz), 5.04-5.07 (m, 2H), 5.85 (ddt, 1H, J=17.0, 10.0, 7.0 Hz), 6.87-6.90 (m, 2H), 6.94-6.97 (m, 2H), 7.31-7.35 (m, 2H), 7.44-7.47 (m, 2H), 7.54 (br.s, 1H); $^{13}$C NMR (75 MHz, CDCl$_3$): δ 24.4, 38.5, 117.5, 118.7, 119.6, 121.7, 129.0, 132.9, 133.6, 133.7, 153.1, 156.7, 168.4; HRMS (FAB) calcd for $C_{17}H_{17}NO_2S$ (M$^+$) 299.0980, found 299.0980.

Conversion from compounds 40, 42a, and 42b to compounds 4f, 43-44 respectively was followed by the same method as described in Scheme 6.

Compound 4f ($R_1$=4-NO$_2$, $R_2$=H). $^1$H NMR (500 MHz, CDCl$_3$): δ 2.51 (dd, 1H, J=4.5, 2.5 Hz), 2.83 (t, 1H, J=4.5 Hz), 3.28 (dd, 1H, J=14.0, 7.0 Hz), 3.35 (m, 1H), 3.41 (dd, 1H, J=14.0, 4.0 Hz), 7.16-7.17 (m, 2H), 7.23-7.25 (m, 2H), 7.99-8.01 (m, 2H), 8.28-8.30 (m, 2H); $^{13}$C NMR (125 MHz, CDCl$_3$): δ 45.7, 45.8, 59.6, 119.1, 119.6, 126.2, 131.0, 134.9, 144.0, 160.2, 160.8; HRMS (FAB) calcd for $C_{15}H_{14}NO_6S$ (M+H$^+$) 336.0542, found 336.0545.

Compound 5f ($R_1$=4-NO$_2$, $R_2$=H). $^1$H NMR (500 MHz, CDCl$_3$): δ 2.58 (dd, 1H, J=6.0, 2.0 Hz), 3.10 (m, 1H), 3.31 (dd, 1H, J=14.0, 7.5 Hz), 3.52 (dd, 1H, J=14.0, 6.5 Hz), 7.15-7.18 (m, 2H), 7.23-7.26 (m, 2H), 7.97-8.00 (m, 2H), 8.28-8.31 (m, 2H); $^{13}$C NMR (125 MHz, CDCl$_3$): δ 24.0, 26.0, 62.5, 119.1, 119.8, 126.2, 131.2, 134.4, 160.3, 160.8; $^{13}$C NMR (125 MHz, acetone-d$_6$): δ 24.5, 27.2, 62.6, 120.2, 121.0, 127.1, 132.3, 136.2, 145.0, 161.1, 162.4; HRMS (FAB) calcd for $C_{15}H_{14}NO_5S_2$ (M$^+$H$^+$) 352.0313, found 352.0297.

Compound 4g=compound 43a ($R_1$=4-CH$_3$SO$_2$NH, $R_2$=H). $^1$H NMR (300 MHz, CDCl$_3$): δ 2.49 (dd, 1H, J=5.1, 1.8 Hz), 2.83 (m, 1H), 3.06 (s, 3H), 3.27-3.36 (m, 3H), 6.77 (br.s, 1H), 7.08-7.11 (m, 4H), 7.28-7.33 (m, 2H), 7.88-7.93 (m, 2H); $^{13}$C NMR (125 MHz, acetone-d$_6$): δ 39.4, 45.9, 46.6, 59.9, 118.3, 122.3, 123.6, 131.6, 134.6, 136.5, 152.7, 163.5; HRMS (FAB) calcd for $C_{16}H_{17}NO_6S_2$ (M$^+$) 383.0497, found 383.0496.

Compound 5g=compound 44a ($R_1$=4-CH$_3$SO$_2$NH, $R_2$=H). $^1$H NMR (300 MHz, CDCl$_3$): δ 2.17 (dd, 1H, J=5.1, 1.8 Hz), 2.55 (dd, 1H, J=6.3, 1.2 Hz), 3.06 (s, 3H), 3.07 (m, 1H), 3.22 (dd, 1H, J=14.1, 7.8 Hz), 3.50 (dd, 1H, J=14.1, 5.7 Hz), 6.72 (br.s, 1H), 7.08-7.12 (m, 4H), 7.30-7.33 (m, 2H), 7.87-7.91 (m, H); $^{13}$C NMR (125 MHz, acetone-d$_6$): δ 24.4, 27.2, 39.3, 62.6, 118.4, 122.3, 123.6, 131.9, 133.9, 136.4, 152.7, 163.6; HRMS (FAB) calcd for $C_{16}H_{17}NO_5S_3$ (M$^+$) 399.0269, found 399.0268.

Compound 4h=compound 43b ($R_1$=4-CH$_3$CONH, $R_2$=H). $^1$H NMR (300 MHz, CDCl$_3$): δ 2.20 (s, 3H), 2.48 (dd, 1H, J=4.5, 1.5 Hz), 2.82 (m, 1H), 3.26-3.34 (m, 3H), 7.03-7.08 (m, 4H), 7.41 (br.s, 1H), 7.55-7.58 (m, 2H), 7.85-7.88 (m, 2H); $^{13}$C NMR (75 MHz, CDCl$_3$): δ 24.1, 45.7, 45.8, 59.8, 117.6, 120.8, 122.0, 130.4, 133.0, 135.4, 151.1, 163.0, 168.5; HRMS (FAB) calcd for C$_{17}$H$_{18}$NO$_5$S (M$^+$H$^+$) 348.0906, found 348.0913.

Compound 5h=compound 44b (R$_1$=4-CH$_3$CONH, R$_2$=H). $^1$H NMR (300 MHz, CDCl$_3$): δ 2.16 (dd, 1H, J=5.1, 1.8 Hz), 2.20 (s, 3H), 2.54 (dd, 1H, J=6.3, 1.5 Hz), 3.06 (m, 1H), 3.19 (dd, 1H, J=14.1, 7.8 Hz), 3.52 (dd, 1H, J=14.1, 5.7 Hz), 7.03-7.08 (m, 4H), 7.52 (br.s, 1H), 7.56-7.59 (m, 2H), 7.84-7.87 (m, 2H); $^{13}$C NMR (125 MHz, CDCl$_3$): δ 24.1, 24.4, 26.0, 62.6, 117.4, 121.0, 121.8, 130.7, 131.6, 135.2, 150.7, 163.1, 168.6; HRMS (FAB) calcd for C$_{17}$H$_{18}$NO$_4$S$_2$ (M$^+$H$^+$) 364.0677, found 364.0651

Conversion from compound 29a to compounds 3i-5i was followed by the same method as described in Schemes 8 and 11.

Compound 21b (R$_1$=4-CH$_3$SO$_2$NH, 2-pyridyl, R$_2$=H). $^1$H NMR (500 MHz, CDCl$_3$) δ 2.96 (s, 3H), 3.03 (br.s., 3H), 3.10 (br.s., 3H), 6.96 (d, J=9.0 Hz, 1H), 7.12 (d, J=8.8 Hz, 2H), 7.51 (d, J=8.8 Hz, 2H), 7.77 (dd, J=8.8, 2.8 Hz, 1H), 7.99 (d, J=2.8 Hz, 1H); HRMS calcd for C$_{25}$H$_{30}$N$_5$O$_6$S (M+H$^+$) 528.1917, found 528.1920.

Compound 4i (R$_1$=4-CH$_3$SO$_2$NH, 2-pyridyl, R$_2$=H). $^1$H NMR (500 MHz, 5% CD$_3$OD in CD$_2$Cl$_2$) δ 2.46 (dd, J=4.6, 2.0 Hz, 1H), 2.79 (t, J=4.4 Hz, 1H), 2.96 (s, 3H), 3.24-3.40 (m, 3H), 7.03 (d, J=8.8 Hz, 1H), 7.29 (d, J=8.4 Hz, 2H), 7.79 (dd, J=8.8, 2.8 Hz, 1H), 7.93 (d, J=8.6 Hz, 2H), 8.05 (d, J=3.0 Hz, 1H); $^{13}$C NMR (126 MHz, 5% CD$_3$OD in CD$_2$Cl$_2$) δ 39.7, 46.2, 46.3, 60.1, 113.9, 121.3, 130.8, 132.0, 134.7, 134.9, 141.1, 159.9, 160.0 (s); HRMS calcd for C$_{15}$H$_{17}$N$_2$O$_6$S$_2$ (M+H$^+$) 385.0528, found 385.0531.

Compound 5i (R$_1$=4-CH$_3$SO$_2$NH, 2-pyridyl, R$_2$=H). $^1$H NMR (500 MHz, 5% CD$_3$OD in CD$_2$Cl$_2$) δ 2.16 (dd, J=5.2, 1.8 Hz, 1H), 2.53 (dd, J=6.6, 1.8 Hz, 1H), 2.97 (s, 3H), 3.06 (m, 1H), 3.25 (dd, J=14.4, 7.6 Hz, 1H), 3.52 (dd, J=14.4, 6.0 Hz, 1H), 7.04 (dd, J=8.8, 0.4 Hz, 1H), 7.31 (d, J=8.6 Hz, 2H), 7.79 (dd, J=8.8, 2.8 Hz, 1H), 7.92 (d, J=8.8 Hz, 2H), 8.04 (d, J=2.8 Hz, 1H); $^{13}$C NMR (126 MHz, 5% CD$_3$OD in CD$_2$Cl$_2$) δ 24.5, 26.5, 39.8, 63.0, 113.8, 121.4, 131.0, 131.9, 134.4, 134.7, 141.1, 159.9, 160.1 (s); HRMS calcd for C$_{15}$H$_{17}$N$_2$O$_5$S$_3$ (M+H) 401.0300, found 401.0290.

Compound 48. 2-(4-Bromophenoxy)-phenol was prepared by reported method. A mixture of phenol (2.65 g, 10.0 mmol) and K$_2$CO$_3$ (1.45 g, 10.5 mmol) in DMF (20 mL) was stirred for 0.5 hours, and then benzylbromide (1.56 mL, ml3.0 mmol) was added. The reaction mixture was stirred at room temperature for 3 hours, then was diluted with ethyl acetate and water. The layers were separated and the aqueous layer was extracted with ethyl acetate. The combined organic layer was washed with water, 2 N HCl, sat'd NaHCO$_3$, and brine, dried under anhydrous MgSO$_4$, filtered, and dried under reduced pressure. The residue was purified by column chromatography to give the desired product as a white solid (3.00 g, 84%). $^1$H NMR (500 MHz, CDCl$_3$) δ 5.06-5.13 (m, 2H), 6.85 (d, J=9.0 Hz, 2H), 7.00 (t, J=9.0 Hz, 1H), 7.05-7.23 (m, 5H), 7.26-7.37 (m, 3H), 7.42 (d, J=9.0 Hz, 2H); $^{13}$C NMR (126 MHz, CDCl$_3$) δ 70.6, 114.6, 115.3, 118.6, 121.9, 122.4, 125.7, 127.2, 128.0, 128.6, 132.5, 136.8, 144.9, 150.7, 157.9;

Conversion from compound 48 to compounds 52a-55a was followed by the same method as described in Scheme 5.

Compound 2j=compound 52a (R$_1$=2-benzyloxy, R$_2$=H). $^1$H NMR (500 MHz, CDCl$_3$) δ 3.07 (ddd, J=44.7, 13.8, 5.4 Hz, 2H), 3.68 (ddd, J=19.9, 11.2, 4.4 Hz, 1H), 3.83-3.95 (m, 1H), 5.10 (s, 2H), 6.93 (d, J=8.6 Hz, 2H), 7.02 (t, J=7.6 Hz, 1H), 7.05-7.25 (m, 5H), 7.27-7.36 (m, 3H), 7.41 (d, J=8.6 Hz, 2H); $^{13}$C NMR (126 MHz, CDCl$_3$) δ 40.1, 48.1, 69.5, 70.8, 115.3, 117.5, 121.9, 122.4, 125.7, 126.6, 127.1, 127.9, 128.5, 132.1, 133.4, 136.8, 144.7, 150.7, 158.5.

Compound 3j (R$_1$=2-benzyloxy, R$_2$=H). $^1$H NMR (500 MHz, CDCl$_3$) δ 2.43 (dd, J=4.8, 2.4 Hz, 1H), 2.78 (t, J=4.4 Hz, 1H), 3.22 (dd, J=14.0, 5.2 Hz, 1H), 3.26-3.30 (m, 1H), 5.04-5.08 (m, 2H), 7.03-7.08 (m, 3H), 7.09-7.21 (m, 4H), 7.22-7.33 (m, 4H), 7.87 (d, J=8.8 Hz, 2H); $^{13}$C NMR (126 MHz, CDCl$_3$) δ 46.0, 46.1, 59.8, 70.7, 115.1, 116.5, 122.0, 123.1, 126.8, 127.1, 128.1, 128.6, 130.4, 131.9, 136.4, 143.2, 150.7, 163.4;

Compound 4j=compound 53a (R$_1$=2-benzyloxy, R$_2$=H). $^1$H NMR (500 MHz, CDCl$_3$) δ 2.47 (dd, J=5.0, 2.6 Hz, 1H), 2.76 (t, J=3.8 Hz, 1H), 2.88 (dd, J=14.0, 6.2 Hz, 1H), 3.12 (dd, J=13.6, 5.6 Hz, 1H), 3.16-3.20 (m, 1H), 5.09-5.12 (m, 2H), 6.95 (d, J=9.0 Hz, 2H), 7.03 (td, J=7.6, 1.6 Hz, 6H), 7.08-7.25 (m, 5H), 7.47 (d, J=8.8 Hz, 2H); $^{13}$C NMR (126 MHz, CDCl$_3$) δ 38.2, 47.4, 51.1, 70.6, 115.1, 117.2, 121.7, 122.3, 125.5, 127.0, 127.2, 127.8, 128.4, 133.7, 136.7, 144.6, 150.6, 158.2;

Compound 4jj=compound 54a (R$_1$=2-hydroxy, R$_2$=H). Compound 4j (0.50 g, 1.3 mmol) was stirred in the presence of Pd(OH)$_2$ (0.15 g) in ethylacetate/i-PrOH (20 mL) for 0.5 h in the atmosphere of H2. The reaction mixture was filtered through a layer of celite and the filtrate was concentrated under reduced pressure. The residue was purified by column chromatography to give the desired product (0.28 g, 70%). $^1$H NMR (500 MHz, CDCl$_3$) δ 2.45 (dd, J=3.4, 1.8 Hz, 1H), 2.77-2.83 (m, 1H), 3.24-3.30 (m, 3H), 6.89-6.95 (m, 1H), 6.97-7.02 (m, 1H), 7.04-7.10 (m, 3H), 7.11-7.18 (m, 1H), 7.82 (d, J=9.0 Hz, 2H); $^{13}$C NMR (126 MHz, CDCl$_3$) δ 46.0, 59.7, 117.2, 117.5, 121.3, 126.9, 130.7, 132.7, 141.4, 148.2, 162.5;

Compound 5j (R$_1$=2-benzyloxy, R$_2$=H). $^1$H NMR (500 MHz, CDCl$_3$) δ 2.10 (dd, J=5.0, 1.6 Hz, 1H), 2.49 (d, J=6.2 Hz, 1H), 3.04 (m, 1H), 3.13 (dd, J=14.1, 8.1 Hz, 1H), 3.55 (dd, J=14.2, 5.2 Hz, 1H), 5.07 (s, 2H), 7.04-7.09 (m, 3H), 7.11-7.17 (m, 3H), 7.23-7.31 (m, 5H), 7.85 (d, J=8.8 Hz, 2H); $^{13}$C NMR (126 MHz, CDCl$_3$) δ24.5, 26.3, 62.8, 70.7, 115.1, 116.6, 122.1, 123.0, 126.9, 127.1, 128.2, 128.6, 130.6, 131.4, 136.4, 143.2, 150.7, 163.5.

Compound 5jj=compound 55a (R$_1$=2-hydroxy, R$_2$=II). $^1$H NMR (500 MHz, CDCl$_3$) δ 2.15 (dd, J=5.0, 1.6 Hz, 1H), 2.53 (dd, J=6.0, 1.4 Hz, 8H), 3.01-3.08 (m, 1H), 3.18 (dd, J=14.2, 7.8 Hz, 1H), 3.50 (dd, J=14.4, 5.8 Hz, 1H), 5.78-5.85 (m, 1H), 6.94 (td, J=8.0, 1.6 Hz, 1H), 7.00 (dd, J=8.0, 1.2 Hz, 1H), 7.06-7.20 (m, 4H), 7.83 (d, J=8.8 Hz, 2H); $^{13}$C NMR (126 MHz, CDCl$_3$) δ 24.4, 26.2, 62.8, 117.5, 117.5, 121.1, 121.4, 126.9, 130.9, 132.4, 141.5, 148.1, 162.4.

Compounds of Scheme 12.

Compound 51. $^1$H NMR (500 MHz, CDCl$_3$) δ 5.06-5.08 (m, 2H), 6.85 (d, J=9.0 Hz, 2H), 6.97-7.00 (m, 4H), 7.34-7.50 (m, 7H); $^{13}$C NMR (126 MHz, CDCl$_3$) δ 70.7, 115.0, 116.2, 119.5, 121.0, 127.7, 128.2, 128.8, 132.7, 137.1, 150.0, 155.5, 157.9.

Conversion from compound 51 to compounds 52b-55b was followed by the same method as described in Scheme 5.

Compound 2k=compound 52b (R=4-benzyloxy, R$_2$=H). $^1$H NMR (500 MHz, CDCl$_3$) δ 3.05 (ddd, J=44.5, 13.8, 5.5 Hz, 2H), 3.67 (ddd, J=17.6, 11.0, 4.5 Hz, 2H), 5.06 (s, 2H), 6.90 (d, J=8.6 Hz, 2H), 6.98 (s, 4H), 7.34-7.47 (m, 7H); $^{13}$C NMR (126 MHz, CDCl$_3$) δ 39.9, 48.1, 69.6, 70.7, 116.2, 118.4, 121.2, 127.2, 127.6, 128.2, 128.8, 133.4, 137.1, 149.9, 155.5, 158.5.

Compound 3k (R$_1$=4-benzyloxy, R$_2$=H). $^1$H NMR (500 MHz, CDCl$_3$) δ 2.49 (dd, J=4.8, 2.8 Hz, 1H), 2.79 (t, J=4.5 Hz, 1H), 2.88 (dd, J=13.8, 5.9 Hz, 1H), 3.10 (dd, J=13.8, 4.8 Hz, 1H), 3.15-3.21 (m, 1H), 5.08 (s, 2H), 6.92 (d, J=8.6 Hz, 4H), 7.00 (s, 2H), 7.34-7.49 (m, 8H); $^{13}$C NMR (126 MHz, CDCl$_3$) δ 38.2, 47.5, 51.2, 70.6, 116.1, 118.2, 121.1, 127.6, 127.7, 128.1, 128.7, 133.8, 137.0, 149.9, 158.3.

Compound 4k=compound 53b (R$_1$=4-benzyloxy, R$_2$=H). $^1$H NMR (500 MHz, CDCl$_3$) δ 2.48 (dd, J=5.0, 1.9 Hz, 1H), 2.82 (dd, J=6.2, 2.8 Hz, 1H), 3.22-3.37 (m, 3H), 5.09 (s, 2H), 7.02-7.09 (m, 4H), 7.33-7.38 (m, 1H), 7.40-7.43 (m, 9H), 7.45-7.47 (m, 9H), 7.87 (d, J=9.0 Hz, 2H); $^{13}$C NMR (126 MHz, CDCl$_3$) δ 46.0, 59.8, 70.6, 116.4, 117.1, 122.0, 127.6, 128.3, 128.8, 130.6, 132.1, 136.8, 148.2, 156.4, 163.8.

Compound 4kk=compound 54b (R$_1$=4-hydroxy, R$_2$=H). $^1$H NMR (500 MHz, CDCl$_3$) δ 2.47 (dd, J=5.5, 1.4 Hz, 1H), 2.81 (dd, J=4.5, 2.4 Hz, 1H), 3.23-3.35 (m, 3H), 6.86 (d, J=9.0 Hz, 2H), 6.92 (d, J=9.0 Hz, 2H), 7.02 (d, J=9.0 Hz, 2H), 7.82 (d, J=9.0 Hz, 2H); $^{13}$C NMR (126 MHz, CDCl$_3$) δ 46.0, 59.8, 116.8, 117.0, 122.1, 130.6, 131.6, 147.3, 154.2, 163.6.

Compound 5k (R$_1$=4-benzyloxy, R$_2$=H). $^1$H NMR (500 MHz, CDCl$_3$) δ 2.18 (dd, J=5.2, 1.7 Hz, 1H), 2.56 (dd, J=6.2, 1.4 Hz, 1H), 3.08 (m, 1H), 3.19 (dd, J=14.1, 7.9 Hz, 1H), 3.54 (dd, J=14.1, 5.5 Hz, 1H), 5.11 (s, 2H), 7.06 (s, 5H), 7.08 (d, J=9.0 Hz, 2H), 7.35-7.51 (m, 4H), 7.87 (d, J=9.0 Hz, 2H); $^{13}$C NMR (126 MHz, CDCl$_3$) δ 24.4, 26.3, 62.8, 70.7, 116.4, 117.2, 121.9, 127.6, 128.2, 128.8, 130.8, 131.6, 136.8, 148.2, 156.4, 163.8.

Compound 5kk=compound 55b (R$_1$=4-hydroxy, R$_2$=H). $^1$H NMR (500 MHz, CDCl$_3$) δ 2.17 (dd, J=5.2, 1.7 Hz, 1H), 2.55 (dd, J=6.2, 1.7 Hz, 1H), 3.02-3.11 (m, 1H), 3.20 (dd, J=14.5, 7.9 Hz, 1H), 3.54 (dd, J=14.5, 5.9 Hz, 1H), 6.90 (d, J=8.6 Hz, 2H), 6.97 (d, J=9.0 Hz, 2H), 7.06 (d, J=9.0 Hz, 2H), 7.88 (d, J=9.0 Hz, 2H); $^{13}$C NMR (126 MHz, CDCl$_3$) δ 24.4, 26.2, 62.8, 117.0, 117.2, 122.2, 130.8, 131.2, 147.9, 153.5, 164.0.

Compounds of Scheme 13.

Synthesis of compounds 57 (=compound 21a), 58 (compound 3d) is described in Scheme 8. Conversion from compound 58 to compounds 59-61 was followed by the same method as described in Schemes 5 and 12.

Compound 4d=compound 59. $^1$H NMR (500 MHz, CDCl$_3$) δ 2.48 (dd, J=5.4, 2.0 Hz, 1H), 2.81 (t, J=4.4 Hz, 1H), 3.29-3.34 (m, 3H), 5.05-5.08 (m, 2H), 6.70 (dd, J=10.2, 2.2 Hz, 1H), 6.73 (t, J=2.2 Hz, 1H), 6.88 (dd, J=8.4, 2.4 Hz, 1H), 7.10 (d, J=8.8 Hz, 2H), 7.29-7.46 (m, 6H), 7.89 (d, J=8.8 Hz, 2H); $^{13}$C NMR (126 MHz, CDCl$_3$) δ 45.9, 45.9, 59.6, 70.2, 107.4, 111.8, 112.7, 117.8, 127.5, 128.2, 128.7, 130.5, 130.8, 132.6, 136.4, 155.8, 160.3, 162.6.

Compound 4dd=compound 60 (R$_1$=3-hydroxy, R$_2$=H). $^1$H NMR (500 MHz, CDCl$_3$) δ 2.48 (dd, J=4.5, 1.7 Hz, 1H), 2.82 (1,1H), 3.31 (m, 3H), 6.48 (br.s., 1H), 6.57 (t, J=2.4 Hz, 1H), 6.60 (ddd, J=8.3, 2.1, 0.7 Hz, 1H), 6.71 (ddd, J. 8.3, 2.4, 1.0 Hz, 1H), 7.08 (d, J=8.6 Hz, 2H), 7.23 (t, J=7.9 Hz, 1H), 7.85 (d, J=9.0 Hz, 2H); $^{13}$C NMR (126 MHz, CDCl$_3$) δ 46.1, 59.8, 108.0, 112.4, 112.6, 118.0, 130.6, 131.0, 132.2, 155.9, 157.8, 162.9.

Compound 5d (R$_1$=3-benzyloxy, R$_2$=H). $^1$H NMR (500 MHz, CDCl$_3$) δ 2.18 (dd, J=5.0, 1.4 Hz, 1H), 2.56 (d, J=5.2 Hz, 1H), 3.09 (m, 1H), 3.21 (dd, J=14.3, 7.9 Hz, 1H), 3.55 (dd, J=14.2, 5.6 Hz, 1H), 5.09 (s, 2H), 6.69-6.76 (m, 2H), 6.90 (dd, J=8.3, 2.1 Hz, 1H), 7.13 (d, J=8.8 Hz, 2H), 7.33-7.38 (m, 2H), 7.40-7.46 (m, 4H), 7.89 (d, J=8.8 Hz, 2H); $^{13}$C NMR (126 MHz, CDCl$_3$) δ 24.4, 26.2, 62.7, 70.3, 107.4, 111.9, 112.8, 118.0, 127.6, 128.3, 128.8, 130.8, 130.9, 132.1, 136.5, 156.0, 160.4, 162.7.

Compound 5dd=compound 61 (R$_1$=3-hydroxy, R$_2$=H). $^1$H NMR (500 MHz, CDCl$_3$) δ 2.12 (m, 1H), 2.50 (m, 1H), 3.02 (m, 1H), 3.21 (dd, J=14.1, 7.6 Hz, 1H), 3.50 (dd, J=14.1, 5.9 Hz, 1H), 6.60 (m, 2H), 6.73 (d, J=7.9 Hz, 1H), 6.86 (br.s., 1H), 7.08 (d, J=9.0 Hz, 2H), 7.22 (t, J=8.6 Hz, 1H), 7.83 (d, J=9.0 Hz, 2H); $^{13}$C NMR (126 MHz, CDCl$_3$) δ 24.3, 26.1, 62.6, 107.9, 112.2, 112.6, 118.0, 130.7, 131.0, 131.4, 155.8, 157.8, 162.9.

Compounds of Scheme 14.

Compound 63. Synthesis of compound 63 was done by the similar method for the preparation of compound 2e using 4-hydroxymethylphenyl-boronic acid (62) and compound 19. $^1$H NMR (500 MHz, CDCl$_3$) δ 2.89 (br.s., 1H), 2.94-3.03 (m, 1H), 3.08 (dd, J=13.8, 5.9 Hz, 1H), 3.58-3.66 (m, 2H), 3.85-3.91 (m, 1), 4.54 (d, J=17.6 Hz, 1H), 4.61 (s, 1H), 6.78 (t, J=8.6 Hz, 1H), 6.91 (t, J=7.9 Hz, 2H), 6.97 (d, J=8.3 Hz, 1H), 7.18 (dd, J=10.0, 8.3 Hz, 1H), 7.31 (t, J=9.0 Hz, 1H), 7.37 (d, J=8.6 Hz, 1H); $^{13}$C NMR (126 MHz, CDCl$_3$) δ 39.8, 48.1, 65.1, 69.6, 116.7, 119.5, 119.5, 125.5, 128.4, 128.7, 129.0, 129.2, 133.3, 135.7, 157.3 (s).

Conversion from compound 63 to compounds 64-33 was followed by the same method as described in Scheme 5.

Compound 3l. $^1$H NMR (500 MHz, CDCl$_3$) δ 2.47 (dd, J=4.8, 2.8 Hz, 1H), 2.74 (t, J=4.3 Hz, 1H), 2.80 (br s, 1H), 2.86 (dd, J=13.8, 5.9 Hz, 2H), 3.06 (dd, J=13.8, 5.2 Hz, 1H), 3.13 (m, 1H), 4.61 (s, 2H), 6.91 (d, J=8.6 Hz, 2H), 6.97 (d, J=8.6 Hz, 2H); $^{13}$C NMR (126 MHz, CDCl$_3$) δ 37.9, 47.4, 51.2, 64.5, 119.1, 119.2, 128.7, 133.4, 136.6, 156.0, 157.0.

Compound 4l=compound 64. $^1$H NMR (500 MHz, CDCl$_3$) δ 2.43 (dd, J=5.0, 2.2 Hz, 1H), 2.76 (dd, J=4.8, 3.8 Hz, 1H), 3.25 (m, 3H), 4.64 (s, 2H), 7.02 (dd, J=8.6, 7.9 Hz, 4H), 7.37 (d, J=8.6 Hz, 2H), 7.82 (d, J=9.0 Hz, 2H); $^{13}$C NMR (126 MHz, CDCl$_3$) δ 45.9, 45.9, 59.5, 64.3, 117.6, 120.5, 128.9, 130.5, 132.3, 138.1, 153.9, 162.9.

Compound 5l=compound 33. $^1$H NMR (500 MHz, CDCl$_3$) δ 2.14 (dd, J=5.2, 1.7 Hz, 1H), 2.41 (br.s., 1H), 2.52 (d, J=5.2 Hz, 1H), 3.03 (m, 1H), 3.18 (dd, J=14.1, 7.6 Hz, 1H), 3.49 (dd, J=14.3, 5.7 Hz, 2H), 4.69 (s, 2H), 7.07 (dd, J=8.6, 6.9 Hz, 4H), 7.41 (d, J=8.6 Hz, 2H), 7.84 (d, J=9.0 Hz, 2H); $^{13}$C NMR (126 MHz, CDCl$_3$) δ 24.3, 26.2, 62.7, 64.5, 117.8, 120.6, 129.1, 130.8, 131.9, 138.2, 154.1, 163.0.

Compounds of Scheme 15.

Compound 66=compound 10b. The synthesis of compound 10b was described previously. Conversion from compound 10b to compounds 4m-5m was followed by the same method as described in Scheme 6.

Compound 4m. $^1$H NMR (500 MHz, CDCl$_3$): δ 2.47 (dd, 1H, J=5.0, 2.0 Hz), 2.82 (m, 1H), 3.26-3.33 (m, 3H), 3.65 (s, 2H), 3.72 (s, 3H), 7.03-7.05 (m, 2H), 7.08-7.10 (m, 2H), 7.32-7.34 (m, 2H), 7.86-7.88 (m, 2H); $^{13}$C NMR (125 MHz, CDCl$_3$): δ 40.3, 45.8, 52.1, 59.6, 117.6, 120.6, 130.5, 130.9, 131.1, 132.4, 153.8, 162.8, 171.8; HRMS (FAB) calcd for C$_{18}$H$_{18}$O$_6$S (M$^+$) 362.0824, found 362.0829.

Compound 5m=compound 67. $^1$H NMR (500 MHz, CDCl$_3$): δ 2.15 (dd, 1H, J=5.5, 2.0 Hz), 2.53 (dd, 1H, J=6.5, 2.0 Hz), 3.05 (m, 1H), 3.17 (dd, 1H, J=14.5, 7.0 Hz), 3.51 (dd, 1H, J=14.5, 5.5 Hz), 3.65 (s, 2H), 3.72 (s, 3H), 7.03-7.05 (m, 2H), 7.08-7.10 (m, 2H), 7.33-7.34 (m, 2H), 7.85-7.86 (m, 2H); $^{13}$C NMR (125 MHz, CDCl$_3$): δ 24.2, 26.0, 40.3, 52.1, 62.6, 117.7, 120.5, 130.7, 130.9, 131.1, 131.9, 153.8, 162.8, 171.8; HRMS (FAB) calcd for C$_{18}$H$_{19}$O$_5$S$_2$ (M+H$^+$) 379.0674, found 379.0645.

Compound 36a (R$_1$=R$_2$=H, n=1). To a stirred solution of 5m (312 mg, 0.83 mmol) in toluene (11 mL) was added bis(tributyltin)oxide (1.05 mL, 2.06 mmol) at room temperature, and the mixture was stirred at 80° C. for 12 h. The solution was cooled to room temperature and was concentrated to dryness under reduced pressure. The residue was dissolved in acetonitrile, and the solution was washed with hexane (3×) and concentrated under reduced pressure to leave the crude tin ester (532 mg) as a pale-yellow oil. Subsequently, tin ester was passed through a C$_{18}$-reverse phase silica gel pad (ODS silica gel 20g, washed with water, 1:2 water/acetonitrile and acetonitrile) to afford a mixture of 5m and 36a, which was purified by silica gel column chromatography (chloroform/methanol=30/1 to 10/1) to give 36a (195 mg, 65%) as a white solid with the recovery of some of 5m (38 mg, 12%). nip 133-134° C.; $^1$H NMR (500 MHz, CDCl$_3$): δ 2.16 (d, 1H, J=4.0 Hz), 2.54 (d, 1H, J-5.5 Hz), 3.06 (m, 1H), 3.19 (dd, 1H, J-14.0, 8.0 Hz), 3.52 (dd, 1H, J=14.0, 6.0 Hz), 3.68 (s, 2H), 7.05 (br d, 2H, J=8.5 Hz), 7.10 (br d, 2H, J=8.5 Hz), 7.35 (brd, 2H, J=8.5 Hz), 7.86 (br d, 2H, J=8.5 Hz); $^{13}$C NMR (125 MHz, CDCl$_3$): δ 24.2, 26.0, 40.2, 62.6, 117.8, 120.5, 130.2, 130.7, 131.3, 132.0, 154.1, 162.7, 177.1; HRMS (FAB) calcd for C$_{17}$H$_{17}$O$_5$S$_2$ (M+H$^+$) 365.0517, found 365.0495; Rf value=0.2 (chloroform/methanol 10/1).

Compounds of Scheme 16.

Compound 69a (R$_1$=R$_2$=H). This material was prepared in the same manner as described for 11b in Scheme 7, starting from 68a. $^1$H NMR (500 MHz, CDCl$_3$) δ 2.46 (s, 3H), 4.08 (s, 2H), 7.27-7.33 (m, 5H), 7.38 (d, J=7.0 Hz, 2H), 7.43 (d, J=7.6 Hz, 2H).

Conversion from compound 69a to compound 70a was followed by the same method as described in Scheme 6.

Compound 70a (R$_1$=R$_2$=H). $^1$H NMR (500 MHz, CDCl$_3$) δ 2.16 (dd, J=5.2, 1.8 Hz, 1H), 2.54 (dd, J=6.2, 1.6 Hz, 1H), 3.06 (m, 1H), 3.17 (dd, J=14.3, 8.1 Hz, 1H), 3.56 (dd, J=14.2, 5.4 Hz, 1H), 4.11 (s, 2H), 7.20 (d, J=7.0 Hz, 2H), 7.28 (d, J=7.2 Hz, 1H), 7.35 (t, J=7.5 Hz, 2H), 7.43 (d, J=8.6 Hz, 2H), 7.87 (d, J=8.2 Hz, 2H); $^{13}$C NMR (126 MHz, CDCl$_3$) δ 24.4, 26.2, 41.9, 62.6, 126.8, 128.7, 128.9, 129.1, 130.0, 136.4, 139.4, 148.4 (s).

Compound 75a (R—=R$_2$=H). This material was prepared in the same manner as described for 11b in Scheme 7, starting from 74a. $^1$H NMR (300 MHz, CDCl$_3$) δ 2.42 (s, 3H), 7.39-7.60 (m, 5H), 7.68-7.81 (m, 4H).

Conversion from compound 75a to compound 76a was followed by the same method as described in Scheme 6.

Compound 76a (R$_1$=R$_2$=H). $^1$H NMR (500 MHz, CDCl$_3$) δ 2.19 (dd, J=5.1, 1.7 Hz, 1H), 2.57 (dd, J=6.2, 1.8 Hz, 1H), 3.11 (m, 1H), 3.31 (dd, J=14.4, 7.6 Hz, 1H), 3.57 (dd, J=14.4, 6.0 Hz, 1H), 7.54 (t, J=7.8 Hz, 2H), 7.66 (t, J=7.4 Hz, 1H), 7.81 (d, J=7.4 Hz, 2H), 7.98 (d, J=8.2 Hz, 2H), 8.08 (d, J=8.2 Hz, 2H); $^{13}$C NMR (126 MHz, CDCl$_3$) δ 24.3, 26.0, 62.6, 128.7, 128.9, 130.3, 130.7, 133.7, 136.5, 141.8, 142.9, 195.3.

Compounds of Scheme 17.

Compound 77a (R$_1$=H). Compound 20a (2.00 g, 12.0 mmol) was dissolved in CH$_2$Cl$_2$ (10 mL) in ice-water bath. m-CPBA (13.0 g, 58.0 mmol, 77%) was added to the reaction mixture and was stirred at room temperature for 3 days. m-Chlorobenzoic acid was filtered and washed with 10% sodium thiosulfate, and brine. The organic layer was dried under anhydrous MgSO$_4$, filtered, and concentrated under reduced pressure. The residue was purified by column chromatography to give the desired product as a white solid (1.80 g, 70%).

Compound 78a (R$_1$=H). $^1$H NMR (500 MHz, CDCl$_3$) δ 2.05 (dd, J 5.2, 2.1 Hz, 1H), 2.45 (dd, J=6.2, 2.1 Hz, 1H), 2.94-3.01 (m, 1H), 3.11 (dd, J=14.1, 7.9 Hz, 1H), 3.47 (dd, J=14.1, 5.5 Hz, 1H), 6.91 (d, J=9.0 Hz, 2H), 7.69 (d, J=8.6 Hz, 2H); $^{13}$C NMR (126 MHz, CDCl$_3$) δ 24.2, 26.2, 62.7, 116.3, 128.2, 130.7, 162.6.

Compound 79a (R$_1$=H, R$_2$=benzyl). $^1$H NMR (500 MHz, CDCl$_3$) δ 2.12 (dd, J=5.2, 1.6 Hz, 1H), 2.50 (dd, J=6.2, 1.6 Hz, 1H), 3.01-3.08 (m, 1H), 3.15 (dd, J=14.2, 8.0 Hz, 1H), 3.51 (dd, J=14.2, 5.4 Hz, 1H), 5.16 (s, 2H), 7.11 (d, J=8.8 Hz, 2H), 7.36-7.45 (m, 5H), 7.85 (d, J=8.8 Hz, 2H); $^{13}$C NMR (126 MHz, CDCl$_3$) δ 24.4, 26.3, 62.7, 70.5, 115.6, 127.6, 128.6, 128.9, 130.3, 130.7, 135.7, 163.3.

Compounds of Scheme 18.

Compound 84a (R$_1$=R$_2$=H). To a solution of Mg (0.33 g, 13.6 mmol) in anhydrous THE (4 mL), biphenylbromide (3.25 g, 12.8 mmol) in THF (6 mL) was added and the resulting solution was refluxed for 0.5 hours. Then the reaction mixture was diluted with THF (10 mL) and cooled down to −78° C. CuBr DMS (0.26 g, 1.29 mmol) was added and stirred for 20 minutes, followed by the addition of epichlorohydrin (1.6 mL, 19.2 mmol). The reaction mixture was stirred for 1 hour while the reaction temperature was slowly increased to room temperature. The reaction was quenched by addition of sat'd NH$_4$Cl solution and extracted with EtOAc. The combined organic layers were washed with H$_2$O, 5% HCl, and brine. After removal of solvent, the residue was used for the next reaction without further purification. A suspension of crude 83a (3.55 g, 14.4 mmol) and K$_2$CO$_3$ (5.98 g, 43.3 mmol) in 1:1 solution of MeOH: THF (60 mL) was stirred for 1 hour and then was diluted with diethylether. The suspension was filtered and the filtrate was concentrated and the residue was purified by column chromatography to afford pure 84a (2.37 g, 88%).

Compound 85a (R$_1$=R$_2$=H). Vinylmagnesium bromide (19.0 mL, 1.0 M in THF) in THF (5 mL) was added CuBr.DMS (0.11 g, 0.55 mmol) at −78° C. After 20 minutes, compound 84a (1.15 g, 5.48 mmol) was added to the reaction mixture and stirred for additional 1 hour at −78° C. Stirring was continued for 3 hours, while the reaction was warmed to 0° C. After quenching the reaction with addition of sat'd NH$_4$Cl at 0° C. and the solution was stirred for 0.5 hours and extracted with EtOAc. After washing with water and brine, organic layer was concentrated and purified by column chromatography (1.06 g, 82%).

Compound 86a (R$_1$=R$_2$=H). A solution of compound 85a (1.00 g, 4.20 mmol) and Et$_3$N (0.73 mL, 5.27 mmol) was added methanesulfonyl chloride (0.39 mL, 5.04 mmol) and was stirred for 1 hour. Water was added to the reaction mixture, which was subsequently extracted with EtOAc. The organic layer was washed with sat'd NaHCO$_3$, 1 M KHSO$_4$, water and brine and evaporated to dryness. The crude material was used for the next reaction without further purification. A solution of crude material and potassium thioacetate (2.49 g, 21.8 mmol) in DMF (40 mL) was stirred at 50° C. for 17 hours. The reaction mixture was then diluted with ether/water and layers were separated. Combined organic layers were washed with NaHCO$_3$, H$_2$O and brine and dried. The residue was purified by column chromatography to give the desired product (0.79 g, 64%) as a semi solid Compound 87a (R$_1$=R$_2$=H, R=Bn). t-BuOK (0.79 g, 7.04 mmol) was added to a solution of compound 86a (0.52 g, 1.76 mmol) in 1:2 solution of MeOH:THF (10 mL) and the resulting suspension was stirred for 15 minutes, followed by addition of benzyl chloride (1.62 mL, 14.1 mmol). After 3 hours, the reaction was quenched with ammonium hydroxide and was extracted with diethyl ether. The organic layer was washed with water, 5% RCl, and brine. The crude product was purified by column chromatography to give the desired product (0.55 g, 91%) as a colorless oil.

Compound 88a (R$_1$=R$_2$=H, R=Bn). This compound was prepared in the same manner as described in Scheme 5.

Compounds of Scheme 19.

Conversion from compound 90a to compound 96a was followed by the same method as described in Scheme 14.

Compound 91a (R$_1$=R$_2$=H).
Compound 92a (R$_1$=R$_2$=H).
Compound 93a (R$_1$=R$_2$=H).

Compound 94a ($R_1$=$R_2$=H).
Compound 95a ($R_1$=$R_2$=H, $R_3$=Bn).
Compound 96a (R, —$R_2$=H, $R_3$=Bn).
Compounds of Scheme 20.

2-Amino-3-bromo-5-nitrophenol (98). A solution of 2-amino-5-nitrophenol (97, 24 g, 156 mmol) in $CH_3CN$ (1 L) was treated with NBS (28.8 g, 160.8 mmol) at room temperature. After stirring for 1 hour, the solvent was removed to afford brown precipitate, which was taken up with ethyl acetate:hexane (1:1). The precipitate was filtered and was used for the next step without further purification (33 g, 91%). A small amount of sample was purified by column chromatography on silica gel for analysis; $^1H$ NMR (500 MHz, $CD_3OD$): δ 4.93 (brs, 3H), 7.50 (d, 1H, J=2.4 Hz), 7.89 (d, 1H, J=2.4 Hz); $^{13}C$ NMR (125 MHz, $CD_3OD$): δ 105.5, 108.7, 121.8, 138.5, 143.7, 144.8; HRMS (FAB) calcd for $C_6H_5BrN_2O_3$ ($M^+$) 231.9484, found 231.9479.

3-Bromo-5-nitrophenol (99). Compound 98 (33.0 g, 0.14 mol) was treated with sulfuric acid (13.7 mL) and was refluxed in EtOH (550 mL) for 0.5 hours, followed by addition of $NaNO_2$ (23.8 g, 0.35 mol). The resulting mixture was refluxed for additional 1 hour and the volatile was evaporated. The residue was taken up with ethyl acetate and water. The layers were separated and the organic layer was washed with water, saturated sodium bicarbonate, and brine. After removal of solvent, the residue was purified by column chromatography on silica gel to afford the title compound (26 g, 85%); $^1H$ NMR (500 MHz, $CD_3OD$): δ 5.00 (brs, 1H), 7.58 (dd, 1H, J=1.7, 2.3 Hz), 7.47 (t, 1H, J=2.1 Hz), 7.69 (t, 1H, J=1.9 Hz); $^{13}C$ NMR (125 MHz, $CD_3OD$): δ 110.5, 118.1, 123.7, 125.6, 151.0, 160.5; HRMS (FAB) calcd for $C_6H_4BrNO_3$ ($M^+$) 216.9375, found 216.9374.

Compound 100a ($R_1$=iPr). A mixture of compound 99 (4.36 g, 20.0 mmol), $K_2CO_3$ (5.5 g, 40.0 mmol), and 2-iodopropane (4.0 mL, 40.0 mmol) in DMF (20 mL) was stirred at room temperature overnight. The solution was diluted with ethyl acetate and washed with water and brine, dried over $MgSO_4$, and the volatile was removed under reduced pressure. The residue was purified by column chromatography to yield the desired product (4.7 g, 90%); $^1H$ NMR (500 MHz, $CDCl_3$): δ 1.38 (d, 6H, J=6.0 Hz), 4.62 (septet, 1H, J=6.0 Hz), 7.33 (t, 1H, J=2.0 Hz), 7.64 (t, 1H, J=2.1 Hz), 7.91 (t, 1H, J=1.8 Hz); $^{13}C$ NMR (125 MHz, $CDCl_3$): δ 21.9, 71.7, 109.3, 118.7, 123.1, 125.4, 149.7, 159.2; HRMS (FAB) calcd for $C_9H_{10}BrNO_3$ ($M^+$) 258.9844, found 258.9829.

Compound 101a ($R_1$=iPr, $R_2$=4-Cl). Compound 100a (4.7 g, 18.1 mmol) dissolved in toluene (45 mL) was treated with sodium carbonate (18 mL, 2 M solution) and ethanol (12 mL). 4-Chlorophenylboronic acid (3.06 g, 20.1 mmol) was then added to the mixture followed by tetrakis(triphenylphosphine)palladium(0) (0.6 g, 0.54 mmol). The resulting mixture was refluxed for 3 hours. Brine was added (60 mL) and the mixture was extracted with $CH_2Cl_2$. The volatile was evaporated under reduced pressure and the residue was purified by column chromatography to afford the title compound (4.1 g, 77%); $^1H$ NMR (500 MHz, $CDCl_3$): δ 1.41 (d, 6H, J=6.0 Hz), 4.70 (septet, 1H, J=6.0 Hz), 7.37 (dd, 1H, J=1.6, 2.4 Hz), 7.47 (d, 2H, J=8.8 Hz), 7.53 (d, 2H, J=8.8 Hz), 7.69 (t, 1H, J=2.1 Hz), 7.97 (t, 1H, J=1.7 Hz); $^{13}C$ NMR (125 MHz, $CDCl_3$): δ 22.0, 71.2, 108.5, 114.1, 121.3, 128.5, 129.4, 134.9, 137.3, 142.4, 149.8, 159.0; HRMS (FAB) calcd for $C_{15}H_{14}ClNO_3$ ($M^+$) 291.0662, found 291.0688.

Compound 102a ($R_1$=iPr, $R_2$=H). Compound 101a (4.0 g, 13.7 mmol) dissolved in ethyl acetate:ethanol (1:1, mL) was stirred for 4 hours in the presence of Pd/C under hydrogen atmosphere. The reaction mixture was filtered through a small layer of Celite and washed with THF and ethanol. The combined filtrate was concentrated under reduced pressure and the residue was used for the next reaction without further purification (3.1 g, quantitative); $^1H$ NMR (500 MHz, $CDCl_3$): δ 1.35 (d, 6H, J=6.0 Hz), 4.62 (septet, 1H, J=6.0 Hz), 7.10 (dt, 2H, J=1.9, 10.9 Hz), 7.32 (t, 1H, J=1.5 Hz), 7.35-7.43 (m, 4H), 7.55 (dd, 2H, J=1.5, 8.4 Hz), 10.64 (brs, 1H); $^{13}C$ NMR (125 MHz, $CDCl_3$): δ 22.1, 70.8, 109.3, 114.0, 115.7, 127.4, 128.4, 129.1, 131.2, 139.6, 144.7, 159.5; HRMS (FAB) calcd for $C_{15}H_{17}NO$ ($MH^+$) 228.1388, found 228.1372.

Compound 103a ($R_1$=iPr, $R_2$=4-Cl). $^1H$ NMR (500 MHz, $CDCl_3$) δ 1.38 (d, J=5.9 Hz, 6H), 2.45 (s, 3H), 4.61 (m, 1H), 6.96 (s, 1H), 7.11 (s, 1H), 7.17 (s, 1H), 7.40 (d, J=8.4 Hz, 2H), 7.50 (d, J=8.4 Hz, 2H); $^{13}C$ NMR (126 MHz, $CDCl_3$) δ 22.2, 30.4, 70.5, 116.4, 120.1, 125.1, 128.6, 129.1, 129.5, 134.0, 138.7, 142.3, 158.7, 194.0.

Compound 104a ($R_1$=iPr, $R_2$=H). $^1H$ NMR (500 MHz, $CDCl_3$) δ 1.37 (d, J=5.9 Hz, 6H), 2.17 (dd, J=4.9, 1.5 Hz, 1H), 2.53 (d, J=5.9 Hz, 1H), 3.06 (m, 1H), 3.23 (dd, J=14.3, 7.4 Hz, 1H), 3.55 (dd, J=14.3, 5.9 Hz, 1H), 4.67 (m, 1H), 7.32 (s, 1H), 7.36 (s, 1H), 7.41 (d, J=8.4 Hz, 2H), 7.51 (d, J=8.4 Hz, 2H), 7.63 (s, 1H); $^{13}C$ NMR (126 MHz, $CDCl_3$) δ 22.0, 24.3, 26.1, 62.5, 71.1, 113.3, 118.8, 120.8, 128.5, 129.3, 134.8, 137.5, 140.4, 143.0, 159.0.

Compounds of Scheme 21.

Compound 105a ($R_1$=$R_2$=H). Compound 14a (2.45 g, 13.2 mmol) was dissolved in THF (10 mL) and treated with triethylamine (2.2 mL, 15.8 mmol). Allylsulfonyl chloride (2.2 g, 15.8 mmol) in THF (5 mL) was slowly added dropwise to the above solution at ice-water temperature over 0.5 hours. The resulting mixture was stirred for 1 hour, while the temperature was gradually warmed to room temperature. Additional triethylamine (2.2 mL, 15.8 mmol) was added to the reaction mixture and the resultant solution was stirred for 0.5 h. The reaction mixture was filtered through a small layer of silica gel and the volatile was evaporated. The residue was taken up in ethyl acetate and washed with water, 5% $NaHCO_3$, and brine. The organic layer was dried over $MgSO_4$, and evaporated. The residue was purified by column chromatography on silica gel to afford the desired product (2.73 g, 75%); $^1H$ NMR (500 MHz, $CDCl_3$) δ 3.87 (d, J=7.4 Hz, 2H), 5.32 (d, J=17.3 Hz, 1H), 5.43 (d, J=10.4 Hz, 1H), 5.88 (m, 1H), 6.78 (dd, J=8.4, 2.0 Hz, 1H), 6.97 (s, 1H), 6.99-7.07 (m, 2H), 7.16 (t, J=7.4 Hz, 1H), 7.28 (t, J=8.2 Hz, 1H), 7.37 (t, J=7.9 Hz, 2H), 7.48 (br.s., 1H); $^{13}C$ NMR (126 MHz, $CDCl_3$) δ 55.7, 110.8, 114.8, 114.9, 119.3, 123.9, 125.0, 130.0, 130.7, 138.5, 156.5, 158.5.

Conversion from compound 105a to compounds 106a-107a was followed by the same method as described in Scheme 6.

Compound 106a ($R_1$=$R_2$=$R_3$=H). $^1H$ NMR (500 MHz, $CDCl_3$) δ 3.24 (dd, J=14.8, 3.0 Hz, 1H), 3.33 (dd, J=14.8, 8.9 Hz, 1H), 3.52 (dd, J=11.9, 6.4 Hz, 1H), 3.63 (dd, J=12.4, 4.0 Hz, 1H), 4.32 (m, 1H), 6.71 (m, 1H), 6.98-7.01 (m, 4H), 7.11 (t, J=7.4 Hz, 1H), 7.20 (dd, J=8.4 Hz, 1H), 7.32 (t, J=8.4, 7.4 Hz, 2H); $^{13}C$ NMR (126 MHz, $CDCl_3$) δ 50.4, 53.4, 65.3, 67.7, 111.5, 114.9, 115.6, 119.3, 123.9, 129.9, 130.7, 138.3, 156.4, 158.3.

Compound 106b (R=$R_2$=H, $R_3$=Me). $^1H$ NMR (500 MHz, $CDCl_3$) δ 2.4 (s, 3H), 3.1-3.3 (m, 2H), 3.9 (d, J=4.0 Hz, 1H), 4.0 (d, J=4.9 Hz, 2H), 4.5 (br.s., 1H), 6.8 (d, J=8.9 Hz, 1H), 6.9-7.0 (m, 1H), 7.0 (d, J=7.9 Hz, 1H), 7.1 (t, J=7.4 Hz, 1H), 7.2 (t, J=8.4 Hz, 1H), 7.5 (s, 1H), 7.8 (d, J=8.4 Hz, 1H); $^{13}C$ NMR (126 MHz, $CDCl_3$) δ 21.8, 52.7, 65.4, 71.8, 111.9, 115.3, 115.9, 119.4, 123.9, 128.1, 130.0, 130.2, 130.7, 131.9, 138.0, 145.6, 156.5, 158.4.

Compound 107a ($R_1=R_2=R_3=H$). 1H NMR (500 MHz, CDCl$_3$) δ 2.32 (d, J=5.4 Hz, 1H), 2.64 (d, J=5.9 Hz, 1H), 3.19 (m, 1H), 3.26 (dd, J=14.3, 7.4 Hz, 1H), 3.57 (dd, J=14.1, 5.7 Hz, 1H), 6.77-6.83 (m, 2H), 6.91 (s, 1H), 6.97 (d, J=8.4 Hz, 1H), 7.05 (d, J=8.4 Hz, 2H), 7.18 (t, J=7.4 Hz, 1H), 7.28-7.32 (m, 1H), 7.39 (t, J=7.7 Hz, 1H); $^{13}$C NMR (126 MHz, CDCl$_3$) δ 24.8, 26.7, 57.9, 110.5, 114.6, 115.1, 119.6, 124.2, 130.1, 131.0, 137.9, 156.4, 158.9.

Compounds of Scheme 23.

Synthesis of compounds 111a-118a was followed by the same method 110 as described in Schemes 21 and 22.

Compound 111a ($R_1$=iPr, $R_2$=H). 1H NMR (500 MHz, CDCl$_3$) δ 31.41 (d, J=5.9 Hz, 6H), 3.92 (d, J=7.9 Hz, 2H), 4.65 (m, 1H), 5.37 (d, J=17.3 Hz, 1H), 5.48 (d, J=10.4 Hz, 1H), 5.95 (m, 1H), 6.88 (m, 1H), 6.97 (s, 1H), 7.04 (m, 1H), 7.41 (d, J=7.4 Hz, 1H), 7.47 (t, J=7.4 Hz, 2H), 7.59 (d, J=6.9 Hz, 2H); $^{13}$C NMR (125 MHz, CDCl$_3$): δ 22.2, 55.6, 70.4, 106.8, 111.5, 111.7, 125.1, 125.2, 127.3, 128.0, 129.0, 138.4, 140.4, 143.9, 159.3; HRMS (FAB) calcd for C is H$_{21}$NO$_3$S (MH$^+$) 332.1320, found 332.1313.

Compound 112a ($R_1$=iPr, $R_2$=H, $R_3$=Me). Compound 111a (3.0 g, 9.1 mmol) was treated with sodium hydride (0.54 g, 13.6 mmol, 60%) in DMF (20 mL) in ice-water bath. The resulting suspension was stirred for 1 µl while the temperature was gradually warmed to room temperature. Iodomethane (1.7 mL, 27.2 mmol) was added to above mixture and the resultant solution was stirred at room temperature overnight. After dilution with ethyl acetate, the organics was washed with water, 1 N HCl, and brine and was dried over MgSO$_4$. After removal of solvent, the residue was purified by short-path column chromatography on silica gel to yield the desired compound (2.9 g, 91%); $^1$H NMR (500 MHz, CDCl$_3$): δ 1.41 (d, 6H, J=6.0 Hz), 3.20 (s, 3H), 3.80 (d, 2H, J=7.9 Hz), 4.61 (septet, 1H, J=5.9 Hz), 5.41 (m, 2H), 5.95 (m, 1H), 6.92 (s, 1H), 7.00 (m, 1H), 7.18 (m, 1H), 7.40-7.60 (m, 6H); $^{13}$C NMR (125 MHz, CDCl$_3$): δ 22.1, 39.2, 54.8, 70.6, 106.8, 113.1, 113.6, 117.1, 117.2, 123.7, 127.2, 127.9, 128.5, 128.9, 129.1, 139.0, 140.6, 142.2, 159.0; HRMS (FAB) calcd for C$_{19}$H$_{24}$NO$_3$S (MH$^+$) 346.1477, found 346.1480.

Compound 113a ($R_1$=iPr, $R_2$=H, $R_3$=H). $^1$H NMR (500 MHz, CDCl$_3$) δ 1.32 (d, J=5.9 Hz, 6H), 3.20 (dd, J=14.3, 2.5 Hz, 1H), 3.33 (dd, J=14.6, 9.2 Hz, 1H), 3.50 (dd, J=11.6, 6.2 Hz, 1H), 3.62 (dd, J=11.6, 3.2 Hz, 1H), 4.34 (m, J=3.0 Hz, 1H), 4.57 (m, 1H), 6.85 (m, 1H), 6.91 (m, 1H), 7.04 (m, 1H), 7.30 (t, J=8.4, 7.4 Hz, 1H), 7.37 (t, J=7.4 Hz, 2H), 7.52 (d, J=7.9 Hz, 2H); $^{13}$C NMR (126 MHz, CDCl$_3$) δ 22.1, 53.4, 58.6, 65.5, 67.9, 70.5, 107.9, 112.0, 112.4, 127.3, 128.0, 129.0, 138.3, 140.4, 143.9, 159.2.

Compound 113b ($R_1$=iPr, $R_2$=H, $R_3$=Me). $^1$H NMR (300 MHz, CDCl$_3$): δ 1.35 (d, 6H, J=6.0 Hz), 3.15-3.25 (m, 2H), 3.31, 3.34 (2s, 3H), 3.51-3.68 (m, 3H), 3.83 (brs, 1H), 4.61 (septet, 1H, J=6.0 Hz), 6.92 (m, 1H), 7.01 (dt, 1H, J=1.8, 15.6), 7.14 (dt, 1H, J=1.6, 9.8), 7.35-7.56 (m, 5H); $^{13}$C NMR (75 MHz, CDCl$_3$): δ 22.1, 22.2, 38.7, 52.8, 65.5, 67.5, 70.7, 113.5, 113.6, 114.1, 114.2, 117.4, 117.5, 127.3, 128.0, 128.6, 129.0, 129.1, 138.9, 140.4, 142.4, 159.1; HRMS (FAB) calcd for C$_{19}$H$_{25}$NO$_5$S (M$^+$) 379.1453, found 379.1462.

Compound 114a ($R_1$=iPr, $R_2$=H, $R_3$=H). $^1$H NMR (500 MHz, CDCl$_3$) δ 1.38 (d, J=5.9 Hz, 6H), 2.32 (dd, J=3.5, 1.5 Hz, 1H), 2.63 (dd, J=4.9, 1.0 Hz, 1H), 3.21 (m, 1H), 3.28 (dd, J=14.3, 7.4 Hz, 1H), 3.61 (dd, J=14.1, 5.7 Hz, 1H), 4.62 (m, 1H), 6.84 (s, 1H), 6.94 (s, 1H), 7.01 (s, 1H), 7.08 (s, 1H), 7.39 (t, J=7.4 Hz, 1H), 7.45 (t, J=7.4 Hz, 2H), 7.56 (d, J=7.4 Hz, 2H); $^{13}$C NMR (126 MHz, CDCl$_3$) δ 22.2, 24.8, 26.7, 57.7, 70.5, 106.8, 111.4, 111.9, 127.3, 128.1, 129.0, 138.0, 140.4, 144.2, 159.4.

Compound 114b ($R_1$=iPr, $R_2$=1H, $R_3$=Me). $^1$H NMR (500 MHz, CDCl$_3$) δ 1.39 (dd, J=5.9, 1.5 Hz, 6H), 2.40 (m, 1H), 2.67 (d, J=5.9 Hz, 1H), 3.05 (dt, J=13.9, 8.4 Hz, 1H), 3.19 (m, 1H), 3.41 (d, J=2.5 Hz, 3H), 3.57 (td, J=13.1, 5.4 Hz, 1H), 6.94 (t, J=2.5 Hz, 1H), 6.99 (t, J=2.0 Hz, 1H), 7.04 (t, J=2.0 Hz, 1H), 7.13 (t, J=2.0 Hz, 1H), 7.16 (t, J=1.5 Hz, 1H), 7.40-7.49 (m, 4H), 7.56 (d, J=6.9 Hz, 2H); $^{13}$C NMR (125 MHz, CDCl$_3$): δ 22.2, 25.3, 26.7, 38.9, 56.1, 70.5, 113.0, 113.7, 113.9, 117.0, 117.1, 127.4, 128.1, 128.6, 129.1, 129.2, 142.5, 142.7, 143.7, 159.0; HRMS (FAB) calcd for C$_{19}$H$_{24}$NO$_3$S$_2$ (MH$^+$) 378.1198, found 378.1200.

Compound 116a ($R_1$=iPr, $R_2$=4-Cl, $R_3$=Me). $^1$H NMR (500 MHz, CDCl$_3$) δ 1.31 (d, J=5.9 Hz, 6H), 2.67 (dd, J=20.8, 7.4 Hz, 2H), 3.17 (t, J=7.2 Hz, 3H), 3.68 (d, J=10.9 Hz, 3H), 4.51-4.58 (m, 1H), 5.03-5.13 (m, 2H), 5.67-5.78 (m, 1H), 6.75 (s, 1H), 6.77 (s, 1H), 6.95 (s, 1H), 7.31 (d, J=8.4 Hz, 2H), 7.42 (d, J=8.4 Hz, 2H); $^{13}$C NMR (126 MHz, CDCl$_3$) δ 21.9, 30.9, 31.9, 36.3 (d, J=3.6 Hz), 50.6 (d, J=7.1 Hz), 69.9, 108.9 (d, J=3.6 Hz), 109.6, 112.9 (d, J=3.6 Hz), 120.1, 120.3, 127.0, 127.1, 128.3, 128.7, 129.6, 131.9, 133.4, 139.4, 141.7, 145.8 (d, J=5.3 Hz), 158.7.

Compound 117a ($R_1$=iPr, $R_2$=4-Cl, $R_3$=Me). $^1$H NMR (500 MHz, CDCl$_3$) δ 1.35 (d, J=5.9 Hz, 6H), 3.18 (dd, J=17.3, 7.9 Hz, 3H), 3.44 (dd, J=11.4, 5.9 Hz, 1H), 3.53-3.63 (m, 1H), 3.70 (d, J=11.4 Hz, 3H), 4.01 (s, 1H), 4.08-4.15 (m, 1H), 4.54-4.62 (m, 1H), 6.76-6.81 (m, 2H), 6.96 (s, 1H), 7.37 (d, J=8.4 Hz, 2H), 7.46 (d, J=8.4 Hz, 2H); $^{13}$C NMR (126 MHz, CDCl$_3$) δ 22.1, 30.1, 36.2 (d, J=3.6 Hz), 53.6, 66.8 (d, J=16.0 Hz), 67.0 (d, J=16.0 Hz), 67.2 (d, J=3.6 Hz), 70.2 (d, J=1.8 Hz), 109.3 (d, J=3.6 Hz), 109.7 (d, J=3.6 Hz), 110.0, 110.1, 110.8, 113.1 (d, J=3.6 Hz), 113.7 (d, J=2.7 Hz), 128.5, 129.0 (d, J=1.8 Hz), 129.9, 133.8 (d, J=5.3 Hz), 139.4 (d, J=3.6 Hz), 142.1 (d, J=14.3 Hz), 145.6 (t, J=4.9 Hz), 159.0 (d, J=8.0 Hz).

Compound 118a ($R_1$=iPr, $R_2$=4-Cl, $R_3$=Me). $^1$H NMR (500 MHz, CDCl$_3$) δ 1.35 (d, J=5.9 Hz, 6H), 1.94 (m, 0.5H), 2.24 (td, J=15.7, 6.2 Hz, 0.25H), 2.37 (td, J=15.3, 5.4 Hz, 0.25H), 2.46 (m, 0.5H), 2.52 (m, 0.5H), 2.78 (m, 1H), 3.18 (m, 1H), 3.23 (d, J=7.9 Hz, 3H), 3.77 (dd, J=11.4, 7.9 Hz, 3H), 4.59 (m, 1H), 6.78-6.86 (m, 1H), 6.95-7.03 (m, 1H), 7.34-7.41 (m, J=8.4 Hz, 1H), 7.42-7.48 (m, J=7.7, 7.7 Hz, 3H), 7.54 (t, J=7.4 Hz, 1H), 7.66 (dd, J=11.9, 6.9 Hz, 1H); $^{13}$C NMR (126 MHz, CDCl$_3$) δ 22.1, 29.5 (d, J=4.5 Hz), 30.5 (d, J=4.5 Hz), 36.1 (d, J=4.5 Hz), 36.4 (d, J=4.5 Hz), 46.8, 47.3 (d, J=6.2 Hz), 47.5 (d, J=8.0 Hz), 50.7 (d, J=7.1 Hz), 50.8 (d, J=6.2 Hz), 70.2 (d, J=1.8 Hz), 109.2 (d, J=3.6 Hz), 109.9 (d, J=3.6 Hz), 110.0, 110.4, 113.2 (d, J=3.6 Hz), 113.9 (d, J=3.6 Hz), 127.3, 128.5, 128.6, 128.7, 129.0 (d, J=2.7 Hz), 132.1 (t, J=2.7 Hz), 132.1, 132.2, 133.8 (d, J=6.2 Hz), 139.5 (d, J=2.7 Hz), 142.1, 142.2, 145.6 (dd, J=8.0, 4.5 Hz), 159.0 (d, J=6.2 Hz).

Compounds of Scheme 24.

Compound 121a ($R_1$=Bn, $R_2$=$R_3$=H). Biphenylsulfonyl chloride (1.59 g, 6.30 mmol) was added to a solution of compound 119a (1.00 g, 6.61 mmol) in 3:1 mixture of THF: water in ice-water bath. The resulting mixture was stirred at room temperature overnight. Sodium bicarbonate (0.56 g, 6.94 mmol) was added and the resulting solution was stirred for 3 h and solvent was concentrated. The resultant was diluted with EtOAc and water and then layers were separated. The organic layer was washed with 5% HCl and water and was concentrated to dryness. The crude product was purified by column chromatography to give the desired product (1.97 g, 81%).

Compound 122a ($R_1$=Bn, $R_2$=$R_3$=H). Methanesulfonyl chloride (0.58 mL, 7.42 mmol) was added to a solution of compound 121a (1.82 g, 4.95 mmol) and Et$_3$N (1.72 mL, 12.4 mmol) in acetonitrile (30 mL) in ice-water bath and stirred for 10 min. After stirring at room temperature for additional 10 min, the reaction mixture was diluted with 200 mL of MeOH and cooled down to ice-water bath. Potassium carbonate (1.37 g/10 mL water) was added to the reaction mixture and stirred for 3 h at room temperature. Organic solvents were removed and then diluted with EtOAc and water. The layers were separated and the organic layer was washed with water and brine and concentrated. The crude product was purified by column chromatography to give the desired product (1.27 g, 73%).

Compound 123a ($R_1$=Bn, $R_2$=$R_3$=H, n=1). Vinyl magnesium bromide (4.5 mL, 1.0 M in THF) was added to a solution of CuI (85 mg, 0.45 mmol) in THF (3 mL) at −78° C. After 20 minutes, compound 122a (313 mg, 0.90 mmol) was added to the reaction mixture. The reaction mixture was slowly warmed to room temperature over 1.5 hours. After quenching with 5% HCl, the reaction mixture was extracted with EtOAc and organic layer was washed with 5% HCl and brine and volume was reduced. The crude product was purified by column chromatography to give the desired product (237 mg, 70%) as a yellow oil.

Compound 123b ($R_1$=Bn, $R_2$=$R_3$=H, n=2). This material was prepared in the same manner as described for 123a, with the exception that allylmagnesium bromide was used in place of vinylmagnesium bromide.

Conversion from compound 123 to compound 124, 125 was followed by the same method as described in Scheme 5.

Compound 124a ($R_1$=Bn, $R_2$=$R_3$=H, n=1).
Compound 124b ($R_1$=Bn, $R_2$=$R_3$=H, n=2).
Compound 125a ($R_1$=Bn, $R_2$=$R_3$=H, n=1).
Compound 125b ($R_1$=Bn, $R_2$=$R_3$=H, n=2).

Compounds of Scheme 25.

Compound 130a ($R_1$=Bn, $R_2$=$R_3$=H). A solution of compound 129a (183 mg, 1.25 mmol), 107a (330 mg, 1.31 mmol), and $Bt_3N$ (0.21 mL, 1.50 mmol) in $CH_2Cl_2$ (6 mL) was stirred for 1 h at room temperature. The reaction mixture was washed with water and organic solvent was concentrated. The crude product was purified by column chromatography to give the desired product (389 mg, 86%) as a white solid.

Conversion from compound 130a to compound 131a was followed by the same method as described in Scheme 5.

Compound 131a ($R_1$=Bn, $R_2$=$R_3$=H).

Compounds of Scheme 26.

Compound 133a ($R_1$=Bn, $R_2$=$R_3$=H). Compound 132 (1.17 mL, 11.9 mmol) was added to a solution of phenoxyphenylmagnesium bromide (3.30 g, 12.0 mmol) in anhydrous THF (20 mL) in ice-water bath. After 15 minutes, stirring was continued at room temperature for 1 h and reaction was quenched with sat'd $NH_4Cl$ solution. After extraction with EtOAc, the organic layer was washed with water and brine. The crude product was purified by column chromatography to give the desired product (2.39 g, 79%) as a white solid.

Compound 134a ($R_1$=Bn, $R_2$=$R_3$=H). A mixture of compound 133a (100 mg, 0.39 mmol), TPAP (14 mg, 0.039 mmol), and NMO (138 mg, 1.30 mmol) in $CH_2Cl_2$ (mL) was stirred for 5 minutes and concentrated to dryness. The crude product was purified by column chromatography to give the desired product (88 mg, 89%) as a white solid.

Compound 135a ($R_1$=Bn, $R_2$=$R_3$=H). A mixture of compound 134a (88 mg, 0.35 mmol) and NBS (68 mg, 0.39 mmol) in 3:1 solution of THF:water was stirred at room temperature for 1 hour. 2.5 N NaOH (280 µL) was added to the reaction mixture and stirred for 3 h. The reaction mixture was diluted with diethyl ether and washed with brine. The crude product was purified by column chromatography to give the desired product (75 mg, 81%) as a colorless oil.

Conversion from compound 135a to compound 136a was followed by the same method as described in Scheme 5.

Compound 136a ($R_1$=Bn, $R_2$=$R_3$=H).

Compound 137a ($R_1$=Bn, $R_2$=$R_3$=H). A mixture of compound 136a (66 mg, 0.23 mmol), $NH_2OH$—HCl (24.2 mg, 0.38 mmol), and NaOAc (28.6 mg, 0.38 mmol) in 2:1 solution of EtOH:water was stirred at room temperature for 2 h. Additional batch of $NH_2OH$—HCl and NaOAc was to the reaction mixture and stirring was continued for 4 h. The resulting solution was diluted with EtOAc and water and layers were separated. Organic layer was washed with sat'd $NaHCO_3$, water and brine. The crude product was purified by column chromatography to give the desired product (53 mg, 76%) as a colorless oil.

Compounds of Scheme 27.

Preparation of compounds 139a-143a was followed by the same method as described in Scheme 22.

Compound 139a ($R_1$=$R_2$=H).
Compound 140a ($R_1$=$R_2$=H).
Compound 141a ($R_1$=$R_2$=H).
Compound 142a ($R_1$=$R_2$=H).
Compound 143a ($R_1$=$R_2$=H).

Compounds of Scheme 28.

Compound 150a ($R^1$=H). A solution of compound 149a (1.10 g, 5.12 mmol) in THF (5 mL) was added dropwise to a stirred suspension of KH (230 mg, 5.63 mmol) in THF (10 mL) at room temperature, and the whole was stirred at the same temperature for 5 minutes. A hexane solution of triethylborane (1.0 M, 6.4 mL, 6.4 mmol) was added to the reaction mixture at room temperature, and the whole was stirred at the same temperature for 5 minutes. After addition of allylbromide (1.43 mL, 15.4 mmol) at room temperature, the reaction mixture was stirred at the same temperature for 36 hours. After addition of water, the solvent was removed under reduced pressure, and the resultant residue was partitioned with $CH_2Cl_2$ and water. The aqueous layer was extracted with $CH_2Cl_2$, and the combined organic layers were washed with water and brine, and then dried over $Na_2SO_4$.

After concentration under reduced pressure, the resultant residue was purified by silica gel column chromatography (ethyl acetate:hexane=1:30) to give the desired product (837 mg, 64%) as a pale yellow solid with recovery of compound 149a (254 mg, 23%); Compound 150a: $^1$H NMR (500 MHz, $CDCl_3$): δ 1.83-1.88 (m, 2H), 1.93-1.97 (m, 2H), 2.50-2.55 (m, 2H), 2.62-2.65 (m, 2H), 2.75-2.78 (m, 2H), 3.12 (t, 2H, J=7.5 Hz), 5.02 (dq, 1H, J=10.5, 1.0 Hz), 5.10 (dq, 1H, J=17.0, 2.0 Hz), 5.93 (ddt, 1H, J=17.0, 10.5, 6.5 Hz), 7.43 (d, 1H, J=8.0 Hz), 7.85 (dd, 1H, J=8.0, 1.5 Hz), 8.01 (d, 1H, J=1.5 Hz); $^{13}$C NMR (125 MHz, $CDCl_3$): δ 8.5, 37.8, 110.7, 113.3, 115.2, 118.0, 122.5, 132.2, 133.3, 137.5, 154.0, 158.1, 199.0; HRMS (FAB) calcd for $C_{17}H_{19}O_2$ (M+H$^+$) 255.1385, found 255.1402.

Compound 149a: m.p. 66-67° C.; $^1$H NMR (300 MHz, $CDCl_3$): δ 1.82-1.90 (m, 2H), 1.92-2.00 (m, 2H), 2.61-2.67 (m, 2H), 2.65 (s, 3H), 2.75-2.80 (m, 2H), 7.43 (d, 1H, J=8.4 Hz), 7.84 (dd, 1H, J=1.2, 8.4 Hz), 8.00 (d, 1H, J=1.2 Hz); $^{13}$C NMR (75 MHz, $CDCl_3$): δ20.2, 22.4, 22.6, 23.5, 26.6, 110.9, 113.3, 117.8, 122.8, 132.4, 133.2, 153.9, 158.1, 197.6; HRMS (FAB) calcd for $C_{14}H_{15}O_2$ (M+H$^+$) 215.1072, found 215.1056.

Compound 151a ($R_1$=H). NBS (650 mg, 3.66 mmol) was added to a stirred solution of compound 150a (780 mg, 3.05 mmol) in THF-water (3:1, 15 mL) at room temperature, and the whole was stirred at the same temperature for 1 hour in the dark. Aqueous 2.5 M NaOH (3.7 mL, 9.25 mmol) was added at room temperature, and the whole was stirred at the same temperature for 30 minutes. After addition of a few drops of allyl alcohol, the mixture was stirred for 10 minutes. After dilution with ether and brine, the aqueous layer was extracted with ether. The combined organic layers were washed with water and brine, dried over MgSO$_4$ and concentrated under reduced pressure.

The resultant residue was purified by silica gel column chromatography (1% triethylamine in ethyl acetate:hexane=1:8) to give the title compound (540 mg, 65%) as a white solid; $^1$H NMR (500 MHz, CDCl$_3$): δ 1.83-1.90 (m, 3H), 1.93-1.98 (m, 2H), 2.19 (m, 1H), 2.56 (dd, 1H, J=2.5, 5.0 Hz), 2.62-2.65 (m, 2H), 2.76-2.81 (m, 3H), 3.08 (m, 1H), 3.20 (t, 2H, J=7.5 Hz), 7.44 (d, 1H, J=8.0 Hz), 7.86 (dd, 1H, J=1.0, 8.0 Hz), 8.02 (d, 1H, J=1.0 Hz); $^{13}$C NMR (125 MHz, CDCl$_3$): δ 4.6, 47.4, 51.7, 110.7, 113.4, 118.0, 122.5, 132.0, 133.4, 154.0, 158.3, 198.5; HRMS (FAB) calcd for C$_{17}$H$_{19}$O$_3$ (M+H$^+$) 271.1334, found 271.1343.

Compound 152a (R$_1$=H). Thiourea (349 mg, 4.60 mmol) was added to a stirred solution of compound 151a (500 mg, 1.84 mmol) in MeOH (11 mL) at room temperature, and the whole was stirred at the same temperature overnight. After concentration under reduced pressure, the resultant was dissolved in ethyl acetate. The ethyl acetate solution was washed with water and brine, dried over Na$_2$SO$_4$, and concentrated under reduced pressure. The resultant residue was purified by silica gel column chromatography (ethyl acetate:hexane=1:20) to give the desired product (410 mg, 78%) as a white solid; $^1$H NMR (500 MHz, CDCl$_3$): δ 1.72 (m, 1H), 1.84-1.88 (m, 2H), 1.93-1.98 (m, 2H), 2.25 (dd, 1H, J=1.0, 5.5 Hz), 2.52 (m, 1H), 2.56 (dd, 1H, J=1.0, 6.5 Hz), 2.62-2.65 (m, 2H), 2.76-2.79 (m, 2H), 3.07 (m, 1H), 3.19-3.29 (m, 2H), 7.43 (d, 1H, J=8.5 Hz), 7.86 (dd, 1H, J=1.5, 8.5 Hz), 8.02 (d, 1H, J=1.5 Hz); $^{13}$C NMR (125 MHz, CDCl$_3$): δ 20.9, 22.4, 22.6, 23.6, 26.3, 31.0, 35.7, 38.0, 110.7, 113.4, 118.0, 122.5, 132.0, 133.4, 154.0, 158.3, 198.6; HRMS (FAB) calcd for C$_{17}$H$_{19}$O$_2$S (M+H$^+$) 287.1106, found 287.1104.

Compound 153a (R$^1$=H). A solution of hydroxylamine hydrochloride (266 mg, 3.82 mmol) and sodium acetate (314 mg, 3.82 mmol) in water (1 mL) was added dropwise to a stirred solution of compound 152a (365 mg, 1.27 mmol) in EtOH—CH$_2$Cl$_2$ (3:1, 12 mL) at room temperature, and the whole was stirred at the same temperature for 6 h. After dilution with water, the mixture was extracted with ethyl acetate. The combined organic layers were washed with water and brine, dried over Na$_2$SO$_4$, and concentrated under reduced pressure. The resultant residue was purified by silica gel column chromatography (ethyl acetate:hexane=1:10) to give the desired product (320 mg, 83%) as a white solid; $^1$H NMR (500 MHz, CDCl$_3$): δ 1.76 (m, 1H), 1.83-1.87 (m, 2H), 1.92-1.97 (m, 2H), 2.14-2.21 (m, 2H), 2.48 (d, 1H, J=6.5 Hz), 2.62 (t, 2H, J=6.0 Hz), 2.75 (t, 2H, J=6.0 Hz), 2.96 (qn, 1H, J=6.5 Hz), 3.02 (m, 1H), 3.14 (m, 1H), 7.40 (d, 1H, J=7.5 Hz), 7.50 (d, 1H, J=7.5 Hz), 7.67 (s, 1H), 9.02 (s, 1H); $^{13}$C NMR (125 MHz, CDCl$_3$): δ 20.4, 22.5, 22.8, 23.5, 25.9, 26.0, 33.3, 35.5, 108.8, 113.0, 118.3, 120.5, 130.0, 130.4, 154.4, 155.7, 158.9; HRMS (FAB) calcd for C$_{17}$H$_{20}$O$_2$NS (M+H$^+$) 302.1215, found 302.1212.

Compounds of Scheme 29.

Compound 155a (R$_1$=3-benzyloxy). A mixture of 3-benzyloxybenzaldehyde (9.5 g, 44.7 mmol) and ethyl cyanoacetate (5.2 mL, 48.9 mmol) in benzene (50 mL) was refluxed in the presence of catalytic amount of piperidine (0.5 mL) for 4 h. Evaporation of solvent under reduced pressure resulted in precipitate which was purified by recrystallisation from ethanol (11.0 g, 80%); $^1$H NMR (400 MHz, CDCl$_3$): δ 1.42 (t, 3H, J=7.20 Hz), 4.40 (q, 1H, J=7.0 Hz), 5.14 (s, 2H), 7.19 (dd, 1H, J=2.4, 8.0 Hz), 7.35-7.67 (m, 9H), 8.22 (s, 1H); $^{13}$C NMR (100 MHz, CDCl$_3$): δ 14.3, 63.0, 70.3, 103.3, 115.7, 121.0, 124.6, 127.8, 128.4, 128.8, 130.5, 132.8, 136.4, 155.2, 159.2, 162.6; HRMS (ESI) calcd for C$_{19}$H$_{17}$NNaO$_3$ (M+Na$^+$) 330.1106, found 330.1112.

Compound 156a (R$_1$=3-benzyloxy, R$_2$=H). Potassium cyanide (2.85 g, 43.8 mmol) dissolved in water (5 mL) was added to a solution of compound 155a (7.5 g, 24.4 mmol) in EtOH (40 mL). After reflux for 4 h, the reaction mixture was cooled down and was diluted with 1 N NaOH (25 mL) and 15% NaCl (400 mL), followed by extraction with CH$_2$Cl$_2$. The volatile was evaporated under reduced pressure and the residue was purified by column chromatography on silica gel to afford the desired product (5.8 g, 91%); $^1$H NMR (400 MHz, CDCl$_3$): δ 2.96 (d, 2H, J=6.8 Hz), 4.13 (t, 1H, J=6.8 Hz), 5.10 (s, 2H), 7.00-7.04 (m, 3H), 7.36-7.46 (m, 5H); $^{13}$C NMR (100 MHz, CDCl$_3$): δ 24.8, 34.2, 70.4, 114.2, 115.4, 115.9, 117.9, 119.8, 127.8, 128.4, 128.9, 131.1, 133.8, 136.4, 159.7; HRMS (ES) calcd for C$_{17}$H$_{14}$N$_2$NaO (M+Na$^+$) 285.1004, found 285.1010.

Compound 157a (R$_1$=3-benzyloxy, R$_2$=H). Dibal-H (52.5 mL, 52.5 mmol, 1.0 N solution in toluene) was added dropwise to a solution of compound 156a (5.3 g, 20.2 mmol) in benzene (140 mL) at ice-water temperature. The resulting mixture was stirred for 2 h, while the temperature was gradually warmed to room temperature over 2 h. Sodium dihydrogen phosphate (350 mL, 1.5 N aqueous solution) was added dropwise to the above solution and the resulting solution was refluxed for 1 hour. The reaction mixture was filtered through a layer of Celite and washed with ethyl acetate. The layers of the combined filtrate were separated and the organic layer was washed with water, brine, dried over MgSO$_4$, and evaporated under reduced pressure. The residue was purified by column chromatography on silica gel to afford the desired product (2.0 g, 40%); $^1$H NMR (400 MHz, CDCl$_3$): δ 5.15 (s, 2H), 7.00-7.04 (m, 3H), 7.36-7.46 (m, 5H), 8.27 (brs, 1H); $^{13}$C NMR (100 MHz, CDCl$_3$): δ 70.1, 106.7, 111.8, 112.2, 115.0, 118.3, 119.1, 124.8, 127.8, 128.1, 128.8, 129.8, 137.3, 137.5, 159.3; HRMS (ES) calcd for C$_{17}$H$_{15}$NNaO (M+Na$^+$) 272.1051, found 272.1056.

Compound 158a (R$_1$=3-benzyloxy, R$_2$=H, n=1, X=O). Glycidol (2.6 mL, 40.0 mmol) dissolved in ethyl acetate (200 mL) was treated with triethylamine (5.6 mL, 40.2 mmol). Diphosgene (4.6 mL, 38.4 mmol) was slowly added to the above solution at −20° C., and the reaction mixture was stirred at room temperature for 2 h. The precipitate was filtered off and the filtrate was evaporated. The residue was purified by short-path column chromatography on silica gel yielding 2,3-epoxypropyl chloroformate. Pyrrole 144a (2.0 g, 8.0 mmol) in anhydrous acetonitrile (30 mL) was treated with NaH (0.64 g, 16.0 mmol, 60%) at ice-water temperature. The resulting mixture was stirred while temperature was gradually warmed to room temperature over 1 hour. After cooling in ice-bath, 2,3-epoxypropyl chloroformate (2.2 g, 16.4 mmol) in acetonitrile (5 mL) was added to the reaction mixture and was stirred while the temperature was gradually warmed to room temperature over 2 h. After stirring at 50° C. for additional 1 hour, the resulting mixture was filtered through a small layer of silica gel and the filtrate was evaporated. The residue was taken up in ethyl acetate and was washed with water, brine, and dried over MgSO$_4$.

After removal of solvent, the residue was purified by column chromatography on silica gel to afford the desired product (1.5 g, 55%); $^1$H NMR (400 MHz, CDCl$_3$): δ 2.73 (dd, 1H, J=2.4, 4.9 Hz), 2.92 (dd, 1H, J=4.0, 4.9 Hz), 3.35 (sextet**, 1H, J=3.2 Hz), 4.19 (dd, 1H, J=6.5, 12.2 Hz), 4.71 (dd, 1H, J=3.2, 12.2 Hz), 5.11 (s, 2H), 6.59 (dd, 1H, J=1.6, 3.2 Hz), 6.89 (dd, 1H, J=2.8, 8.4 Hz), 7.16-7.49 (m, 9H), 7.58 (m, 1H); $^{13}$C NMR (100 MHz, CDCl$_3$): δ 44.8, 49.3, 68.1, 70.3, 111.7, 112.6, 113.3, 116.3, 118.7, 121.3, 127.8, 128.2, 128.9, 130.1, 135.6, 137.2, 150.3, 159.4; HRMS (ESI) calcd for $C_{21}H_{19}NNaO_4$ (4+Na$^+$) 372.1212, found 372.1215.

Compound 158b ($R_1$=3-hydroxy, $R_2$=H, n=1, X=O). Compound 158a (0.7 g, 2.0 mmol) was stirred for 2 hours in the presence of Pd(OH)$_2$ (0.2 g) in ethyl acetate:THF (1:1, 15 mL) under hydrogen atmosphere. The reaction mixture was filtered through a layer of celite and washed with methanol. The filtrate was evaporated under reduced pressure and the residue was purified by column chromatography on silica gel to afford the desired product (0.35 g, 67%); $^1$H NMR (400 MHz, CDCl$_3$): δ 2.74 (dd, 1H, J=2.8, 4.5 Hz), 2.93 (dd, 1H, J=4.1, 4.8 Hz), 3.36 (m, 1H), 4.20 (dd, 1H, J=6.5, 12.2 Hz), 4.72 (dd, 1H, J=2.4, 12.2 Hz), 6.56 (dd, 1H, J=1.6, 4.0 Hz), 6.73 (dd, 1H, J=2.4, 8.0 Hz), 7.00-7.26 (m, 4H), 7.33 (m, 1H), 7.55 (m, 1H); $^{13}$C NMR (100 MHz, CDCl$_3$): δ 45.0, 49.5, 68.1, 111.8, 112.7, 114.2, 118.1, 121.3, 130.2, 135.6, 150.3, 156.5; HRMS (ESI) calcd for $C_{14}H_{13}NNaO_4$ M+Na$^+$) 282.0742, found 282.0752.

Compound 158c ($R_1$=3-hydroxy, $R_2$=H, n=1, X=S). A mixture of compound 158b (300 mg, 1.2 mmol) and thiourea (120 mg, 1.6 mmol) in anhydrous methanol (10 mL) was stirred at room temperature overnight. The volatile was evaporated under reduced pressure and the residue was purified by column chromatography on silica gel to afford the desired product (200 mg, 63%); $^1$H NMR (400 MHz, CDCl$_3$): δ 2.37 (dd, 1H, J=1.6, 5.7 Hz), 2.61 (d, 1H, J=5.7 Hz), 3.26 (quintet, 1H, J=5.7 Hz), 4.40 (dd, 1H, J=7.3, 11.4 Hz), 4.48 (dd, 1H, J=6.5, 11.3 Hz), 6.56 (dd, 1H, J=1.6, 3.2 Hz), 6.74 (dd, 1H, J=2.4, 8.1 Hz), 7.02 (dd, 1H, J=1.6, 2.4 Hz), 7.12 (d, 1H, J=8.1 Hz), 7.22-7.26 (m, 2H), 7.36-7.46 (m, 5H), 7.33 (dd, 1H, J=1.6, 3.3 Hz), 7.55 (m, 1H), 8.27 (brs, 1H); $^{13}$C NMR (100 MHz, CDCl$_3$): δ 24.0, 30.5, 71.3, 111.7, 112.7, 116.2, 118.4, 121.3, 128.5, 130.2, 135.7, 150.2, 156.2; HRMS (ESI) calcd for $C_{14}H_{13}NNaO_3S$ (M+Na$^+$) 298.0514, found 298.0522.

Compounds 159a-f were prepared in the same manner as described for 158, with the exception that were used epichlorohydrin and 3,4-epoxybutylchloride in place of 2,3-epoxypropylchloroformate.

Compound 159a ($R_1$=3-benzyloxy, $R_2$=H, n=1, X=O).
Compound 159b ($R_1$=3-hydroxy, $R_2$=H, n=1, X=O).
Compound 159c ($R_1$=3-hydroxy, $R_2$=H, n=1, X=S).
Compound 159d ($R_1$=3-benzyloxy, $R_2$=H, n=2, X=O).
Compound 159e ($R_1$=3-hydroxy, $R_2$=H, n=2, X=O).
Compound 159f ($R_1$=3-hydroxy, $R_2$-=H, n-2, X=S).

Example 4

Other Compounds of the Invention

Figure 9:
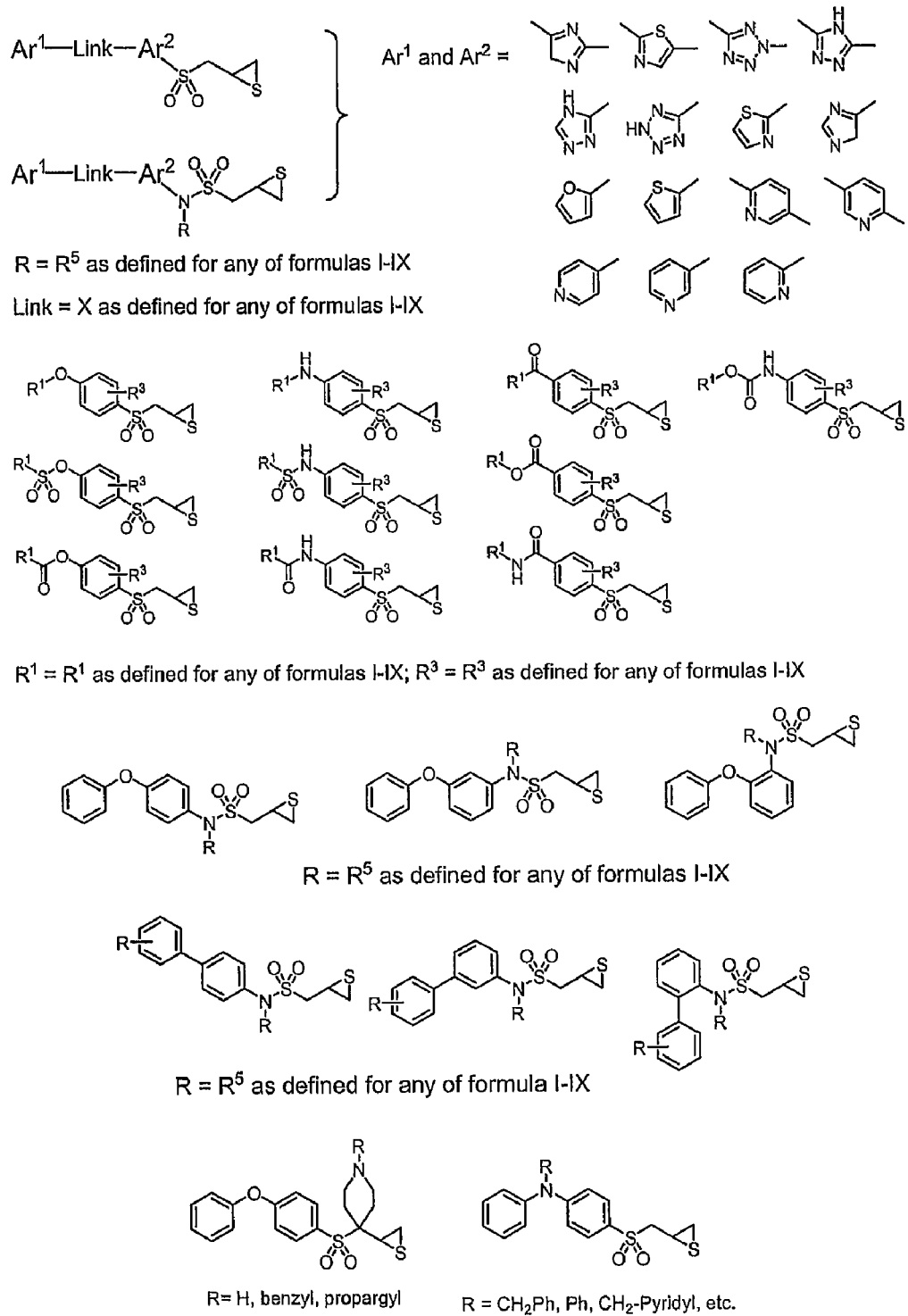
FIG. 9 illustrates certain specific and general compounds of the invention, according to various embodiments.

FIG. 9 illustrates several other species and classes of compounds of the invention. These compounds can be prepared according to the methods described in Example 3, by using appropriate starting materials, and by using other techniques well know to those of skill in the art.

All publications, patents, and patent documents referred to herein are incorporated by reference, as though individually incorporated by reference. The invention has been described with reference to various specific and preferred embodiments and techniques. However, it will be apparent to those skilled in the art that many variations and modifications may be made while remaining within the spirit and scope of the invention.

What is claimed is:

1. A compound of formula I:

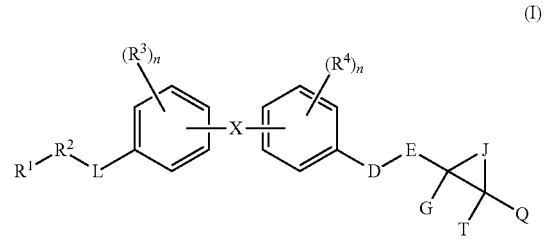

wherein
$R^1$ is $(C_1$-$C_6)$alkyl, halo$(C_1$-$C_6)$alkyl, $(C_1$-$C_6)$alkoxy, aryl$(C_1$-$C_6)$alkyl, heteroaryl$(C_1$-$C_6)$alkyl, aryl$(C_1$-$C_6)$alkoxy, heteroaryl$(C_1$-$C_6)$alkoxy, aryl, heteroaryl, hydroxy, $SR^5$, $NR^5R^5$, or absent;
$R^2$ is $CH_2$, carbonyl, $SO_2$, or OH;
L is $CH_2$, $NR^5$, or O;
$R^3$ and $R^4$ are each independently hydroxy, $(C_1$-$C_6)$alkyl, $(C_1$-$C_6)$alkoxy, $(C_1$-$C_6)$alkanoyl, $(C_1$-$C_6)$alkanoyloxy, aryl, heteroaryl, carboxy, cyano, nitro, halo, trifluoromethyl, trifluoromethoxy, $SR^5$, $SO_2N(R_5)_2$, $NR^5R^5$, or $CO_2R^5$;
each n is independently 0 to 4;
each $R^5$ is independently H, $(C_1$-$C_6)$alkyl, $(C_1$-$C_6)$alkanoyl, $(C_6$-$C_{10})$aroyl, aryl, aryl$(C_1$-$C_6)$alkyl, heteroaryl, heteroaryl$(C_1$-$C_6)$alkyl, or a nitrogen protecting group;
X is O;
D is S, SO, $SO_2$, C=N—OH, or carbonyl;
E is a direct bond, or $(C_1$-$C_6)$alkyl;
J is S, O, or $NR^5$;
G, T, and Q are each independently H, $(C_1$-$C_6)$alkyl, or cyano;
any alkyl, amino, aryl, heteroaryl, or cycloalkyl is optionally substituted with 1 to about 5 $(C_1$-$C_6)$alkyl, $(C_1$-$C_6)$alkoxy, aryl, heteroaryl, aryl$(C_1$-$C_6)$alkyl, heteroaryl$(C_1$-$C_6)$alkyl, nitro, halo, amino, or hydroxy groups;
or a pharmaceutically acceptable salt thereof;
provided that when L is $CH_2$ or O, and $R^2$ is $CH_2$, $R^1$ is not $(C_1$-$C_6)$alkyl;
when L is O and $R^2$ is carbonyl, $R^1$ is not $(C_1$-$C_6)$alkyl; and
when L is $NR^5$, $R^2$ is not $CH_2$.

2. The compound of claim 1 wherein $R^1$ is $(C_1$-$C_6)$alkyl, $(C_1$-$C_6)$alkoxy, heteroaryl$(C_1$-$C_6)$alkoxy, halo$(C_1$-$C_6)$alkyl, aryl$(C_1$-$C_6)$alkyl, or aryl; and $R^2$ is $CH_2$, carbonyl, or $SO_2$.

3. The compound of claim 1 wherein L is $CH_2$, O, or $NR^5$ wherein $R^5$ is H, $(C_1$-$C_6)$alkyl, or a nitrogen protecting group.

4. The compound of claim 1 wherein $R^3$ is hydroxy, halo, amino, hydroxyphenyl, halophenyl, or $SO_2N(R_5)_2$ wherein each $R^5$ of $R^3$ is H.

5. The compound of claim 1 wherein $R^4$ is hydroxy, halo, amino, or $SO_2N(R_5)_2$ wherein each $R^5$ of $R^4$ is H.

6. The compound of claim 1 wherein D is $SO_2$, or carbonyl.

7. The compound of claim 1 wherein E is a direct bond, $CH_2$, or $(C_1$-$C_6)$alkyl, optionally substituted with 1 to 5 halo groups.

8. The compound of claim 1 wherein J is S, O, or NH.

9. The compound of claim 1 wherein G, T, and Q are each H.

10. The compound of claim 1 wherein the compound of formula I is a compound of the formula:

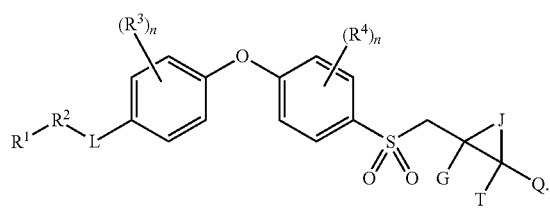

11. The compound of claim 10 wherein J is S or O; the groups G, T, and Q are each H; and each n is 0.

12. The compound of claim 10 wherein L is $CH_2$, $R^2$ is carbonyl, and $R^1$ is $(C_1-C_6)$alkoxy, aryl$(C_1-C_6)$alkoxy, heteroaryl$(C_1-C_6)$alkoxy, or hydroxy.

13. The compound of claim 10 wherein L is $NR^5$ wherein $R^5$ is H, $R^2$ is $SO_2$ or carbonyl, and $R^1$ is $(C_1-C_6)$alkyl or $(C_1-C_6)$alkoxy.

14. The compound of claim 10 wherein L is O, $R^2$ is $SO_2$ or carbonyl, and $R^1$ is $(C_1-C_6)$alkyl or optionally substituted aryl.

15. The compound

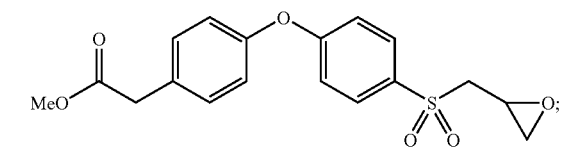

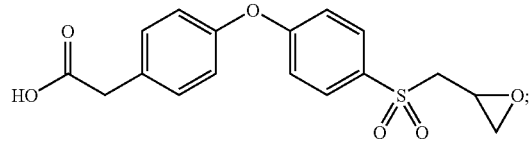

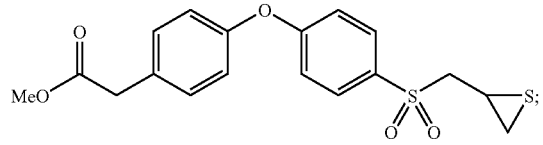

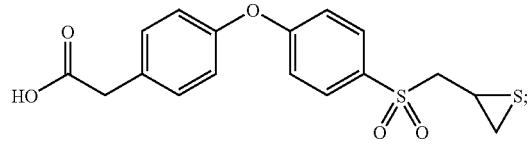

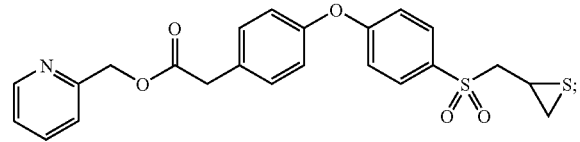

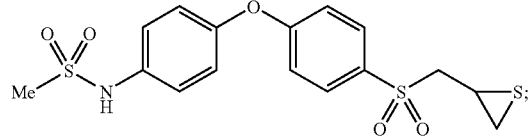

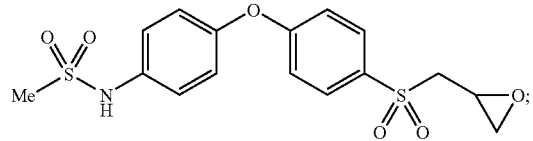

-continued

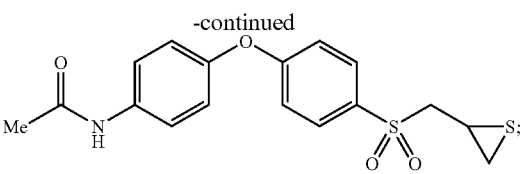

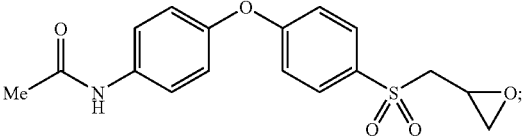

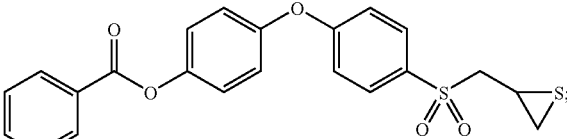

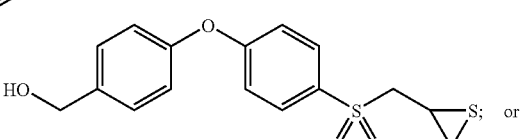

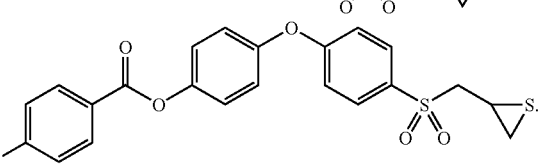

16. The compound

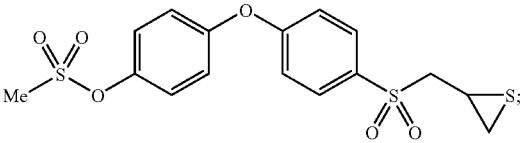

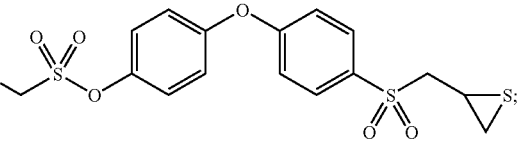

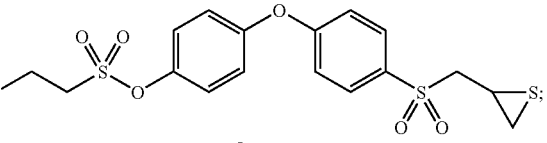

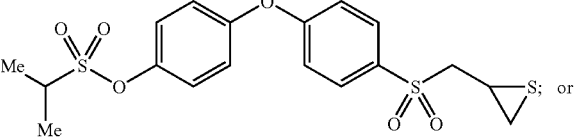

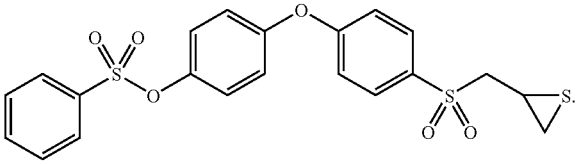

17. A pharmaceutical composition comprising a compound of claim 1 and a pharmaceutically acceptable carrier.

18. A composition comprising a compound of claim 1 and a chemotherapeutic agent.

19. A method of inhibiting a matrix metalloproteinase in a cell comprising contacting a cell with an amount of a compound of claim 1 that is effective to inhibit a matrix metalloproteinase.

20. The method of claim 19 wherein the contacting is in vitro or in vivo.

* * * * *